(12) United States Patent
Zhu et al.

(10) Patent No.: US 11,192,891 B2
(45) Date of Patent: Dec. 7, 2021

(54) DIAZASPIRO ROCK INHIBITORS

(71) Applicant: BRISTOL-MYERS SQUIBB COMPANY, Princeton, NJ (US)

(72) Inventors: Yeheng Zhu, Stockton, NJ (US);
Sunita V. Dewnani, Somerset, NJ (US);
William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 22 days.

(21) Appl. No.: 16/760,682

(22) PCT Filed: Nov. 1, 2018

(86) PCT No.: PCT/US2018/058611
§ 371 (c)(1),
(2) Date: Apr. 30, 2020

(87) PCT Pub. No.: WO2019/089868
PCT Pub. Date: May 9, 2019

(65) Prior Publication Data
US 2021/0188848 A1    Jun. 24, 2021

Related U.S. Application Data

(60) Provisional application No. 62/581,116, filed on Nov. 3, 2017.

(51) Int. Cl.
| | | |
|---|---|---|
| *C07D 471/10* | (2006.01) | |
| *A61K 31/438* | (2006.01) | |
| *A61K 9/00* | (2006.01) | |
| *C07D 487/10* | (2006.01) | |

(52) U.S. Cl.
CPC .......... *C07D 471/10* (2013.01); *A61K 9/0019* (2013.01); *A61K 9/0053* (2013.01); *C07D 487/10* (2013.01)

(58) Field of Classification Search
CPC .. C07D 471/10; C07D 487/10; A61K 31/438; A61P 9/00; A61P 29/00
USPC .................... 546/16; 548/410; 514/278, 409
See application file for complete search history.

(56) References Cited

FOREIGN PATENT DOCUMENTS

| | | |
|---|---|---|
| WO | WO2010065803 A1 | 6/2010 |
| WO | WO2011143148 A1 | 11/2011 |
| WO | WO2011143150 A1 | 11/2011 |
| WO | WO2014113620 A2 | 7/2014 |
| WO | WO2014134388 A1 | 9/2014 |
| WO | WO2014134391 A1 | 9/2014 |
| WO | WO2015002915 A1 | 1/2015 |
| WO | WO2015002926 A1 | 1/2015 |
| WO | WO2016010950 A1 | 1/2016 |
| WO | WO2016028971 A1 | 2/2016 |
| WO | WO2016112236 A1 | 7/2016 |
| WO | WO2016144936 A1 | 9/2016 |
| WO | WO2017123860 A1 | 7/2017 |
| WO | WO2017205709 A1 | 11/2017 |
| WO | WO2018009622 A1 | 1/2018 |
| WO | WO2018009625 A1 | 1/2018 |
| WO | WO2018009627 A1 | 1/2018 |
| WO | WO2018102325 A1 | 6/2018 |
| WO | WO2019014300 A1 | 1/2019 |
| WO | WO2019014303 A1 | 1/2019 |
| WO | WO2019014304 A1 | 1/2019 |
| WO | WO2019014308 A1 | 1/2019 |
| WO | WO2019089868 A1 | 5/2019 |

*Primary Examiner* — Charanjit Aulakh
(74) *Attorney, Agent, or Firm* — Hong Liu

(57) ABSTRACT

The present invention provides compounds of Formula (I): or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

12 Claims, No Drawings

DIAZASPIRO ROCK INHIBITORS

CROSS REFERENCE TO RELATED APPLICATIONS

This application is a 371 of International Application No. PCT/US2018/058611, filed on Nov. 1, 2018, which is entitled to priority pursuant to 35 U.S.C. § 119(e) to U.S. provisional patent application No. 62/581,116, filed Nov. 3, 2017, which is incorporated herein in its entirety.

FIELD OF THE INVENTION

The present invention relates generally to novel diazaspiro compounds and their analogues thereof, which are inhibitors of Rho kinases, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as ACTIN® organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotensin II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.* 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa. H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada. T. et al., *J. Am. Coll. Cardio.*, 45:599-607 (2005)), pulmonary hypertension (Fukumoto, Y. et al., *Heart*, 91:391-392 (2005)), angina (Shimokawa. H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima. H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol Ther.*, 18:67-74 (2005)), cancer (Rattan, R. et al., *J. Neurosci. Res.*, 83:243-255 (2006); Lepley. D. et al., *Cancer Res.*, 65:3788-3795 (2005)), fibrotic diseases (Jiang. C. et al., *Int. J. Mol.*

Sci., 13:8293-8307 (2012); Zhou, L. et al., *Am. J. Nephrol.*, 34:468-475 (2011)), as well as neurological disorders, such as spinal-cord injury, Alzheimer's disease, multiple sclerosis, stroke and neuropathic pain (Mueller, B. K. et al., *Nat. Rev. Drug Disc.*, 4:387-398 (2005); Sun, X. et al., *J Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the U.S., with coronary heart disease accounting for ~1 in 6 deaths overall in the U.S. Contributing to these numbers, it was found that ~33.5% of the adult U.S. population was hypertensive, and it was estimated that in 2010 ~6.6 million U.S. adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

There are many reports of ROCK inhibitors under investigation (see, for example, US 2012/0122842 A1 US 2010/0041645 A1, US 2008/0161297 A1, and Hu, E. et al., *Exp. Opin. Ther. Targets*, 9:715-736 (2005)). Reports also include WO2014/113620, WO 2014/134388, WO 2014/134391, WO2015/002915, WO2015/002926, WO2016/010950, WO2016/028971, WO2016/112236, WO2016/144936, and WO2017/123860, all of which are assigned to the present applicant. However, fasudil is the only marketed ROCK inhibitor at this time. An i.v. formulation was approved in Japan for treatment of cerebral vasospasm. Thus, there remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel diazaspiro compounds and their analogues, including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above.

Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimers disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

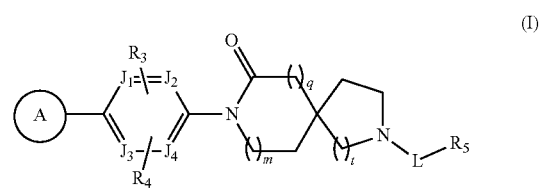

or stereoisomers, tautomers, pharmaceutically acceptable salts, solvates, or prodrugs thereof, wherein Ring A is selected from

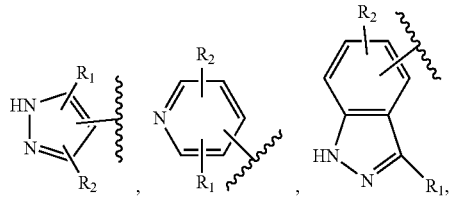

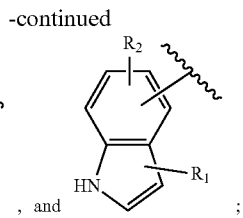
, and $J_1$, $J_2$, $J_3$, and $J_4$ are independently selected from N, $CR_3$, and $CR_4$; provided no more than two of $J_1$, $J_2$, $J_3$, and $J_4$ are N;

L is selected from —C(O)—, —C(O)NH—, and —S(O)$_p$—;

$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—$C_{3-6}$ carbocyclyl substituted with 0-3 $R_e$, and —(CH$_2$)$_r$-heterocyclyl substituted with 0-3 $R_e$;

$R_3$, at each occurrence, is independently selected from H, F, Cl, Br, CN, $C_{1-4}$ alkyl substituted with 0-3 $R_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—$C_{3-6}$carbocyclyl substituted with 0-3 $R_e$, and —(CH$_2$)$_r$-heterocyclyl substituted with 0-3 $R_e$;

$R_4$, at each occurrence, is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is selected from $C_{3-10}$ carbocyclyl substituted with 0-5 $R_6$ and heterocyclyl comprising carbon atoms and 1-6 heteroatoms selected from N, $NR_{6a}$, S, and O, and substituted with 0-6 $R_6$;

$R_6$, at each occurrence, is independently selected from F, Cl, Br, =O, $C_{1-4}$alkyl, $C_{2-4}$alkenyl, $C_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_7$R$_7$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$C(=O)NR$_a$R$_a$, —(CHR$_d$)$_r$OC(=O)R$_b$, —(CHR$_d$)$_r$—$C_{3-6}$cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 $R_e$;

$R_{6a}$ is selected from H, $C_{1-4}$alkyl, $C_{2-4}$alkenyl, $C_{2-4}$alkynyl, —S(O)$_p$R$_c$, —S(O)$_p$NR$_a$R$_a$, —C(=O)OR$_b$, —C(=O)R$_b$, —C(=O)NR$_a$R$_a$, —(CHR$_d$)$_r$—$C_{3-6}$cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 $R_e$;

$R_7$, at each occurrence, is independently selected from H, $C_{1-6}$ alkyl substituted with 1-5 $R_a$, $C_{2-6}$ alkenyl substituted with 1-5 $R_a$, $C_{2-6}$ alkynyl substituted with 1-5 $R_a$, —(CH$_2$)$_r$—$C_{3-10}$carbocyclyl substituted with 1-5 $R_a$, and —(CH)$_r$-heterocyclyl substituted with 1-5 $R_a$; or $R_7$ and $R_7$ together with the nitrogen atom to which they are both attached form a heterocyclic ring substituted with 1-5 $R_a$;

$R_a$, at each occurrence, is independently selected from H, C(=O)OR$_b$, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—$C_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, NO$_2$, =O, $C_{1-6}$ alkyl substituted with 1-5 $R_f$, $C_{2-6}$ alkenyl, $C_{2-6}$ alkynyl, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$, —(CH$_2$)$_r$NR$_f$R$_f$, —(CH$_2$)$_r$—$C_{3-6}$cycloalkyl substituted with 1-5 $R_f$, —O(CH$_2$)$_r$—$C_{3-6}$cycloalkyl substituted with 1-5 $R_f$, —(CH$_2$)$_r$-heterocyclyl substituted with 1-5 Rr, —O(CH$_2$)$_r$-heterocyclyl substituted with 1-5 $R_f$, —(CH$_2$)$_r$-aryl substituted with 1-5 $R_f$, —O(CH$_2$)$_r$-aryl substituted with 1-5 $R_f$, —(CH$_2$)$_r$-heteroaryl substituted with 1-5 $R_f$, and —O(CH$_2$)$_r$-heteroaryl substituted with 1-5 $R_f$;

$R_f$, at each occurrence, is independently selected from H, F, Cl, Br, CN, NO$_2$, =O, $C_{1-5}$alkyl (optionally substituted with F, Cl, Br, OH, $OC_{1-4}$ alkyl, $NR_gR_g$), —(CH$_2$)$_r$—$C_{3-10}$carbocyclyl and —(CH$_2$)-heterocyclyl, or $R_f$ and $R_f$ together with the nitrogen atom to which they are both attached form a heterocyclic ring optionally substituted with $C_{1-4}$alkyl;

$R_g$, at each occurrence, is independently selected from H and $C_{1-5}$alkyl;

m is an integer of zero, 1 or 2;

p is an integer of zero, 1 or 2;

q is an integer of zero or 1;

r is an integer of zero, 1, 2, 3 or 4; and t is an integer of zero, 1 or 2.

In another aspect, the present invention provides compounds of Formula (I), or stereoisomers, tautomers, pharmaceutically acceptable salts, solvates, or prodrugs thereof, wherein $R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

$R_3$, at each occurrence, is independently selected from H, F, Cl, Br, CN, $C_{1-4}$ alkyl substituted with 0-3 $R_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$N-R$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—$C_{3-6}$ carbocyclyl substituted with 0-3 $R_e$, and —(CH$_2$)$_r$-heterocyclyl substituted with 0-3 $R_e$;

R₄, at each occurrence, is independently selected from H, F, Cl, Br, OH, CN, and C₁₋₄ alkyl substituted with 0-3 $R_e$;
R₅ is selected from
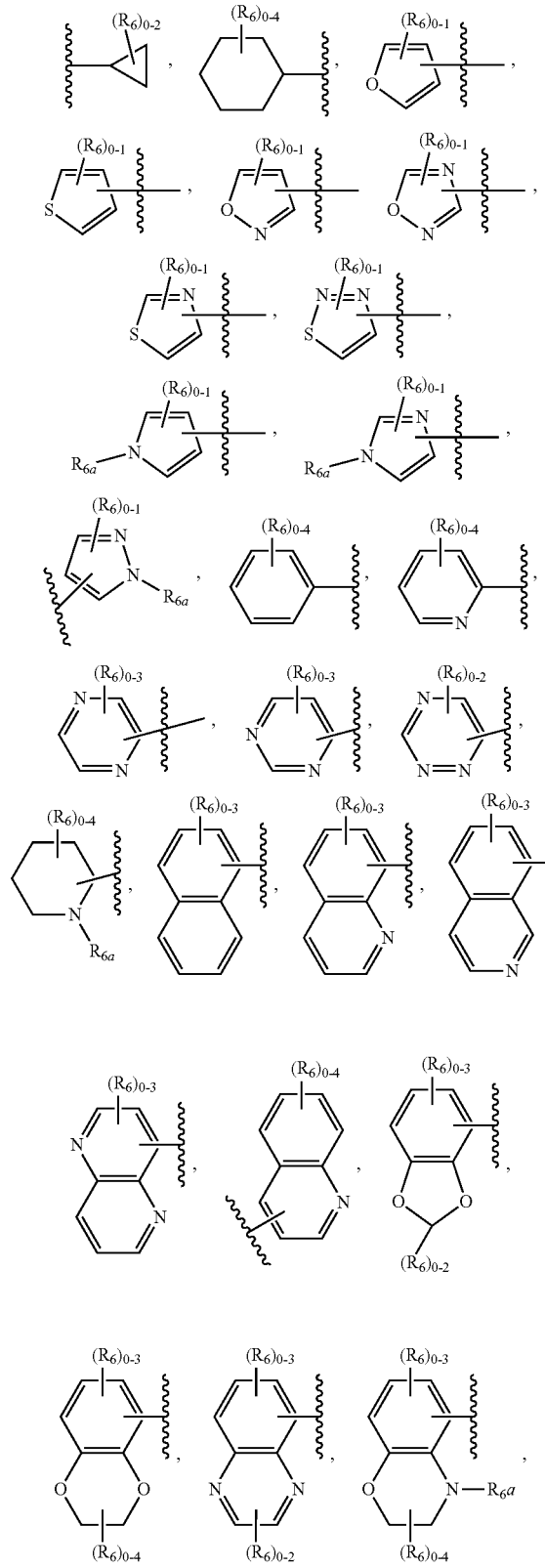
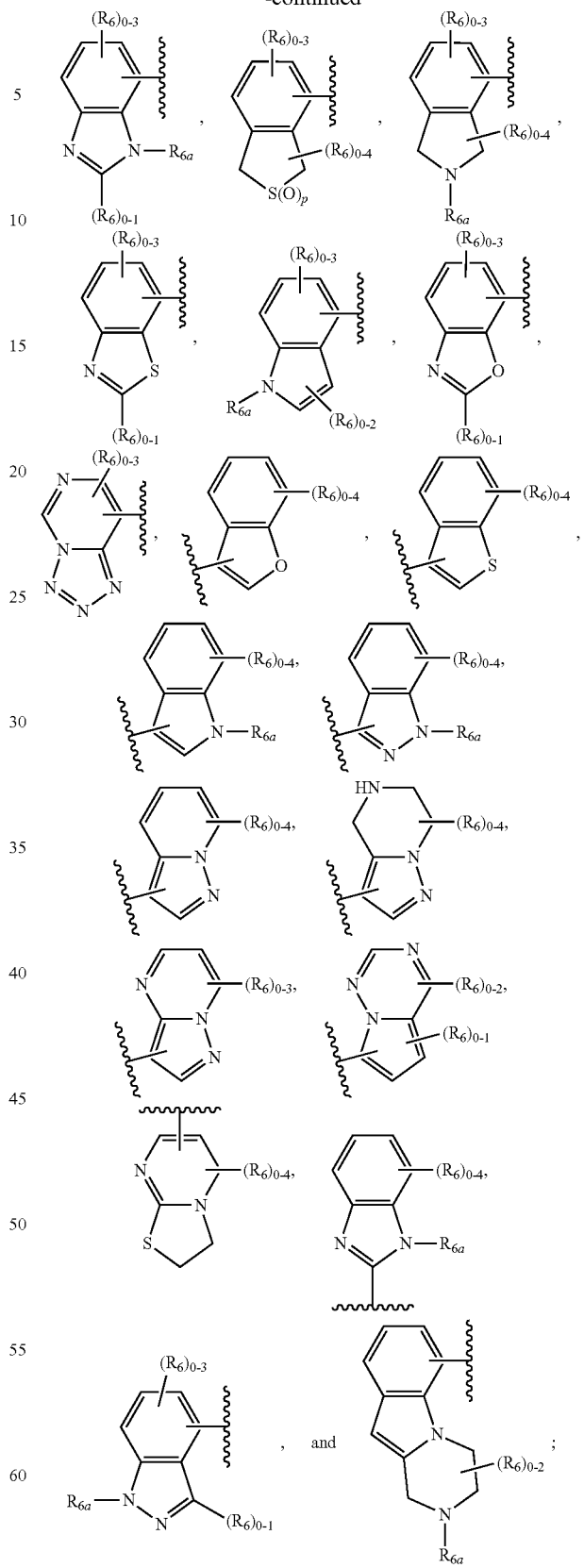
R₆, at each occurrence, is independently selected from F, Cl, Br, =O, C₁₋₄alkyl, C₂₋₄alkenyl, C₂₋₄alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —C(=O)NR$_a$R$_a$—(CHR$_d$)$_r$OC(=O)R$_b$, —(CHR$_d$)$_r$—C$_{3-6}$cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 R$_e$;

R$_{6a}$, at each occurrence, is independently selected from H, C$_{1-4}$alkyl. —S(O)$_p$R$_c$, —S(O)$_p$NR$_a$R$_a$, —C(=O)OR$_b$, —C(=O)R$_b$, —C(=O)NR$_a$R$_a$, —(CHR$_d$)$_r$—C$_{3-6}$cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_7$, at each occurrence, is independently selected from H, C$_{1-6}$ alkyl substituted with 1-5 R$_a$, C$_{2-6}$ alkenyl substituted with 1-5 R$_a$, C$_{2-6}$ alkynyl substituted with 1-5 R$_a$, —(CH$_2$)$_r$—C$_{3-10}$carbocyclyl substituted with 1-5 R$_a$, and —(CH$_2$)$_r$-heterocyclyl substituted with 1-5 R$_a$; or R$_7$ and R$_7$ together with the nitrogen atom to which they are both attached form a heterocyclic ring substituted with 1-5 R$_a$;

R$_a$, at each occurrence, is independently selected from H, $_r$C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$, —(CH$_2$)$_r$NR$_f$R$_f$, —(CH$_2$)$_r$—C$_{3-6}$cycloalkyl substituted with 1-5 R$_f$, —O(CH$_2$)$_r$—C$_{3-6}$cycloalkyl substituted with 1-5 Rr, —(CH$_2$)-heterocyclyl substituted with 1-5 Rr, —O(CH$_2$)$_r$-heterocyclyl substituted with 1-5 Rr, —(CH$_2$)$_r$-aryl substituted with 1-5 R$_f$, —O(CH$_2$)$_r$-aryl substituted with 1-5 R$_f$, —(CH$_2$)$_r$-heteroaryl substituted with 1-5 R$_f$, and —O(CH$_2$)$_r$-heteroaryl substituted with 1-5 R$_f$;

R$_f$, at each occurrence, is independently selected from H, F, Cl, Br, CN, OH, C$_{1-5}$alkyl (optionally substituted with F, Cl, Br, OH and OC$_{1-4}$ alkyl, —NR$_g$R$_g$), —(CH$_2$)$_r$—C$_{3-10}$carbocyclyl, and —(CH$_2$)$_r$-heterocyclyl, or R$_f$ and R$_f$ together with the nitrogen atom to which they are both attached form a heterocyclic ring optionally substituted with C$_{1-4}$alkyl;

R$_g$, at each occurrence, is independently selected from H and C$_{1-5}$alkyl; and other variables are as defined in Formula (I).

In another aspect, the present invention provides compounds of Formula (II):

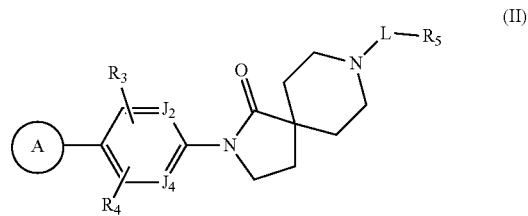

or stereoisomers, tautomers, pharmaceutically acceptable salts, solvates, or prodrugs thereof, wherein Ring A is selected from

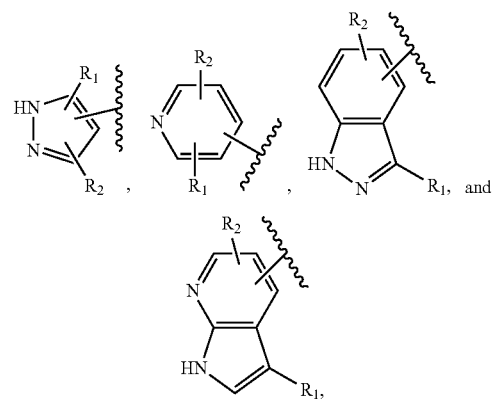

J$_2$ and J$_4$ are independently selected from N, CR$_3$, and CR$_4$;

L is selected from —C(O)— and —S(O)$_p$—;

R$_1$, at each occurrence, is independently selected from H, F, Cl, Br, CN, NR$_a$R$_a$, and C$_{1-4}$alkyl substituted with 0-4 R$_e$;

R$_2$, at each occurrence, is independently selected from H, F, Cl, Br, OH, CN, NR$_a$R$_a$, and C$_{1-4}$alkyl substituted with 0-4 R$_e$;

R$_3$, at each occurrence, is independently selected from H, F, Cl, Br, CN, C$_{1-4}$ alkyl substituted with 0-3 R$_e$, —(CH$_2$)$_r$R$_b$, and —C$_{3-6}$cycloalkyl;

R$_4$, at each occurrence, is independently selected from H, F, Cl, Br, OH, CN, OC$_{1-4}$ alkyl substituted with 0-3 R$_e$, and C$_{1-4}$ alkyl substituted with 0-3 R$_e$;

R$_5$ is selected from

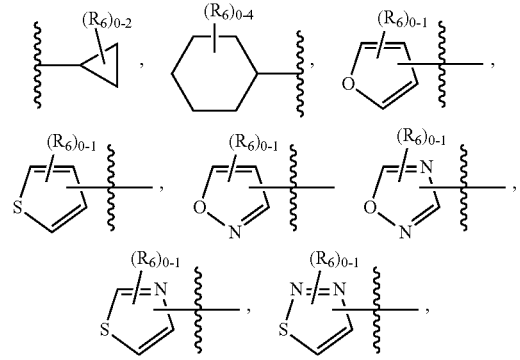

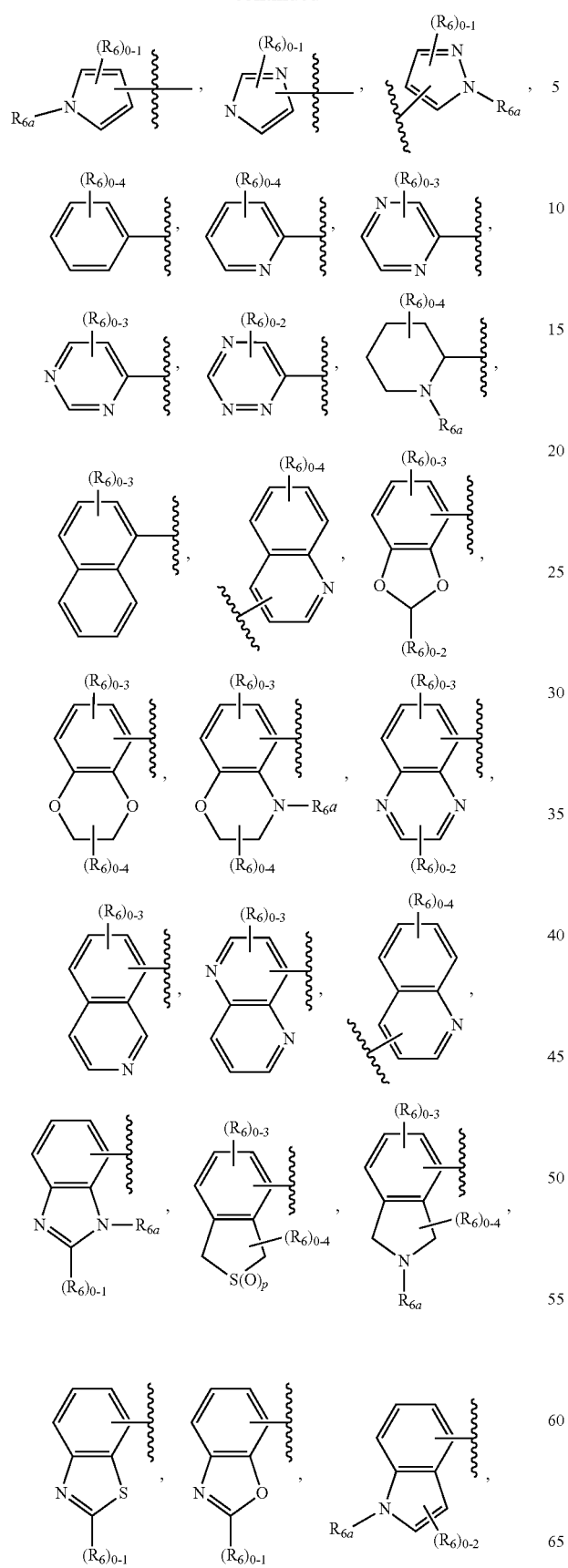
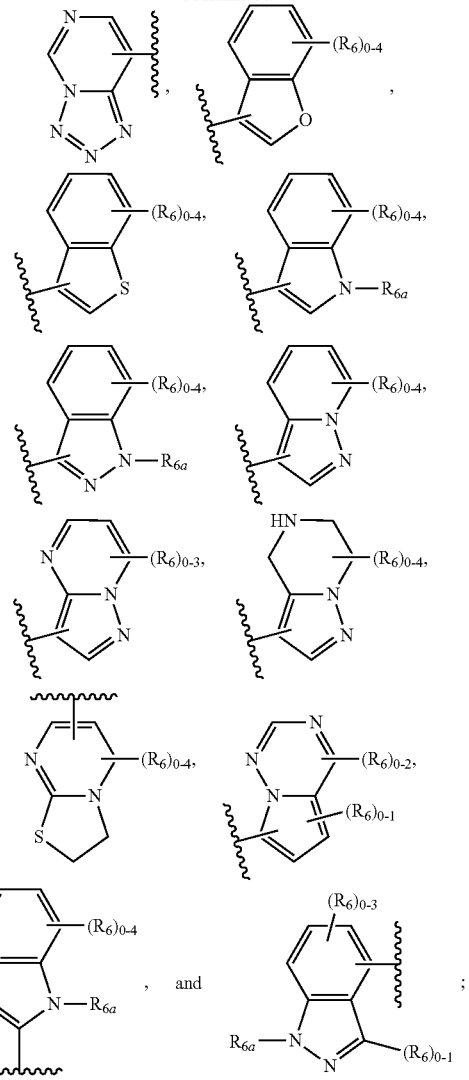

$R_6$, at each occurrence, is independently selected from F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$C(=O)NR_aR_a$—$(CHR_d)_rOC(=O)R_b$, —$(CHR_d)_r$—$C_{3-6}$cycloalkyl, —$(CHR_d)_r$-heterocyclyl, —$(CHR_d)$-aryl, and —$(CHR_d)_r$-heteroaryl, wherein said alkyl, alkenyl, alkynyl, cycloalkyl, heterocyclyl, aryl, or heteroaryl is substituted with 0-4 $R_e$;

$R_{6a}$, at each occurrence, is independently selected from H, $C_{1-4}$alkyl, —$S(O)_pR_e$, —$S(O)_pNR_aR_a$, —$C(=O)OR_b$, —$C(=O)R_b$, —$C(=O)NR_aR_a$, —$(CHR_d)_r$—$C_{3-6}$cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_7$, at each occurrence, is independently selected from H, $C_{1-6}$ alkyl substituted with 0-5 $R_a$, $C_{2-6}$ alkenyl substituted with 1-5 $R_a$, $C_{2-6}$ alkynyl substituted with 1-5 $R_a$, —$(CH_2)_r$—$C_{3-10}$carbocyclyl substituted with 1-5 $R_a$, and —$(CH_2)_r$-heterocyclyl substituted with 1-5 $R_a$; or $R_7$ and $R_7$ together with the nitrogen atom to which they are both attached form a heterocyclic ring substituted with 1-5 $R_a$;

R$_a$, at each occurrence, is independently selected from H, C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl:

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, CO$_2$H, —(CH$_2$)$_r$OR$_f$, S(O)$_p$R$_f$, S(O)$_p$NR$_f$R$_f$, NR$_f$S(O)$_p$R$_d$, —(CH$_2$)$_r$NR$_f$R$_f$, —(CH$_2$)$_r$—C$_{3-6}$cycloalkyl, —O(CH$_2$)$_r$—C$_{3-6}$cycloalkyl, —(CH$_2$)$_r$-heterocyclyl, —O(CH$_2$)$_r$-heterocyclyl, —(CH$_2$)$_r$-aryl, and —O(CH$_2$)$_r$-aryl;

R$_f$ at each occurrence, is independently selected from H, F, Cl, Br, CN, OH, C$_{1-5}$ alkyl (optionally substituted with F, Cl, Br, OH, and OC$_4$ alkyl, —NR$_g$R$_g$), —(CH$_2$)$_r$—C$_{3-6}$cycloalkyl, and —(CH$_2$)$_r$-phenyl;

R$_g$, at each occurrence, is independently selected from H and C$_{1-5}$alkyl; and other variables are as defined in Formula (I).

In another aspect, the present invention provides compounds of Formula (III):

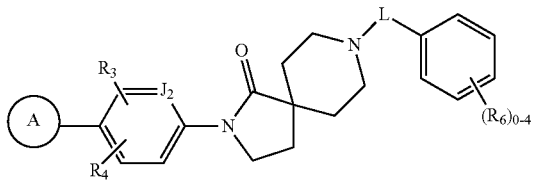

(III)

or stereoisomers, tautomers, pharmaceutically acceptable salts, solvates, or prodrugs thereof, wherein
Ring A is selected from

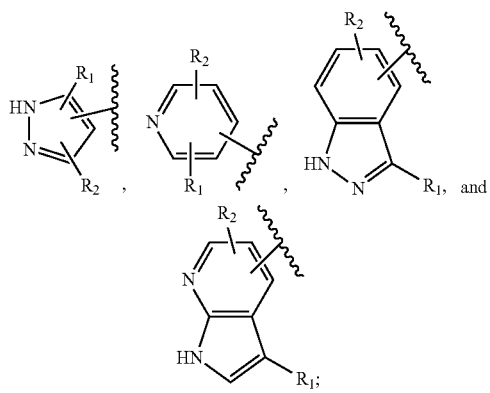

J is selected from N, CR$_3$, and CR$_4$:

L is selected from —C(O)— and —S(O)$_p$—;

R$_1$, at each occurrence, is independently selected from H, F, Cl, Br, CN, NR$_a$R$_a$, and C$_{1-4}$alkyl substituted with 0-4 R$_e$:

R$_2$, at each occurrence, is independently selected from H and C$_{1-4}$alkyl substituted with 0-4 R$_e$;

R$_3$, at each occurrence, is independently selected from H, F, Cl, Br, CN, C$_{1-4}$ alkyl substituted with 0-3 R$_e$, —(CH$_2$)$_r$OR$_b$, and —C$_{3-6}$cycloalkyl;

R$_4$, at each occurrence, is independently selected from H, F, Cl, Br, OH, CN, OC$_{1-4}$ alkyl substituted with 0-3 R$_e$, and C$_{1-4}$ alkyl substituted with 0-3 R$_e$;

R$_6$, at each occurrence, is independently selected from F, Cl, Br, C$_{1-4}$ alkyl, —(CH$_2$)OR$_b$, —(CH$_2$)$_r$CN, —(CH$_2$)$_r$NR$_7$R$_7$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)OC(=O)R$_b$, —(CH$_2$)$_r$C(=O)NR$_a$R$_a$, —(CH$_2$)$_r$—C$_{3-6}$cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$;

R$_7$, at each occurrence, is independently selected from H, C$_{1-6}$ alkyl substituted with 1-5 R$_a$, C$_{2-6}$ alkenyl substituted with 1-5 R$_a$, C$_{2-6}$ alkynyl substituted with 1-5 R$_a$, —(CH$_2$)$_r$—C$_{3-10}$carbocyclyl substituted with 1-5 R$_a$, and —(CH$_2$)$_r$-heterocyclyl substituted with 1-5 R$_a$; or R$_7$ and R$_7$ together with the nitrogen atom to which they are both attached form a heterocyclic ring substituted with 1-5 R$_a$;

R$_a$, at each occurrence, is independently selected from H, C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{1-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, CO$_2$H, —(CH$_2$)$_r$OR$_f$, S(O)$_p$R$_f$, S(O)$_p$NR$_f$R$_f$, NR$_f$S(O)$_p$R$_d$, —(CH$_2$)$_r$NR$_f$R$_f$, —(CH$_2$)$_r$—C$_{3-6}$cycloalkyl, —O(CH$_2$)$_r$—C$_{3-6}$cycloalkyl, —(CH$_2$)$_r$-heterocyclyl, —O(CH$_2$)$_r$-heterocyclyl, —(CH$_2$)$_r$-aryl, and —O(CH$_2$)$_r$-aryl;

R$_f$ at each occurrence, is independently selected from H, F, Cl, Br, CN, OH, C$_{1-5}$ alkyl (optionally substituted with F, Cl, Br, OH, OC$_{1-4}$ alkyl, NR$_g$R$_g$), —(CH$_2$)—C$_{3-6}$cycloalkyl, and —(CH$_2$)$_r$-phenyl;

R$_g$, at each occurrence, is independently selected from H and C$_{1-5}$alkyl; and other variables are as defined in Formula (I).

In another aspect, the present invention provides compounds of Formula (IV):

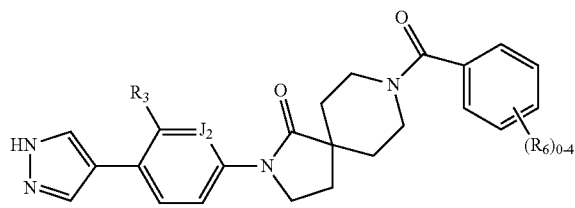

(IV)

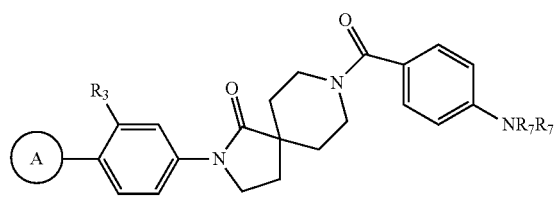

(V)

or stereoisomers, tautomers, pharmaceutically acceptable salts, solvates, or prodrugs thereof, wherein Ring A is selected from

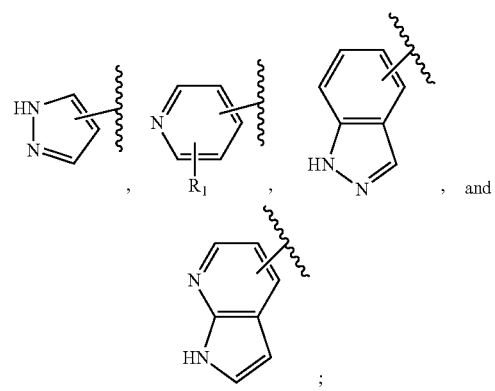

$R_1$ is selected from H, F, Cl, Br, $NR_aR_a$, and $C_{1-4}$alkyl;

$R_3$ is $—OC_{1-3}$ alkyl;

$R_7$, at each occurrence, is independently selected from H, $C_{1-6}$ alkyl substituted with 1-5 $R_a$; or $R_7$ and $R_7$ together with the nitrogen atom to which they are both attached form a heterocyclic ring selected from

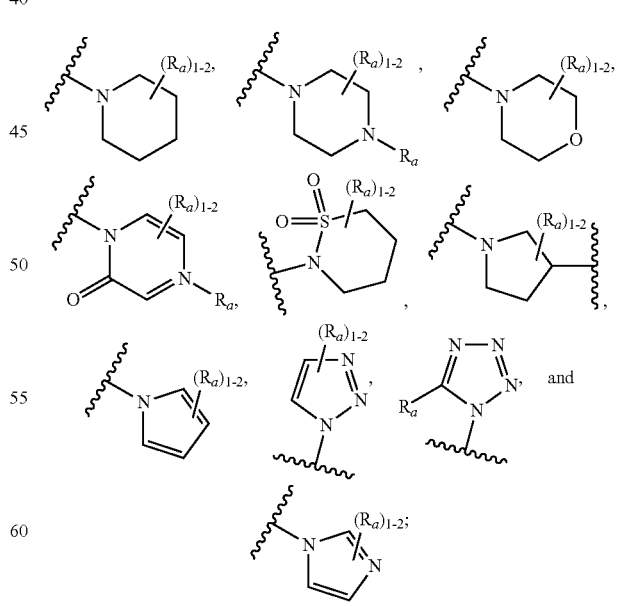

$R_a$, at each occurrence, is independently selected from H, C(=O)$OR_b$, $C_{1-6}$ alkyl substituted with 0-5 $R_e$, —(CH$_2$)$_r$—C$_{3-6}$cycloalkyl substituted with 0-5 $R_e$, or stereoisomers, tautomers, pharmaceutically acceptable salts, solvates, or prodrugs thereof, wherein $J_2$ is selected from N and CH;

$R_3$ is selected from H, CN, $C_{1-4}$ alkyl, $—OC_{1-3}$ alkyl, and $—C_{3-6}$cycloalkyl;

$R_6$, at each occurrence, is independently selected from F, Cl, Br, $C_{1-4}$ alkyl, —(CH$_2$)$_r$OR$_b$, —(CH$_2$)$_r$NR$_7$R$_7$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$C(=O)NR$_a$R$_a$, —(CH$_2$)$_r$—C$_{3-6}$cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 $R_e$;

$R_7$, at each occurrence, is independently selected from H, $C_{1-6}$ alkyl substituted with 1-5 $R_a$, $C_{2-6}$ alkenyl substituted with 1-5 $R_a$, $C_{2-6}$ alkynyl substituted with 1-5 $R_a$, —(CH$_2$)$_r$—C$_{3-10}$carbocyclyl substituted with 1-5 $R_a$, and —(CH$_2$)$_r$-heterocycyl substituted with 1-5 $R_a$; or $R_7$ and $R_7$ together with the nitrogen atom to which they are both attached form a heterocyclic ring substituted with 1-5 $R_a$:

$R_a$, at each occurrence, is independently selected from H, C(=O)$OR_b$, $C_{1-6}$ alkyl substituted with 0-5 $R_e$, —(CH$_2$)$_r$—C$_{3-6}$cycloalkyl substituted with 0-5 $R_e$, —(CH$_2$)$_r$-aryl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_e$, at each occurrence, is independently selected from F, Cl, Br, CN, NO$_2$, =O, $C_{1-6}$ alkyl substituted with 1-5 $R_f$, CO$_2$H, OR$_f$, NHS(O)$_p$C$_{1-4}$alkyl, NR$_f$R$_f$, —(CH$_2$)$_r$—C$_{3-6}$cycloalkyl, —O(CH$_2$)$_r$—C$_{3-6}$cycloalkyl, —(CH$_2$)$_r$-heterocyclyl, —O(CH$_2$)$_r$-heterocyclyl, —(CH$_2$)$_r$-aryl, and —O(CH$_2$)$_r$-aryl:

$R_f$, at each occurrence, is independently selected from H, F, Cl, Br, CN, =O, $C_{1-5}$ alkyl (optionally substituted with F, Cl, Br, OH, OC$_4$ alkyl, NR$_g$R$_g$), —(CH$_2$)$_r$—C$_{3-6}$cycloalkyl, and —(CH$_2$)$_r$-phenyl;

$R_g$, at each occurrence, is independently selected from H and $C_{1-5}$alkyl; and r is an integer of zero, 1, 2 or 3.

In another aspect, the present invention provides compounds of Formula (V):

—(CH$_2$)$_r$-aryl substituted with 0-5 R$_e$, and —(CH$_2$)$_r$-heterocyclyl substituted with 0-5 R$_e$;

R$_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_e$, at each occurrence, is independently selected from F, Cl, Br, CN, NO$_2$, =O, C$_{1-6}$ alkyl substituted with 1-4 R$_f$, CO$_2$H, OR$_f$, NHS(O)$_p$C$_{1-4}$alky, NR$_f$R$_f$, —(CH$_2$)$_r$—C$_{3-6}$cycloalkyl, —(CH$_2$)$_r$-heterocyclyl, —CH$_2$)$_r$-aryl, —O(CH$_2$)$_r$—C$_{3-6}$cycloalkyl, —O(CH$_2$)$_r$-heterocyclyl, and —O(CH$_2$)$_r$-aryl;

R$_f$, at each occurrence, is independently selected from H, H, F, Cl, Br, CN, OH, C$_{1-5}$ alkyl (optionally substituted with F, Cl, Br, OH, OC$_{1-4}$ alkyl, NR$_g$R$_g$), —(CH$_2$)$_r$—C$_{3-6}$cycloalkyl, and —(CH$_2$)-phenyl;

R$_g$, at each occurrence, is independently selected from H and C$_{1-5}$alkyl; and r is an integer of zero, 1, 2 or 3.

In another aspect, the present invention provides compounds of Formula (VI):

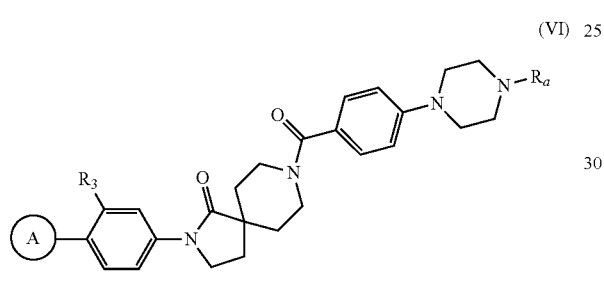

(VI)

or stereoisomers, tautomers pharmaceutically acceptable salts, solvates, or prodrugs thereof, wherein Ring A is selected from

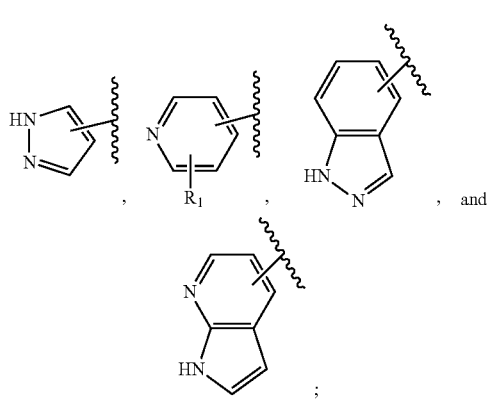

;

R$_1$ is selected from H, F, Cl, Br, NR$_a$R$_a$, and C$_{1-4}$alkyl;

R$_3$ is —OC$_{1-4}$ alkyl;

R$_a$ is selected from H, C(=O)OC$_{1-4}$alkyl, C$_{1-6}$alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;

R$_e$, at each occurrence, is independently selected from F, Cl, Br, CN, NO$_2$, =O, C$_{1-4}$ alkyl CO$_2$H, OR$_f$, NHS(O)$_p$ C$_{1-4}$alkyl, NR$_f$R$_f$, —(CH$_2$)$_r$—C$_{3-6}$cycloalkyl, —(CH$_2$)$_r$-heterocyclyl, —(CH$_2$)$_r$-aryl. —O(CH$_2$)$_r$—C$_{3-6}$cycloalkyl, —O(CH$_2$)$_r$-heterocyclyl, and —O(CH$_2$)$_r$-aryl;

R$_f$, at each occurrence, is independently selected from H, F, Cl, Br, CN, OH, C$_{1-5}$ alkyl (optionally substituted with F, Cl, Br, OH, OC$_{1-4}$ alkyl, NR$_g$R$_g$), and —(CH$_2$)$_r$-phenyl;

R$_g$, at each occurrence, is independently selected from H and C$_{1-5}$alkyl; and r is an integer of zero, 1, 2 or 3.

In another aspect, the present invention provides compounds of Formula (VI), or stereoisomers, tautomers, pharmaceutically acceptable salts, solvates, or prodrugs thereof, wherein R$_a$ is selected from H, C(=O)OC$_{1-4}$alkyl, C$_{1-6}$ alkyl substituted with 0-5 R$_e$, —(CH$_2$)$_r$—C$_{3-6}$cycloalkyl substituted with 0-5 R$_e$, —(CH$_2$)$_r$-phenyl substituted with 0-5 R$_e$, and —(CH$_2$)$_r$-heterocyclyl wherein the heterocyclyl is selected from

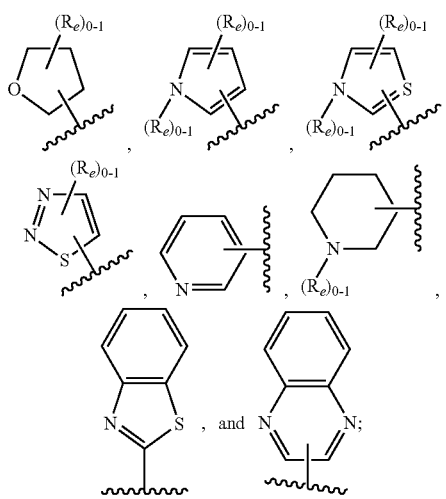

R$_e$, at each occurrence, is independently selected from F, Cl, Br, CN, NO$_2$, =O, C$_{1-6}$ alkyl substituted with 1-4 R$_f$, OR$_f$NHS(O)$_p$C$_{1-4}$alkyl, NR$_f$R$_f$, —(CH$_2$)$_r$—C$_{3-6}$cycloalkyl, —(CH$_2$)$_r$-heterocyclyl, —(CH$_2$)$_r$-aryl, —O(CH$_2$)$_r$—C$_{3-6}$cycloalkyl, —O(CH$_2$)$_r$-heterocyclyl, and —O(CH$_2$)$_r$-aryl;

R$_f$, at each occurrence, is independently selected from H, F, Cl, Br, CN, OH, and C$_{1-5}$ alkyl (optionally substituted with F, Cl, Br, OH OC$_{1-4}$ alkyl, and NR$_g$R$_g$), and —(CH$_2$)$_r$-phenyl;

R$_g$, at each occurrence, is independently selected from H and C$_{1-4}$alkyl; and r is an integer of zero, 1, 2 or 3.

In another aspect, the present invention provides compounds of Formula (VII):

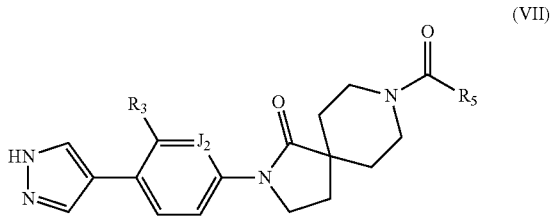

(VII)

or stereoisomers, tautomers, pharmaceutically acceptable salts, solvates, or prodrugs thereof, wherein.

$R_5$ is selected from

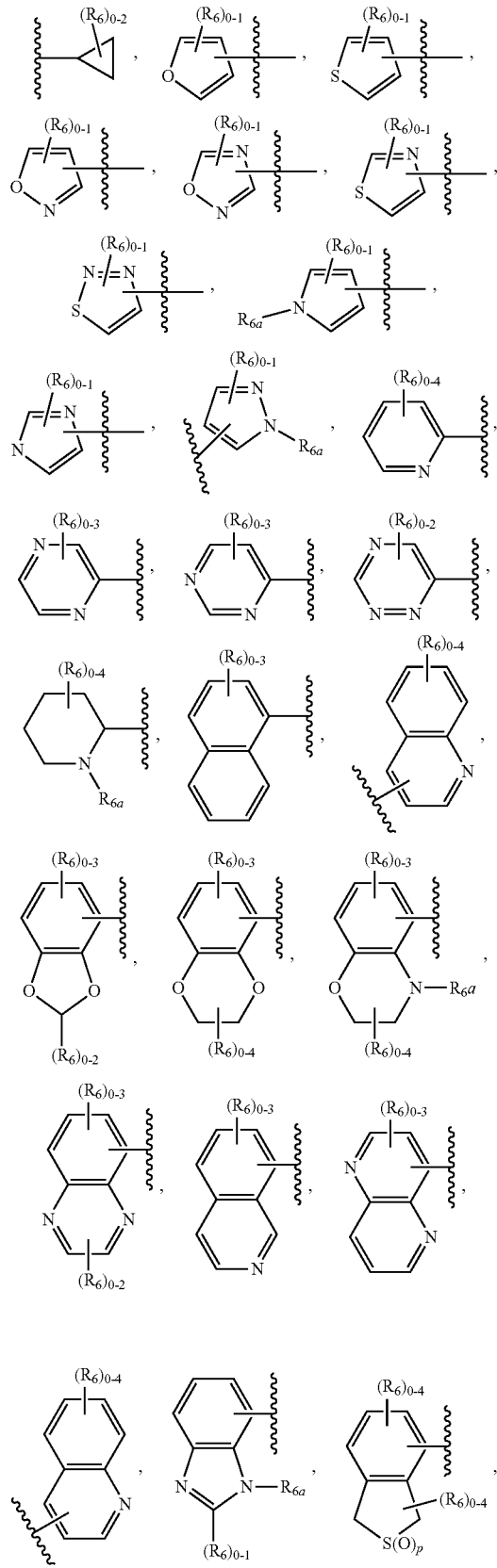

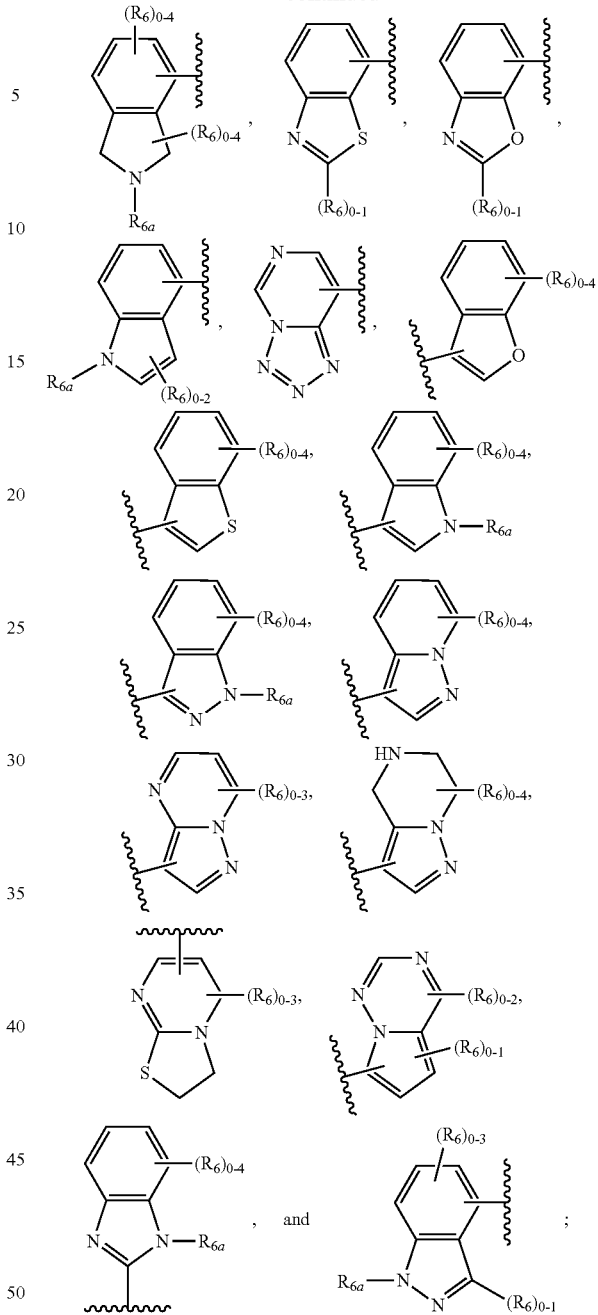

$R_6$, at each occurrence, is independently selected from F, Cl, Br, $C_{1-4}$alkyl, $C_{2-4}$alkenyl, $C_{2-4}$alkynyl, nitro, $-(CH_2)_rS(O)_pR_c$, $-(CH_2)_rS(O)NR_aR_a$, $-(CH_2)_rNR_aS(O)_pR_c$, $-(CH_2)_rOR_b$, $-(CH_2)_rCN$, $-(CH_2)_rNR_aR_a$, $-(CH_2)_rNR_aC(=O)R_b$, $-(CH_2)_rNR_aC(=O)NR_aR_a$, $-(CH_2)_rC(=O)OR_b$, $-(CH_2)_rC(=O)R_b$, $-C(=O)NR_aR_a$ $-(CH_2)_rOC(=O)R_b$, $-(CH_2)_r-C_{3-6}$cycloalkyl, $-(CH_2)$heterocyclyl, $-(CH_2)$-aryl, and $-(CH_2)_r$-heteroaryl, wherein said alkyl, alkenyl, alkynyl, cycloalkyl, heterocyclyl, aryl, or heteroaryl is substituted with 0-4 $R_e$;

$R_{6a}$, at each occurrence, is independently selected from H, $C_{1-4}$alkyl, $-S(O)_pR_c$, $-S(O)_pNR_aR_a$, $-C(=O)OR_b$, $-C(=O)R_b$, $-C(=O)NR_aR_a$, $-(CH_2)_r-C_{3-6}$-cycloalkyl, $-(CH_2)_r$-heterocyclyl, $-(CH_2)_r$-aryl, and —(CH$_2$)$_r$-heteroaryl, wherein said alkyl, cycloalkyl, heterocyclyl, aryl, or heteroaryl is substituted with 0-4 R$_e$;

p is an integer of zero, 1 or 2;

r is an integer of zero, 1, 2 or 3; and other variables are as defined in Formula (I).

In another aspect, the present invention provides compounds of Formula (VII), or stereoisomers, tautomers, pharmaceutically acceptable salts, solvates, or prodrugs thereof, wherein R$_5$ is selected from

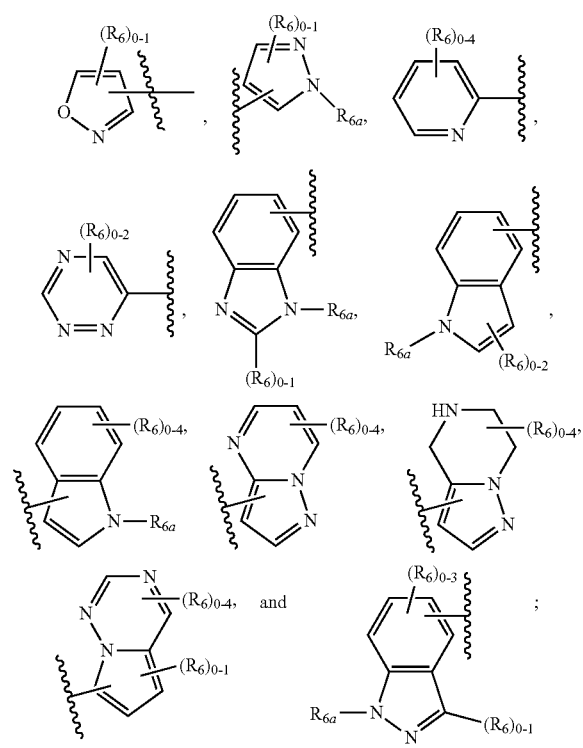

R$_6$, at each occurrence, is independently selected from F, Cl, Br, =O, C$_{1-4}$alkyl, OR$_b$, C$_{3-6}$cycloalkyl, heterocyclyl, aryl and heteroaryl wherein said alkyl, cycloalkyl, heterocyclyl, aryl, or heteroaryl is substituted with 0-4 R$_e$;

R$_{6a}$, at each occurrence, is independently selected from H and C$_{1-4}$ alkyl; and other variables are as defined in Formula (VI).

In another aspect, the present invention provides compounds of Formula (VIII):

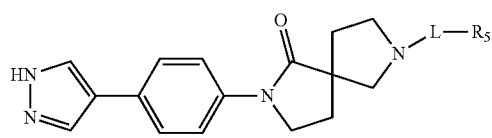

(VIII)

or stereoisomers, tautomers, pharmaceutically acceptable salts, solvates, or prodrugs thereof, wherein L is selected from —C(O)— and —S(O)$_p$—;

R$_5$ is selected from

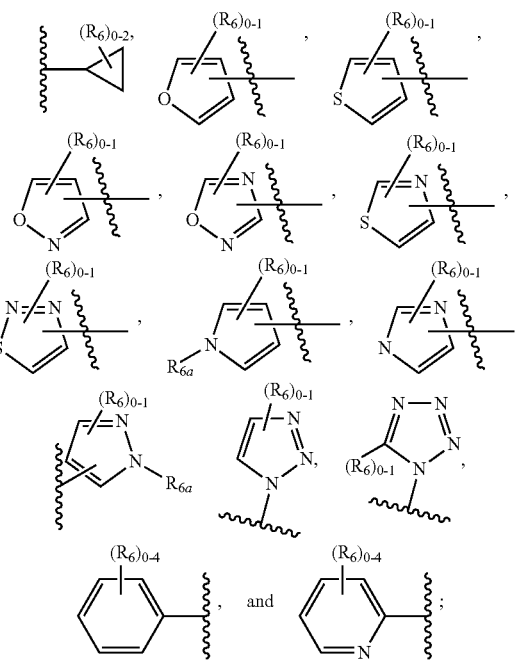

R$_6$, at each occurrence, is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)OR$_b$, —(CHR$_d$)$_r$CN, and —(CHR$_d$)$_r$NR$_a$R$_a$;

R$_{6a}$, at each occurrence, is independently selected from H and C$_{1-4}$alkyl;

R$_a$, at each occurrence, is independently selected from H and C$_{1-6}$ alkyl substituted with 0-5 R$_e$;

R$_b$, at each occurrence, is independently selected from H and C$_{1-6}$ alkyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, CO$_2$H, —(CH$_2$)$_r$OR$_f$, S(O)$_p$R$_f$, S(O)$_p$NR$_f$R$_f$, NR$_f$S(O)$_p$C$_{1-4}$alkyl, —(CH$_2$)$_r$NR$_f$R$_f$, —(CH$_2$)$_r$—C$_{3-6}$cycloalkyl, —(CH$_2$)$_r$-heterocyclyl, and —(CH$_2$)$_r$-aryl;

R$_f$, at each occurrence, is independently selected from H, F, Cl, Br, CN, OH, C$_{1-5}$ alkyl (optionally substituted with F, Cl, Br, OH, and OC$_{1-4}$ alkyl, NR$_g$R$_g$), C$_{3-6}$cycloalkyl, and phenyl;

R$_g$, at each occurrence, is independently selected from H and C$_{1-5}$alkyl;

p is an integer of zero, 1 or 2; and r is an integer of zero, 1, 2 or 3.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments.

In another aspect, the present invention provides a compound selected from any subset list of compounds exemplified in the present application.

In another embodiment, the compounds of the present invention have ROCK $IC_{50}$ values≤10 µM.

In another embodiment, the compounds of the present invention have ROCK $IC_{50}$ values≤1 µM.

In another embodiment, the compounds of the present invention have ROCK $IC_{50}$ values≤0.1 µM.

In another embodiment, the compounds of the present invention have ROCK $IC_{50}$ values≤0.05 µM.

In another embodiment, the compounds of the present invention have ROCK $IC_{50}$ values≤0.01 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state. i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms.

Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly. "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN. $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N-+O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted.

The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th Edition, Mack Publishing Company, Easton. Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs, Elsevier* (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988); and e) Kakeya. N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994): Testa, B. et al., *Hydrolysis in Drug and Prodrug Metabolism, Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "IL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "H" for proton, "S" for delta, "s" for singlet, "d" for doublet, "t" for triplet, "q" for quartet, "m" for multiplet, "br" for broad, "Hz" for hertz, and "α", "β", "R" "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn Benzyl
Boc tert-butyloxycarbonyl
AcOH or HOAc acetic acid
BOP reagent benzotriazol-1-yloxytris(dimethylamino)phosphonium hexafluorophosphate
CBz carbobenzyloxy
CH$_2$Cl$_2$ dichloromethane
CH$_3$CN or ACN acetonitrile
CDCl$_3$ deutero-chloroform
CHCl$_3$ chloroform
DCM dichloromethane
DEA diethylamine
DIC or DIPCDI diisopropylcarbodiimide
DIEA, DIPEA or Hunig's base diisopropylethylamine
DMAP 4-dimethylaminopyridine
DME 1,2-dimethoxyethane
DMF dimethyl formamide
DMSO dimethyl sulfoxide
cDNA complimentary DNA
EDTA ethylenediaminetetraacetic acid
Et$_3$N or TEA triethylamine
EtOAc ethyl acetate
Et$_2$O diethyl ether
EtOH ethanol
HCl hydrochloric acid
Hex Hexane
K$_2$CO$_3$ potassium carbonate
KOAc potassium acetate
K$_3$PO$_4$ potassium phosphate
LAH lithium aluminum hydride
LG leaving group
MeOH methanol
MgSO$_4$ magnesium sulfate
MsOH or MSA methylsulfonic acid
NaOAc sodium acetate
NaCl sodium chloride
NaH sodium hydride
NaHCO$_3$ sodium bicarbonate
Na$_2$CO$_3$ sodium carbonate
Na$_2$SO$_4$ sodium sulfate
NH$_4$Cl ammonium chloride
OTf triflate or trifluoromethanesulfonate
Pd/C palladium on carbon
PG protecting group
i-PrOH or IPA Isopropanol
rt Room temperature RT or $t_R$ retention time
SiO$_2$ silica oxide
TEA triethylamine
TFA trifluoroacetic acid
THF tetrahydrofuran
T3P® propane phosphonic acid anhydride IV. Biology In Vitro Assays The effectiveness of compounds of the present invention as ROCK inhibitors can be determined in a 30 μL assay containing 20 mM HEPES, pH 7.5, 20 mM MgCl$_2$, 0.015% Brij-35.4 mM DTT, 5 μM ATP and 1.5 μM peptide substrate (FITC-AHA-AKRRRLSSLRA-OH) (SEQ ID No. 1). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Remington's Pharmaceutical Sciences, 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like, for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container: (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al., (*Protective Groups in Organic Synthesis*, 4th Edition, Wiley-Interscience (2006)).

Representative 2,8-diazaspiro[4.5]decan-1-one compounds Ig of this invention can be prepared as shown in Scheme 1. Starting from tert-butyl 1-oxo-2,8-diazaspiro [4.5]decane-8-carboxylate 1a, coupling with 1b using Xanphos, $Pd_2(dba)_3$ and $Cs_2CO_3$ gives 1c. Suzuki coupling with 4-(4,4,5,5-tetramethyl-1,3,2-dioxaborolan-2-yl)-1-((2-(trimethylsilyl)ethoxy)methyl)-1H-pyrazole using XPhos Generation 3 catalyst gives 1d. Then the protecting Boc group is selectively removed followed by coupling with either acetyl chlorides or carboxylic acids to yield 1f. The protecting SEM group is then removed to give 1g.

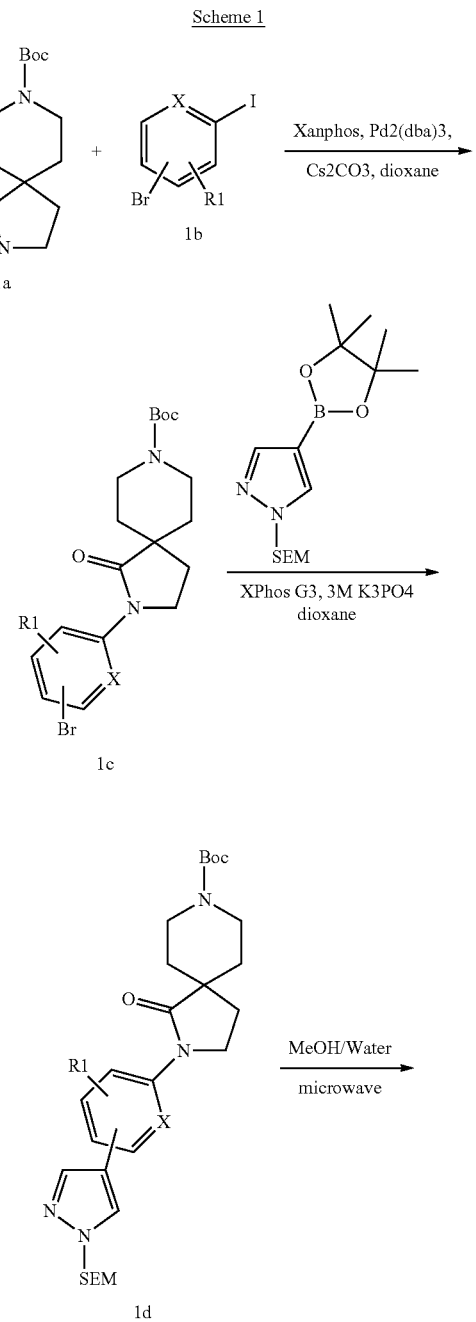

Scheme 1

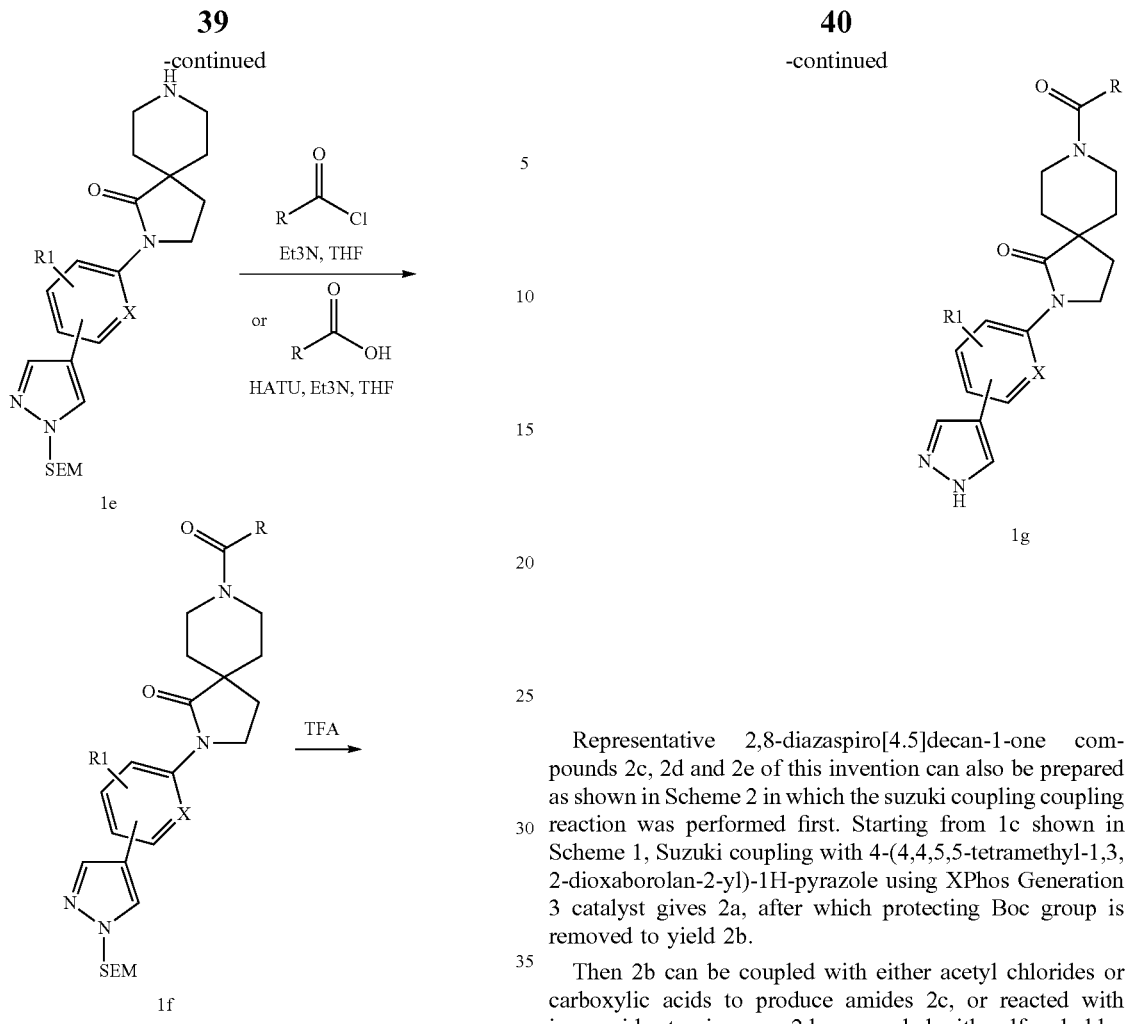

Representative 2,8-diazaspiro[4.5]decan-1-one compounds 2c, 2d and 2e of this invention can also be prepared as shown in Scheme 2 in which the suzuki coupling coupling reaction was performed first. Starting from 1c shown in Scheme 1, Suzuki coupling with 4-(4,4,5,5-tetramethyl-1,3,2-dioxaborolan-2-yl)-1H-pyrazole using XPhos Generation 3 catalyst gives 2a, after which protecting Boc group is removed to yield 2b.

Then 2b can be coupled with either acetyl chlorides or carboxylic acids to produce amides 2c, or reacted with isocyanides to give urea 2d, or coupled with sulfonyl chlorides to give sulfonamides 2e.

Scheme 2

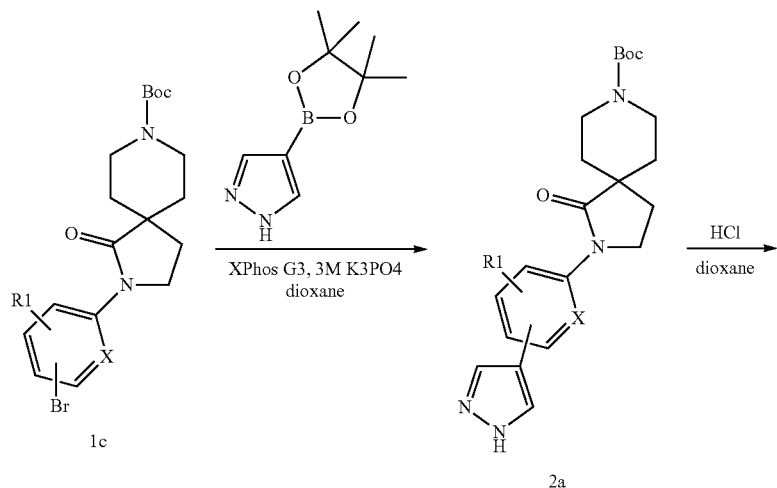

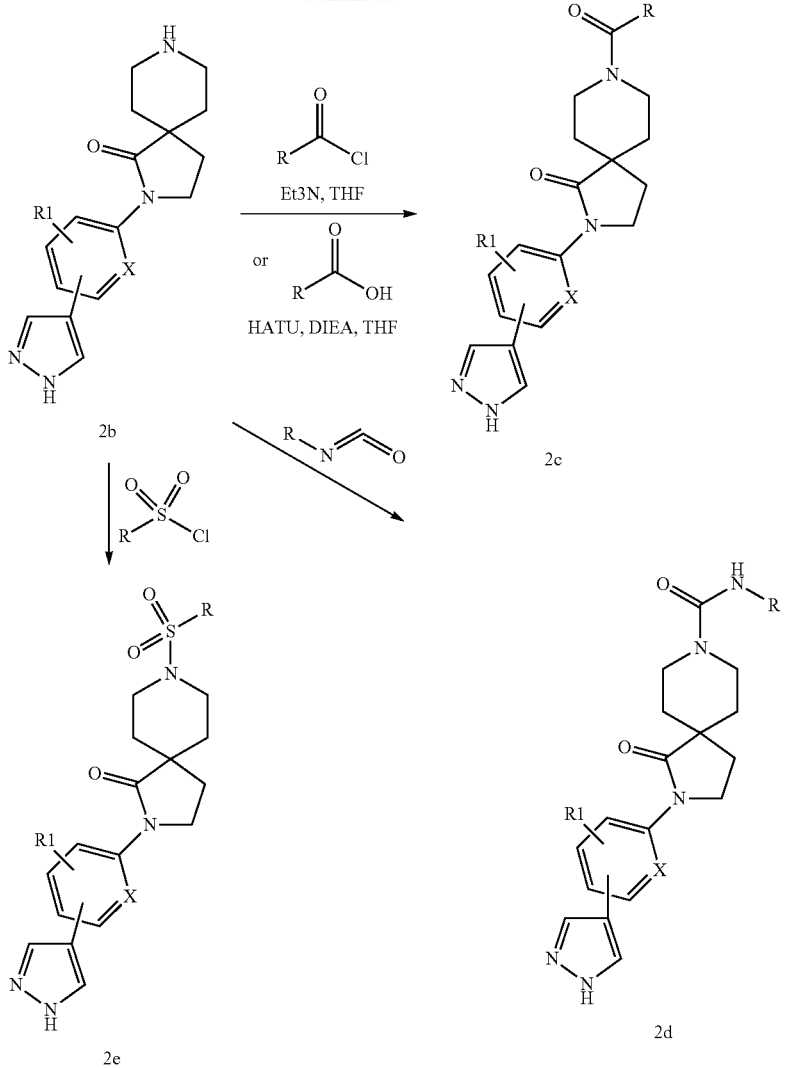

Representative 2,8-diazaspiro[4.5]decan-1-one compounds 3c of this invention can also be prepared as shown in Scheme 3 in which the Suzuki coupling of the hinge aryl group was performed in the last step of the synthesis. Deprotecting Boc group of 1c yields 3a, which can be coupled with either acetyl chlorides or carboxylic acids to give 3b. Suzuki coupling of 3b with aryl boronic acids or boronic esters to give 3c.

Scheme 3

-continued

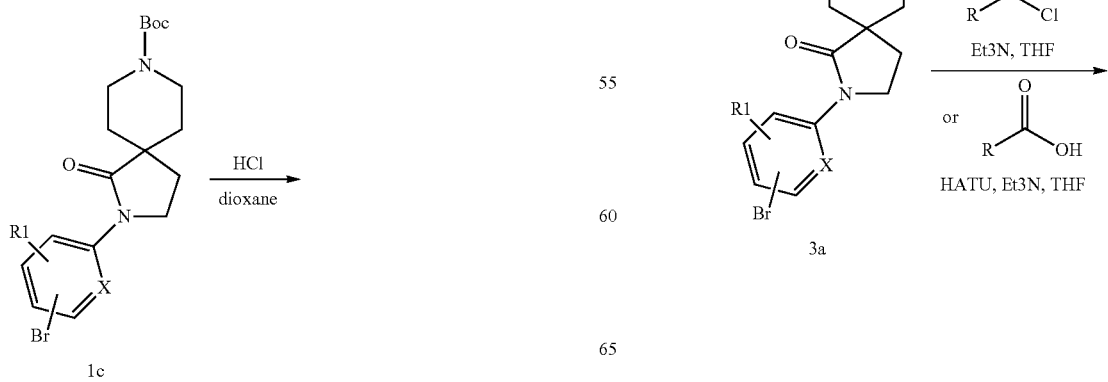

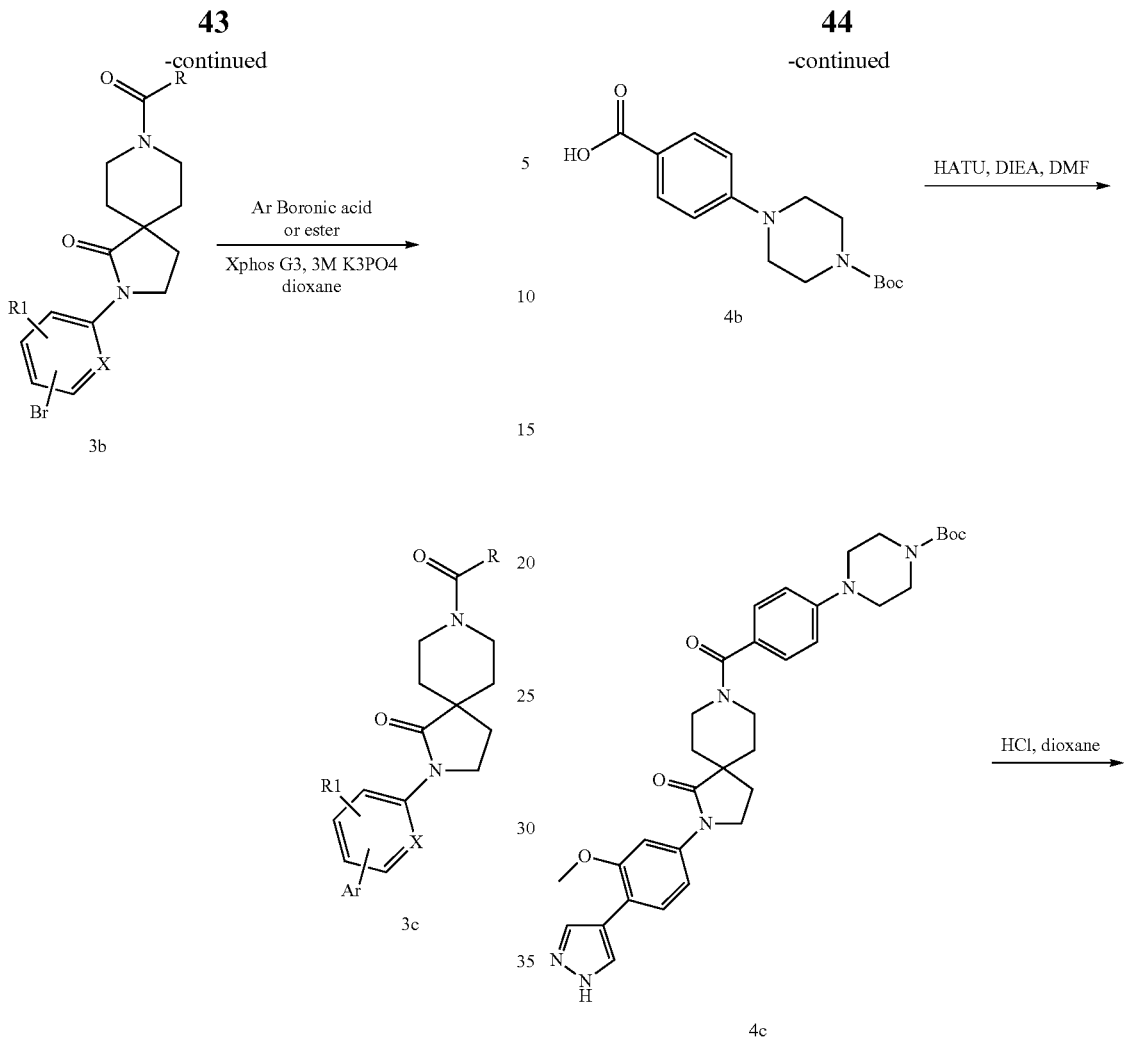
Representative 2-(3-methoxy-4-(1H-pyrazol-4-yl)phenyl)-8-(4-(piperazin-1-yl)benzoyl)-2,8-diazaspiro[4.5]decan-1-one compounds 4e of this invention can be prepared as shown in Scheme 4. Coupling of 4a and 4b followed by deprotecting Boc group produces 4d. Then 4e can be synthesized via reductive-amination of 4d with aldehydes and ketones.
Scheme 4
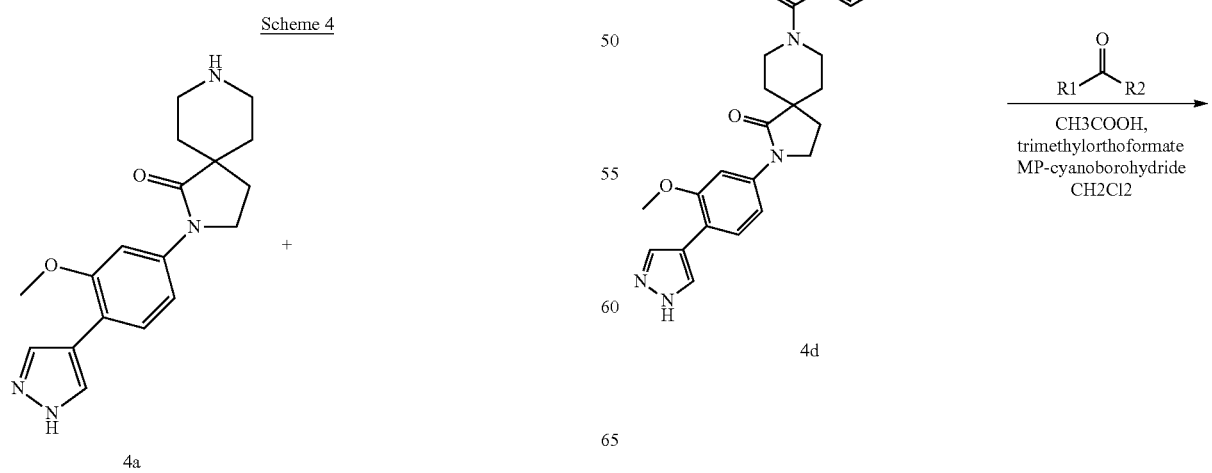

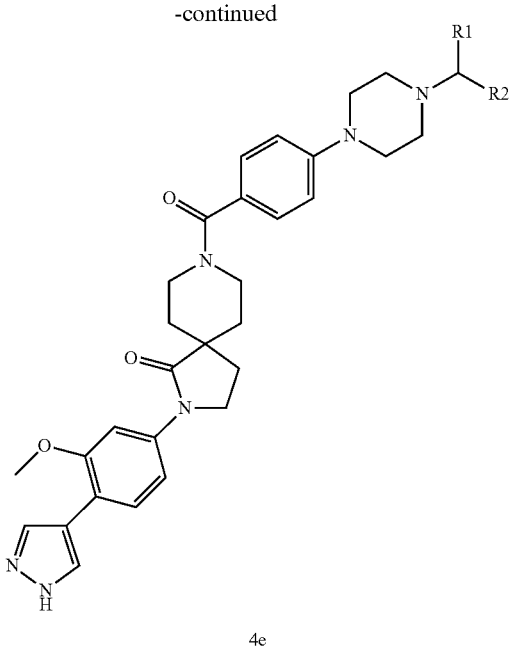

4e

Purification method A:

The crude material was purified via preparative LC/MS with the following conditions:
Column: XBridge C18, 19×200 mm, 5-μm particles;
Mobile Phase A: 5:95 acetonitrile:water with 10-mM ammonium acetate; Mobile Phase
B: 95:5 acetonitrile:water with 10-mM ammonium acetate; Gradient: 15-55% B over 20 minutes, then a 5-minute hold at 100% B; Flow: 20 mL/min. Fractions containing the desired
product were combined and dried via centrifugal evaporation.

Purification Method B:

The crude material was purified via preparative LC/MS with the following conditions:
Column: XBridge C18, 19×200 mm, 5-μm particles;
Mobile Phase A: 5:95 acetonitrile:water with 10-mM ammonium acetate; Mobile Phase B: 95:5 acetonitrile:water with 10-mM ammonium
acetate: Gradient: 15-100% B over 20 minutes, then a 2-minute hold at 100% B; Flow: 20 mL/min. Fractions containing the desired
product were combined and dried via centrifugal evaporation.

Purification Method C:

The crude material was purified via preparative LC/MS with the following conditions: Column: XBridge C18, 19×200 mm, 5-μm particles:
Mobile Phase A: 5:95 acetonitrile:water with 10-mM ammonium acetate; Mobile Phase B: 95:5 acetonitrile:water with 10-mM ammonium
acetate: Gradient: 0-20% B over 19 minutes, then a 5-minute hold at 100% B; Flow: 20 mL/min. Fractions containing the desired product
were combined and dried via centrifugal evaporation.

Analytical Retention Time Method 1: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75-minute hold at 100% B; Flow: 1.0 mL/min; Detection: UV at 220 nm.

Analytical Retention Time Method 2: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Intermediate 1: Preparation of tert-butyl 2-(4-bromophenyl)-1-oxo-2,8-diazaspiro[4.5]decane-8-carboxylate

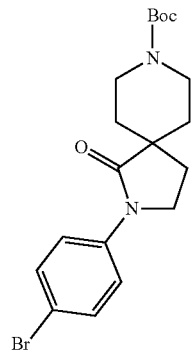 [SMILES: CC(C)(C)OC(=O)N1CCC2(CC1)CCN(c1ccc(Br)cc1)C2=O]

In a sealable reaction tube was added 1-bromo-4-iodobenzene (1112 mg, 3.93 mmol), tert-butyl 1-oxo-2,8-diazaspiro[4.5]decane-8-carboxylate (500 mg, 1.966 mmol), cesium carbonate (1281 mg, 3.93 mmol) and dioxane (3932 μl). The reaction was purged with nitrogen. Then 9,9-dimethyl-4,5-bis(diphenylphosphino)xanthene (171 mg, 0.295 mmol) and $Pd_2(dba)_3$ (90 mg, 0.098 mmol) was added and nitrogen gas was bubbled through reaction for 1 min. The reaction was sealed and stirred at 100° C. overnight. The reaction was partitioned between EtOAc (50 ml) and water (30 ml). The organic layer was separated, washed with water (2×30 ml) and brine (30 ml), dried over $MgSO_4$, filtered and concentrated. The residue was purified using ISCO system (0-100% EtOAc/Hex gradient) to give tert-butyl 2-(4-bromophenyl)-1-oxo-2,8-diazaspiro[4.5]decane-8-carboxylate (740 mg, 1.663 mmol, 85% yield) as a beige solid.

$^1$H NMR (500 MHz, DMSO-$d_6$) δ 7.72-7.64 (m, 2H), 7.61-7.51 (m, 2H), 3.91-3.83 (m, 2H), 3.80 (t, J=7.0 Hz, 2H), 2.98 (br. s., 2H), 2.09 (t, J=7.0 Hz, 2H), 1.62 (td, J=12.4, 4.4 Hz, 2H), 1.54-1.47 (m, 2H), 1.42 (s, 9H). $^{13}$C NMR (500 MHz, DMSO-$d_6$) δ 177.4, 154.4, 139.4, 131.9, 121.8, 116.3, 79.2, 44.9, 44.7, 32.1, 28.6, 28.0 MS (ESI) m/z: 411.0 (M+H)$^+$.

Intermediate 2: Preparation of tert-butyl 2-(4-bromo-3-methoxyphenyl)-1-oxo-2,8-diazaspiro[4.5]decane-8-carboxylate

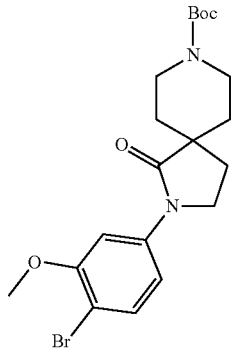 [SMILES: COc1cc(N2CCC3(CCN(C(=O)OC(C)(C)C)CC3)C2=O)ccc1Br]

In a sealable reaction tube was added 1-bromo-4-iodo-2-methoxybenzene (2461 mg, 7.86 mmol), tert-butyl 1-oxo-2,8-diazaspiro[4.5]decane-8-carboxylate (1000 mg, 3.93 mmol), cesium carbonate (2562 mg, 7.86 mmol) and dioxane (7864 μl). The reaction was purged with nitrogen. Then 9,9-dimethyl-4,5-bis(diphenylphosphino)xanthene (341 mg, 0.590 mmol), $Pd_2(dba)_3$ (180 mg, 0.197 mmol) was added and nitrogen was bubbled through reaction for 1 min. The reaction was sealed and stirred at 100° C. overnight. The reaction was partitioned between EtOAc (50 ml) and water (30 ml). The organic layer was separated, washed with water (2×30 ml) and brine (30 ml), dried over $MgSO_4$, filtered and concentrated. The residue was purified using ISCO system (0-100% EtOAc/Hex gradient) to give tert-butyl 2-(4-bromo-3-methoxyphenyl)-1-oxo-2,8-diazaspiro[4.5]decane-8-carboxylate (1.6 g, 3.64 mmol, 93% yield) as a beige solid. $^1$H NMR (500 MHz, DMSO-$d_6$) δ 7.67 (d, J=2.2 Hz, 1H), 7.55 (d, J=8.5 Hz, 1H), 7.12 (dd, J=8.8, 2.5 Hz, 1H), 3.96-3.78 (m, 7H), 3.10-2.84 (m, 2H), 2.10 (t, J=6.9 Hz, 2H), 1.62 (dd, J=12.0, 4.0 Hz, 2H), 1.51 (d, J=13.5 Hz, 2H), 1.42 (s, 9H). MS (ESI) m-z: 439.0, 441.0 (M+H)$^+$.

Intermediate 3: Preparation of 2-(4-(1H-pyrazol-4-yl)phenyl)-2,8-diazaspiro[4.5]decan-1-one, TFA

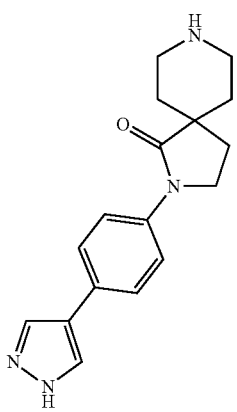 [SMILES: O=C1N(c2ccc(-c3cn[nH]c3)cc2)CCC12CCNCC2]

3A. Preparation of tert-butyl 1-oxo-2-(4-(1-((2-(trimethylsilyl)ethoxy)methyl)-1H-pyrazol-4-yl)phenyl)-2,8-diazaspiro[4.5]decane-8-carboxylate

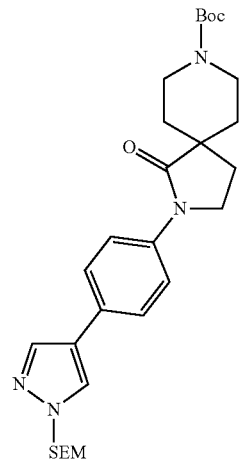 [SMILES: CC(C)(C)OC(=O)N1CCC2(CC1)CCN(c1ccc(-c3cnn(COCC[Si](C)(C)C)c3)cc1)C2=O]

To a microwave vial was added Intermediate 1 (1000 mg, 2.443 mmol), 4-(4,4,5,5-tetramethyl-1,3,2-dioxaborolan-2-yl)-1-((2-(trimethylsilyl)ethoxy)methyl)-1H-pyrazole (951 mg, 2.93 mmol), 3M tripotassium phosphate (2.443 mL, 7.33 mmol), dioxane (10 mL) and methanesulfonato(2-dicyclohexylphosphino-2',4',6'-tri-i-propyl-1,1'-biphenyl)(2'-amino-1,1'-biphenyl-2-yl)palladium(II) (103 mg, 0.122 mmol). The reaction was purged with argon and sealed. The reaction was then subjected to microwave oven and stirred at 120° C. for 45 min. The reaction was partitioned between EtOAc (30 ml) and water (20 ml). The organic layer was separated, washed with water (15 ml) and brine (15 ml), dried over $MgSO_4$, filtered and concentrated. The residue was purified using ISCO system (0-100% EtOAc/Hex gradient) to give tert-butyl 1-oxo-2-(4-(1-((2-(trimethylsilyl)ethoxy)methyl)-1H-pyrazol-4-yl)phenyl)-2,8-diazaspiro[4.5]decane-8-carboxylate (760 mg, 1.443 mmol, 59.1% yield) as an off-white solid. MS (ESI) m/z: 527.3 (M+H)$^+$.

3B. Preparation of 2-(4-(1H-pyrazol-4-yl)phenyl)-2,8-diazaspiro[4.5]decan-1-one, TFA

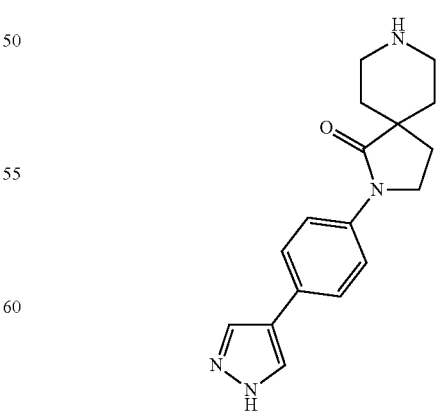

To around bottom flask was added intermediate 3A (20 mg, 0.038 mmol), $CH_2Cl_2$ (0.5 mL) and TFA (0.5 mL). The reaction was stirred at rt for 3 hr. The reaction was concentrated and purified using prep-HPLC. The desired fraction was concentrated to give 2-(4-(1H-pyrazol-4-yl)phenyl)-2,8-diazaspiro[4.5]decan-1-one, TFA (10 mg, 0.024 mmol, 62.9% yield) as a beige solid. $^1$H NMR (500 MHz, METHANOL-d$_4$) δ 7.99 (br. s., 2H), 7.64 (s, 4H), 3.94 (q, J=6.2 Hz, 2H), 3.61-3.50 (m, 2H), 3.26-3.15 (m, 2H), 2.28-2.21 (m, 2H), 2.19-2.07 (m, 2H), 1.95-1.76 (m, 2H); MS (ESI) m/z: 297.1 (M+H)$^+$. ROCK2 IC$_{50}$=1010 nM Intermediate 4: Preparation of 2-(3-methoxy-4-(1H-pyrazol-4-yl)phenyl)-2,8-diazaspiro[4.5]decan-1-one, 2 HCl

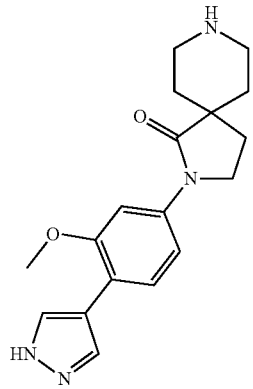 [SMILES: COc1cc(N2CCC3(CCNCC3)C2=O)ccc1-c1cn[nH]c1]

4A. Preparation of tert-butyl 2-(4-(1-(tert-butoxycarbonyl)-1H-pyrazol-4-yl)-3-methoxyphenyl)-1-oxo-2,8-diazaspiro[4.5]decane-8-carboxylate

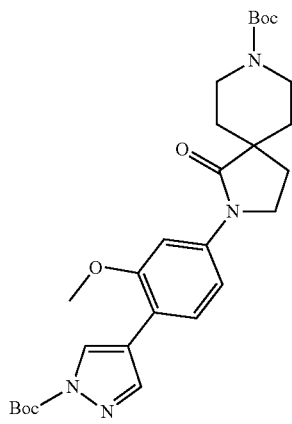 [SMILES: COc1cc(N2CCC3(CCN(C(=O)OC(C)(C)C)CC3)C2=O)ccc1-c1cnn(C(=O)OC(C)(C)C)c1]

To a round bottle flask was added Intermediate 2 (1.8 g, 4.10 mmol), tert-butyl 4-(4,4,5,5-tetramethyl-1,3,2-dioxaborolan-2-yl)-1H-pyrazole-1-carboxylate (1.808 g, 6.15 mmol), 3M tripotassium phosphate (4.10 mL, 12.29 mmol), dioxane (10 mL) and chloro(2-dicyclohexylphosphino-2',4',6'-triisopropyl-1,1'-biphenyl)[2-(2'-amino-1,1'-biphenyl)]palladium(II) (0.226 g, 0.287 mmol). The reaction was purged with nitrogen then stirred at 80° C. for 4 hr. The reaction was partitioned between EtOAc (50 ml) and water (20 ml). The organic layer was separated, washed with water (20 ml) and brine (30 ml), dried over MgSO$_4$, filtered and concentrated. The residue was purified using ISCO system (0-100% EtOAc/Hex gradient) to give tert-butyl 2-(4-(1-(tert-butoxycarbonyl)-1H-pyrazol-4-yl)-3-methoxyphenyl)-1-oxo-2,8-diazaspiro[4.5]decane-8-carboxylate (1.98 g, 3.76 mmol, 92% yield) as an off-white solid. $^1$H NMR (500 MHz, DMSO-d$_6$) δ 8.54 (d, J=0.6 Hz, 1H), 8.30 (d, J=0.8 Hz, 1H), 7.74 (d, J=8.5 Hz, 1H), 7.67 (d, J=2.2 Hz, 1H), 7.21 (dd, J=8.5, 2.2 Hz, 1H), 3.91 (s, 3H), 3.88-3.83 (m, 3H), 3.10-2.88 (m, 2H), 2.11 (t, J=7.0 Hz, 2H), 1.68-1.62 (m, 2H), 1.61 (s, 9H), 1.51 (d, J=13.2 Hz, 2H), 1.42 (s, 9H); MS (ESI) m/z: 527.2 (M+H)$^+$.

4B. Preparation of 2-(3-methoxy-4-(1H-pyrazol-4-yl)phenyl)-2,8-diazaspiro[4.5]decan-1-one, 2 HCl

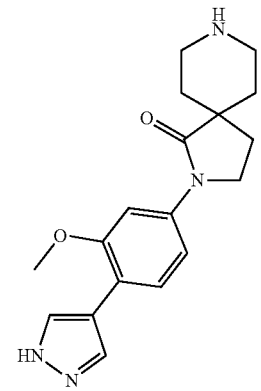

To a round bottom flask was added Intermediate 4A (1.98 g, 3.76 mmol), dioxane (10 mL) and 4N HCl (2.285 mL, 75 mmol) in dioxane. The reaction was stirred at rt overnight. The reaction was concentrated to give 2-(3-methoxy-4-(H-pyrazol-4-yl)phenyl)-2,8-diazaspiro[4.5]decan-1-one, 2 HCl (1.5 g, 3.76 mmol, 100% yield) as an off-white solid. MS (ESI) m/z: 327.0 (M+H)$^+$.

Intermediate 5: Preparation of 2-(3-methoxy-4-(1H-pyrazol-4-yl)phenyl)-8-(4-(piperazin-1-yl)benzoyl)-2,8-diazaspiro[4.5]decan-1-one, 2 HCl

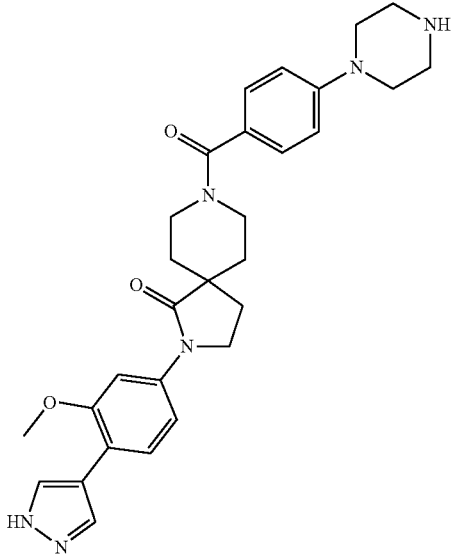 [SMILES: COc1cc(N2CCC3(CCN(C(=O)c4ccc(N5CCNCC5)cc4)CC3)C2=O)ccc1-c1cn[nH]c1]

5A. Preparation of tert-butyl 4-(4-(2-(3-methoxy-4-(1H-pyrazol-4-yl)phenyl)-1-oxo-2,8-diazaspiro[4.5]decane-8-carbonyl)phenyl)piperazine-1-carboxylate

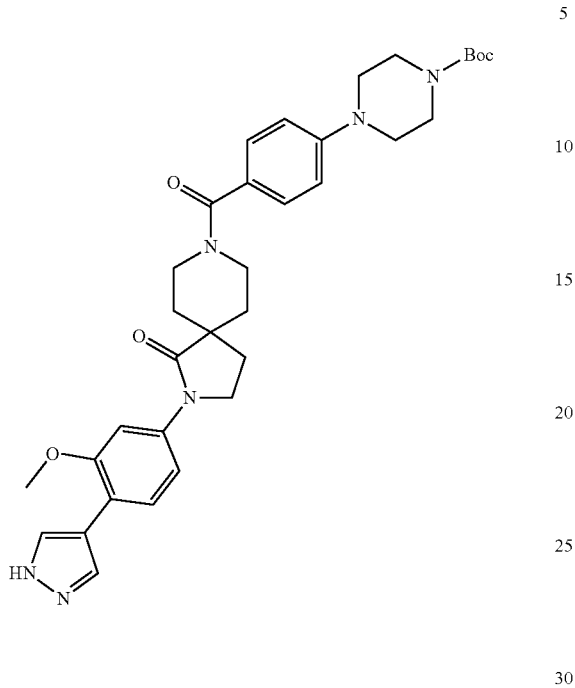

To a 1-dram vial was added 4-(4-(tert-butoxycarbonyl)piperazin-1-yl)benzoic acid (345 mg, 1.127 mmol), THF (5 mL), HATU (514 mg, 1.352 mmol) and Et$_3$N (0.785 mL, 5.63 mmol). The reaction was stirred at rt for 10 min and then Intermediate 4 (450 mg, 1.127 mmol) was added and the reaction was continued for 4 hr. The reaction was partitioned between EtOAc (20 ml) and water (15 ml). The organic layer was separated, washed with brine (15 ml), dried over MgSO$_4$, filtered and concentrated. The residue was purified using ISCO system (0-1000% EtOAc/Hex gradient, then 0-20% MeOH/CH$_2$Cl$_2$ gradient) to give tert-butyl 4-(4-(2-(3-methoxy-4-(1H-pyrazol-4-yl)phenyl)-1-oxo-2,8-diazaspiro[4.5]decane-8-carbonyl)phenyl)piperazine-1-carboxylate (500 mg, 0.813 mmol, 72.2% yield) as a light beige solid. $^1$H NMR (500 MHz, DMSO-d$_6$) δ 8.09 (br. s., 1H), 7.93 (br. s., 1H), 7.64-7.57 (m, 2H), 7.31 (d, J=8.8 Hz, 2H), 7.15 (dd, J=8.4, 2.1 Hz, 1H), 6.98 (d, J=8.8 Hz, 2H), 3.92-3.83 (m, 5H), 3.52-3.42 (m, 4H), 3.28 (s, 4H), 3.22-3.19 (m, 4H), 2.15 (t, J=6.9 Hz, 2H), 1.78-1.67 (m 2H), 1.57 (d, J=12.9 Hz, 2H), 1.43 (s, 9H); MS (ESI) m/z: 615.1 (M+H)$^+$.

5B. Preparation of 2-(3-methoxy-4-(1H-pyrazol-4-yl)phenyl)-8-(4-(piperazin-1-yl)benzoyl)-2,8-diazaspiro[4.5]decan-1-one, 2 HCl

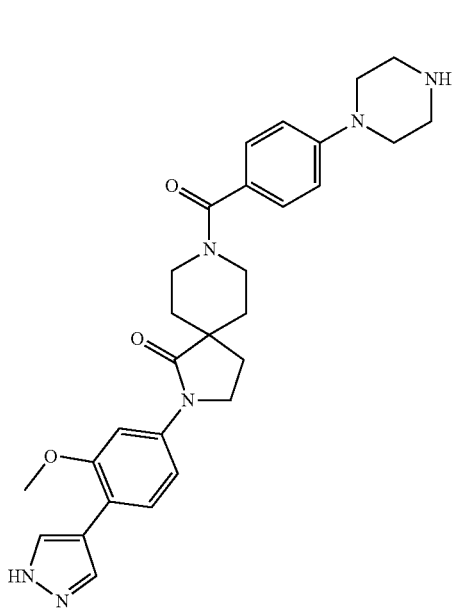 [SMILES: COc1cc(N2CCC3(CCN(C(=O)c4ccc(N5CCNCC5)cc4)CC3)C2=O)ccc1-c1cn[nH]c1]

To a round bottom flask was added Intermediate 5A (380 mg, 0.618 mmol), dioxane (3 mL) and 4N HCl (0.019 mL, 0.618 mmol) in dioxane. The reaction was stirred at rt for 4 hr. The reaction was concentrated to give 2-(3-methoxy-4-(H-pyrazol-4-yl)phenyl)-8-(4-(piperazin-1-yl)benzoyl)-2,8-diazaspiro[4.5]decan-1-one, 2 HCl (350 mg, 0.596 mmol, % % yield) as a white solid. MS (ESI) m/z: 515.0 (M+H)$^+$.

Intermediate 6: Preparation of 2-(4-bromphenyl)-8-(4-(4-methylpiperazin-1-yl)benzoyl)-2,8-diazaspiro[4.5]decan-1-one

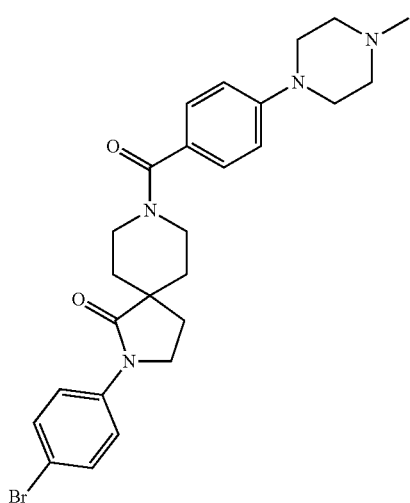 [SMILES: CN1CCN(c2ccc(C(=O)N3CCC4(CC3)CCN(c3ccc(Br)cc3)C4=O)cc2)CC1]

6A. Preparation of 2-(4-bromophenyl)-2,8-diazaspiro[4.5]decan-1-one, HCl

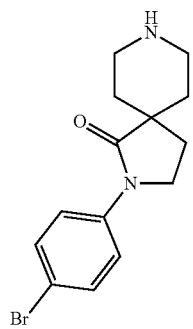 [SMILES: O=C1N(c2ccc(Br)cc2)CCC12CCNCC2]

To a round bottom flask was added Intermediate 1 (630 mg, 1.539 mmol), dioxane (5 ml) and 4N HCl (7696 µl, 30.8 mmol) in dioxane. The reaction was stirred at rt for 3 hr. The reaction was concentrated to give 2-(4-bromophenyl)-2,8-diazaspiro[4.5]decan-1-one, HCl (530 mg, 1.533 mmol, 100% yield) as a light colored solid. MS (ESI) m/z: 308.8, 310.8 (M+H)$^+$.

6B. Preparation of 2-(4-bromphenyl)-8-(4-(4-methylpiperazin-1-yl)benzoyl-2,8-diazaspiro[4.5]decan-1-one

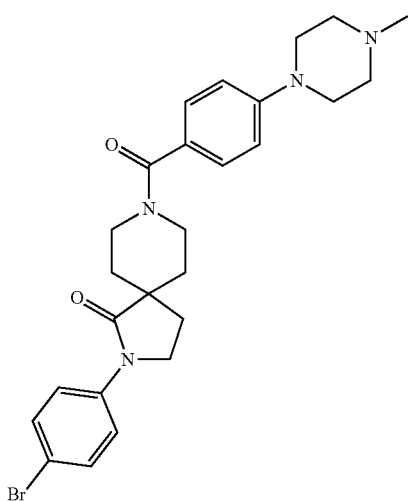 [SMILES: CN1CCN(c2ccc(C(=O)N3CCC4(CC3)CCN(c3ccc(Br)cc3)C4=O)cc2)CC1]

To around bottom flask was added 4-(4-methylpiperazin-1-yl)benzoic acid (147 mg, 0.665 mmol), THF (10 mL), HATU (304 mg, 0.798 mmol) and Et$_3$N (0.464 mL, 3.33 mmol). The reaction was stirred at rt for 10 min and then 6A (230 mg, 0.665 mmol) was added and the reaction was continued for 2 hr. The reaction was concentrated and the residue was purified using ISCO system (0-15% MeOH/CH$_2$Cl$_2$ gradient) to give 2-(4-bromophenyl)-8-(4-(4-methylpiperazin-1-yl)benzoyl)-2,8-diazaspiro[4.5]decan-1-one (305 mg, 0.596 mmol, 90% yield) as an off-white solid. $^1$H NMR (500 MHz, DMSO-d$_6$) δ 7.71-7.63 (m, 2H), 7.59-7.53 (m, 2H), 7.31 (d, J=8.8 Hz, 2H), 6.99 (d, J=8.8 Hz, 2H), 4.17-3.85 (m, 2H), 3.82 (t, J=6.9 Hz, 2H), 3.35-3.28 (m, 7H), 3.18 (br. s., 2H), 2.84-2.66 (m, 2H), 2.44 (br. s., 2H), 2.14 (t, J=6.9 Hz, 2H), 1.77-1.65 (m, 2H), 1.57 (d, J=12.7 Hz, 2H); MS (ESI) m/z: 511.0, 513.0 (M+H)$^+$.

Intermediate 7: Preparation of 2-(4-(1H-pyrazol-4-yl)benzyl)-2,7-diazaspiro[3.5]nonan-1-one, 2 HCl

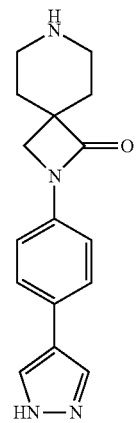

2-(4-(1H-pyrazol-4-yl)phenyl)-2,7-diazaspiro[3.5]nonan-1-one, 2 HCl (20 mg, 0.056) was prepared in a similar manner as the procedure described in Intermediate 3, using tert-butyl 1-oxo-2,7-diazaspiro[3.5]nonane-7-carboxylate (150 mg, 0.624 mmol); MS (ESI) m/z: 283.0 (M+H)$^+$.

Intermediate 8: Preparation of 2-(3-methoxy-4-(1H-pyrazol-4-yl)phenyl)-2,8-diazaspiro[4.5]decan-3-one, 2HCl

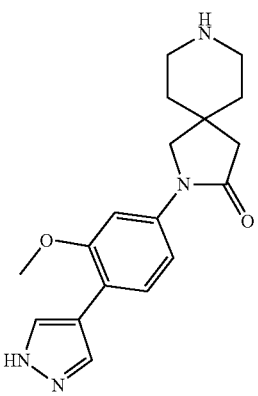 [SMILES: COc1cc(N2CC3(CCNCC3)CC2=O)ccc1-c1cn[nH]c1]

2-(3-methoxy-4-(1H-pyrazol-4-yl)phenyl)-2,8-diazaspiro[4.5]decan-3-one, 2 HCl (70 mg, 0.167 mmol) was prepared in a similar manner as the procedure described in Intermediate 4, using tert-butyl 3-oxo-2,8-diazaspiro[4.5]decane-8-carboxylate (150 mg, 0.59 mmol). MS (ESI) m/z: 327.1 (M+H)$^+$.

EXAMPLES

Example 1: Preparation of 8-benzoyl-2-[4-(1H-pyrazol-4-yl)phenyl]-2,8-diazaspiro[4.5]decan-1-one

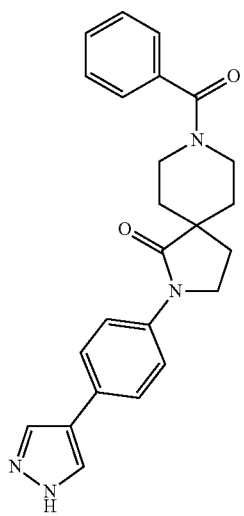 [SMILES: O=C(c1ccccc1)N1CCC2(CC1)CCN(c1ccc(-c3cn[nH]c3)cc1)C2=O]

1A: Preparation of 8-benzoyl-2-(4-bromophenyl)-2,8-diazaspiro[4.5 decan]-1-one

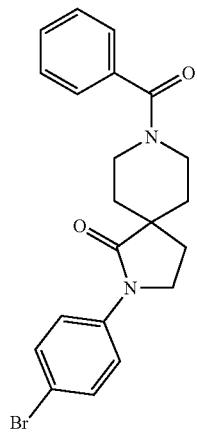 [SMILES: O=C(c1ccccc1)N1CCC2(CC1)CCN(c1ccc(Br)cc1)C2=O]

To a round bottom flask was added Intermediate 3 (8 mg, 0.110 mmol), THF (2 mL), Hunig's base (0.115 mL, 0.660 mmol) and benzoyl chloride (23.18 mg, 0.165 mmol). The reaction was stirred at rt for 15 min. The reaction was partitioned between EtOAc (30 ml) and water (20 ml). The organic layer was separated, washed with water (20 ml) and brine (20 ml), dried over MgSO₄, filtered and concentrated. The residue was purified using ISCO system (0-100% EtOAc/Hex gradient) to give 8-benzyl-2-(4-bromophenyl)-2,8-diazaspiro[4.5]decan-1-one (45 mg, 0.109 mmol, 99% yield) as an off-white solid. $^1$H NMR (500 MHz, DMSO-$d_6$) δ 7.72-7.65 (m, 2H), 7.60-7.54 (m, 2H), 7.50-7.43 (m, 3H), 7.42-7.37 (m, 2H), 3.82 (br. s., 2H), 3.27-3.10 (m, 2H), 2.14 (br. s., 2H), 1.81-1.45 (m, 4H); MS (ESI) m/z: 412.9, 414.9 (M+H)$^+$.

1B: Preparation of 8-benzoyl-2-[4-(1H-pyrazol-4-yl)phenyl]-2,8-diazaspiro[4.5]decan-1-one

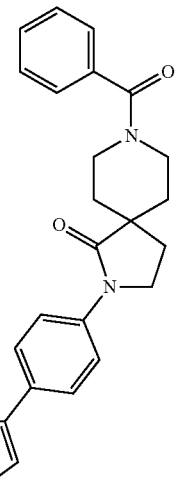

To a microwave vial was added 1A (45 mg, 0.109 mmol), 4-(4,4,5,5-tetramethyl-1,3,2-dioxaborolan-2-yl)-1H-pyrazole (42.3 mg, 0.218 mmol), tripotassium phosphate (0.145 mL, 0.436 mmol), Dioxane (2 mL) and methanesulfonato (2-dicyclohexylphosphino-2',4',6'-tri-i-propyl-1,1'-biphenyl)(2'-amino-1,1'-biphenyl-2-yl)palladium(II) (9.22 mg, 10.89 μmol). The reaction was purged with argon and sealed. The reaction was then subjected to microwave oven and stirred at 120° C. for 35 min. The reaction was partitioned between EtOAc (10 ml) and water (5 ml). The organic layer was separated, washed with brine (5 ml), dried and concentrated. The residue was purified using purification Method A to give 8-benzoyl-2-[4-(H-pyrazol-4-yl)phenyl]-2,8-diazaspiro[4.5]decan-1-one (6.6 mg, 0.016 mmol, 14.8% yield). $^1$H NMR (500 MHz, DMSO-$d_6$) δ 8.11 (br. s., 1H), 7.91 (br. s., 1H), 7.69-7.56 (m, 4H), 7.51-7.36 (m, 5H), 3.82 (br. s., 2H), 3.52 (br. s., 2H), 3.33-3.05 (m, 2H), 2.14 (br. s., 2H), 1.90-1.40 (m, 4H); MS (ESI) m/z: 400.8 (M+H)$^+$; Anal. HPLC Retention time: 1.3 (Method 1); ROCK 2 IC$_{50}$=326 nM.

Example 2: Preparation of 8-(benzenesulfonyl)-2-[4-(1H-pyrazol-4-yl)phenyl]-2,8-diazaspiro[4.5]decan-1-one

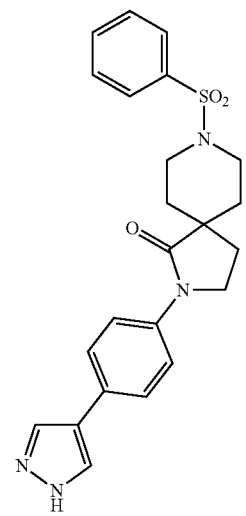 [SMILES: O=C1N(c2ccc(-c3cn[nH]c3)cc2)CCC12CCN(S(=O)(=O)c1ccccc1)CC2]

2A: Preparation of 2-(4-bromphenyl)-8-(phenylsulfonyl)-2,8-diazaspiro[4.5]decan-1-one

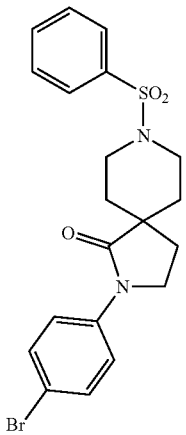 [SMILES: O=C1N(c2ccc(Br)cc2)CCC12CCN(S(=O)(=O)c1ccccc1)CC2]

To a round bottom flask was added Intermediate (38 mg, 0.110 mmol), THF (2 mL), Hunig's Base (0.115 mL, 0.660 mmol) and benzenesulfonyl chloride (29.1 mg, 0.165 mmol). The reaction was stirred at rt for 15 min. The reaction was partitioned between EtOAc (30 ml) and water (20 ml). The organic layer was separated, washed with water (20 ml) and brine (20 ml), dried over MgSO$_4$, filtered and concentrated. The residue was purified using ISCO system (0-100% EtOAc/Hex gradient) to give 2-(4-bromophenyl)-8-(phenylsulfonyl)-2,8-diazaspiro[4.5]decan-1-one (38 mg, 0.085 mmol, 77% yield) as an off-white solid. MS (ESI) m: 448.9, 450.9 (M+H)$^+$.

2B: Preparation of 8-(benzenesulfonyl)-2-[4-(1H-pyrazol-4-yl)phenyl]-2,8-diazaspiro[4.5]decan-1-one

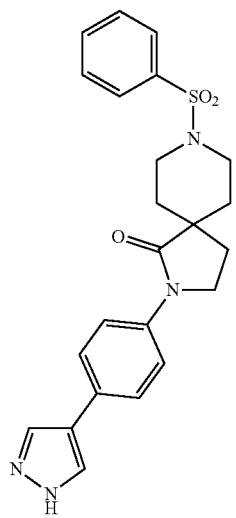 [SMILES: O=C1N(c2ccc(-c3cn[nH]c3)cc2)CCC12CCN(S(=O)(=O)c1ccccc1)CC2]

To a microwave vial was added 2A (37 mg, 0.082 mmol), 4-(4,4,5,5-tetramethyl-1,3,2-dioxaborolan-2-yl)-1H-pyrazole (32.0 mg, 0.165 mmol), 3M tripotassium phosphate (0.110 mL, 0.329 mmol), Dioxane (2 mL) and methanesulfonato(2-dicyclohexylphosphino-2',4',6'-tri-i-propyl-1,1'-biphenyl)(2'-amino-1,1'-biphenyl-2-yl)palladium(II) (6.97 mg, 8.23 µmol). The reaction was purged with argon and sealed. The reaction was then subjected to microwave oven and stirred at 120° C. for 35 min. The reaction was partitioned between EtOAc (10 ml) and water (5 ml). The organic layer was separated, washed with brine (5 ml), dried over MgSO$_4$ and concentrated. The residue purified using purification Method A to give 8-(benzenesulfonyl)-2-[4-(1H-pyrazol-4-yl)phenyl]-2,8-diazaspiro[4.5]decan-1-one (6.8 mg, 0.015 mmol, 18.8% yield). $^1$H NMR (500 MHz, DMSO-d$_6$) δ 8.16-8.01 (m, 1H), 8.00-7.84 (m, 1H), 7.79-7.71 (m, 3H), 7.69-7.64 (m, 2H), 7.58 (s, 4H), 3.72 (br t, J=6.9 Hz, 2H), 3.51 (br d, J=12.1 Hz, 2H), 2.66-2.54 (m, 2H), 1.86 (br t, J=6.8 Hz, 2H), 1.82-1.73 (m, 2H), 1.61 (br d, J=13.4 Hz, 2H); MS (ESI) m/z: 437.2 (M+H)$^+$; Anal. HPLC Retention time: 1.51 (Method 1); ROCK2 IC$_{50}$=330 nM.

Example 3: Preparation of 8-(2-methoxybenzoyl)-2-[4-(1H-pyrazol-4-yl)phenyl]-2,8-diazaspiro[4.5]decan-1-one

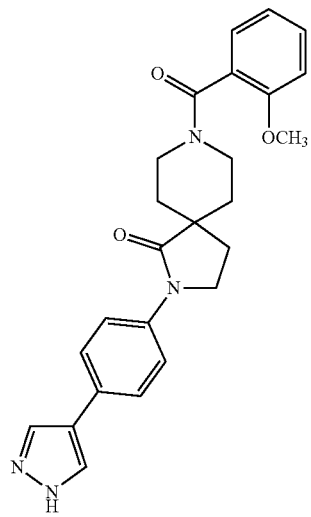 [SMILES: COc1ccccc1C(=O)N1CCC2(CC1)CCN(c1ccc(-c3cn[nH]c3)cc1)C2=O]

3A: Preparation of 2-(4-(1-((2-(trimethylsilyl)ethoxy)methyl)-1H-pyrazol-4-yl)phenyl)-2,8-diazaspiro[4.5]decan-1-one

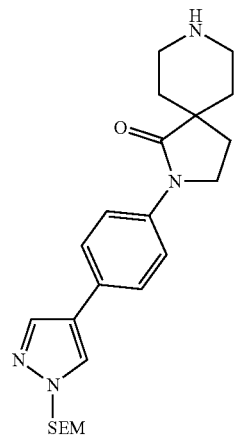 [SMILES: C[Si](C)(C)CCOCn1cc(-c2ccc(N3CCC4(CCNCC4)C3=O)cc2)cn1]

To a microwave vial was added Intermediate 3A (595 mg, 1.130 mmol). MeOH (8 mL) and H$_2$O (45 mL). The reaction was stirred at 150° C. for 90 min. The reaction was extracted with EtOAc (3×20 ml). The combined EtOAc was dried over MgSO$_4$, filtered and concentrated to give 2-(4-(1-((2-(trimethylsilyl)ethoxy)methyl)-1H-pyrazol-4-yl)phenyl)-2,8-diazaspiro[4.5]decan-1-one (295 mg, 0.691 mmol, 61.2% yield) as an off-white solid. (ESI) m/z: 427.1 (M+H)$^+$.

3B: Preparation of 8-(2-methoxybenzoyl)-2-[4-(1H-pyrazol-4-yl)phenyl]-2,8-diazaspiro[4.5]decan-1-one

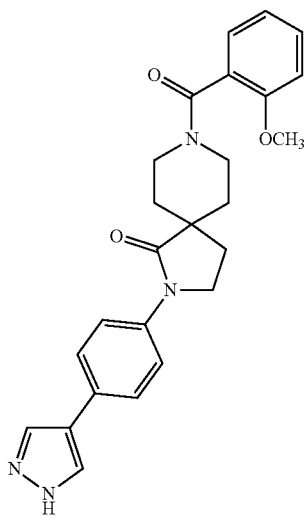 [SMILES: COc1ccccc1C(=O)N1CCC2(CC1)CCN(c1ccc(-c3cn[nH]c3)cc1)C2=O]

To a round bottom flask was added 3A (25 mg, 0.059 mmol), THF (1 mL), 2-methoxybenzoyl chloride (11.00 mg, 0.064 mmol) and Et$_3$N (0.012 mL, 0.088 mmol). The reaction was stirred at rt for 1 hr. The reaction was concentrated and then CH$_2$Cl$_2$ (0.5 mL) and TFA (0.5 mL) was added and then the reaction was stirred at rt overnight. The reaction was concentrated and the residue was purified using purification Method A to give 8-(2-methoxybenzoyl)-2-[4-(1H-pyrazol-4-yl)phenyl]-2,8-diazaspiro[4.5]decan-1-one (11.6 mg, 0.026 mmol, 45.1% yield). $^1$H NMR (500 MHz, DMSO-d$_6$) δ 8.24-7.85 (m, 2H), 7.75-7.55 (m, 4H), 7.40 (br s, 1H), 7.29-6.92 (m, 3H), 4.49-4.28 (m, 1H), 3.91-3.76 (m, 4H), 3.33 (br d, J=8.8 Hz, 1H), 3.21-2.99 (m, 2H), 2.24-2.01 (m, 2H), 1.83-1.39 (m, 4H); MS (ESI) m/z: 431.3 (M+H)$^+$; Anal. HPLC Retention time: 1.43 (Method 1); ROCK2 IC$_{50}$=160 nM Example 4: Preparation of 8-(4-methoxybenzoyl)-2-[4-(1H-pyrazol-4-yl)phenyl]-2,8-diazaspiro[4.5]decan-1-one

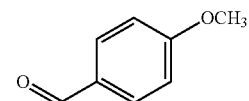

8-(4-methoxybenzoyl)-2-[4-(1H-pyrazol-4-yl)phenyl]-2,8-diazaspiro[4.5]decan-1-one (12.2 mg, 0.027 mmol, 46.9% yield) was prepared in a similar manner as the procedure described in Example 3, using 4-methoxybenzoyl chloride (11.00 mg, 0.064 mmol). $^1$H NMR (500 MHz, DMSO-d$_6$) δ 8.24-7.82 (m, 2H), 7.68-7.57 (m, 4H), 7.37 (d, J=8.5 Hz, 2H), 6.99 (d, J=8.4 Hz, 2H), 3.82 (br. s., 2H), 3.78 (s, 3H), 3.69-3.60 (m, 2H), 2.55 (m, 2H), 2.13 (br. s., 2H), 1.70 (br. s., 2H), 1.56 (br. s., 2H); MS (ESI) m/z: 431.3 (M+H)$^+$; Anal. HPLC Retention time: 1.32 (Method 2); ROCK2 IC$_{50}$=21 nM.

Example 5: Preparation of 8-(3-methoxybenzoyl)-2-[4-(1H-pyrazol-4-yl)phenyl]-2,8-diazaspiro[4.5]decan-1-one

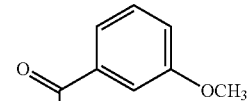
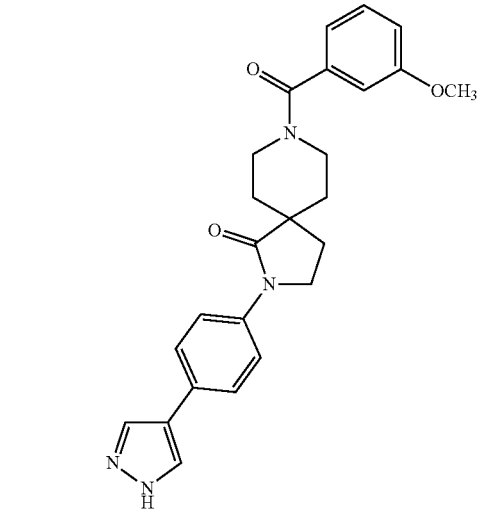 [SMILES: COc1cccc(C(=O)N2CCC3(CC2)CCN(c2ccc(-c4cn[nH]c4)cc2)C3=O)c1]

8-(3-methoxybenzoyl)-2-[4-(1H-pyrazol-4-yl)phenyl]-2,8-diazaspiro[4.5]decan-1-one (9.6 mg, 0.021 mmol, 36.5% yield) was prepared in a similar manner as the procedure described in Example 3, using 3-methoxybenzoyl chloride (11.00 mg, 0.064 mmol). $^1$H NMR (500 MHz, DMSO-$d_6$) δ 8.11 (br. s., 1H), 7.94 (br. s., 1H), 7.72-7.55 (m, 4H), 7.37 (t, J=7.9 Hz, 1H), 7.02 (dd, J=8.2, 2.1 Hz, 1H), 6.96-6.88 (m, 2H), 3.82 (br. s., 2H), 3.78 (s, 3H), 3.58-3.52 (m, 2H), 3.31-3.03 (m, 2H), 2.13 (br. s., 2H), 1.66 (br. s., 3H), 1.51 (br. s., 1H); MS (ESI) m/z: 431.3 (M+H)$^+$; Anal. HPLC Retention time: 1.49 (Method 1); ROCK2 IC$_{50}$=85 nM.

Example 6: Preparation of 8-(1-methyl-1H-indazole-3-carbonyl)-2-[4-(1H-pyrazol-4-yl)phenyl]-2,8-diazaspiro[4.5]decan-1-one

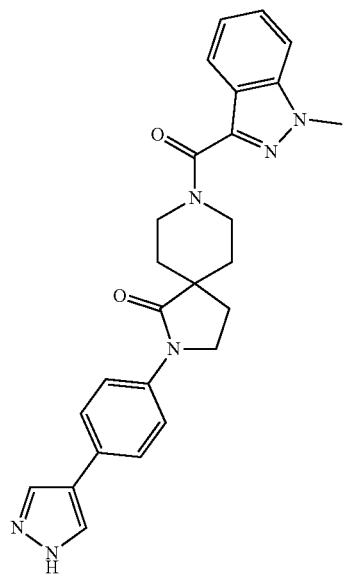 [SMILES: Cn1nc(C(=O)N2CCC3(CC2)CCN(c2ccc(-c4cn[nH]c4)cc2)C3=O)c2ccccc21]

To a round bottom flask was added 3A (25 mg, 0.059 mmol), THF (1 mL), 1-methyl-1H-indazole-3-carboxylic acid (10.32 mg, 0.059 mmol), HATU (26.7 mg, 0.070 mmol) and Et$_3$N (0.012 mL, 0.088 mmol). The reaction was stirred at rt overnight. The reaction was partitioned between EtOAc (20 ml) and water (15 ml). The organic layer was separated, washed with brine (15 ml), dried over MgSO$_4$, filtered and concentrated. To the residue was added CH$_2$Cl$_2$ (0.5 mL) and TFA (0.5 mL). The reaction was stirred at rt for 4 hr. The reaction was concentrated and purified using Purification Method A to give 8-(1-methyl-1H-indazole-3-carbonyl)-2-[4-(1H-pyrazol-4-yl)phenyl]-2,8-diazaspiro[4.5]decan-1-one (10.2 mg, 0.022 mmol, 37.5% yield). $^1$H NMR (500 MHz, DMSO-$d_6$) δ 8. 8.14 (br. s., 1H), 7.93 (d, J=8.1 Hz, 2H), 7.74-7.57 (m, 5H), 7.47 (t, J=7.6 Hz, 1H), 7.26 (t, J=7.4 Hz, 1H), 4.55 (br. s., 1H), 4.47 (br. s., 1H), 4.10 (s, 3H), 3.85 (br. s., 2H), 3.65-3.56 (m, 1H), 3.16 (d, J=5.7 Hz, 2H), 2.19 (d, J=6.0 Hz, 2H), 1.86-1.73 (m, 2H), 1.68 (br. s., 1H), 1.60 (br. s., 1H); MS (ESI) m/z: 455.0 (M+H)$^+$; Anal. HPLC Retention time: 1.34 (Method 2); ROCK2 IC$_{50}$=143 nM.

Example 7: Preparation of 8-cyclopropanecarbonyl-2-[4-(1H-pyrazol-4-yl)phenyl]-2,8-diazaspiro[4.5]decan-1-one 8-Cyclopropanecarbonyl-2-[4-(1H-pyrazol-4-yl)phenyl]-2,8-diazaspiro[4.5]decan-1-one (9.9 mg, 0.027 mmol, 45.4% yield) was prepared in a similar manner as the procedure described in Example 3, using cyclopropanecarbonyl chloride (6.13 mg, 0.059 mmol). $^1$H NMR (500 MHz, DMSO-$d_6$) δ 8.15 (br. s., 1H), 7.91 (br. s., 1H), 7.72-7.54 (m, 4H), 4.21 (br. s., 2H), 3.84 (t, J=6.9 Hz, 2H), 3.33 (br. s., 1H), 2.90 (br. s., 1H), 2.14 (t, J=6.9 Hz, 2H), 2.00 (t, J=6.1 Hz, 1H), 1.73 (br. s., 1H), 1.63-1.44 (m, 3H), 0.72 (br. s., 4H); MS (ESI) m/z: 365.2 (M+H)$^+$; Anal. HPLC Retention time: 1.11 Method 1; ROCK2 IC$_{50}$=875 nM.

Example 8: Preparation of 8-(3-fluoro-2-methoxybenzoyl)-2-[4-(1H-pyrazol-4-yl)-phenyl]-2,8-diazaspiro[4.5]decan-1-one

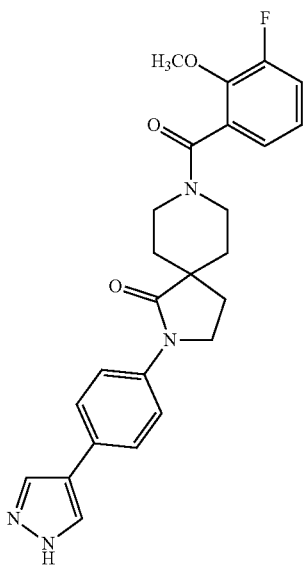 [SMILES: COc1c(F)cccc1C(=O)N1CCC2(CC1)CCN(c1ccc(-c3cn[nH]c3)cc1)C2=O]

8-(3-Fluoro-2-methoxybenzoyl)-2-[4-(1H-pyrazol-4-yl)phenyl]-2,8-diazaspiro[4.5]decan-1-one (7.6 mg, 0.017 mmol, 47.2% yield) was prepared in a similar manner as the procedure described in Example 6, using 3-fluoro-2-methoxybenzoic acid (5.98 mg, 0.035 mmol). $^1$H NMR (500 MHz, DMSO-$d_6$) δ 8.15 (br. s., 1H), 7.90 (br. s., 1H), 7.76-7.54 (m, 4H), 7.40-7.27 (m, 1H), 7.17 (br. s., 1H), 7.12-6.96 (m, 1H), 4.37 (br. s., 1H), 3.99-3.71 (m, 5H), 3.42 (s, 1H), 3.21-3.04 (m, 2H), 2.24-2.04 (m, 2H), 1.80-1.57 (m, 3H), 1.48 (d, J=12.5 Hz, 1H); MS (ESI) m/z: 449.3 (M+H)$^+$; Anal. HPLC Retention time: 1.48 (Method 1); ROCK2 IC$_{50}$=112 nM.

Example 9: Preparation of 8-(4-fluoro-2-methoxybenzoyl)-2-[4-(1H-pyrazol-4-yl)phenyl]-2,8-diazaspiro[4.5]decan-1-one

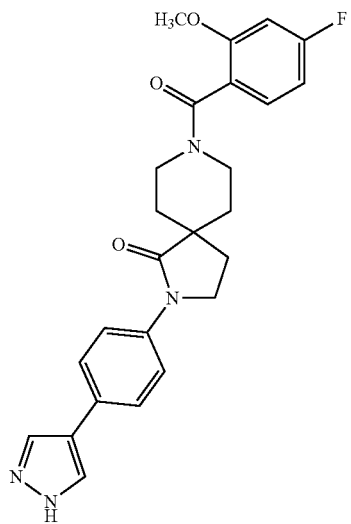 [SMILES: COc1cc(F)ccc1C(=O)N1CCC2(CC1)CCN(c1ccc(-c3cn[nH]c3)cc1)C2=O]

8-(4-Fluoro-2-methoxybenzoyl)-2-[4-(1H-pyrazol-4-yl)phenyl]-2,8-diazaspiro[4.5]decan-1-one (7.6 mg, 0.017 mmol, 28.3% yield) was prepared in a similar manner as the procedure described in Example 6, using 4-fluoro-2-methoxybenzoic acid (9.97 mg, 0.059 mmol). $^1$H NMR (500 MHz, DMSO-$d_6$) δ 8.16 (br. s., 1H), 7.99-7.79 (m, 1H), 7.72-7.54 (m, 4H), 7.34-7.13 (m, 1H), 7.01 (d, J=11.0 Hz, 1H), 6.84 (br. s., 1H), 4.33 (d, J=13.7 Hz, 1H), 3.91-3.69 (m, 5H), 3.47-3.31 (m, 1H), 3.23-3.00 (m, 2H), 2.26-2.00 (m, 2H), 1.82-1.52 (m, 3H), 1.46 (d, J=12.8 Hz, 1H); MS (ESI) m/z: 449.1 (M+H)$^+$; Anal. HPLC Retention time: 1.47 (Method 1); ROCK2 IC$_{50}$=241 nM.

Example 10: Preparation of 2-[4-(1H-pyrazol-4-yl)phenyl]-8-[4-(trifluoromethoxy)benzoyl]-2,8-diazaspiro[4.5]decan-1-one

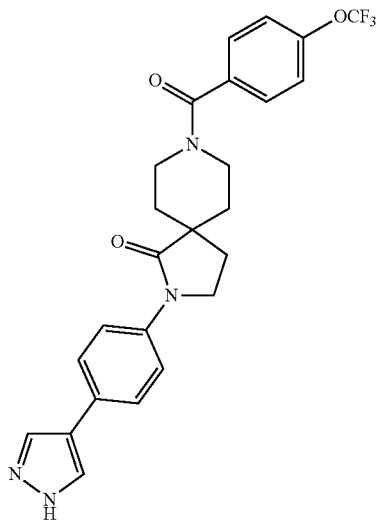 [SMILES: O=C(c1ccc(OC(F)(F)F)cc1)N1CCC2(CC1)CCN(c1ccc(-c3cn[nH]c3)cc1)C2=O]

2-[4-(1H-pyrazol-4-yl)phenyl]-8-[4-(trifluoromethoxy)benzoyl]-2,8-diazaspiro[4.5]decan-1-one (14.5 mg, 0.030 mmol, 36.1% yield) was prepared in a similar manner as the procedure described in Example 6, using 4-(trifluoromethoxy)benzoic acid (16.9 mg, 0.082 mmol). $^1$H NMR (500 MHz, DMSO-$d_6$) δ 8.16 (br. s., 1H), 7.93 (br. s., 1H), 7.70-7.64 (m, 2H), 7.63-7.59 (m, 2H), 7.56 (d, J=8.5 Hz, 2H), 7.45 (d, J=8.2 Hz, 2H), 4.40-4.21 (m, 1H), 3.83 (br. s., 2H), 3.30-3.07 (m, 1H), 2.60-2.45 (m, 2H), 2.23-2.06 (m, 2H), 1.87-1.60 (m, 3H), 1.53 (br. s., 1H); MS (ESI) m/z: 485.2 (M+H)$^+$; Anal. HPLC Retention time: 1.74 (Method 2); ROCK2 IC$_{50}$=95 nM.

Example 11: Preparation of 8-(3-fluoro-4-methoxybenzoyl)-2-[4-(1H-pyrazol-4-yl)phenyl]-2,8-diazaspiro[4.5]decan-1-one

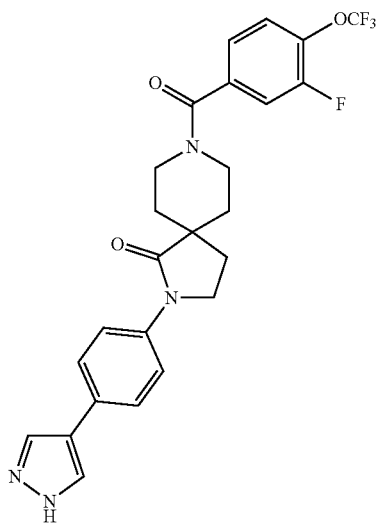 [SMILES: O=C(c1ccc(OC(F)(F)F)c(F)c1)N1CCC2(CC1)CCN(c1ccc(-c3cn[nH]c3)cc1)C2=O]

8-(3-fluoro-4-methoxybenzoyl)-2-[4-(1H-pyrazol-4-yl)phenyl]-2,8-diazaspiro[4.5]decan-1-one (15.8 mg, 0.035 mmol, 58.9% yield) was prepared in a similar manner as the procedure described in Example 6, using 3-fluoro-4-methoxybenzoic acid (9.97 mg, 0.059 mmol). ¹H NMR (500 MHz, DMSO-d₆) δ 8.13 (br. s., 1H), 7.91 (br. s., 1H), 7.71-7.55 (m, 4H), 7.28 (d, J=11.6 Hz, 1H), 7.23 (br. s., 2H), 4.23 (q, J=5.2 Hz, 2H), 3.87 (s, 3H), 3.84-3.80 (m, 2H), 3.68-3.63 (m, 2H), 2.13 (br. s., 2H), 1.72 (br. s., 2H), 1.57 (br. s., 2H); MS (ESI) m/z: 449.2 (M+H)⁺; Anal. HPLC Retention time: 1.53 (Method 1); ROCK2 EC₅₀=16 nM.

Example 12: Preparation of 2-[3-methoxy-4-(1H-pyrazol-4-yl)phenyl]-8-(2-methoxybenzoyl)-2,8-diazaspiro[4.5]decan-1-one

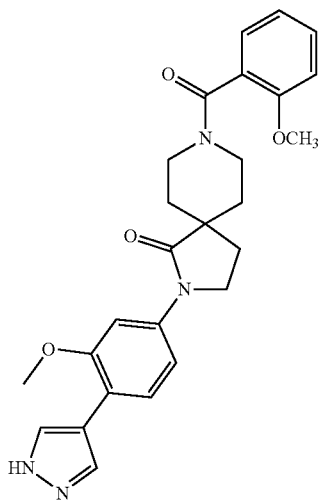 [SMILES: COc1ccccc1C(=O)N1CCC2(CC1)CCN(c1ccc(-c3cn[nH]c3)c(OC)c1)C2=O]

12A: Preparation of 2-(4-bromo-3-methoxyphenyl)-8-(2-methoxybenzoyl)-2,8-diazaspiro[4.5]decan-1-one

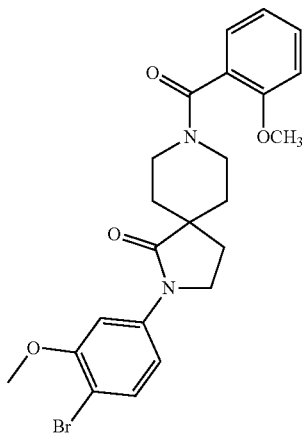 [SMILES: COc1cc(N2CCC3(CCN(C(=O)c4ccccc4OC)CC3)C2=O)ccc1Br]

To a round bottom flask was added Intermediate 2 (50 mg, 0.114 mmol), and 4N HCl (1.423 mL, 5.69 mmol) in Dioxane (0.5 mL). The reaction was stirred at rt for 30 min. The reaction was concentrated. Then the reaction was dissolved in THF (1.5 mL) and Et₃N (0.095 mL, 0.683 mmol) and 2-methoxybenzoyl chloride (23.30 mg, 0.137 mmol) was added to the reaction. The reaction was stirred at rt for 15 min. The reaction was then partitioned between EtOAc (20 ml) and water (10 ml). The organic layer was separated, washed with water (10 ml) and brine (10 ml), dried over MgSO₄, filtered and concentrated. The residue was purified using ISCO system (0-100% EtOAc/Hex gradient) to give 2-(4-bromo-3-methoxyphenyl)-8-(2-methoxybenzoyl)-2,8-diazaspiro[4.5]decan-1-one (50 mg, 0.106 mmol, 93% yield) as a beige solid. ¹H NMR (500 MHz, DMSO-d₆) δ 7.67 (dd, J=10.5, 1.9 Hz, 1H), 7.55 (d, J=8.5 Hz, 1H), 7.43-7.36 (m, 1H), 7.24-7.14 (m, 1H), 7.14-7.07 (m, 2H), 7.01 (q, J=7.4 Hz, 1H), 4.36 (dd, J=17.6, 13.8 Hz, 1H), 3.85 (d, J=5.0 Hz, 4H), 3.82-3.78 (m, 3H), 3.39-3.32 (m, 1H), 3.21-3.01 (m, 2H), 2.24-2.04 (m, 2H), 1.83-1.53 (m, 3H), 1.46 (d, J=12.9 Hz, 1H), 1.33-1.24 (m, 1H); MS (ESI) m/z: 473.0, 475.0 (M+H)⁺.

12B: Preparation of 2-[3-methoxy-4-(1H-pyrazol-4-yl)phenyl]-8-(2-methoxybenzoyl)-2,8-diazaspiro[4.5]decan-1-one

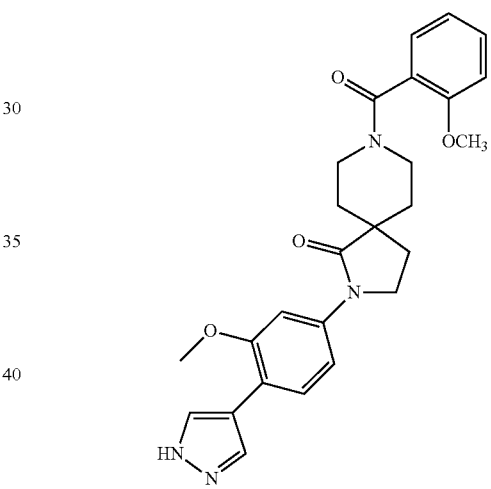

To a microwave vial was added 2-(4-bromo-3-methoxyphenyl)-8-(2-methoxybenzoyl)-2,8-diazaspiro[4.5]decan-1-one (60 mg, 0.127 mmol), 4-(4,4,5,5-tetramethyl-1,3,2-dioxaborolan-2-yl)-1H-pyrazole (73.8 mg, 0.380 mmol), tripotassium phosphate (0.169 mL, 0.507 mmol), Dioxane (3 mL) and methanesulfonato(2-dicyclohexylphosphino-2′,4′,6′-tri-i-propyl-1,1′-biphenyl)(2′-amino-1,1′-biphenyl-2-yl)palladium(II) (10.73 mg, 0.013 mmol). The reaction was purged with argon and sealed. The reaction was then subjected to microwave oven and stirred at 120° C. for 30 min. The reaction was partitioned between EtOAc (50 ml) and water (20 ml). The organic layer was separated, washed with water (20 ml) and brine (30 ml), dried over MgSO₄, filtered and concentrated. The residue was purified using Purification Method A to give 2-[3-methoxy-4-(1H-pyrazol-4-yl)phenyl]-8-(2-methoxybenzoyl)-2,8-diazaspiro[4.5]decan-1-one (21.6 mg, 0.046 mmol, 36.3% yield). ¹H NMR (500 MHz, DMSO-d₆) δ 8.30-7.78 (m, 2H), 7.61 (d, J=9.7 Hz, 2H), 7.40 (d, J=4.0 Hz, 1H), 7.26-7.06 (m, 3H), 7.01 (q, J=7.6 Hz, 1H), 4.51-4.25 (m, 1H), 3.98-3.66 (m, 7H), 3.54-3.27 (m, 2H), 3.22-2.97 (m, 2H), 2.28-2.00 (m, 2H), 1.83-1.52 (m, 3H), 1.46 (d, J=12.5 Hz, 1H); MS (ESI) m/z: 461.0 (M+H)+; Anal. HPLC Retention time: 1.5 (Method 1); ROCK2 IC$_{50}$=54 nM.

Example 13: Preparation of 2-[3-methoxy-4-(1H-pyrazol-4-yl)phenyl]-8-(4-methoxybenzoyl)-2,8-diazaspiro[4.5]decan-1-one

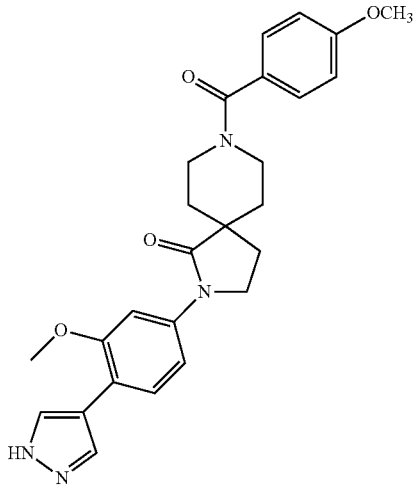 [SMILES: COc1ccc(C(=O)N2CCC3(CC2)CCN(c2ccc(-c4cn[nH]c4)c(OC)c2)C3=O)cc1]

2-[3-Methoxy-4-(1H-pyrazol-4-yl)phenyl]-8-(4-methoxybenzoyl)-2,8-diazaspiro[4.5]decan-1-one (19.6 mg, 0.042 mmol, 43.9% yield) was prepared in a similar manner as the procedure described in Example 10, using 4-methoxybenzoyl chloride (23.3 mg, 0.137 mmol). $^1$H NMR (500 MHz, DMSO-d$_6$) δ 8.02 (br. s., 2H), 7.64-7.52 (m, 2H), 7.37 (d, J=8.5 Hz, 2H), 7.19-7.10 (m, 1H), 6.99 (d, J=8.5 Hz, 2H), 3.86-3.81 (m, 4H), 3.79 (s, 3H), 3.60 (br. s., 1H), 3.17 (s, 2H), 2.53 (d, J=19.2 Hz, 2H), 2.14 (br. s., 2H), 1.72 (br. s., 2H), 1.58 (br. s., 2H); MS (EST) m/z: 461.0 (M+H)+. Anal; HPLC Retention time: 1.52 (Method 1); ROCK2 IC$_{50}$=8 nM.

Example 14: Preparation of 8-(3-fluoro-4-methoxybenzoyl)-2-[3-methoxy-4-(1H-pyrazol-4-yl)phenyl]-2,8-diazaspiro[4.5]decan-1-one

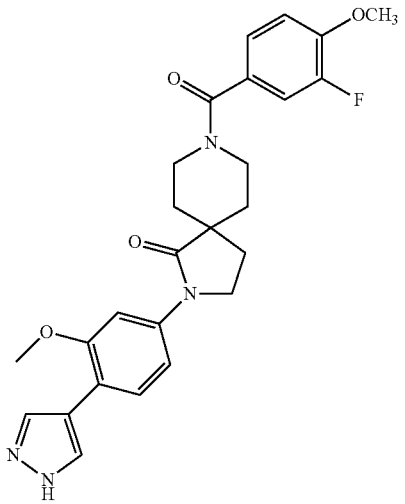 [SMILES: COc1ccc(C(=O)N2CCC3(CC2)CCN(c2ccc(-c4cn[nH]c4)c(OC)c2)C3=O)cc1F]

To a round bottom flask was added 3-fluoro-4-methoxybenzoic acid (8.52 mg, 0.050 mmol), THF (1 mL), HATU (22.85 mg, 0.060 mmol) and Et$_3$N (0.035 mL, 0.250 mmol). The reaction was stirred at rt for 10 min and then Intermediate 4 (20 mg, 0.050 mmol) was added and the reaction. The reaction was continued for 2 hr. The reaction was partitioned between EtOAc (20 ml) and water (15 ml). The organic layer was separated, washed with brine (15 ml), dried over MgSO$_4$, filtered and concentrated. The residue was purified using Purification method A to give 8-(3-fluoro-4-methoxybenzoyl)-2-[3-methoxy-4-(1H-pyrazol-4-yl)phenyl]-2,8-diazaspiro[4.5]decan-1-one (4.1 mg, 0.0081 mmol, 16.1% yield).). $^1$H NMR (500 MHz, DMSO-d$_6$) δ 8.10-7.93 (m, 2H), 7.62-7.58 (m, 2H), 7.30 (d, J=11.6 Hz, 1H), 7.23 (br. s., 2H), 7.15 (d, J=8.5 Hz, 1H), 3.91-3.84 (m, 8H), 3.42 (br. s., 2H), 3.17 (d, J=5.2 Hz, 2H), 2.14 (br. s., 2H), 1.75 (d, J=13.1 Hz, 2H), 1.59 (br. s., 2H); MS (ESI) m/z: 479.1 (M+H)+; Anal. HPLC Retention time: 1.53 (Method 1); ROCK2 IC$_{50}$=8 nM.

Example 15: Preparation of 8-[4-(hydroxymethyl)benzoyl]-2-[3-methoxy-4-(1H-pyrazol-4-yl)phenyl]-2,8-diazaspiro[4.5]decan-1-one

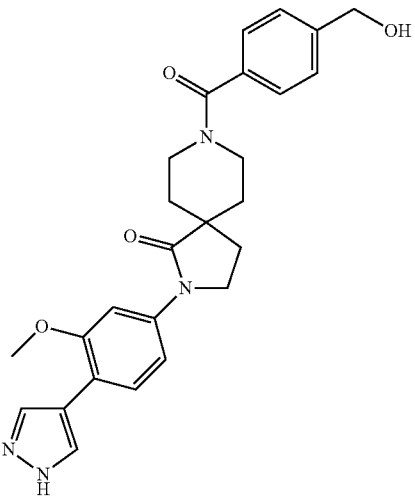 [SMILES: COc1cc(N2CCC3(CCN(C(=O)c4ccc(CO)cc4)CC3)C2=O)ccc1-c1cn[nH]c1]

8-[4-(Hydroxymethyl)benzoyl]-2-[3-methoxy-4-(1H-pyrazol-4-yl)phenyl]-2,8-diazaspiro[4.5]decan-1-one (12.4 mg, 0.026 mmol, 52.7% yield) was prepared in a similar manner as the procedure described in Example 14, using 4-(hydroxymethyl)benzoic acid (7.62 mg, 0.050 mmol). $^1$H NMR (500 MHz, DMSO-d$_6$) δ 8.01 (br. s., 2H), 7.62-7.54 (m, 2H), 7.42-7.33 (m, 4H), 7.14 (d, J=8.5 Hz, 1H), 4.53 (d, J=5.2 Hz, 2H), 3.93-3.82 (m, 5H), 3.60 (br. s., 2H), 3.17 (d, J=5.2 Hz, 2H), 2.14 (br. s., 2H), 1.71 (br. s., 4H); MS (ESI) m/z: 461.1 (M+H)+; Anal. HPLC Retention time: 1.22 (Method 1); ROCK2 IC$_{50}$=53 nM.

Example 16: Preparation of 2-[3-methoxy-4-(1H-pyrazol-4-yl)phenyl]-8-(5-methoxypyridine-2-carbonyl)-2,8-diazaspiro[4.5]decan-1-one

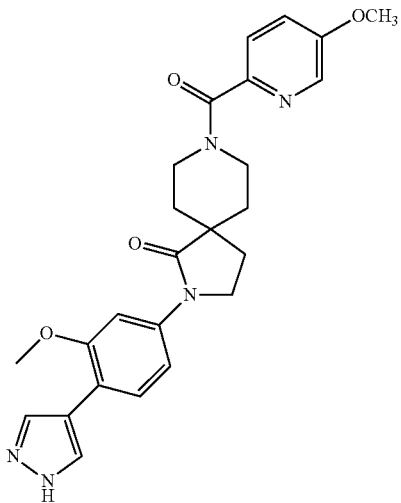 [SMILES: COc1ccc(C(=O)N2CCC3(CC2)CCN(c2ccc(-c4cn[nH]c4)c(OC)c2)C3=O)nc1]

2-[3-Methoxy-4-(1H-pyrazol-4-yl)phenyl]-8-(5-methoxypyridine-2-carbonyl)-2,8-diazaspiro[4.5]decan-1-one (15.8 mg, 0.034 mmol, 67% yield) was prepared in a similar manner as the procedure described in Example 14, using 5-methoxypicolinic acid (7.67 mg, 0.050 mmol). $^1$H NMR (500 MHz, DMSO-$d_6$) δ 8.29 (d, J=2.4 Hz, 1H), 8.02 (br. s., 2H), 7.70-7.56 (m, 3H), 7.51 (dd, J=8.6, 2.5 Hz, 1H), 7.15 (d, J=8.4 Hz, 1H), 4.36 (d, J=13.2 Hz, 1H), 3.87 (d, J=6.1 Hz, 1H), 3.36-3.22 (m, 1H), 3.13 (t, J=11.0 Hz, 9H), 2.16 (dd, J=17.7, 6.6 Hz, 2H), 1.84-1.71 (m, 2H), 1.65 (d, J=12.5 Hz, 1H), 1.52 (d, J=11.6 Hz, 1H); MS (ESI) m/z: 461.9 (M+H)$^+$; Anal. HPLC Retention time: 1.41 (Method 1); ROCK2 IC$_{50}$=13 nM.

Example 17: Preparation of 8-(2-fluoro-4-methoxybenzoyl)-2-[3-methoxy-4-(1H-pyrazol-4-yl)phenyl]-2, diazaspiro[4.5]decan-1-one

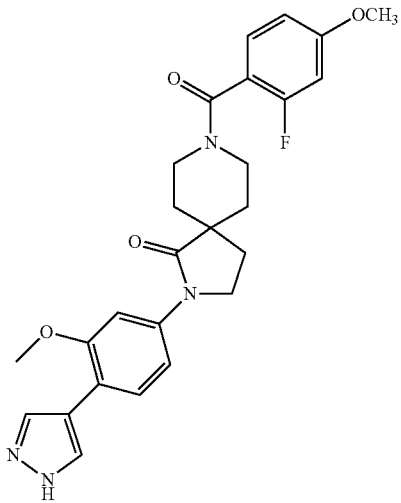 [SMILES: COc1ccc(C(=O)N2CCC3(CC2)CCN(c2ccc(-c4cn[nH]c4)c(OC)c2)C3=O)c(F)c1]

8-(2-Fluoro-4-methoxybenzoyl)-2-[3-methoxy-4-(1H-pyrazol-4-yl)phenyl]-2,8-diazaspiro[4.5]decan-1-one (9.1 mg, 0.019 mmol, 37.2% yield) was prepared in a similar manner as the procedure described in Example 14, using 2-fluoro-4-methoxybenzoic acid (8.52 mg, 0.050 mmol). $^1$H NMR (500 MHz, DMSO-$d_6$) δ 8.17-7.77 (m, 2H), 7.67-7.56 (m, 2H), 7.32 (t, J=8.2 Hz, 1H), 7.14 (d, J=8.5 Hz, 1H), 6.98-6.78 (m, 3H), 4.19 (br. s., 1H), 3.92-3.82 (m, 6H), 3.80 (s, 3H), 3.12 (br. s., 2H), 2.13 (dd, J=13.9, 7.2 Hz, 3H), 1.83-1.59 (m, 3H), 1.51 (d, J=11.9 Hz, 1H); MS (ESI) m/z: 478.9 (M+H)$^+$; Anal. HPLC Retention time: 1.47 (Method 1); ROCK2 IC$_{50}$=8 nM.

Example 18: Preparation of 8-(4-chlorobenzoyl-2-[3-methoxy-4-(1H-pyrazol-4-yl)phenyl]-2,8-diazaspiro[4.5]decan-1-one

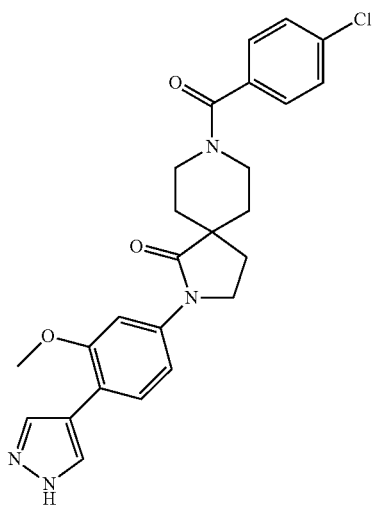 [SMILES: COc1cc(N2CCC3(CCN(C(=O)c4ccc(Cl)cc4)CC3)C2=O)ccc1-c1cn[nH]c1]

8-(4-Chlorobenzoyl)-2-[3-methoxy-4-(1H-pyrazol-4-yl)phenyl]-2,8-diazaspiro[4.5]decan-1-one (21.1 mg, 0.044 mmol, 88% yield) was prepared in a similar manner as the procedure described in Example 14, using 4-chlorobenzoic acid (7.84 mg, 0.050 mmol). $^1$H NMR (500 MHz, DMSO-$d_6$) δ 8.18-7.92 (m, 2H), 7.65-7.56 (m, 2H), 7.53 (d, J=8.2 Hz, 2H), 7.44 (d, J=8.2 Hz, 2H), 7.30-7.00 (m, 2H), 3.94-3.76 (m, 5H), 3.34-3.03 (m, 2H), 2.55 (s, 2H), 2.25-2.09 (m, 2H), 1.81-1.44 (m, 4H); MS (ESI) m/z: 464.9 (M+H)$^+$; Anal. HPLC Retention time: 1.7 (Method 1); ROCK2 IC$_{50}$=62 nM.

Example 19: Preparation of 8-(4-cyclopropylbenzoyl)-2-[3-methoxy-4-(1H-pyrazol-4-yl)phenyl]-2,8-diazaspiro[4.5]decan-1-one

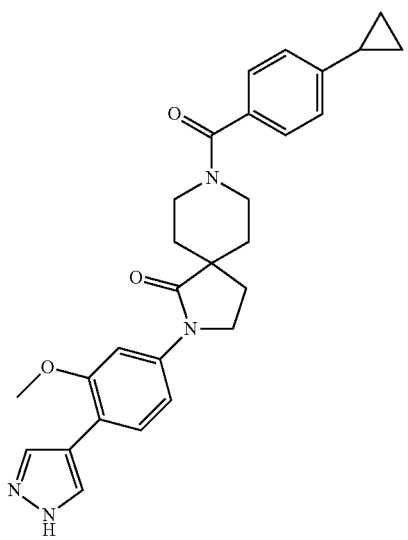 [SMILES: COc1cc(N2CCC3(CCN(C(=O)c4ccc(C5CC5)cc4)CC3)C2=O)ccc1-c1cn[nH]c1]

8-(4-Cyclopropylbenzoyl)-2-[3-methoxy-4-(H-pyrazol-4-yl)phenyl]-2,8-diazaspiro[4.5]decan-1-one (11.2 mg, 0.023 mmol, 46.6% yield) was prepared in a similar manner as the procedure described in Example 14, using 4-cyclopropylbenzoic acid (8.12 mg, 0.050 mmol). $^1$H NMR (500 MHz, DMSO-$d_6$) δ 7.99 (br. s., 2H), 7.67-7.53 (m, 2H), 7.28 (d, J=8.0 Hz, 2H), 7.14 (d, J=8.0 Hz, 3H), 3.86 (s, 5H), 3.51-3.38 (m, 1H), 3.17 (br. s., 1H), 2.55 (s, 2H), 2.14 (br. s., 2H), 1.99-1.90 (m, 1H), 1.83-1.38 (m, 4H), 0.99 (d, J=6.6 Hz, 2H), 0.71 (d, J=5.1 Hz, 2H); MS (ESI) m/z: 471.3 (M+H)$^+$; Anal. HPLC Retention time: 1.58 (Method 1); ROCK2 IC$_{50}$=10 nM

Example 20: Preparation of 8-(4-ethylbenzoyl)-2-[3-methoxy-4-(1H-pyrazol-4-yl)phenyl]-2,8-diazaspiro[4.5]decan-1-one

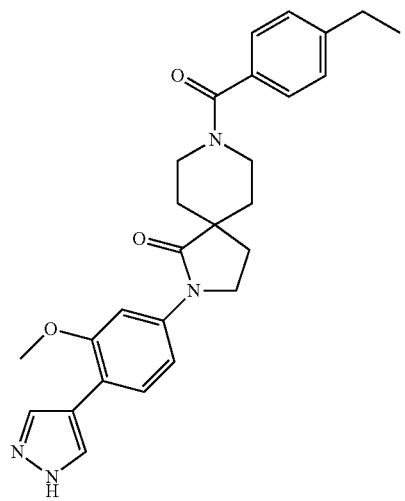 [SMILES: CCc1ccc(C(=O)N2CCC3(CC2)CCN(c2ccc(-c4cn[nH]c4)c(OC)c2)C3=O)cc1]

8-(4-Ethylbenzoyl)-2-[3-methoxy-4-(1H-pyrazol-4-yl)phenyl]-2,8-diazaspiro[4.5]decan-1-one (21.3 mg, 0.046 mmol, 91% yield) was prepared in a similar manner as the procedure described in Example 14, using 4-ethylbenzoic acid (7.52 mg, 0.050 mmol). $^1$H NMR (500 MHz, DMSO-$d_6$) δ 8.02 (br. s., 2H), 7.66-7.53 (m, 2H), 7.31 (q, J=7.9 Hz, 4H), 7.14 (d, J=8.1 Hz, 1H), 3.86 (s, 5H), 3.35-3.02 (m, 1H), 2.64 (q, J=7.6 Hz, 2H), 2.55 (s, 2H), 2.14 (br. s., 2H), 1.83-1.45 (m, 4H), 1.20 (t, J=7.5 Hz, 3H); MS (ESI) m/z: 458.9 (M+H)$^+$; Anal. HPLC Retention time: 1.79 (Method 1); ROCK2 IC$_{50}$=50 nM

Example 21: Preparation of 8-[4-(dimethylamino)benzoyl]-2-[3-methoxy-4-(1H-pyrazol-4-yl)phenyl]-2,8-diazaspiro[4.5]decan-1-one

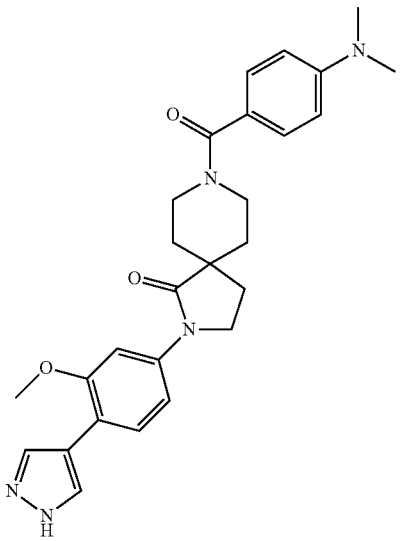 [SMILES: COc1cc(N2CCC3(CCN(C(=O)c4ccc(N(C)C)cc4)CC3)C2=O)ccc1-c1cn[nH]c1]

8-[4-(Dimethylamino)benzoyl]-2-[3-methoxy-4-(1H-pyrazol-4-yl)phenyl]-2,8-diazaspiro[4.5]decan-1-one (18.4 mg, 0.038 mmol, 76% yield) was prepared in a similar manner as the procedure described in Example 14, using 4-(dimethylamino)benzoic acid (8.27 mg, 0.050 mmol). $^1$H NMR (500 MHz, DMSO-$d_6$) δ 8.23-7.79 (m, 2H), 7.69-7.55 (m, 2H), 7.28 (d, J=8.6 Hz, 2H), 7.14 (d, J=6.9 Hz, 1H), 6.72 (d, J=8.7 Hz, 2H), 3.93-3.77 (m, 4H), 3.52 (d, J=5.6 Hz, 2H), 3.17 (d, J=5.0 Hz, 2H), 3.00-2.85 (m, 6H), 2.25-2.06 (m, 2H), 1.78-1.64 (m, 2H), 1.56 (d, J=12.9 Hz, 2H); MS (ESI) m/z: 474.4 (M+H)$^+$; Anal. HPLC Retention time: 1.43 (Method 1); ROCK2 IC$_{50}$=16 nM.

Example 22: Preparation of 8-(3-chloro-4-methoxy-benzoyl)-2-[3-methoxy-4-(1H-pyrazol-4-yl)phenyl]-2,8-diazaspiro[4.5]decan-1-one

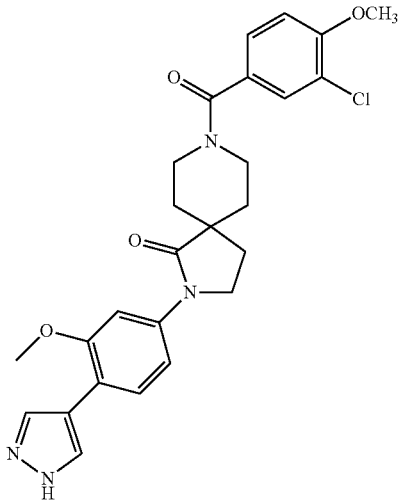 [SMILES: COc1ccc(C(=O)N2CCC3(CC2)CCN(c2ccc(-c4cn[nH]c4)c(OC)c2)C3=O)cc1Cl]

8-(3-Chloro-4-methoxybenzoyl)-2-[3-methoxy-4-(1H-pyrazol-4-yl)phenyl]-2,8-diazaspiro[4.5]decan-1-one (21.2 mg, 0.042 mmol, 84% yield) was prepared in a similar manner as the procedure described in Example 14, using 3-chloro-4-methoxybenzoic acid (9.35 mg, 0.050 mmol). $^1$H NMR (500 MHz, DMSO-d$_6$) δ 8.16-7.83 (m, 2H), 7.62 (d, J=5.3 Hz, 2H), 7.49 (s, 1H), 7.40 (d, J=8.4 Hz, 1H), 7.22 (d, J=8.5 Hz, 1H), 7.15 (d, J=8.5 Hz, 1H), 3.90 (s, 3H), 3.87 (s, 5H), 3.44-3.15 (m, 2H), 2.55 (s, 2H), 2.22-2.09 (m, 2H), 1.73 (br. s., 2H), 1.59 (br. s., 2H); MS (ESI) m/z: 495.2 (M+H)$^+$; Anal. HPLC Retention time: 1.45 (Method 1); ROCK2 IC$_{50}$=6 nM.

Example 23: Preparation of 4-{2-[3-methoxy-4-(1H-pyrazol-4-yl)phenyl]-1-oxo-2,8-diazaspiro[4.5]decane-8-carbonyl}benzamide

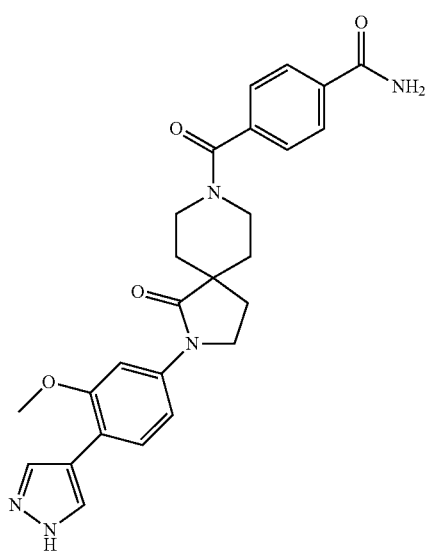 [SMILES: COc1cc(N2CCC3(CCN(C(=O)c4ccc(C(N)=O)cc4)CC3)C2=O)ccc1-c1cn[nH]c1]

4-{2-[3-Methoxy-4-(1H-pyrazol-4-yl)phenyl]-1-oxo-2,8-diazaspiro[4.5]decane-8-carbonyl}benzamide (10.5 mg, 0.022 mmol, 57.8% yield) was prepared in a similar manner as the procedure described in Example 14, using 4-carbamoylbenzoic acid (6.20 mg, 0.038 mmol). $^1$H NMR (500 MHz, DMSO-d$_6$) δ 8.16-7.87 (m, 5H), 7.67-7.56 (m, 2H), 7.48 (d, J=7.8 Hz, 3H), 7.14 (d, J=8.4 Hz, 2H), 3.86 (s, 2H), 3.31-3.10 (m, 1H), 2.51 (br. s., 5H), 2.14 (br. s., 2H), 1.85-1.38 (m, 4H); MS (ESI) m/z: 474.3 (M+H)$^+$; ROCK2 IC$_{50}$=36 nM.

Example 24: Preparation of methyl 4-{2-[3-methoxy-4-(1H-pyrazol-4-yl)phenyl]-1-oxo-2,8-diazaspiro[4.5]decane-8-carbonyl}benzoate

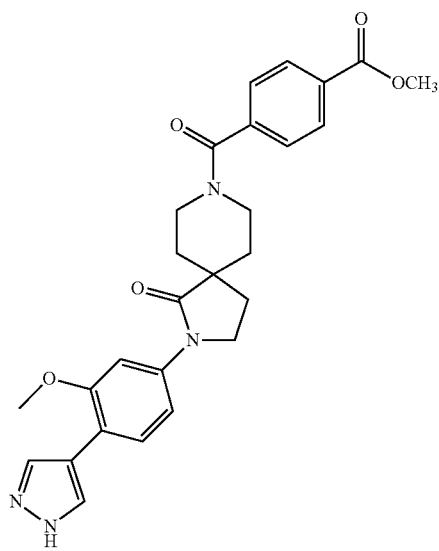 [SMILES: COC(=O)c1ccc(C(=O)N2CCC3(CC2)CCN(c2ccc(-c4cn[nH]c4)c(OC)c2)C3=O)cc1]

Methyl 4-{2-[3-methoxy-4-(1H-pyrazol-4-yl)phenyl]-1-oxo-2,8-diazaspiro[4.5]decane-8-carbonyl}benzoate (40 mg, 0.078 mmol) was prepared in a similar manner as the procedure described in Example 14, using 4-(methoxycarbonyl)benzoic acid (22.56 mg, 0.125 mmol). $^1$H NMR (500 MHz, DMSO-d$_6$) δ 8.10-7.93 (m, 2H), 7.62-7.58 (m, 2H), 7.30 (d, J=1.6 Hz, 1H), 7.23 (br. s., 2H), 7.15 (d, J=8.5 Hz, 1H), 3.91-3.84 (m, 8H), 3.42 (br. s., 2H), 3.17 (d, J=5.2 Hz, 2H), 2.14 (br. s., 2H), 1.75 (d, J=13.1 Hz, 2H), 1.59 (br. s., 2H); MS (ESI) m/z: 479.1 (M+H)$^+$; ROCK2 IC$_{50}$=23 nM.

Example 25: Preparation of 4-{2-[3-methoxy-4-(1H-pyrazol-4-yl)phenyl]-1-oxo-2,8-diazaspiro[4.5]decane-8-carbonyl}benzoic acid

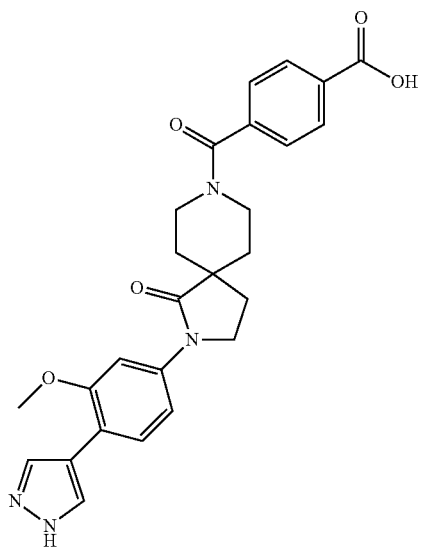 [SMILES: COc1cc(N2CCC3(CCN(C(=O)c4ccc(C(=O)O)cc4)CC3)C2=O)ccc1-c1cn[nH]c1]

To a round bottom flask was added Example 24 (55 mg, 0.113 mmol). THF (1 mL), water (0.1 mL) and LiOH (2.70 mg, 0.113 mmol). The reaction was stirred at rt overnight. The reaction was concentrated to give 4-(2-(3-methoxy-4-(1H-pyrazol-4-yl)phenyl)-1-oxo-2,8-diazaspiro[4.5]decane-8-carbonyl)benzoic acid, lithium salt (48 mg, 0.090 mmol, 80% yield) as a white solid. MS (ESI) m/z: 475.1 (M+H)$^+$; ROCK2 IC$_{50}$=1430 nM Example 26: Preparation of N-(cyclopropylmethyl)-4-{2-[3-methoxy-4-(1H-pyrazol-4-yl)phenyl]-1-oxo-2,8-diazaspiro[4.5]decane-8-carbonyl}benzamide

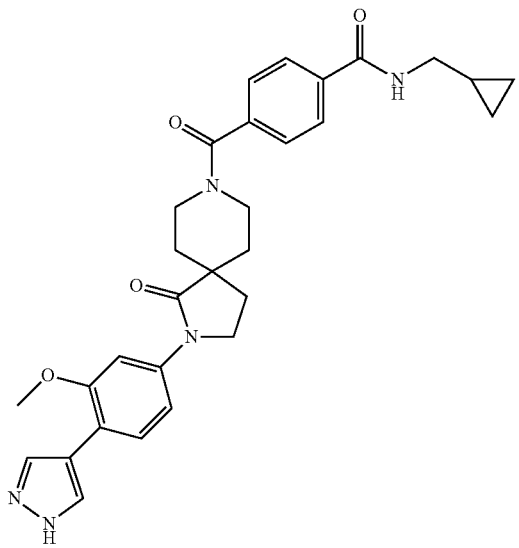 [SMILES: COc1cc(N2CCC3(CCN(C(=O)c4ccc(C(=O)NCC5CC5)cc4)CC3)C2=O)ccc1-c1cn[nH]c1]

To a round bottom flask was added cyclopropylmethanamine (2.70 mg, 0.038 mmol), HATU (21.64 mg, 0.057 mmol), DMF (0.5 mL), Et$_3$N (0.016 mL, 0.114 mmol) followed by Example 25 (18 mg, 0.038 mmol). The reaction was stirred at rt overnight. The reaction was filtered using Purification Method A to give N-(cyclopropymethyl)-4-{2-[3-methoxy-4-(1H-pyrazol-4-yl)phenyl]-1-oxo-2,8-diazaspiro[4.5]decane-8-carbonyl}benzamide (4.4 mg, 0.0077 mmol, 20.2% yield). $^1$H NMR (500 MHz, DMSO-d$_6$) δ 8.43 (br t, J=5.3 Hz, 1H), 7.79 (br s, 2H), 7.69 (br d, J=8.2 Hz, 2H), 7.41-7.33 (m, 2H), 7.26 (br d, J=8.2 Hz, 2H), 6.92 (dd, J=8.5, 1.8 Hz, 1H), 3.75-3.54 (m, 5H), 3.16-2.86 (m, 6H), 1.92 (br s, 2H), 1.59-1.38 (m, 3H), 1.30 (br s, 1H), 0.87-0.70 (m, 1H), 0.21 (br d, J=6.7 Hz, 2H), 0.01 (br d, J=4.6 Hz, 2H); MS (ESI) m/z: 528.3 (M+H)$^+$; Anal. HPLC Retention time: 1.28 (Method 1); ROCK2 IC$_{50}$=119 nM Example 27: Preparation of 8-[2-chloro-4-(4-methylpiperazin-1-yl)benzoyl]-2-[3-methoxy-4-(1H-pyrazol-4-yl)phenyl]-2,8-diazaspiro[4.5]decan-1-one

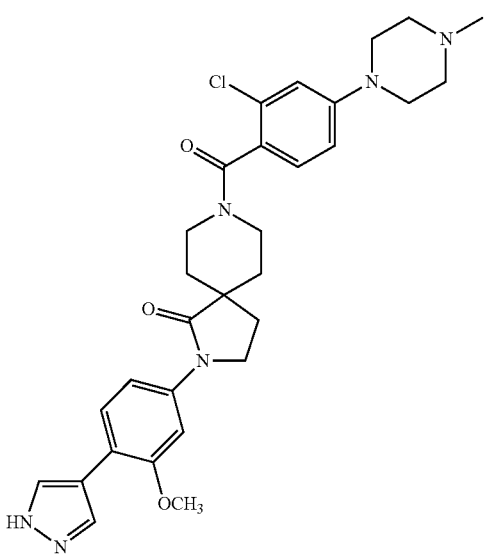 [SMILES: COc1cc(N2CCC3(CCN(C(=O)c4ccc(N5CCN(C)CC5)cc4Cl)CC3)C2=O)ccc1-c1cn[nH]c1]

8-[2-Chloro-4-(4-methylpiperazin-1-yl)benzoyl]-2-[3-methoxy-4-(1H-pyrazol-4-yl)phenyl]-2,8-diazaspiro[4.5]decan-1-one was prepared in a similar manner as the procedure described in Example 14, using 2-chloro-4-(4-methylpiperazin-1-yl)benzoic acid (9.57 mg, 0.038 mmol). $^1$H NMR (500 MHz, DMSO-d$_6$) δ 8.09-7.92 (m, 2H), 8.02 (br. s., 2H), 7.67-7.55 (m, 2H), 7.65-7.54 (m, 2H), 7.21-7.07 (m, 2H), 7.22-7.07 (m, 2H), 7.02-6.88 (m, 2H), 6.97 (d, J=14.4 Hz, 2H), 4.28-4.25 (m, 1H), 3.92-3.79 (m, 6H), 3.95-3.79 (m, 6H), 3.31-3.02 (m, 4H), 2.43 (br. s., 4H), 2.46-2.38 (m, 4H), 2.21 (s, 3H), 2.18-2.04 (m, 2H), 2.17-2.03 (m, 2H), 1.83-1.69 (m, 2H), 1.75 (d, J=12.9 Hz, 2H), 1.64 (d, J=12.4 Hz, 1H), 1.49 (d, J=11.6 Hz, 1H), 1.67-1.43 (m, 2H); MS (ESI) m/z: 563.2 (M+H)$^+$; Anal. HPLC Retention time: 1.03 (Method 2); ROCK2 IC$_{50}$=0.8 nM.

Example 28: Preparation of 8-(2,6-difluoro-4-methoxybenzoyl)-2-[3-methoxy-4-(1H-pyrazol-4-yl)phenyl]-2,8-diazaspiro[4.5]decan-1-one

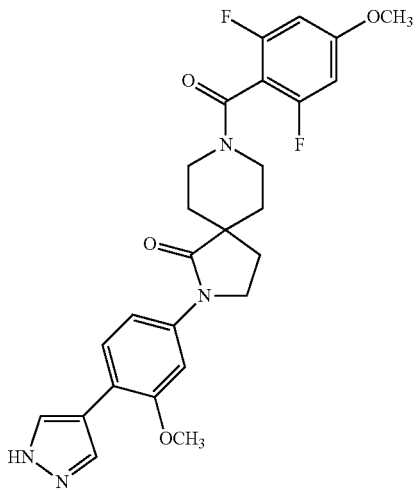 [SMILES: COc1cc(F)c(C(=O)N2CCC3(CC2)CCN(c2ccc(-c4cn[nH]c4)c(OC)c2)C3=O)c(F)c1]

8-(2,6-Difluoro-4-methoxybenzoyl)-2-[3-methoxy-4-(1H-pyrazol-4-yl)phenyl]-2,8-diazaspiro[4.5]decan-1-one (17.6 mg, 0.035 mmol, 92% yield) was prepared in a similar manner as the procedure described in Example 14, using 2,6-difluoro-4-methoxy benzoic acid (7.07 mg, 0.038 mmol). $^1$H NMR (500 MHz, DMSO-$d_6$) δ 8.00 (br. s., 2H), 7.64-7.55 (m, 2H), 7.13 (d, J=8.2 Hz, 1H), 6.84 (t, J=12.2 Hz, 2H), 4.37 (d, J=13.4 Hz, 2H), 3.92-3.75 (m, 8H), 3.32-3.08 (m, 2H), 2.22-2.05 (m, 2H), 1.75-1.45 (m, 4H); MS (ESI) m/z: 497.0 (M+H)$^+$; ROCK2 IC$_{50}$=5 nM,

Example 29: Preparation of 2-[3-methoxy-4-(1H-pyrazol-4-yl)phenyl]-8-(2,4,6-trimethoxybenzoyl)-2,8-diazaspiro[4.5]decan-1-one

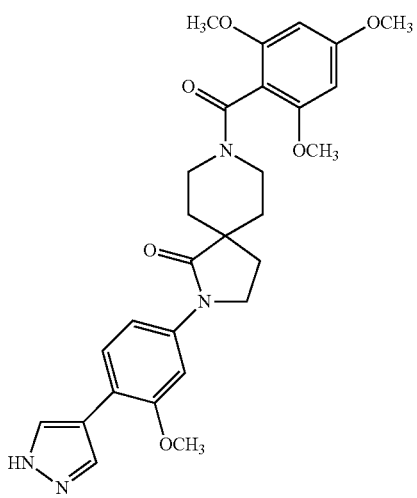 [SMILES: COc1cc(OC)c(C(=O)N2CCC3(CC2)CCN(c2ccc(-c4cn[nH]c4)c(OC)c2)C3=O)c(OC)c1]

2-[3-Methoxy-4-(1H-pyrazol-4-yl)phenyl]-8-(2,4,6-trimethoxybenzoyl)-2,8-diazaspiro[4.5]decan-1-one (13.9 mg, 0.026 mol, 69.7% yield) was prepared in a similar manner as the procedure described in Example 14, using 2,4,6-trimethoxybenzoic acid (7.97 mg, 0.038 mmol). $^1$H NMR (500 MHz, DMSO-$d_6$) δ 8.01 (br. s., 2H), 7.60 (d, J=3.6 Hz, 2H), 7.12 (d, J=8.2 Hz, 1H), 6.26 (d, J=5.3 Hz, 2H), 4.37 (d, J=13.5 Hz, 1H), 3.89-3.67 (m, 1H), 3.11-2.92 (m, 2H), 2.22-2.00 (m, 2H), 1.67 (d, J=11.8 Hz, 2H), 1.57 (d, J=12.8 Hz, 1H), 1.42 (d, J=12.4 Hz, 1H); MS (ESI) m-z: 521.1 (M+H)$^+$; ROCK2 IC$_{50}$=336 nM.

Example 30: Preparation of 4-{2-[3-methoxy-4-(1H-pyrazol-4-yl)phenyl]-1-oxo-2,8-diazaspiro[4.5]decane-8-carbonyl}-3,5-dimethylbenzamide

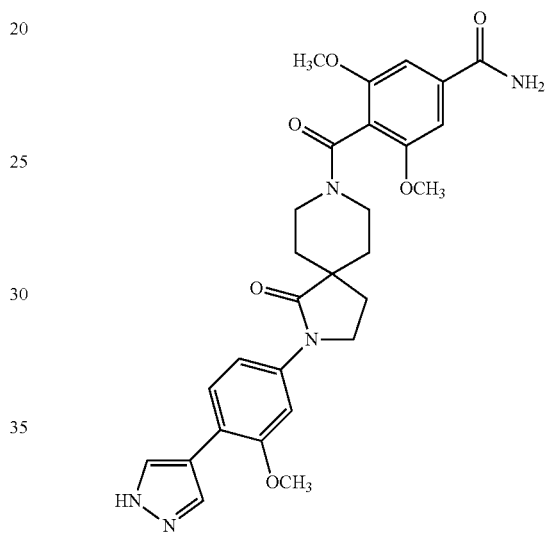

4-{2-[3-Methoxy-4-(1H-pyrazol-4-yl)phenyl]-1-oxo-2,8-diazaspiro[4.5]decane-8-carbonyl}-3,5-dimethylbenzamide (10.2 mg, 0.020 mmol, 52.5% yield) was prepared in a similar manner as the procedure described in Example 14, using 4-carbamoyl-2,6-dimethylbenzoic acid (7.26 mg, 0.038 mmol). $^1$H NMR (500 MHz, DMSO-$d_6$) δ 8.11-7.91 (m, 3H), 7.67-7.54 (m, 4H), 7.32 (br. s., 1H), 7.11 (d, J=7.9 Hz, 1H), 4.46 (d, J=13.1 Hz, 1H), 3.90-3.78 (m, 5H), 3.55 (br. s., 1H), 3.19-3.12 (m, 2H), 2.26 (s, 3H), 2.21-2.09 (m, 5H), 1.72-1.57 (m, 3H), 1.48 (d, J=13.4 Hz, 1H); MS (ESI) m/z: 502.2 (M+H)$^+$; ROCK2 IC$_{50}$=130 nM.

Example 31: Preparation of 8-[4-(4-methylpiperazin-1-yl)benzoyl]-2-[4-(1H-pyrazol-4-yl)phenyl]-2,8-diazaspiro[4.5]decan-1-one

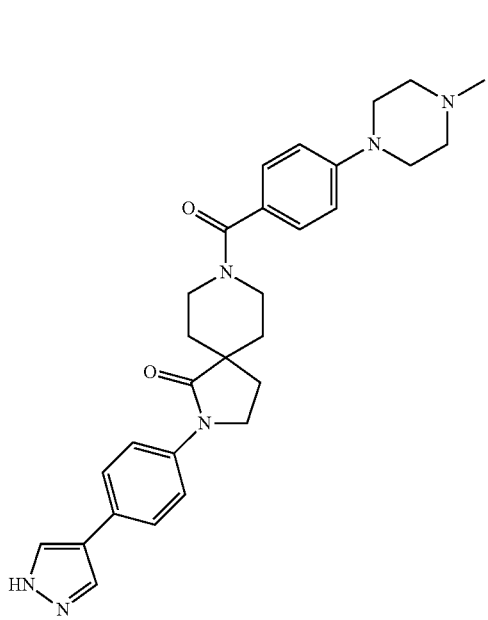 [SMILES: CN1CCN(c2ccc(C(=O)N3CCC4(CC3)CCN(c3ccc(-c5cn[nH]c5)cc3)C4=O)cc2)CC1]

31A. Preparation of 2-(4-bromphenyl)-8-(4-(4-methylpyrazin-1-yl)benzoyl)-2,8-diazaspiro[4.5]decan-1-one

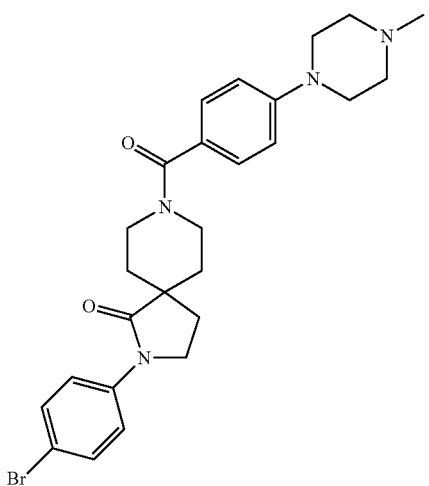 [SMILES: CN1CCN(c2ccc(C(=O)N3CCC4(CC3)CCN(c3ccc(Br)cc3)C4=O)cc2)CC1]

To a round bottom flask was added 4-(4-methylpiperazin-1-yl)benzoic acid (147 mg, 0.665 mmol), THF (10 mL), HATU (304 mg, 0.798 mmol) and Et$_3$N (0.464 mL, 3.33 mmol). The reaction was stirred at rt for 10 min and then Intermediate 3 (230 mg, 0.665 mmol) was added and the reaction was continued for 2 hr. The reaction was concentrated and the residue was purified using ISCO system (0-15% MeOH/CH$_2$Cl$_{2gradient}$) to give 2-(4-bromophenyl)-8-(4-(4-methylpiperazin-1-yl)benzoyl)-2,8-diazaspiro[4.5]decan-1-one (305 mg, 0.596 mmol, 90% yield) as an off-white solid. $^1$H NMR (500 MHz, DMSO-d$_6$) δ 7.71-7.63 (m, 2H), 7.59-7.53 (m, 2H), 7.31 (d, J=8.8 Hz, 2H), 6.99 (d, J=8.8 Hz, 2H), 4.17-3.85 (m, 2H), 3.82 (t, J=6.9 Hz, 2H), 3.35-3.28 (m, 7H), 3.18 (br. s., 2H), 2.84-2.66 (m, 2H), 2.44 (br. s., 2H), 2.14 (t, J=6.9 Hz, 2H), 1.77-1.65 (m, 2H), 1.57 (d, J=12.7 Hz, 2H); MS (ESI) mv: 511.0, 513.0 (M+H)$^+$.

31B. Preparation of 8-[4-(4-methylpiperazin-1-yl)benzoyl]-2-[4-(1H-pyrazol-4-yl)phenyl]-2,8-diazaspiro[4.5]decan-1-one

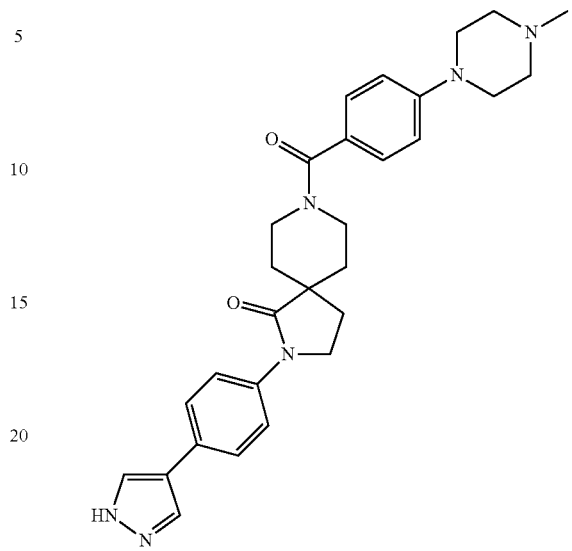

8-[4-(4-Methylpiperazin-1-yl)benzoyl]-2-[4-(1H-pyrazol-4-yl)phenyl]-2,8-diazaspiro[4.5]decan-1-one was prepared in a similar manner as the procedure described in Example 1, using 31A (20 mg, 0.039 mmol). $^1$H NMR (500 MHz, DMSO-d$_6$) δ 8.04 (br. s., 2H), 7.71-7.56 (m, 4H), 7.29 (d, J=8.3 Hz, 2H), 6.96 (d, J=8.5 Hz, 2H), 3.83 (t, J=6.6 Hz, 2H), 3.19 (d, J=19.4 Hz, 4H), 2.55 (s, 2H), 2.44 (br. s., 4H), 2.14 (br. s., 2H), 1.91 (s, 2H), 1.78-1.64 (m, 2H), 1.57 (br. s., 2H); MS (ESI) m/z: 499.4 (M+H)$^+$; Anal. HPLC Retention time: 1.22 Method 1; ROCK2 IC$_{50}$=0.7 nM.

Example 32: Preparation of 2-[4-(2-hydroxypyridin-4-yl)phenyl]-8-[4-(4-methylpiperazin-1-yl)benzoyl]-2,8-diazaspiro[4.5 decan]-1-one

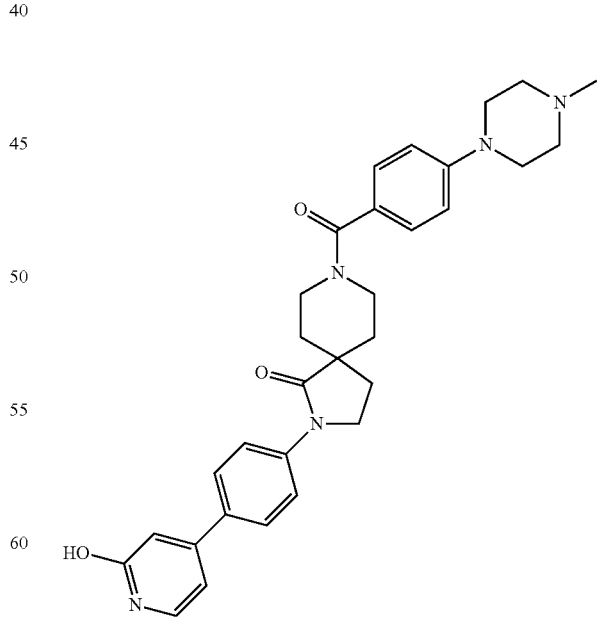

To a microwave vial was added Intermediate 6 (20 mg, 0.039 mmol), 4-(4,4,5,5-tetramethyl-1,3,2-dioxaborolan-2-yl)pyridin-2-ol (17.29 mg, 0.078 mmol), tripotassium phosphate (0.052 mL, 0.156 mmol), Dioxane (3 mL) and methanesulfonato(2-dicyclohexylphosphino-2',4',6'-tri-i-propyl-1,1'-biphenyl)(2'-amino-1,1'-biphenyl-2-yl)palladium(II) (3.31 mg, 3.91 μmol). The reaction was purged with argon and sealed. The reaction was then subjected to microwave oven and stirred at 120° C. for 30 min. The reaction was partitioned between EtOAc (50 ml) and water (20 ml). The organic layer was separated, washed with water (20 ml) and brine (30 ml), dried over MgSO$_4$, filtered and concentrated. The residue was purified using Purification Method A to give 2-[4-(2-hydroxypyridin-4-yl)phenyl]-8-[4-(4-methylpiperazin-1-yl)benzoyl]-2,8-diazaspiro[4.5]decan-1-one (1.6 mg, 0.0027 mmol, 6.7% yield). $^1$H NMR (500 MHz DMSO-d$_6$) δ 7.84-7.78 (m, 2H), 7.78-7.72 (m, 2H), 7.44 (d, J=6.7 Hz, 1H), 7.35 (d, J=8.2 Hz, 2H), 7.05 (d, J=8.5 Hz, 2H), 6.60 (s, 1H), 6.55 (d, J=6.7 Hz, 1H), 3.91-3.85 (m, 2H), 3.44 (d, J=6.1 Hz, 2H), 3.25-3.07 (m, 2H), 2.85 (s, 3H), 2.55 (s, 8H), 2.17 (br. s., 2H), 1.72 (br. s., 2H), 1.60 (br. s., 2H); MS (ESI) m/z: 526.4 (M+H)$^+$; Anal. HPLC Retention time: 0.88 (Method 2); ROCK2 IC$_{50}$=54 nM.

Example 33: Preparation of 2-[4-(3-fluoropyridin-4-yl)phenyl]-8-[4-(4-methylpiperazin-1-yl)benzoyl]-2,8-diazaspiro[4.5]decan-1-one

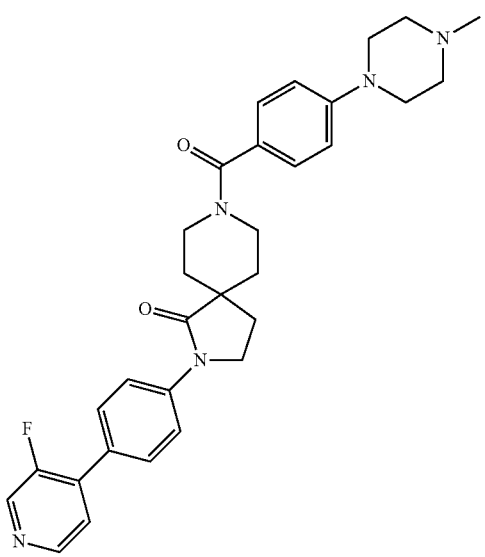 [SMILES: CN1CCN(c2ccc(C(=O)N3CCC4(CC3)CCN(c3ccc(-c5ccncc5F)cc3)C4=O)cc2)CC1]

2-[4-(3-Fluoropyridin-4-yl)phenyl]-8-[4-(4-methylpiperazin-1-yl)benzoyl]-2,8-diazaspiro[4.5]decan-1-one (2.3 mg, 4.3 mmol, 10.9% yield) was prepared in a similar manner as the procedure described in Example 32, using 3-fluoro-4-(4,4,5,5-tetramethyl-1,3,2-dioxaborolan-2-yl)pyridine (17.44 mg, 0.078 mmol). $^1$H NMR (500 MHz, DMSO-d$_6$) δ 8.66 (br. s., 1H), 8.50 (br. s., 1H), 7.88 (d, J=8.6 Hz, 2H), 7.73 (d, J=8.2 Hz, 2H), 7.66 (br. s., 1H), 7.30 (d, J=8.5 Hz, 2H), 6.96 (d, J=8.6 Hz, 2H), 3.89 (t, J=6.7 Hz, 2H), 3.44-3.09 (m, 4H), 2.55-2.51 (m, 4H), 2.44 (br. s., 4H), 2.22 (s, 3H), 2.17 (t, J=6.4 Hz, 2H), 1.80-1.68 (m, 2H), 1.60 (br. s., 2H); MS (ESI) m/z: 528.4 (M+H)$^+$; Anal. HPLC Retention time: 1.01 (Method 2); ROCK2 IC$_{50}$=1.3 nM.

Example 34: Preparation of 2-[4-(1H-indazol-6-yl)phenyl]-8-[4-(4-methylpiperazin-1-yl)benzoyl]-2,8-diazaspiro[4.5]decan-1-one

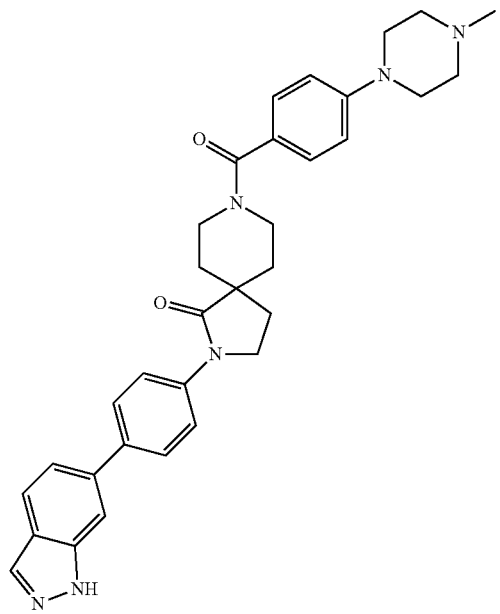 [SMILES: CN1CCN(c2ccc(C(=O)N3CCC4(CC3)CCN(c3ccc(-c5ccc6cn[nH]c6c5)cc3)C4=O)cc2)CC1]

2-[4-(1H-indazol-6-yl)phenyl]-8-[4-(4-methylpiperazin-1-yl)benzoyl]-2,8-diazaspiro[4.5]decan-1-one (9.1 mg, 0.016 mmol, 41.6% yield) was prepared in a similar manner as the procedure described in Example 32, using 6-(4,4,5,5-tetramethyl-1,3,2-dioxaborolan-2-yl)-1H-indazole (19.09 mg, 0.078 mmol). $^1$H NMR (500 MHz, DMSO-d$_6$) δ 13.13 (s, 1H), 8.09 (s, 1H), 7.86-7.70 (m, 6H), 7.43 (d, J=8.5 Hz, 1H), 7.31 (d, J=8.4 Hz, 2H), 6.97 (d, J=8.6 Hz, 2H), 3.89 (t, J=6.7 Hz, 2H), 3.23 (br. s., 2H), 2.58-2.48 (m, 10H), 2.27 (s, 3H), 2.17 (t, J=6.4 Hz, 2H), 1.78-1.68 (m, 2H), 1.59 (d, J=11.6 Hz, 2H); MS (ESI) m/z: 549.2 (M+H)$^+$; Anal. HPLC Retention time: 1.45 (Method 1); ROCK2 IC$_{50}$=106 nM.

Example 35: Preparation of 8-[4-(4-methylpiperazin-1-yl)benzoyl]-2-(4-{1H-pyrrolo[2,3-b]pyridin-4-yl}phenyl)-2,8-diazaspiro[4.5]decan-1-one

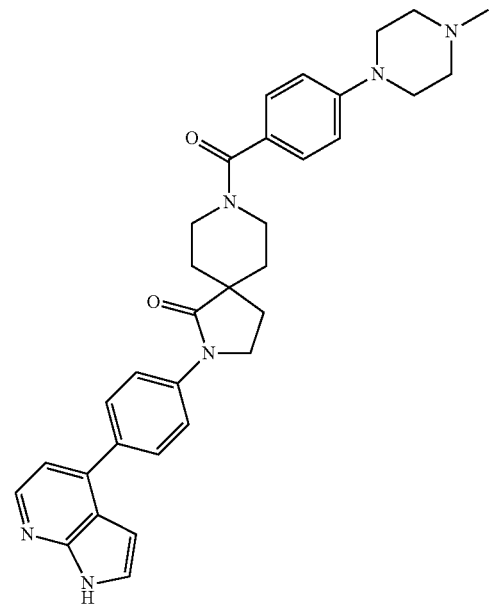 [SMILES: CN1CCN(c2ccc(C(=O)N3CCC4(CC3)CCN(c3ccc(-c5ccnc6[nH]ccc56)cc3)C4=O)cc2)CC1]

8-[4-(4-Methylpiperazin-1-yl)benzoyl]-2-(4-{1H-pyrrolo[2,3-b]pyridin-4-yl}phenyl)-2,8-diazaspiro[4.5]decan-1-one (8.9 mg, 0.016 mmol, 40.7% yield) was prepared in a similar manner as the procedure described in Example 32, using 4-(4,4,5,5-tetramethyl-1,3,2-dioxaborolan-2-yl)-1H-pyrrolo[2,3-b]pyridine (19.09 mg, 0.078 mmol). $^1$H NMR (500 MHz, DMSO-$d_6$) δ 11.77 (br. s., 1H), 8.28 (d, J=4.9 Hz, 1H), 7.92-7.85 (m, 2H), 7.81 (d, J=8.2 Hz, 2H), 7.54 (br. s., 1H), 7.31 (d, J=8.2 Hz, 2H), 7.19 (d, J=4.9 Hz, 1H), 6.97 (d, J=8.5 Hz, 2H), 6.63 (br. s., 1H), 4.31-3.96 (m, 2H), 3.91 (t, J=6.6 Hz, 2H), 3.24-3.14 (m, 4H), 2.51-2.44 (m, 6H), 2.25 (s, 3H), 2.18 (t, J=6.3 Hz, 2H), 1.82-1.68 (m, 2H), 1.60 (d, J=11.3 Hz, 2H); MS (ESI) m/z: 549.1 (M+H)$^+$; Anal. HPLC Retention time: 1.42 (Method 1); ROCK2 IC$_{50}$=0.3 nM.

Example 36: Preparation of 2-[4-(2-aminopyridin-4-yl)phenyl]-8-[4-(4-methylpiperazin-1-yl)benzoyl]-2,8-diazaspiro[4.5]decan-1-one

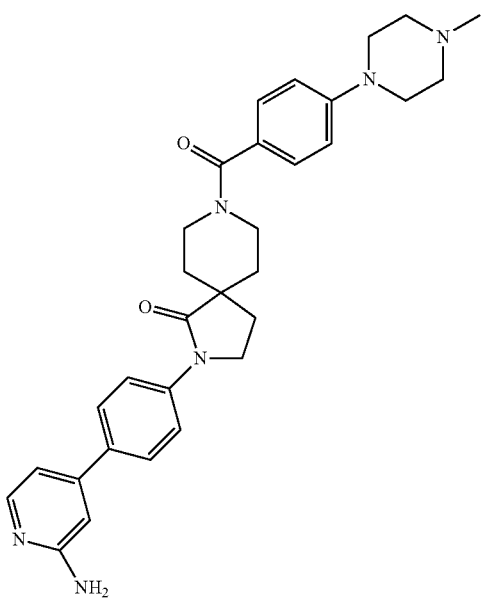 [SMILES: CN1CCN(c2ccc(C(=O)N3CCC4(CC3)CCN(c3ccc(-c5ccnc(N)c5)cc3)C4=O)cc2)CC1]

2-[4-(2-Aminopyridin-4-yl)phenyl]-8-[4-(4-methylpiperazin-1-yl)benzoyl]-2,8-diazaspiro[4.5]decan-1-one (1.4 mg, 0.0026 mmol, 6.6% yield) was prepared in a similar manner as the procedure described in Example 32, using 4-(4,4,5,5-tetramethyl-1,3,2-dioxaborolan-2-yl)pyridin-2-amine (17.21 mg, 0.078 mmol). $^1$H NMR (500 MHz, DMSO-$d_6$) δ 7.95 (d, J=5.2 Hz, 1H), 7.81 (d, J=8.5 Hz, 2H), 7.67 (d, J=8.2 Hz, 2H), 7.29 (d, J=8.2 Hz, 2H), 6.96 (d, J=8.2 Hz, 2H), 6.79 (d, J=5.2 Hz, 1H), 6.71 (s, 1H), 5.93 (s, 2H), 4.28-3.73 (m, 4H), 3.20-3.12 (m, 2H), 2.57-2.47 (m, 6H), 2.22 (s, 3H), 2.16 (t, J=6.6 Hz, 2H), 1.77-1.65 (m, 2H), 1.58 (d, J=12.2 Hz, 2H); MS (ESI) m/z: 525.1 (M+H)$^+$; Anal. HPLC Retention time: 0.76 (Method 2); ROCK2 IC$_{50}$=2.0 nM.

Example 37: Preparation of 2-[4-(1H-indazol-5-yl)phenyl]-8-[4-(4-methylpiperazin-1-yl)benzoyl]-2,8-diazaspiro[4.5]decan-1-one

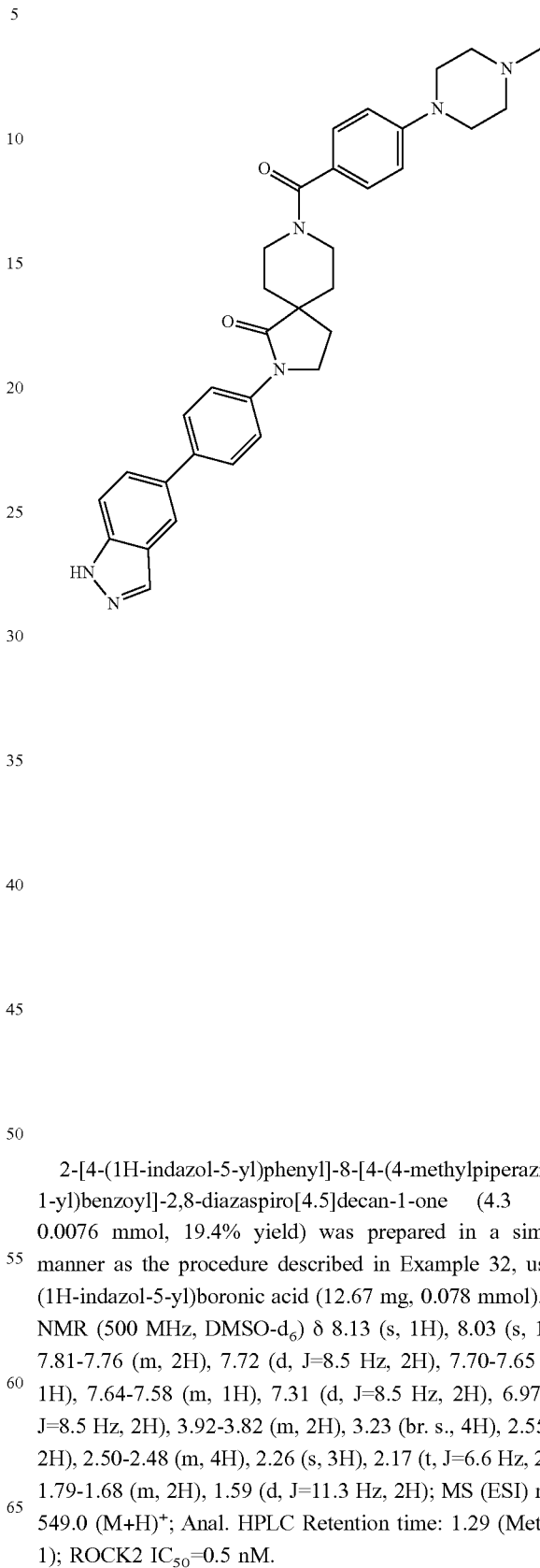

2-[4-(1H-indazol-5-yl)phenyl]-8-[4-(4-methylpiperazin-1-yl)benzoyl]-2,8-diazaspiro[4.5]decan-1-one (4.3 mg, 0.0076 mmol, 19.4% yield) was prepared in a similar manner as the procedure described in Example 32, using (1H-indazol-5-yl)boronic acid (12.67 mg, 0.078 mmol). $^1$H NMR (500 MHz, DMSO-$d_6$) δ 8.13 (s, 1H), 8.03 (s, 1H), 7.81-7.76 (m, 2H), 7.72 (d, J=8.5 Hz, 2H), 7.70-7.65 (m, 1H), 7.64-7.58 (m, 1H), 7.31 (d, J=8.5 Hz, 2H), 6.97 (d, J=8.5 Hz, 2H), 3.92-3.82 (m, 2H), 3.23 (br. s., 4H), 2.55 (s, 2H), 2.50-2.48 (m, 4H), 2.26 (s, 3H), 2.17 (t, J=6.6 Hz, 2H), 1.79-1.68 (m, 2H), 1.59 (d, J=11.3 Hz, 2H); MS (ESI) m/z: 549.0 (M+H)$^+$; Anal. HPLC Retention time: 1.29 (Method 1); ROCK2 IC$_{50}$=0.5 nM.

Example 38: Preparation of 2-[4-(1H-1,2,3-benzotriazol-6-yl)phenyl]-8-[4-(4-methylpiperazin-1-yl)benzoyl]-2,8-diazaspiro[4.5]decan-1-one

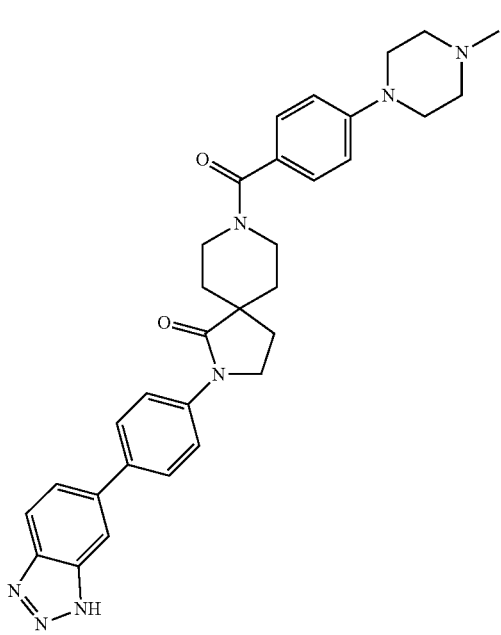 [SMILES: CN1CCN(c2ccc(C(=O)N3CCC4(CC3)CCN(c3ccc(-c5ccc6nn[nH]c6c5)cc3)C4=O)cc2)CC1]

2-[4-(1H-1,2,3-benzotriazol-6-yl)phenyl]-8-[4-(4-methylpiperazin-1-yl)benzoyl]-2,8-diazaspiro[4.5]decan-1-one (5.1 mg, 0.0089 mmol, 22.8% yield) was prepared in a similar manner as the procedure described in Example 32, using 6-(4,4,5,5-tetramethyl-1,3,2-dioxaborolan-2-yl)-1H-benzo[d][1,2,3]triazole (19.17 mg, 0.078 mmol). $^1$H NMR (500 MHz, DMSO-$d_6$) δ 8.34 (s, 1H), 8.08 (s, 1H), 7.94 (d, J=8.9 Hz, 1H), 7.80 (d, J=4.6 Hz, 4H), 7.70 (d, J=8.5 Hz, 1H), 7.30 (d, J=8.5 Hz, 2H), 6.96 (d, J=8.9 Hz, 2H), 3.88 (br. s., 2H), 3.47 (br. s., 2H), 3.24-3.05 (m, 6H), 2.44 (br. s., 4H), 2.21 (s, 3H), 2.17 (br. s., 2H), 1.72 (d, J=11.9 Hz, 2H), 1.58 (d, J=12.2 Hz, 2H); MS (ESI) m/z: 550.1 (M+H)$^+$; Anal. HPLC Retention time: 1.26 (Method 1); ROCK2 IC$_{50}$=116 nM.

Example 39: Preparation of 2-[6-methoxy-5-(1H-pyrazol-4-yl)pyridin-2-yl]-8-(4-methoxybenzoyl)-2,8-diazaspiro[4.5]decan-1-one

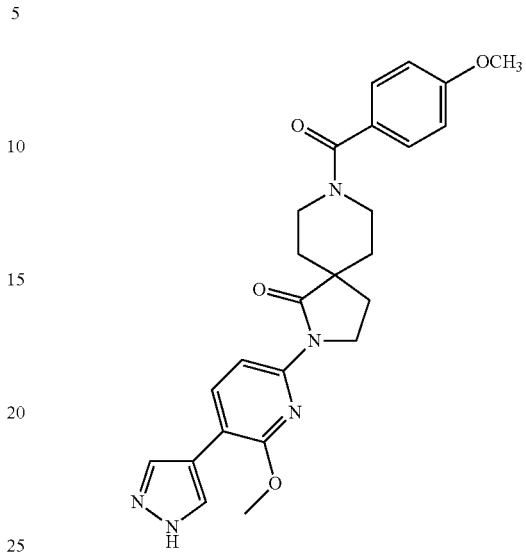

39A: Preparation of tert-butyl 2-(5-bromo-6-methoxypyridin-2-yl)-1-oxo-2,8-diazaspiro[4.5]decane-8-carboxylate

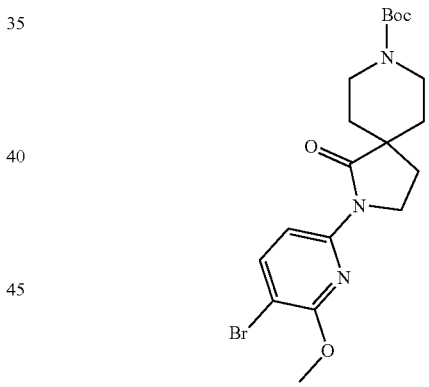

In a sealable reaction tube was mixed 3,6-dibromo-2-methoxypyridine (283 mg, 1.062 mmol), tert-butyl 1-oxo-2,8-diazaspiro[4.5]decane-8-carboxylate (135 mg, 0.531 mmol), cesium carbonate (346 mg, 1.062 mmol) and dioxane (1062 µl). The reaction was purged with N$_2$. Then 9,9-Dimethyl-4,5-bis(diphenylphosphino)xanthene (46.1 mg, 0.080 mmol), Pd$_2$(dba)$_3$ (24.30 mg, 0.027 mmol) was added and N$_2$ was bubbled through reaction for 1 min. The reaction was sealed and stirred at 100° C. overnight. The reaction was partitioned between EtOAc (50 ml) and water (30 ml). The organic layer was separated, washed with water (2×30 ml) and brine (30 ml), dried over MgSO$_4$, filtered and concentrated. The residue was purified using ISCO system (0-100% EtOAc/Hex gradient) to give tert-butyl 2-(5-bromo-6-methoxypyridin-2-yl)-1-oxo-2,8-diazaspiro[4.5]decane-8-carboxylate (225 mg, 0.511 mmol, 96% yield) as a beige solid. MS (ESI) m: 441.9 (M+H)$^+$.

39B: Preparation of tert-butyl 2-(6-methoxy-5-(1H-pyrazol-4-yl)pyridin-2-yl)-1-oxo-2,8-diazaspiro[4.5]decane-8-carboxylate

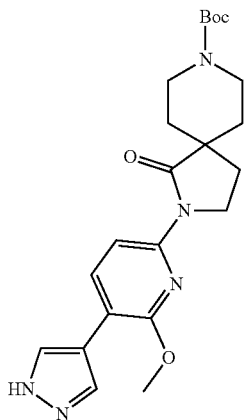 [SMILES: COc1nc(N2CCC3(CCN(C(=O)OC(C)(C)C)CC3)C2=O)ccc1-c1cn[nH]c1]

To a microwave vial was added 39A (230 mg, 0.522 mmol), 4-(4,4,5,5-tetramethyl-1,3,2-dioxaborolan-2-yl)-1H-pyrazole (304 mg, 1.567 mmol), tripotassium phosphate (0.696 mL, 2.089 mmol), Dioxane (3 mL) and methanesulfonato(2-dicyclohexylphosphino-2',4',6'-tri-i-propyl-1,1'-biphenyl)(2'-amino-1,1'-biphenyl-2-yl)palladium(II) (22.11 mg, 0.026 mmol). The reaction was purged with nitrogen and sealed. The reaction was then subjected to microwave oven and stirred at 120° C. for 40 min. The reaction was partitioned between EtOAc (50 ml) and water (20 ml). The organic layer was separated, washed with water (20 ml) and brine (30 ml), dried over MgSO$_4$, filtered and concentrated. The residue was purified using ISCO system (0-100% EtOAc/Hex gradient) to give tert-butyl 2-(6-methoxy-5-(1H-pyrazol-4-yl)pyridin-2-yl)-1-oxo-2,8-diazaspiro[4.5]decane-8-carboxylate (200 mg, 0.468 mmol, 90% yield) as an off-white solid. $^1$H NMR (500 MHz, DMSO-d$_6$) δ 8.21-8.10 (m, 1H), 8.06 (d, J=8.0 Hz 1H), 8.04-7.95 (m, 1H), 7.90 (d, J=8.3 Hz, 1H), 4.04 (t, J=7.2 Hz, 2H), 3.99 (s, 3H), 2.99 (br. s., 2H), 2.09 (t, J=7.0 Hz, 2H), 1.74-1.59 (m, 2H), 1.53 (d, J=13.2 Hz, 2H), 1.43 (s, 9H); MS (ESI) m/z: 427.2 (M+H)$^+$.

39C: Preparation of 2-(6-methoxy-5-(1H-pyrazol-4-yl)pyridin-2-yl)-2,8-diazaspiro[4.5]decan-1-one, 3 HCl

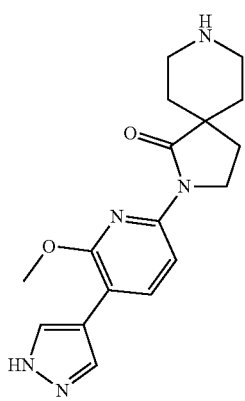 [SMILES: COc1nc(N2CCC3(CCNCC3)C2=O)ccc1-c1cn[nH]c1]

To a round bottom flask was added 39B (100 mg, 0.234 mmol), MeOH, 4N HCl (0.178 mL, 5.85 mmol) in Dioxane (1 mL). The reaction was stirred at rt for 1 hr. The reaction was concentrated to give 2-(6-methoxy-5-(1H-pyrazol-4-yl)pyridin-2-yl)-2,8-diazaspiro[4.5]decan-1-one, 3 HCl (95 mg, 0.218 mmol, 93% yield) as an off-white solid. MS (ESI) m/z: 328.1 (M+H)$^+$.

39D: Preparation of 2-[6-methoxy-5-(1H-pyrazol-4-yl)pyridin-2-yl]-8-(4-methoxybenzoyl)-2,8-diazaspiro[4.5]decan-1-one

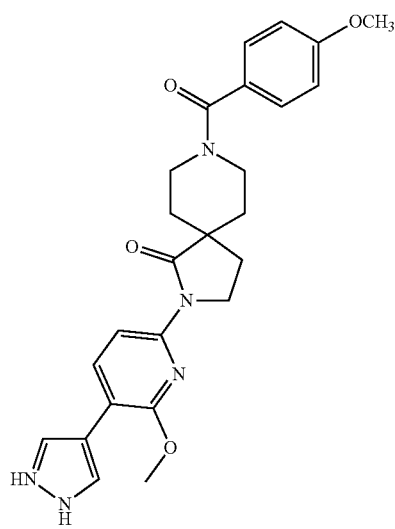 [SMILES: COc1ccc(C(=O)N2CCC3(CC2)CCN(c2ccc(-c4cn[nH]c4)c(OC)n2)C3=O)cc1]

To a round bottom flask was added 39C (20 mg, 0.046 mmol) THF (1 mL), 4-methoxybenzoyl chloride (7.81 mg, 0.046 mmol) and Et$_3$N (0.038 mL, 0.275 mmol). The reaction was stirred at rt for 2 hr. The reaction was concentrated and purified using Purification Method A to give 2-[6-methoxy-5-(H-pyrazol-4-yl)pyridin-2-yl]-8-(4-methoxybenzoyl)-2,8-diazaspiro[4.5]decan-1-one (13.9 mg, 0.029 mmol, 63.1% yield). $^1$H NMR (500 MHz, DMSO-d$_6$) δ 8.05 (d, J=8.1 Hz, 3H), 7.88 (d, J=8.2 Hz, 1H), 7.38 (d. J=8.4 Hz, 2H), 6.99 (d, J=8.4 Hz, 2H), 7.14-6.85 (m, 1H), 4.03 (t, J=6.7 Hz, 2H), 3.97 (s, 3H), 3.79 (s, 3H), 3.66-3.52 (m, 2H), 2.55 (s, 2H), 2.19-2.03 (m, 2H), 1.71 (br. s., 2H), 1.59 (br. s., 2H); MS (ESI) m/z: 462.1 (M+H)$^+$; Anal. HPLC Retention time: 1.58 (Method 2); ROCK2 IC$_{50}$=4 nM.

Example 40: Preparation of 7-(4-methoxybenzoyl)-2-[4-(1H-pyrazol-4-yl)phenyl]-2,7-diazaspiro[3.5]nonan-1-one

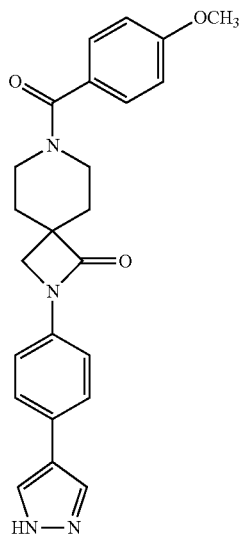 [SMILES: COc1ccc(C(=O)N2CCC3(CC2)CN(c2ccc(-c4cn[nH]c4)cc2)C3=O)cc1]

To a round bottom flask was added Intermediate 7 (10 mg, 0.028 mmol). THF (1 mL), 4-methoxybenzoyl chloride (4.80 mg, 0.028 mmol) and Et$_3$N (0.020 mL, 0.141 mmol). The reaction was stirred at rt for 2 hr. The reaction was concentrated and purified using Purification Method A to give 7-(4-methoxybenzoyl)-2-[4-(H-pyrazol-4-yl)phenyl]-2,7-diazaspiro[3.5]nonan-1-one (6.7 mg, 0.015 mmol, 53.7% yield). $^1$H NMR (500 MHz, DMSO-d$_6$) δ 8.14 (br. s., 1H), 7.90 (br. s., 1H), 7.62 (d, J=8.3 Hz, 2H), 7.43-7.27 (m, 4H), 6.99 (d, J=8.5 Hz, 2H), 3.79 (s, 3H), 3.69-3.37 (m, 3H), 3.17 (d, J=5.2 Hz, 1H), 2.58-2.50 (m, 2H), 1.88 (br. s., 4H); MS (ESI) m/z: 416.9 (M+H)$^+$; Anal. HPLC Retention time: 1.51 (Method 1); ROCK2 IC$_{50}$=132 nM.

Example 41: Preparation of 7-(3-methoxybenzoyl)-2-[4-(1H-pyrazol-4-yl)phenyl]-2,7-diazaspiro[3.5]nonan-1-one

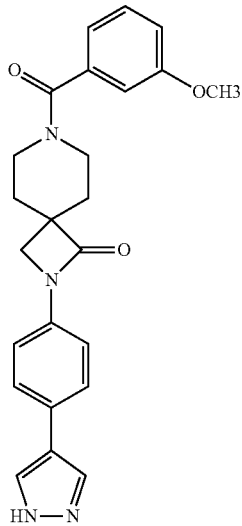 [SMILES: COc1cccc(C(=O)N2CCC3(CC2)CN(c2ccc(-c4cn[nH]c4)cc2)C3=O)c1]

7-(3-Methoxybenzoyl)-2-[4-(1H-pyrazol-4-yl)phenyl]-2,7-diazaspiro[3.5]nonan-1-one (6.8 mg, 0.016 mmol, 56.3% yield) was prepared in a similar manner as the procedure described in Example 40, using 3-methoxybenzoyl chloride (4.80 mg, 0.028 mmol). $^1$H NMR (500 MHz, DMSO-d$_6$) δ 8.36-7.75 (m, 2H), 7.62 (d, J=8.3 Hz, 2H), 7.45-7.22 (m, 3H), 7.10-6.89 (m, 3H), 3.79 (s, 3H), 3.69-3.37 (m, 2H), 2.58-2.50 (m, 4H), 1.99-1.67 (m, 4H); MS (ESI) m/z: 417.1 (M+H)$^+$; Anal. HPLC Retention time: 1.44 (Method 1); ROCK2 IC$_{50}$=285 nM.

Example 42: Preparation of 7-benzoyl-2-[4-(1H-pyrazol-4-yl)phenyl]-2,7-diazaspiro[4.4]nonan-1-one

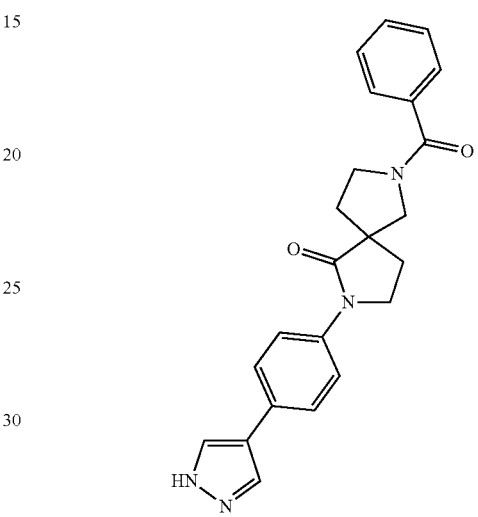

42A: Preparation of tert-butyl 7-(4-bromophenyl)-6-oxo-2,7-diazaspiro[4.4]nonane-2-carboxylate

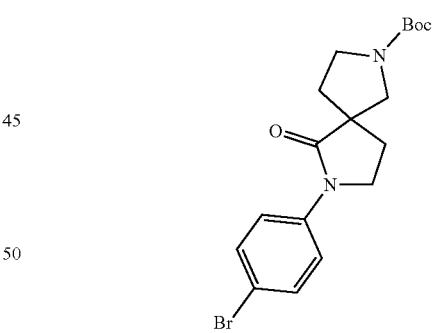

In a sealable reaction tube was mixed 1-bromo-4-iodobenzene (1177 mg, 4.16 mmol), tert-butyl 6-oxo-2,7-diazaspiro[4.4]nonane-2-carboxylate (500 mg, 2.081 mmol), cesium carbonate (1356 mg, 4.16 mmol) and dioxane (4161 µl). The reaction was purged with N$_2$. Then 9,9-Dimethyl-4,5-bis(diphenylphosphino)xanthene (120 mg, 0.208 mmol), Pd$_2$(dba)$_3$ (95 mg, 0.104 mmol) was added and N$_2$ was bubbled through reaction for 1 min. The reaction was sealed and stirred at 100° C. overnight. The reaction was partitioned between EtOAc (50 ml) and water (30 ml). The organic layer was separated, washed with water (2×30 ml) and brine (30 ml), dried over MgSO$_4$, filtered and concentrated. The residue was purified using ISCO system (0-100%

EtOAc/Hex gradient) to give tert-butyl 7-(4-bromophenyl)-6-oxo-2,7-diazaspiro[4.4]nonane-2-carboxylate (740 mg, 1.872 mmol, 90% yield) as a beige solid. ¹H NMR (500 MHz, DMSO-d₆) δ 7.71-7.65 (m, 2H), 7.60-7.54 (m, 2H), 3.82 (t, J=6.9 Hz, 2H), 3.50 (ddd, J=10.6, 8.1, 4.4 Hz, 1H), 3.46-3.40 (m, 1H), 3.37-3.32 (m, 2H), 2.13 (t, J=6.7 Hz, 2H), 2.09-1.99 (m, 1H), 1.92 (d, J=7.4 Hz, 1H), 1.41 (s, 10H); MS (ESI) m/z: 397.0 (M+H)⁺.

42B: Preparation of tert-butyl 6-oxo-7-(4-(1-((2-(trimethylsilyl)ethoxy)methyl)-1H-pyrazol-4-yl)phenyl)-2,7-diazaspiro[4.4]nonane-2-carboxylate

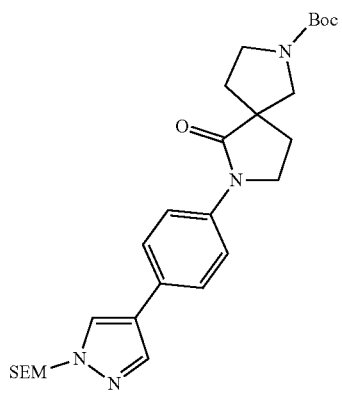 [SMILES: CC(C)(C)OC(=O)N1CCC2(CCN(c3ccc(-c4cnn(COCC[Si](C)(C)C)c4)cc3)C2=O)C1]

To a microwave vial was added 42A (730 mg, 1.847 mmol), 4-(4,4,5,5-tetramethyl-1,3,2-dioxaborolan-2-yl)-1-((2-(trimethylsilyl)ethoxy)methyl)-1H-pyrazole (1198 mg, 3.69 mmol), 3M tripotassium phosphate (2.462 mL, 7.39 mmol), Dioxane (10 mL) and methanesulfonato(2-dicyclohexylphosphino-2',4',6'-tri-i-propyl-1,1'-biphenyl)(2'-amino-1,1'-biphenyl-2-yl)palladium(I) (156 mg, 0.185 mmol). The reaction was purged with argon and sealed. The reaction was then subjected to microwave oven and stirred at 120° C. for 45 min. The reaction was partitioned between EtOAc (50 ml) and water (30 ml). The organic layer was separated, washed with water (30 ml) and brine (30 ml), dried over MgSO₄, filtered and concentrated. The reside was purified using ISCO system (0-100% EtOAc/Hex gradient) to give tert-butyl 6-oxo-7-(4-(1-((2-(trimethylsilyl)ethoxy)methyl)-1H-pyrazol-4-yl)phenyl)-2,7-diazaspiro[4.4]nonane-2-carboxylate (845 mg, 1.648 mmol, 89% yield) as an off-white solid. ¹H NMR (500 MHz, DMSO-d₆) δ 8.36 (d, J=0.6 Hz, 1H), 8.01 (d, J=0.6 Hz, 1H), 7.76-7.70 (m, 2H), 7.69-7.57 (m, 2H), 5.45 (s, 2H), 3.88 (t, J=7.0 Hz, 2H), 3.67-3.58 (m, 2H), 3.57-3.51 (m, 1H), 3.48 (t, J=11.1 Hz, 1H), 3.37 (d, J=11.0 Hz, 2H), 2.17 (t, J=6.6 Hz, 2H), 2.13-2.02 (m, 1H), 1.96 (d, J=7.4 Hz, 1H), 1.45 (s, 9H), 0.94-0.82 (m, 2H), 0.03-0.07 (m, 9H); MS (ESI) m/z: 513.3 (M+H)⁺.

42C: Preparation of 2-(4-(1-((2-(trimethylsilyl)ethoxy)methyl)-1H-pyrazol-4-yl)phenyl)-2,7-diazaspiro[4.4]nonan-1-one

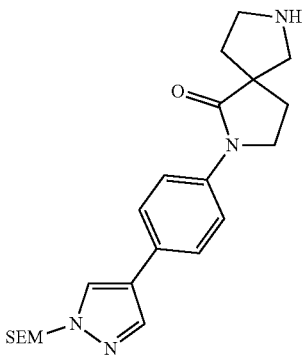 [SMILES: C[Si](C)(C)CCOCn1cc(-c2ccc(N3CCC4(CCNC4)C3=O)cc2)cn1]

To a microwave vial was 42B (275 mg, 0.536 mmol), MeOH (2 mL) and H₂O (8 mL). The reaction was subjected to microwave oven and stirred at 150° C. for 90 min. The reaction was partitioned between EtOAc (40 ml) and water (10 ml). The organic layer was separated, washed with brine (20 ml), dried over MgSO₄, filtered and concentrated to give 2-(4-(1-((2-(trimethylsilyl)ethoxy)methyl)-1H-pyrazol-4-yl)phenyl)-2,7-diazaspiro[4.4]nonan-1-one (160 mg, 0.388 mmol, 72.3% yield) as a beige solid. It was used without further purification. MS (ESI) m/z: 413.2 (M+H)⁺.

42D: Preparation of 7-benzoyl-2-[4-(1H-pyrazol-4-yl)phenyl]-2,7-diazaspiro[4.4]nonan-1-one

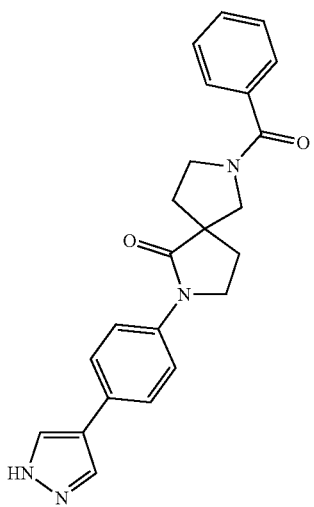 [SMILES: O=C(c1ccccc1)N1CCC2(CCN(c3ccc(-c4cn[nH]c4)cc3)C2=O)C1]

To a round bottom flask was added 42C (28 mg, 0.068 mmol), THF (1.5 mL), benzoyl chloride (14.31 mg, 0.102 mmol) and Hunig's Base (0.047 mL, 0.271 mmol). The reaction was stirred at rt overnight. The reaction was concentrated. Then to the residue was added CH₂Cl₂ (1 ml) and TFA (1 ml). The reaction was stirred at rt for 6 hr. The reaction was concentrated and purified using purification Method A to give 7-benzoyl-2-[4-(1H-pyrazol-4-yl)phenyl]-2,7-diazaspiro[4.4]nonan-1-one (12.3 mg, 0.032 mmol, 46.4% yield). ¹H NMR (500 MHz, DMSO-d₆) δ 8.27-7.80

(m, 2H), 7.73-7.66 (m, 1H), 7.65-7.58 (m, 3H), 7.55 (br. s., 2H), 7.50-7.37 (m, 3H), 3.88 (t, J=6.6 Hz, 1H), 3.84-3.71 (m, 2H), 3.69-3.52 (m, 2H), 3.42 (d, J=9.1 Hz, 1H), 2.27-1.92 (m, 4H); MS (ESI) m/z: 387.1 (M+H)+; Anal. HPLC Retention time: 1.34 (Method 1); ROCK2 IC$_{50}$=1222 nM.

Example 43: Preparation of 7-(2-methoxybenzoyl)-2-[4-(1H-pyrazol-4-yl)phenyl]-2,7-diazaspiro[4.4]nonan-1-one

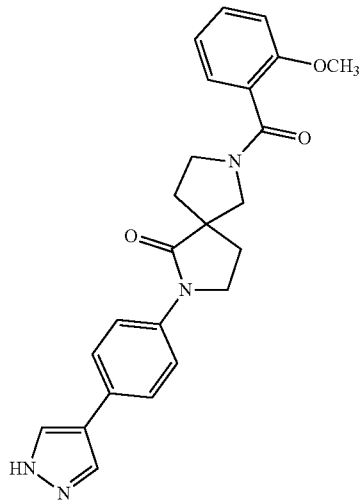 [SMILES: COc1ccccc1C(=O)N1CCC2(CCN(c3ccc(-c4cn[nH]c4)cc3)C2=O)C1]

7-(2-Methoxybenzoyl)-2-[4-(1 H-pyrazol-4-yl)phenyl]-2,7-diazaspiro[4.4]nonan-1-one (9.1 mg, 0.021 mmol, 44.2% yield) was prepared in a similar manner as the procedure described in Example 42, using 2-methoxybenzoyl chloride (12.40 mg, 0.073 mmol). $^1$H NMR (500 MHz, DMSO-d$_6$) δ 8.18-7.89 (m, 2H), 7.74-7.54 (m, 4H), 7.40 (q, J=7.7 Hz, 1H), 7.22 (br t, J=6.6 Hz, 1H), 7.09 (br t, J=9.2 Hz, 1H), 7.00 (q, =7.5 Hz, 1H), 3.94-3.68 (m, 5H), 2.55 (s, 2H), 2.25-1.98 (m, 4H); MS (ESI) m/z: 416.9 (M+H)+; Anal. HPLC Retention time: 1.44 (Method 1); ROCK2 IC$_{50}$=2560 nM.

Example 44: Preparation of 7-(3-methoxybenzoyl)-2-[4-(1H-pyrazol-4-yl)phenyl]-2,7-diazaspiro[4.4]nonan-1-one

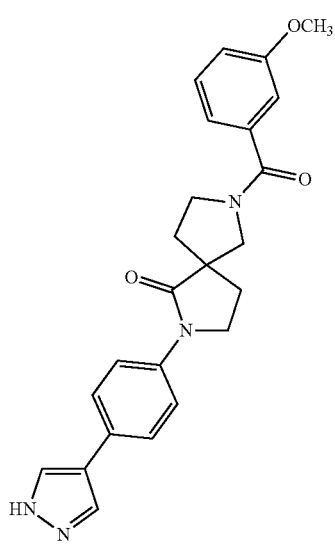 [SMILES: COc1cccc(C(=O)N2CCC3(CCN(c4ccc(-c5cn[nH]c5)cc4)C3=O)C2)c1]

7-(3-Methoxybenzoyl)-2-[4-(1H-pyrazol-4-yl)phenyl]-2,7-diazaspiro[4.4]nonan-1-one (6.6 mg, 0.016 mmol, 32.0% yield) was prepared in a similar manner as the procedure described in Example 42, using 3-methoxybenzoyl chloride (12.40 mg, 0.073 mmol). $^1$H NMR (500 MHz, DMSO-d$_6$) δ 8.17 (br s, 1H), 7.91 (br d, J=6.1 Hz 1H). 7.72-7.55 (m, 4H), 7.37 (q, J=8.0 Hz, 1H), 7.17-6.96 (m, 3H), 3.88 (br t, J=6.5 Hz, 1H), 3.83-3.69 (m, 4H), 3.67-3.54 (m, 2H), 2.28-1.91 (m, 4H); MS (ESI) m/z: 417.2 (M+H)+; Anal. HPLC Retention time: 1.41 (Method 1); ROCK2 IC$_{50}$=444 nM.

Example 45: Preparation of 7-(4-methoxybenzoyl)-2-[4-(1H-pyrazol-4-yl)phenyl]-2,7-diazaspiro[4.4]nonan-1-one

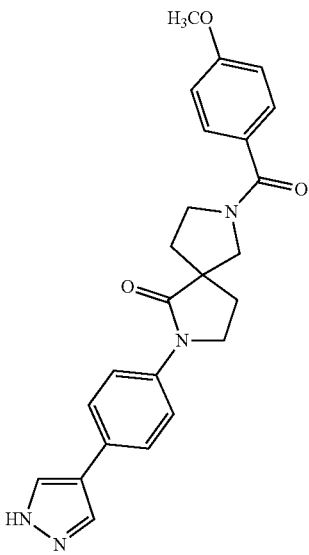 [SMILES: COc1ccc(C(=O)N2CCC3(CCN(c4ccc(-c5cn[nH]c5)cc4)C3=O)C2)cc1]

7-(4-Methoxybenzoyl)-2-[4-(1H-pyrazol-4-yl)phenyl]-2,7-diazaspiro[4.4]nonan-1-one (10.6 mg, 0.025 mmol, 53.6% yield) was prepared in a similar manner as the procedure described in Example 42, using 4-methoxybenzoyl chloride (12.40 mg, 0.073 mmol). $^1$H NMR (500 MHz, DMSO-d$_6$) δ 8.27-7.80 (m, 2H), 7.73-7.66 (m, 1H), 7.65-7.58 (m, 3H), 7.55 (br. s., 2H), 7.50-7.37 (m, 3H), 3.88 (t, J=6.6 Hz, 1H), 3.84-3.71 (m, 2H), 3.69-3.52 (m, 2H), 3.42 (d, J=9.1 Hz, 1H), 2.27-1.92 (m, 4H); MS (ESI) m/z: 417.2 (M+H)+; Anal. HPLC Retention time: 1.39 (Method 1), ROCK2 IC$_{50}$=180 nM.

Example 46: Preparation of 7-(benzenesulfonyl)-2-[4-(1H-pyrazol-4-yl)phenyl]-2,7-diazaspiro[4.4]nonan-1-one

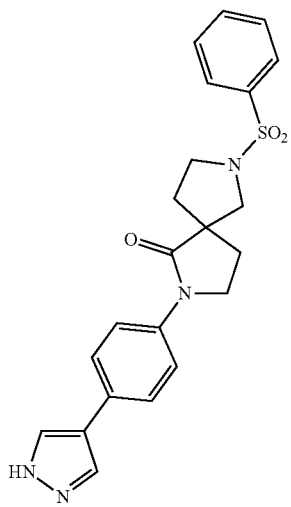 [SMILES: O=C1N(c2ccc(-c3cn[nH]c3)cc2)CCC12CCN(S(=O)(=O)c1ccccc1)C2]

To a round bottom flask was added 42C (28 mg, 0.068 mmol), THF (2 mL), benzenesulfonyl chloride (17.98 mg, 0.102 mmol) and Hunig's Base (0.047 mL, 0.271 mmol). The reaction was stirred at rt overnight. The reaction was concentrated. Then the residue was dissolved in $CH_2Cl_2$ (1 mL) and TFA (1 mL). The reaction was stirred at rt for 6 hr. The reaction was concentrated and the residue was purified using purification Method B to give 7-(benzenesulfonyl)-2-[4-(H-pyrazol-4-yl)phenyl]-2,7-diazaspiro[4.4]nonan-1-one (14.1 mg, 0.033 mmol, 48.7% yield). $^1$H NMR (500 MHz, DMSO-$d_6$) δ 8.02 (br. s., 2H), 7.86 (d, J=7.6 Hz, 2H), 7.78-7.73 (m, 1H), 7.71-7.64 (m, 2H), 7.59 (s, 4H), 3.73 (t, J=6.7 Hz, 2H), 3.33-3.20 (m, 2H), 2.55 (s, 2H), 1.97-1.68 (m, 4H); MS (ESI) m/z: 423.2 (M+H)$^+$; Anal. HPLC Retention time: 1.55 (Method 1); ROCK2 $IC_{50}$=750 nM.

Example 47: Preparation of 2-[3-methoxy-4-(1H-pyrazol-4-yl)phenyl]-8-(4-methoxybenzoyl)-2,8-diazaspiro[4.5]decan-3-one

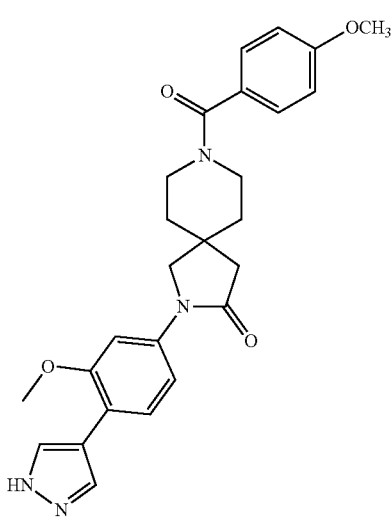 [SMILES: COc1ccc(C(=O)N2CCC3(CC2)CC(=O)N(c2ccc(-c4cn[nH]c4)c(OC)c2)C3)cc1]

To a round bottom flask was added Intermediate 8, 2-(3-methoxy-4-(H-pyrazol-4-yl)phenyl)-2,8-diazaspiro[4.5]decan-3-one, 2 HCl (20 mg, 0.050 mmol), THF (1 mL), 4-methoxy benzoyl chloride (8.54 mg, 0.050 mmol) and $Et_3N$ (0.035 mL, 0.250 mmol). The reaction was stirred at rt for 15 min. The reaction was concentrated and purified using Purification Method B to give 2-[3-methoxy-4-(1H-pyrazol-4-yl)phenyl]-8-(4-methoxybenzoyl)-2,8-diazaspiro[4.5]decan-3-one (8.3 mg, 0.018 mmol, 35.3% yield). $^1$H NMR (500 MHz, DMSO-$d_6$) δ 8.02 (br. s., 2H), 7.60 (d, J=8.3 Hz, 1H), 7.49 (s, 1H), 7.36 (d, J=8.3 Hz, 2H), 7.16 (d, J=8.8 Hz, 1H), 6.99 (d, J=8.4 Hz, 2H), 3.86 (s, 3H), 3.79 (s, 3H), 3.75 (br. s., 2H), 3.48 (d, J=12.9 Hz, 2H), 1.65 (br. s., 4H); MS (ESI) m/z: 461.1 (M+H)$^+$; Anal. HPLC Retention time: 1.38 (Method 1); ROCK2 $IC_{50}$=306 nM.

48: Preparation of 8-[4-(4-methylpiperazin-1-yl)benzoyl]-2-[3-(1H-pyrazol-4-yl)phenyl]-2,8-diazaspiro[4.5]decan-1-one

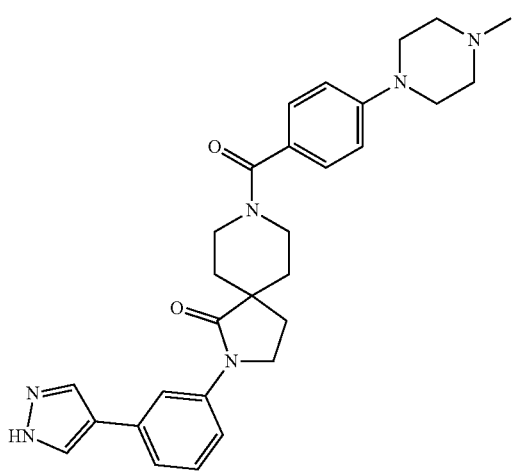 [SMILES: CN1CCN(c2ccc(C(=O)N3CCC4(CC3)CCN(c3cccc(-c5cn[nH]c5)c3)C4=O)cc2)CC1]

48A: Preparation of tert-butyl 2-(3-bromophenyl)-1-oxo-2,8-diazaspiro[4.5]decane-8-carboxylate

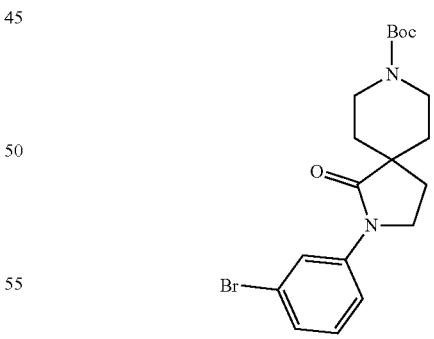

In a sealable reaction tube was mixed 1-bromo-3-iodobenzene (445 mg, 1.573 mmol), tert-butyl 1-oxo-2,8-diazaspiro[4.5]decane-8-carboxylate (200 mg, 0.786 mmol), Cesium carbonate (512 mg, 1.573 mmol) and dioxane (1573 μl). The reaction was purged with $N_2$. Then 9,9-Dimethyl-4,5-bis(diphenylphosphino)xanthene (68.3 mg, 0.118 mmol), $Pd_2(dba)_3$ (36.0 mg, 0.039 mmol) was added and $N_2$ was bubbled through reaction for 1 min. The reaction was sealed and stirred at 100° C. overnight. The reaction was partitioned between EtOAc (50 ml) and water (30 ml). The organic layer was separated, washed with water (2×30 ml) and brine (30 ml), dried over MgSO$_4$, filtered and concentrated. The residue was purified using ISCO system (0-100% EtOAc/Hex gradient) to give tert-butyl 2-(3-bromophenyl)-1-oxo-2,8-diazaspiro[4.5]decane-8-carboxylate (300 mg, 0.733 mmol, 93% yield) as a beige solid. $^1$H NMR (500 MHz, DMSO-d6) 8.13-7.93 (m, 1H), 7.61 (dt, J=6.7, 2.3 Hz, 1H), 7.42-7.24 (m, 2H), 3.93-3.74 (m, 4H), 3.09-2.82 (m, 2H), 2.09 (t, J=7.0 Hz, 2H), 1.62 (td, J=12.4, 4.1 Hz, 2H), 1.55-1.46 (m, 2H), 1.42 (s, 9H); MS (ESI) m/z: 409.0, 411.0 (M+H)$^+$.

48B: Preparation of tert-butyl 2-(3-(1-(tert-butoxycarbonyl)-1H-pyrazol-4-yl)phenyl)-1-oxo-2,8-diazaspiro[4.5]decane-8-carboxylate

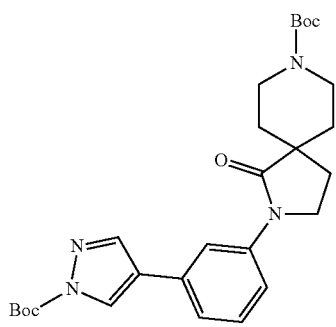 [SMILES: CC(C)(C)OC(=O)N1CCC2(CC1)CCN(c1cccc(-c3cnn(C(=O)OC(C)(C)C)c3)c1)C2=O]

To a round bottle flask was added 48A (300 mg, 0.733 mmol), tert-butyl 4-(4,4,5,5-tetramethyl-1,3,2-dioxaborolan-2-yl)-1H-pyrazole-1-carboxylate (431 mg, 1.466 mmol), tripotassium phosphate (0.733 mL, 2.199 mmol), Dioxane (3 mL) and chloro(2-dicyclohexylphosphino-2',4',6'-triisopropyl-1,1'-biphenyl)[2-(2'-amino-1,1'-biphenyl)]palladium (II) (40.4 mg, 0.051 mmol). The reaction was purged with nitrogen then stirred at 80° C. for 4 hr. The reaction was partitioned between EtOAc (50 ml) and water (20 ml). The organic layer was separated, washed with water (20 ml) and brine (30 ml), dried over MgSO$_4$, filtered and concentrated. The residue was purified using ISCO system (0-100% EtOAc/Hex gradient) to give tert-butyl 2-(3-(1-(tert-butoxycarbonyl)-1H-pyrazol-4-yl)phenyl)-1-oxo-2,8-diazaspiro[4.5]decane-8-carboxylate (320 mg, 0.644 mmol, 88% yield) as an off-white solid. $^1$H NMR (500 MHz, DMSO-d6) 8.73 (s, 1H), 8.29 (s, 1H), 7.89 (d, J=1.7 Hz, 1H), 7.71 (dd, J=8.3, 1.4 Hz, 1H), 7.53 (d, J=7.7 Hz, 1H), 7.46-7.32 (m, 1H), 3.91-3.86 (m, 4H), 3.00 (br. s., 2H), 2.11 (t, J=6.9 Hz, 2H), 1.68-1.60 (m, 11H), 1.51 (d, J=13.2 Hz, 2H), 1.42 (s, 9H); MS (ESI) m/z: 497.1 (M+H)$^+$.

48C: Preparation of 2-(3-(1H-pyrazol-4-yl)phenyl)-2,8-diazaspiro[4.5]decan-1-one

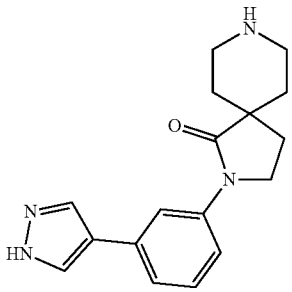 [SMILES: O=C1N(c2cccc(-c3cn[nH]c3)c2)CCC12CCNCC2]

To around bottom flask was added 48B (310 mg, 0.624 mmol), Dioxane (10 mL) and 4N HCl (0.379 mL, 12.48 mmol) in dioxane. The reaction was stirred at rt overnight. The reaction was concentrated to give 2-(3-(H-pyrazol-4-yl)phenyl)-2,8-diazaspiro[4.5]decan-1-one, HCl (221 mg, 0.631 mmol, 100% yield) as an off-white solid. MS (ESI) m/z: 296.9 (M+H)$^+$.

48D: Preparation of 8-[4-(4-methylpiperazin-1-yl)benzoyl]-2-[3-(1H-pyrazol-4-yl)phenyl]-2,8-diazaspiro[4.5]decan-1-one

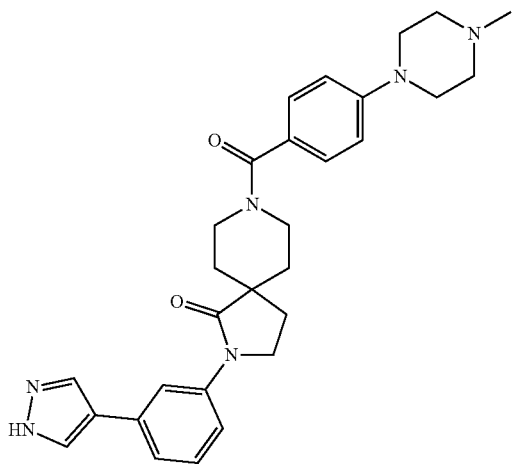 [SMILES: CN1CCN(c2ccc(C(=O)N3CCC4(CC3)CCN(c3cccc(-c5cn[nH]c5)c3)C4=O)cc2)CC1]

To a round bottom flask was added 4-(4-methylpiperazin-1-yl)benzoic acid (8.95 mg, 0.041 mmol), DMF (0.5 mL), HATU (18.53 mg, 0.049 mmol) and Et$_3$N (0.028 mL, 0.203 mmol). The reaction was stirred at rt for 10 min and then 48C (15 mg, 0.041 mmol) was added and the reaction was continued for 2 hr. The reaction was purified using Purification Method A to give 8-[4-(4-methylpiperazin-1-yl)benzoyl]-2-[3-(1H-pyrazol-4-yl)phenyl]-2,8-diazaspiro[4.5]decan-1-one (18.9 mg, 0.037 mmol, 91% yield). $^1$H NMR (500 MHz, DMSO-d6) 8.05 (br. s., 2H), 7.82 (s, 1H), 7.56 (d, J=7.8 Hz, 1H), 7.43-7.25 (m, 4H), 6.96 (d, J=8.5 Hz, 2H), 3.96-3.73 (m, 2H), 3.21 (br. s., 2H), 2.55 (s, 4H), 2.45 (br. s., 4H), 2.22 (s, 3H), 2.15 (t, J=6.4 Hz, 2H), 1.92 (br. s., 2H), 1.78-1.66 (m, 2H), 1.58 (br. s., 2H); MS (EST) m/z: 499.1 (M+H)$^+$; Anal. HPLC Retention time: 1.14 (Method 1); ROCK2 IC$_{50}$=1095 nM.

Example 49: Preparation of 2-[3-(1H-indazol-6-yl)phenyl]-8-[4-(4-methylpiperazin-1-yl)benzoyl]-2,8-diazaspiro[4.5]decan-1-one

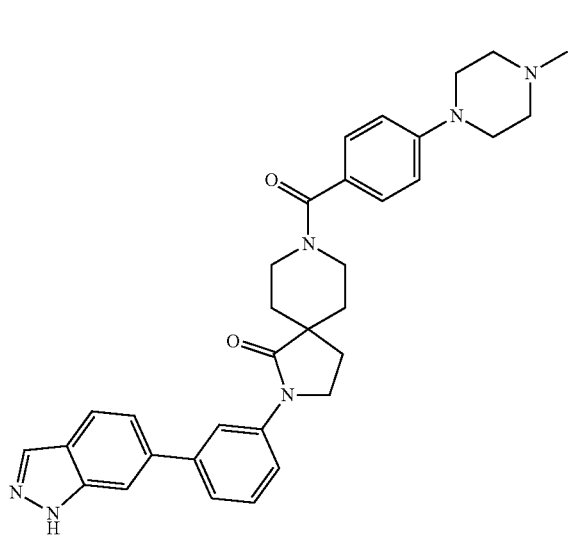 [SMILES: CN1CCN(c2ccc(C(=O)N3CCC4(CC3)CCN(c3cccc(-c5ccc6cn[nH]c6c5)c3)C4=O)cc2)CC1]

49A: Preparation of tert-butyl 2-(3-(1H-indazol-6-yl)phenyl)-1-oxo-2,8-diazaspiro[4.5]decane-8-carboxylate

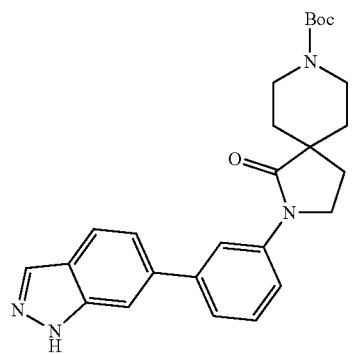 [SMILES: CC(C)(C)OC(=O)N1CCC2(CC1)CCN(c1cccc(-c3ccc4cn[nH]c4c3)c1)C2=O]

To a round bottle flask was added 48A (140 mg, 0.342 mmol), (1H-indazol-6-yl)boronic acid (111 mg, 0.684 mmol), tripotassium phosphate (0.342 mL, 1.026 mmol), Dioxane (3 mL) and chloro(2-dicyclohexylphosphino-2',4',6'-triisopropyl-1,1'-biphenyl)[2-(2'-amino-1,1'-biphenyl)]palladium(II) (18.84 mg, 0.024 mmol). The reaction was purged with nitrogen then stirred at 80° C. for 4 hr. The reaction was partitioned between EtOAc (50 ml) and water (20 ml). The organic layer was separated, washed with water (20 ml) and brine (30 ml), dried over MgSO$_4$, filtered and concentrated. The residue was purified using ISCO system (0-100% EtOAc/Hex gradient) to give tert-butyl 2-(3-(H-indazol-6-yl)phenyl)-1-oxo-2,8-diazaspiro[4.5]decane-8-carboxylate (120 mg, 0.269 mmol, 79% yield) as an off-white solid. $^1$H NMR (500 MHz, DMSO-d6) 13.14 (s, 1H), 8.12 (d, J=1.1 Hz, 2H), 7.87 (d, J=8.6 Hz, 1H), 7.75 (s, 1H), 7.70-7.63 (m, 1H), 7.57-7.48 (m, 2H), 7.43 (dd, J=8.5, 1.4 Hz, 1H), 3.97-3.81 (m, 4H), 3.02 (br. s., 2H), 2.13 (t, J=6.9 Hz, 2H), 1.74-1.62 (m, 2H), 1.59-1.50 (m, 2H), 1.44 (s, 9H); MS (ESI) m/z: 447.0 (M+H)$^+$.

49B: Preparation of 2-(3-(1H-indazol-6-yl)phenyl)-2,8-diazaspiro[4.5]decan-1-one, HCl

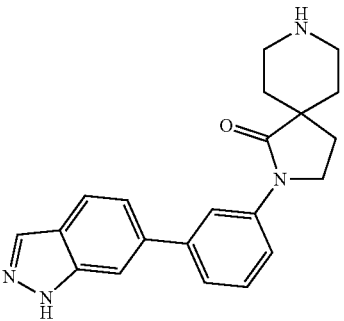 [SMILES: O=C1N(c2cccc(-c3ccc4cn[nH]c4c3)c2)CCC12CCNCC2]

To around bottom flask was added 49A (120 mg, 0.269 mmol), Dioxane (10 mL) and 4N HCl (1.344 mL, 5.37 mmol) in dioxane. The reaction was stirred at rt overnight. The reaction was concentrated to give 2-(3-(H-indazol-6-yl)phenyl)-2,8-diazaspiro[4.5]decan-1-one, HCl (100 mg, 0.261 mmol, 97% yield) as an off-white solid. MS (ESI) m/z: 347.0 (M+H)$^+$.

49C: Preparation of 2-[3-(1H-indazol-6-yl)phenyl]-8-[4-(4-methylpiperazin-1-yl)benzoyl]-2,8-diazaspiro[4.5]decan-1-one

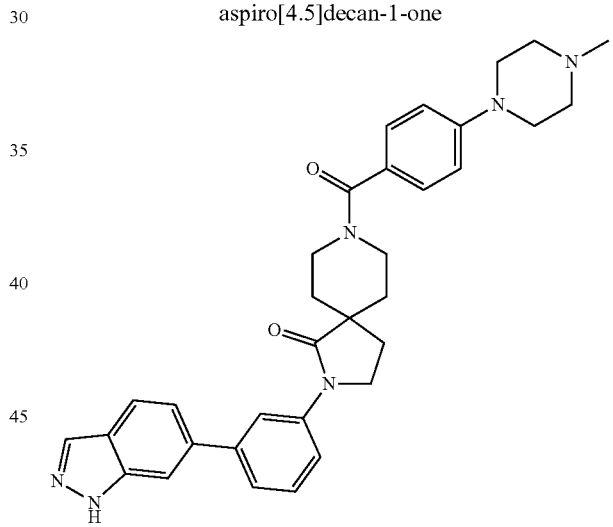

To a 1 dram vial was added 4-(4-methylpiperazin-1-yl)benzoic acid (11.51 mg, 0.052 mmol), DMF (0.5 mL), HATU (23.83 mg, 0.063 mmol) and Et$_2$N (0.036 mL, 0.261 mmol). The reaction was stirred at rt for 10 min and then 49B (20 mg, 0.052 mmol) was added and the reaction was continued for 4 hr. The reaction was partitioned between EtOAc (20 ml) and water (15 ml). The organic layer was separated, washed with brine (15 ml), dried over MgSO$_4$, filtered and concentrated. The residue was purified using Purification Method A to give 2-[3-(1H-indazol-6-yl)phenyl]-8-[4-(4-methylpiperazin-1-yl)benzoyl]-2,8-diazaspiro[4.5]decan-1-one (19.3 mg, 0.034 mmol, 66.0% yield). $^1$H NMR (500 MHz, DMSO-d6) 8.18-8.03 (m, 2H), 7.86 (d, J=8.4 Hz, 1H), 7.75 (s, 1H), 7.64 (br. s., 1H), 7.51 (br. s., 2H), 7.42 (d, J=8.4 Hz, 1H), 7.30 (d, J=8.4 Hz, 2H), 6.96 (d, J=8.5 Hz, 2H), 4.02-3.78 (m, 2H), 3.21 (br. s., 4H), 2.45 (br. s., 4H), 2.22 (s, 2H), 2.17 (t, J=6.6 Hz, 2H), 1.91 (s, 3H), 1.78-1.65 (m, 2H), 1.60 (br. s., 2H); MS (EST) m/z: 549.2 (M+H)+; Anal. HPLC Retention time: 1.32 (Method 2); ROCK2 IC$_{50}$=6.8 nM.

Example 50: Preparation of 2-[3-1H-indazol-6-yl)phenyl]-8-(4-methoxybenzoyl)-2,8-diazaspiro[4.5]decan-1-one

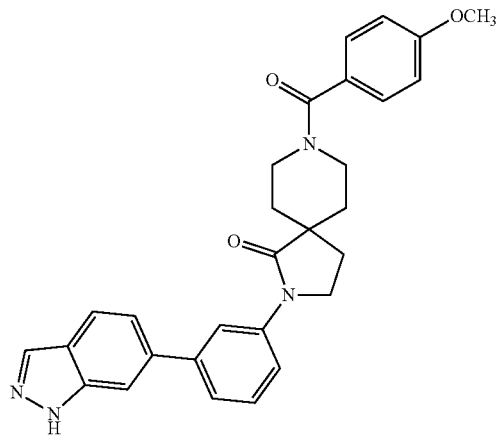 [SMILES: COc1ccc(C(=O)N2CCC3(CC2)CCN(c2cccc(-c4ccc5cn[nH]c5c4)c2)C3=O)cc1]

To a round bottom flask was added 49B (20 mg, 0.052 mmol), DMF (0.5 mL), Et$_3$N (0.022 mL, 0.157 mmol) and 4-methoxybenzoyl chloride (8.91 mg, 0.052 mmol). The reaction was stirred at rt for 15 min. The reaction was purified using Purification Method A to give 2-[3-(H-indazol-6-yl)phenyl]-8-(4-methoxybenzoyl)-2,8-diazaspiro[4.5]decan-1-one (14.6 mg, 0.029 mmol, 54.7% yield). $^1$H NMR (500 MHz, DMSO-d6) 8.11 (s, 1H), 8.07 (br s, 1H), 7.86 (d, J=8.4 Hz, 1H), 7.75 (s, 1H), 7.64 (br s, 1H), 7.53-7.48 (m, 2H), 7.42 (br d, J=8.3 Hz, 1H), 7.38 (br d, J=8.3 Hz, 2H), 7.00 (d, J=8.5 Hz, 2H), 3.91 (br d, J=5.8 Hz, 2H), 3.79 (s, 3H), 3.57-3.53 (m, 3H), 3.27-3.09 (m, 2H), 2.16 (br s, 2H), 1.73 (br s, 2H), 1.60 (br s, 2H); MS (ESI) m/z: 480.1 (M+H)+; Anal. HPLC Retention time: 1.85 (Method 1); ROCK2 IC$_{50}$=1680 nM.

Example 51: Preparation of 2-[3-(1H-indazol-5-yl)phenyl]-8-[4-(4-methyl)piperazin-1-yl)benzoyl]-2,8-diazaspiro[4.5]decan-1-one

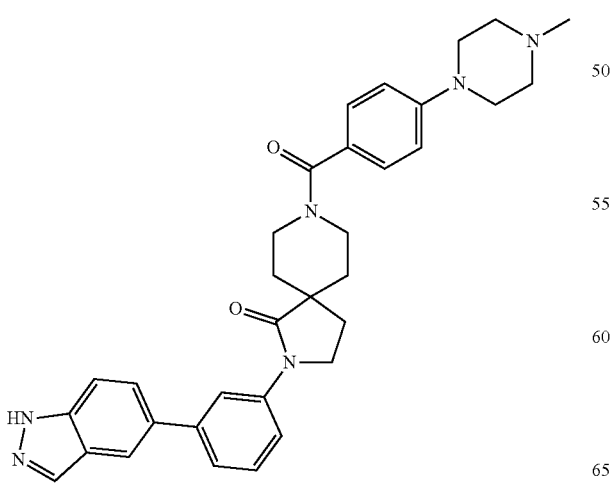

51A: Preparation of tert-butyl 2-(3-(1H-indazol-5-yl)phenyl)-1-oxo-2,8-diazaspiro[4.5]decane-8-carboxylate

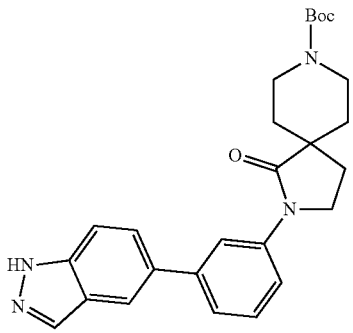 [SMILES: CC(C)(C)OC(=O)N1CCC2(CC1)CCN(c1cccc(-c3ccc4[nH]ncc4c3)c1)C2=O]

To a round bottle flask was added 48A (140 mg, 0.342 mmol), 5-(4,4,5,5-tetramethyl-1,3,2-dioxaborolan-2-yl)-1H-indazole (167 mg, 0.684 mmol), tripotassium phosphate (0.342 mL, 1.026 mmol), Dioxane (3 mL) and chloro(2-dicyclohexylphosphino-2',4',6'-triisopropyl-1,1'-biphenyl)[2-(2'-amino-1,1'-biphenyl)]palladium(II) (18.84 mg, 0.024 mmol). The reaction was purged with nitrogen then stirred at 100° C. for 4 hr. The reaction was partitioned between EtOAc (50 ml) and water (20 ml). The organic layer was separated, washed with water (20 ml) and brine (30 ml), dried over MgSO$_4$, filtered and concentrated. The residue was purified using ISCO system (0-100% EtOAc/Hex gradient) to give tert-butyl 2-(3-(1H-indazol-5-yl)phenyl)-1-oxo-2,8-diazaspiro[4.5]decane-8-carboxylate (70 mg, 0.157 mmol, 45.8% yield) as an off-white solid. $^1$H NMR (500 MHz, DMSO-d6) 13.13 (s, 1H), 8.15 (s, 1H), 8.04 (d, J=7.2 Hz, 2H), 7.70-7.59 (m, 3H), 7.54-7.42 (m, 2H), 3.96-3.81 (m, 4H), 3.00 (br. s., 2H), 2.13 (t, J=6.9 Hz, 2H), 1.66 (td, J=12.4, 4.3 Hz, 2H), 1.53 (d, J=12.9 Hz, 2H), 1.43 (s, 9H); MS (EST) m/z: 447.0 (M+H)+.

51B: Preparation of 2-(3-(1H-indazol-5-yl)phenyl)-2,8-diazaspiro[4.5]decan-1-one, HCl

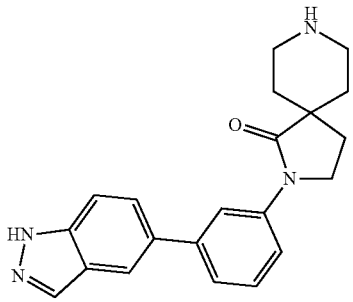 [SMILES: O=C1N(c2cccc(-c3ccc4[nH]ncc4c3)c2)CCC12CCNCC2]

To a round bottom flask was added 51A (70 mg, 0.157 mmol), Dioxane (1) and 4N HCl (784 μl, 3.14 mmol) in dioxane. The reaction was stirred at rt overnight. The reaction was concentrated to give 2-(3-(1H-indazol-5-yl)phenyl)-2,8-diazaspiro[4.5]decan-1-one, HCl (60 mg, 0.157 mmol, 100% yield) as an off-white solid. MS (EST) m/z: 347.0 (M+H)+.

51C: Preparation of 2-[3-(1H-indazol-5-yl)phenyl]-8-[4-(4-methylpiperazin-1-yl)benzoyl]-2,8-diazaspiro[4.5]decan-1-one

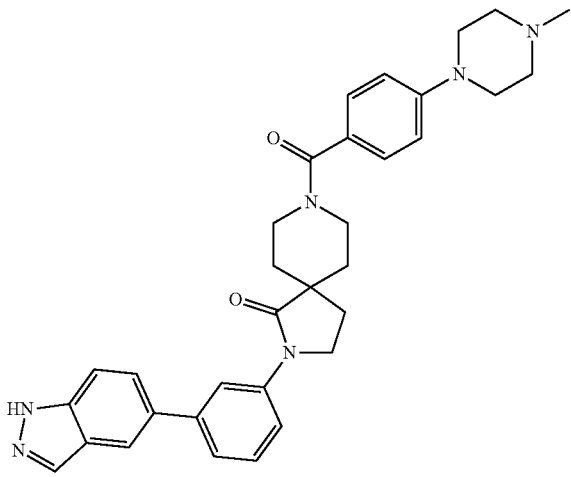 [SMILES: CN1CCN(c2ccc(C(=O)N3CCC4(CC3)CCN(c3cccc(-c5ccc6[nH]ncc6c5)c3)C4=O)cc2)CC1]

To a 1 dram vial was added 4-(4-methylpiperazin-1-yl)benzoic acid (11.51 mg, 0.052 mmol), DMF (0.5 mL), HATU (23.83 mg, 0.063 mmol) and Et$_3$N (0.036 mL, 0.261 mmol). The reaction was stirred at rt for 10 min and then 51B (20 mg, 0.052 mmol) was added and the reaction was continued for 4 hr. The reaction was partitioned between EtOAc (20 ml) and water (15 ml). The organic layer was separated, washed with brine (15 ml), dried over MgSO$_4$, filtered and concentrated. The residue was purified using Purification Method A to give 2-[3-(1H-indazol-5-yl)phenyl]-8-[4-(4-methylpiperazin-1-yl)benzoyl]-2,8-diazaspiro[4.5]decan-1-one (19.1 mg, 0.034 mmol, 64.6% yield). $^1$H NMR (500 MHz, DMSO-d6) 8.14 (s, 1H), 8.02 (br. s., 2H), 7.70-7.57 (m, 3H), 7.47 (d, J=4.6 Hz, 2H), 7.34 (d, J=8.5 Hz, 2H), 7.04 (d, J=8.5 Hz, 2H), 4.08-3.81 (m, 4H), 3.64-3.41 (m, 6H), 3.17 (s, 4H), 2.16 (br. s., 2H), 1.72 (d, J=10.7 Hz, 2H), 1.60 (br. s., 2H), 1.22 (s, 2H); MS (ESI) m/z: 549.1 (M+H)$^+$; Anal. HPLC Retention time: 1.53 (Method 1); ROCK2 IC$_{50}$=14 nM.

Example 52: Preparation of 2-[3-(1H-indazol-5-yl)phenyl]-8-(4-methoxybenzoyl)-2,8-diazaspiro[4.5]decan-1-one

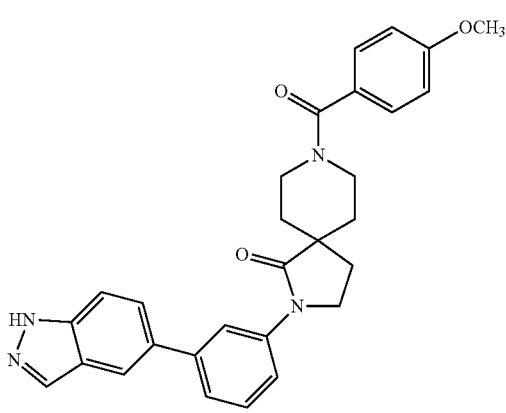 [SMILES: COc1ccc(C(=O)N2CCC3(CC2)CCN(c2cccc(-c4ccc5[nH]ncc5c4)c2)C3=O)cc1]

2-[3-(1H-indazol-5-yl)phenyl]-8-(4-methoxy benzoyl)-2,8-diazaspiro[4.5]decan-1-one (10.1 mg, 0.021 mmol, 39.4% yield) was prepared in a similar manner as the procedure described in Example 51, using 51B (20 mg, 0.052 mmol). $^1$H NMR (500 MHz, DMSO-d$_6$) δ 8.15 (s, 1H), 8.03 (br. s., 2H), 7.72-7.57 (m, 3H), 7.47 (d, J=4.7 Hz, 2H), 7.38 (d, J=8.4 Hz, 2H), 7.00 (d, J=8.4 Hz, 2H), 3.92 (br. s., 2H), 3.79 (s, 3H), 3.17 (d, J=5.0 Hz, 2H), 2.16 (br. s., 2H), 1.73 (br. s., 2H), 1.60 (br. s., 2H); MS (ESI) m/z: 481.1 (M+H)$^+$; Anal. HPLC Retention time: 1.66 (Method 2); ROCK2 IC$_{50}$=1875 nM.

Preparation of Examples 53-205

The following compounds were made in a parallel manner using the following procedure: Reagents were weighed into stubby tubes. Stock solutions were made for reagent addition: Dissolved 2305.8 mg Intermediate 4 in 45.75 mL DMF and DIEA (2 eq). Dissolved 3131.85 mg HATU in 75 mL DMF. To each vial containing reagent acid (0.063 mmol) was added 0.25 ml of the HATU solution in DMF followed by DIEA (0.028 mL, 0.158 mmol). After stirring for 10 min, 0.25 ml of the Intermediate 4 solution was added and the resulting reaction mixture vials were placed in a Bohdan Miniblock XT and were agitated overnight at 400 rpm.

Upon completion, reaction mixtures were purified via preparative LC/MS with the following conditions: Column: XBridge C18, 19×100 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 2-minute hold at 100% B; Flow: 20 mL/min. Fractions containing the desired product were combined and dried via centrifugal evaporation. **Gradient varied for each reaction depending on polarity of compound.

Compound purity was assigned based on the methods below.

Method 1: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75-minute hold at 100% B; Flow: 1.0 mL/min; Detection: UV at 220 nm.

Method 2: Column: Waters Acquit) UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 53: Preparation of 2-[3-methoxy-4-(1H-pyrazol-4-yl)phenyl]-8-[4-(1H-pyrazol-3-yl)benzoyl]-2,8-diazaspiro[4.5]decan-1-one

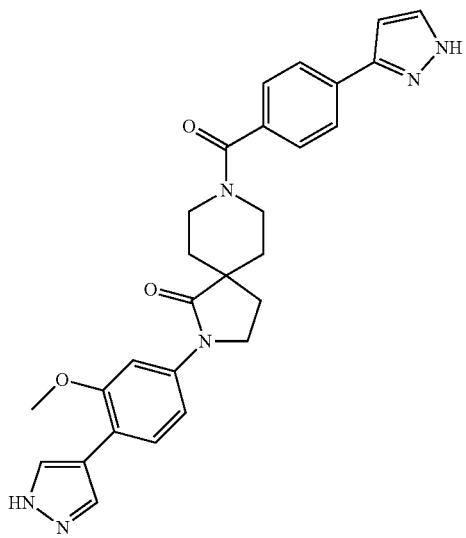 [SMILES: COc1cc(N2CCC3(CCN(C(=O)c4ccc(-c5cc[nH]n5)cc4)CC3)C2=O)ccc1-c1cn[nH]c1]

¹H NMR (500 MHz, DMSO-d₆) δ 8.10 (br s, 1H), 7.94 (br s, 1H), 7.90 (br d, J=6.9 Hz, 2H), 7.81 (br s, 1H), 7.69-7.55 (m, 2H), 7.44 (br d, J=7.0 Hz, 2H), 7.15 (br d, J=7.0 Hz, 1H), 6.78 (br s, 1H), 4.41-4.29 (m, 1H), 3.87 (s, 5H), 3.69 (br d, =9.3 Hz, 1H), 3.35-3.23 (m, 1H), 3.17-3.07 (m, 1H), 2.15 (br s, 2H), 1.85-1.48 (m, 4H); MS ESI m/z 497.2 (M+H); Anal. HPLC Retention time: 1.2 (Method 2); ROCK2 IC₅₀=16.5 nM.

Example 54: Preparation of 2-[3-methoxy-4-(1H-pyrazol-4-yl)phenyl]-8-[5-(pyrrolidin-1-yl)pyridine-2-carbonyl]-2,8-diazaspiro[4.5]decan-1-one

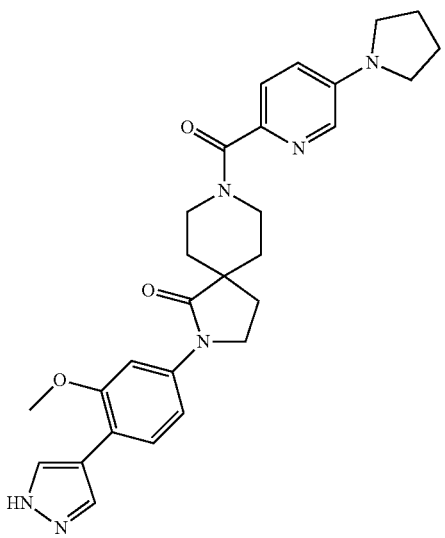 [SMILES: COc1cc(N2CCC3(CCN(C(=O)c4ccc(N5CCCC5)cn4)CC3)C2=O)ccc1-c1cn[nH]c1]

¹H NMR (500 MHz, DMSO-d₆) δ 8.01 (br s, 2H), 7.89 (d, J=2.1 Hz, 1H), 7.65-7.57 (m, 2H), 7.50 (d, J=8.9 Hz, 1H), 7.15 (br d, J=8.2 Hz, 1H), 6.96 (dd, J=8.5, 2.4 Hz, 1H), 4.33 (br s, 1H), 4.20 (br d, J=7.0 Hz, 1H), 3.91-3.81 (m, 5H), 3.31 (br s, 4H), 3.17 (br s, 1H), 3.08 (br s, 1H), 2.16 (br s, 2H), 1.97 (br s, 4H), 1.83-1.71 (m, 2H), 1.68-1.43 (m, 2H); MS ESI n/z 501.3 (M+H); Anal. HPLC Retention time: 1.3 (Method 2); ROCK2 IC₅₀=2.1 nM.

Example 55: Preparation of 4-{2-[3-methoxy-4-(1H-pyrazol-4-yl)phenyl]-1-oxo-2,8-diazaspiro[4.5]decane-8-carbonyl}benzene-1-sulfonamide

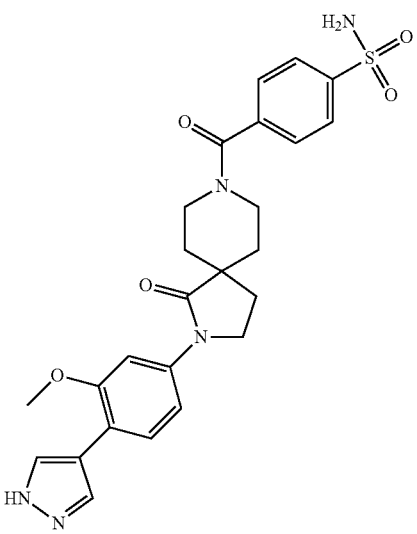 [SMILES: COc1cc(N2CCC3(CCN(C(=O)c4ccc(S(N)(=O)=O)cc4)CC3)C2=O)ccc1-c1cn[nH]c1]

¹H NMR (500 MHz, DMSO-d₆) δ 8.02 (br s, 2H), 7.90 (d, J=8.2 Hz, 2H), 7.61 (br d, J=6.5 Hz, 4H), 7.15 (dd, J=8.5, 1.6 Hz, 1H), 4.34 (br d, J=12.8 Hz, 1H), 3.92-3.79 (m, 5H), 3.17 (br d, J=4.5 Hz, 1H), 2.21-2.08 (m, 2H), 1.83-1.63 (m, 3H), 1.51 (br s, 1H); MS ESI m/z 510 (M+H); Anal. HPLC Retention time: 1.07 (Method 1); ROCK2 IC₅₀=96 nM.

Example 56: Preparation of 2-[3-methoxy-4-(1H-pyrazol-4-yl)phenyl]-8-(pyridine-4-carbonyl)-2,8-diazaspiro[4.5]decan-1-one

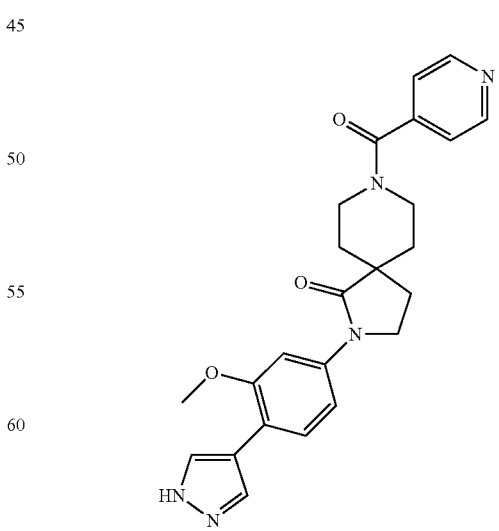

¹H NMR (500 MHz, DMSO-d₆) δ 8.68 (br d, J=5.0 Hz, 2H), 8.02 (br s, 2H), 7.63-7.57 (m, 2H), 7.41 (br d, J=5.5 Hz,

2H), 7.15 (br d, J=8.4 Hz, 1H), 4.32 (br d, J=13.4 Hz, 1H), 3.87 (s, 5H), 3.38 (br s, 1H), 3.28-3.12 (m, 2H), 2.22-2.03 (m, 2H), 1.83-1.64 (m, 3H), 1.52 (br d, J=14.0 Hz, 1H); MS ESI m/z 432.1 (M+H); Anal. HPLC Retention time: 0.86 (Method 1); ROCK2 IC$_{50}$=433 nM.

Example 57: Preparation of 2-[3-methoxy-4-(1H-pyrazol-4-yl)phenyl]-8-(3-phenoxybenzoyl)-2,8-diazaspiro[4.5]decan-1-one

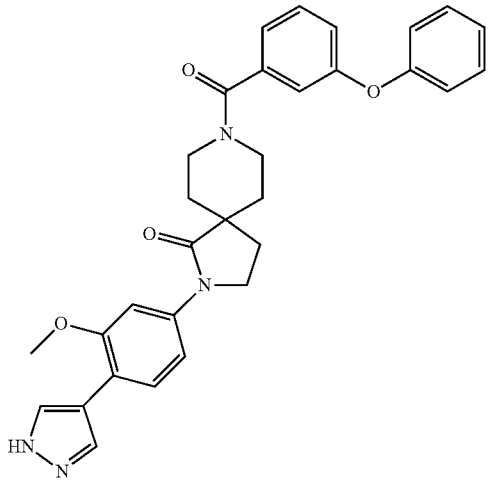 [SMILES: COc1cc(N2CCC3(CCN(C(=O)c4cccc(Oc5ccccc5)c4)CC3)C2=O)ccc1-c1cn[nH]c1]

$^1$H NMR (500 MHz, DMSO-d$_6$) δ 7.66-7.58 (m, 2H), 7.51-7.40 (m, 4H), 7.23-7.05 (m, 7H), 6.95 (s, 1H), 4.35-4.22 (m, 1H), 3.86 (s, 5H), 3.40 (br s, 3H), 2.12 (br d, J=8.8 Hz, 2H), 1.78-1.48 (m, 4H); Anal. HPLC Retention time: 1.84 Method 2; ROCK2 IC$_{50}$=118 nM.

Example 58: Preparation of 2-[3-methoxy-4-(1H-pyrazol-4-yl)phenyl]-8-[3-(trifluoromethyl)benzoyl]-2,8-diazaspiro[4.5]decan-1-one

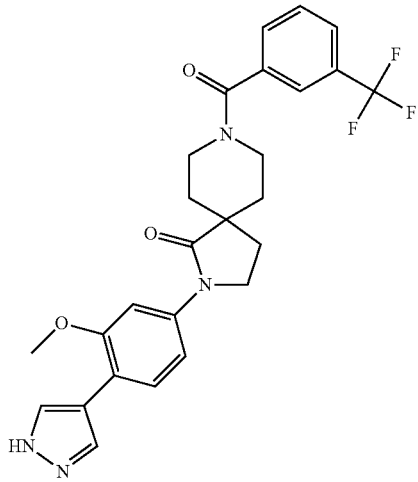 [SMILES: COc1cc(N2CCC3(CCN(C(=O)c4cccc(C(F)(F)F)c4)CC3)C2=O)ccc1-c1cn[nH]c1]

$^1$H NMR (500 MHz, DMSO-d$_6$) δ 8.01 (br s, 2H), 7.84 (br d, J=6.8 Hz, 1H), 7.78-7.68 (m, 3H), 7.63-7.55 (m, 2H), 7.14 (dd, J=8.4, 1.7 Hz, 1H), 4.38-4.20 (m, 1H), 3.93-3.77 (m, 5H), 3.58-3.46 (m, 3H), 2.14 (br d, J=5.5 Hz, 2H), 1.83-1.61 (m, 3H), 1.52 (br d, J=9.6 Hz, 1H); Anal. HPLC Retention time: 1.61 (Method 1); ROCK2 IC$_{50}$=144 nM.

Example 59: Preparation of 8-(4-chlorobenzyl)-2-[3-methoxy-4-(1H-pyrazol-4-yl)phenyl]-2,8-diazaspiro[4.5]decan-1-one

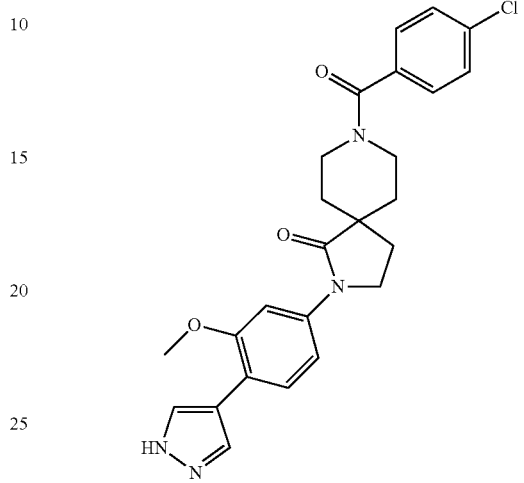

$^1$H NMR (500 MHz, DMSO-d$_6$) δ 8.02 (br s, 2H), 7.65-7.58 (m, 2H), 7.56-7.50 (m, 2H), 7.44 (br d, J=8.3 Hz, 2H), 7.15 (dd, J=8.5, 1.6 Hz, 1H), 4.36-4.25 (m, 1H), 3.93-3.79 (m, 5H), 3.31-3.09 (m, 2H), 2.14 (br s, 2H), 1.80-1.46 (m, 4H); Anal. HPLC Retention time: 1.56 (Method 2); ROCK2 IC$_{50}$=67 nM.

Example 60: Preparation of 2-[3-methoxy-4-(1H-pyrazol-4-yl)phenyl]-8-(4-phenoxybenzoyl)-2,8-diazapsiro[4.5]decan-1-one

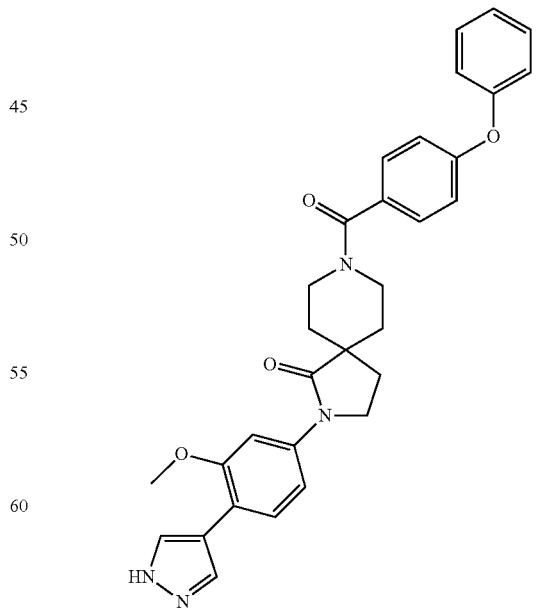

$^1$H NMR (500 MHz, DMSO-d$_6$) δ 8.02 (br s, 2H), 7.64-7.57 (m, 2H), 7.48-7.39 (m, 3H), 7.33 (s, 1H), 7.21 (t,

J=7.4 Hz, 1H), 7.15 (br d, J=8.6 Hz, 1H), 7.10 (br d, J=7.9 Hz, 2H), 7.03 (d, J=8.5 Hz, 2H), 4.36-4.18 (m, 1H), 3.91-3.81 (m, 5H), 3.50-3.39 (m, 1H), 3.34-3.07 (m, 1H), 3.02-2.87 (m, 1H), 2.14 (br s, 2H), 1.79-1.52 (m, 4H); Anal. HPLC Retention time: 1.8 (Method 1); ROCK2 IC$_{50}$=54 nM.

Example 61: Preparation of 8-{[1,1'-biphenyl]-4-carbonyl}-2-[3-methoxy-4-(1H-pyrazol-4-yl)phenyl]-2,8-diazaspiro[4.5]decan-1-one

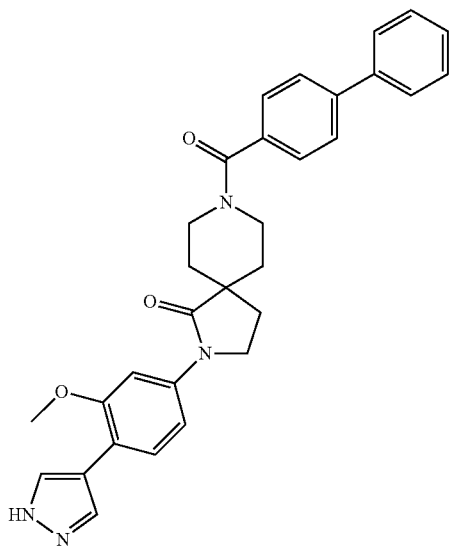 [SMILES: COc1cc(N2CCC3(CCN(C(=O)c4ccc(-c5ccccc5)cc4)CC3)C2=O)ccc1-c1cn[nH]c1]

$^1$H NMR (500 MHz, DMSO-d$_6$) δ 8.02 (br s, 2H), 7.76 (d, J=8.2 Hz, 2H), 7.72 (br d, J=7.5 Hz, 2H), 7.64-7.59 (m, 2H), 7.55-7.46 (m, 4H), 7.44-7.37 (m, 1H), 7.16 (dd, J=8.5, 1.7 Hz, 1H), 4.42-4.29 (m, 1H), 3.87 (s, 5H), 3.75-3.65 (m, 1H), 2.16 (br s, 2H), 1.76 (br s, 2H), 1.56 (br d, J=5.6 Hz, 1H); MS ESI m/z 507.2 (M+H); Anal. HPLC Retention time: 1.77 (Method 1); ROCK2 IC$_{50}$=18 nM.

Example 62: Preparation of 2-[3-methoxy-4-(1H-pyrazol-4-yl)phenyl]-8-(1-methyl-1H-pyrrole-2 carbonyl)-2,8-diazaspiro[4.5]decan-1-one

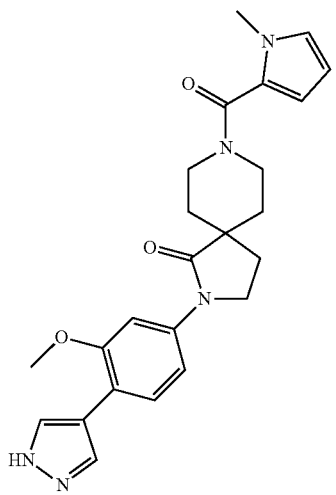 [SMILES: COc1cc(N2CCC3(CCN(C(=O)c4cccn4C)CC3)C2=O)ccc1-c1cn[nH]c1]

$^1$H NMR (500 MHz, DMSO-d$_6$) δ 8.02 (br s, 2H), 7.66-7.56 (m, 2H), 7.15 (dd, J=8.4, 1.6 Hz, 1H), 6.89 (s, 1H), 6.31 (br d, J=2.3 Hz, 1H), 6.04 (t, J=3.0 Hz, 1H), 4.22 (br d, J=13.0 Hz, 2H), 3.90-3.82 (m, 5H), 3.67 (s, 2H), 2.55 (s, 2H), 2.16 (br t, J=6.8 Hz, 2H), 1.79-1.67 (m, 2H), 1.60 (br d, J=13.0 Hz, 2H); MS ESI m/z 867.2 (M+H); Anal. HPLC Retention time: 1.35 (Method 2); ROCK2 IC$_{50}$=1430 nM.

Example 63: Preparation of 8-(furan-2-carbonyl)-2-[3-methoxy-4-(1H-pyrazol-4-yl)phenyl]-2,8-diazaspiro[4.5]decan-1-one

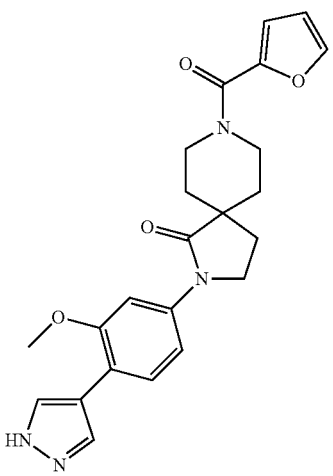 [SMILES: COc1cc(N2CCC3(CCN(C(=O)c4ccco4)CC3)C2=O)ccc1-c1cn[nH]c1]

$^1$H NMR (500 MHz, DMSO-d$_6$) δ 8.02 (s, 2H), 7.85 (s, 1H), 7.62 (dd, J=5.0, 3.2 Hz, 2H), 7.16 (dd, J=8.5, 1.8 Hz, 1H), 7.00 (d, J=3.3 Hz, 1H), 6.64 (dd, J=3.2, 1.6 Hz, 1H), 4.23 (br d, J=13.3 Hz, 2H), 3.76-3.09 (m, 4H), 2.17 (br t, J=6.8 Hz, 2H), 1.76 (s, 2H), 1.63 (br d, J=13.6 Hz, 2H); MS ESI m/z 421.2 (M+H); Anal. HPLC Retention time: 1.24 Method 2; ROCK2 IC$_{50}$=1690 nM.

Example 64: Preparation of 2-[3-methoxy-4-(1H-pyrazol-4-yl)phenyl]-8-(naphthalene-2-carbonyl)-2,8-diazaspiro[4.5]decan-1-one

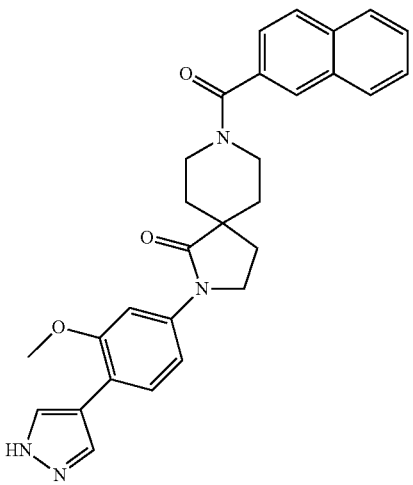 [SMILES: COc1cc(N2CCC3(CCN(C(=O)c4ccc5ccccc5c4)CC3)C2=O)ccc1-c1cn[nH]c1]

¹H NMR (500 MHz, DMSO-d₆) δ 8.07-7.94 (m, 6H), 7.65-7.57 (m, 4H), 7.53 (d, J=8.8 Hz, 1H), 7.16 (dd, J=8.5, 1.6 Hz, 1H), 4.44-4.35 (m, 1H), 4.27 (s, 1H), 3.93-3.81 (m, 5H), 2.16 (br s, 2H), 1.86-1.61 (m, 4H), 1.53 (br d, J=6.4 Hz, 1H); Anal. HPLC Retention time: 1.62 Method 1; ROCK2 IC$_{50}$=104 nM.

Example 65: Preparation of 8-(furan-3-carbonyl)-2-[3-methoxy-4-(1H-pyrazol-4-yl)phenyl]-2,8-diazaspiro[4.5]decan-1-one

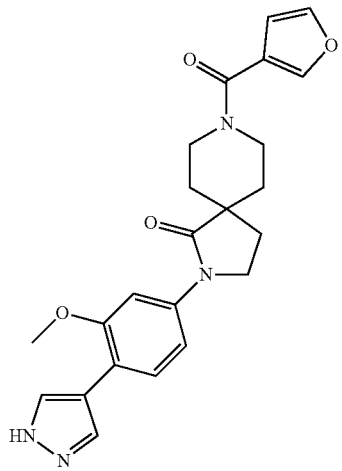 [SMILES: COc1cc(N2CCC3(CCN(C(=O)c4ccoc4)CC3)C2=O)ccc1-c1cn[nH]c1]

¹H NMR (500 MHz, DMSO-d₆) δ 8.17-7.93 (m, 5H), 7.78-7.68 (m, 3H), 7.63-7.56 (m, 2H), 7.15 (br d, J=8.2 Hz, 1H), 4.52 (br d, J=6.1 Hz, 1H), 4.26-4.16 (m, 1H), 3.86 (br s, 5H), 3.48 (br s, 2H), 2.15 (br s, 2H), 1.77-1.67 (m, 2H), 1.59 (br d, J=12.1 Hz, 2H); MS ESI m/z 421.2 (M+H); Anal. HPLC Retention time: 1.31 (Method 1); ROCK2 IC$_{50}$=752 nM.

Example 66: Preparation of 2-[3-methoxy-4-(1H-pyrazol-4-yl)phenyl]-8-(5-methylthiophene-2-carbonyl)-2,8-diazaspiro[4.5]decan-1-one

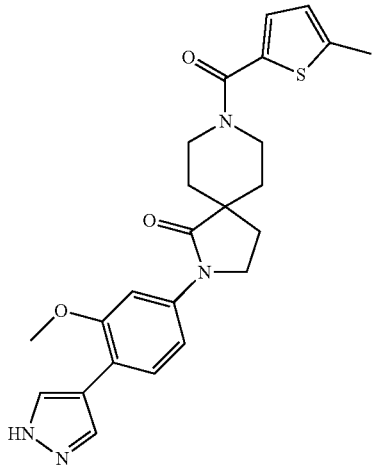 [SMILES: COc1cc(N2CCC3(CCN(C(=O)c4ccc(C)s4)CC3)C2=O)ccc1-c1cn[nH]c1]

¹H NMR (500 MHz, DMSO-d₆) δ 8.02 (br s, 2H), 7.66-7.57 (m, 2H), 7.23 (d, J=3.4 Hz, 1H), 7.16 (br d, J=8.2 Hz, 1H), 6.83 (br d, J=2.8 Hz, 1H), 4.19 (br d, J=11.1 Hz, 2H), 3.93-3.80 (m, 5H), 2.55 (s, 2H), 2.48 (s, 3H), 2.16 (br t, J=6.6 Hz, 2H), 1.79-1.71 (m, 2H), 1.62 (br d, J=13.5 Hz, 2H); MS ESI m/z 451.2 (M+H); Anal. HPLC Retention time: 1.49 (Method 2); ROCK2 IC$_{50}$=372 nM.

Example 67: Preparation of 2-[3-methoxy-4-(1H-pyrazol-4-yl)phenyl]-8-(thiophene-3-carbonyl)-2,8-diazaspiro[4.5]decan-1-one

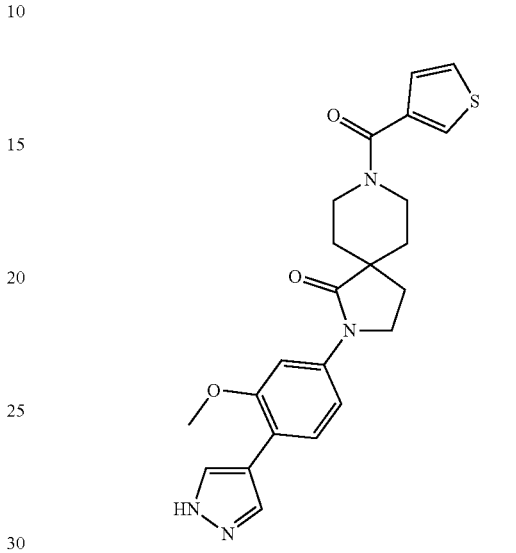

¹H NMR (500 MHz, DMSO-d₆) δ 8.02 (br s, 2H), 7.80 (d, J=1.7 Hz, 1H), 7.68-7.56 (m, 3H), 7.22 (d, J=4.9 Hz, 1H), 7.15 (dd, J=8.4, 1.7 Hz, 1H), 4.41-4.21 (m, 2H), 3.87 (s, 5H), 3.44-3.11 (m, 2H), 2.15 (br s, 2H), 1.75-1.52 (m, 4H); MS ESI m/z 437 (M+H); Anal. HPLC Retention time: 1.3 (Method 2); ROCK2 IC$_{50}$=382 nM.

Example 68: Preparation of 8-(1H-indole-2-carbonyl)-2-[3-methoxy-4-(1H-pyrazol-4-yl)phenyl]-2,8-diazaspiro[4.5]decan-1-one

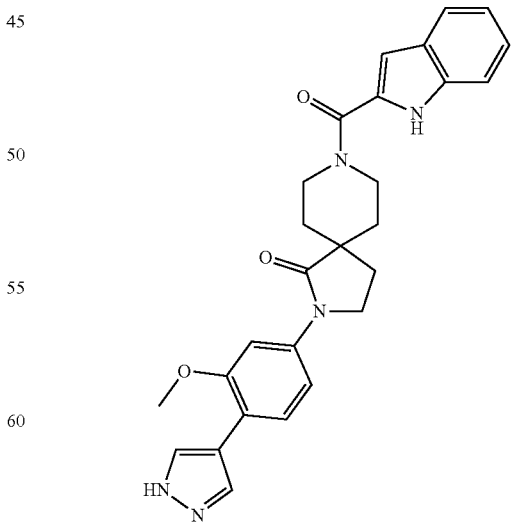

¹H NMR (500 MHz, DMSO-d₆) δ 11.56 (br s, 1H), 8.02 (br s, 2H), 7.61 (br dd, J=9.3,6.1 Hz, 3H), 7.44 (br d, J=8.2

Hz, 1H), 7.24-7.11 (m, 2H), 7.05 (br t, J=7.3 Hz, 1H), 6.81 (s, 1H), 4.36 (br d, J=13.2 Hz, 2H), 3.92-3.80 (m, 4H), 3.74-3.58 (m, 3H), 2.18 (br t, J=6.1 Hz, 2H), 1.84-1.75 (m, 2H), 1.65 (br d, J=12.7 Hz, 2H); MS ESI m/z 470.3 (M+H); Anal. HPLC Retention time: 1.55 (Method 1); ROCK2 IC$_{50}$=467 nM.

Example 69: Preparation of 8-(2H-1,3-benzodioxole-5-carbonyl)-2-[3-methoxy-4-(1H-pyrazol-4-yl)phenyl]-2,8-diazaspiro[4.5]decan-1-one

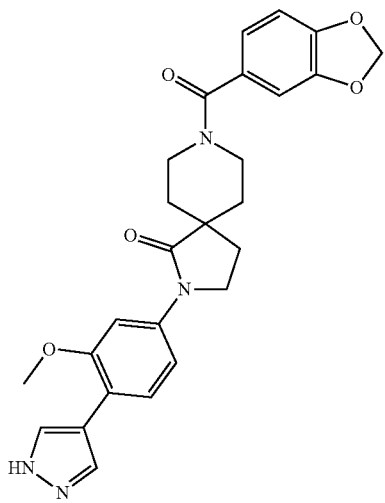 [SMILES: COc1cc(N2CCC3(CCN(C(=O)c4ccc5c(c4)OCO5)CC3)C2=O)ccc1-c1cn[nH]c1]

$^1$H NMR (500 MHz, DMSO-d$_6$) δ 8.02 (br s, 2H), 7.67-7.57 (m, 2H), 7.15 (br d, J=8.2 Hz, 1H), 7.03-6.95 (m, 2H), 6.93-6.89 (m, 1H), 6.08 (s, 2H), 4.07-3.99 (m, 1H), 3.94-3.81 (m, 6H), 3.51-3.32 (m, 1H), 3.26-3.09 (m, 1H), 2.14 (br s, 2H), 1.78-1.66 (m, 2H), 1.63-1.46 (m, 2H); MS ESI m/z 474.9 (M+H); Anal. HPLC Retention time: 1.35 (Method 2); ROCK2 IC$_{50}$=93 nM.

Example 70: Preparation of 8-(1-benzofuran-2-carbonyl)-2-[3-methoxy-4-(1H-pyrazol-4-yl)phenyl]-2,8-diazaspiro[4.5]decan-1-one

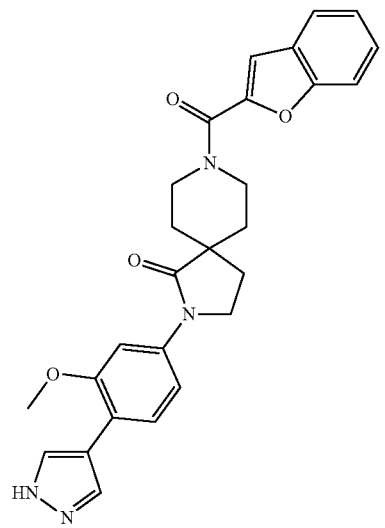 [SMILES: COc1cc(N2CCC3(CCN(C(=O)c4cc5ccccc5o4)CC3)C2=O)ccc1-c1cn[nH]c1]

$^1$H NMR (500 MHz, DMSO-d$_6$) δ 8.17-7.90 (m, 2H), 7.76 (d, J=7.6 Hz, 1H), 7.67 (d, J=8.2 Hz, 1H), 7.63-7.58 (m, 2H), 7.45 (t, J=7.5 Hz, 1H), 7.42 (s, 1H), 7.37-7.30 (m, 1H), 7.16 (br d, J=8.4 Hz, 1H), 4.93 (d, J=5.0 Hz, 1H), 4.70 (t, J=5.6 Hz, 1H), 3.91-3.87 (m, 5H), 3.17 (d, J=5.2 Hz, 2H), 2.19 (br t, J=6.3 Hz, 2H), 1.67 (br d, =13.5 Hz, 2H), 1.50 (br t, J=6.9 Hz, 2H); MS ESI m/z 471.2 (M+H); Anal. HPLC Retention time: 1.57 Method 1; ROCK2 IC$_{50}$=529 nM.

Example 71: Preparation of 2-[3-methoxy-4-(1H-pyrazol-4-yl)phenyl]-8-(pyrazine-2-carbonyl)-2,8-diazaspiro[4.5]decan-1-one

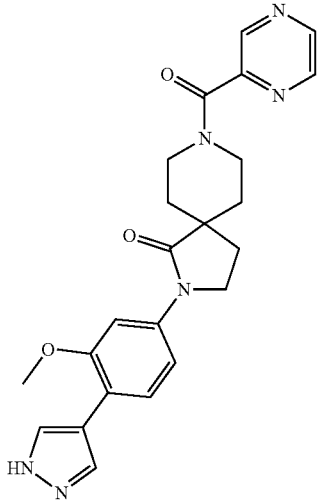 [SMILES: COc1cc(N2CCC3(CCN(C(=O)c4cnccn4)CC3)C2=O)ccc1-c1cn[nH]c1]

$^1$H NMR (500 MHz, DMSO-d$_6$) δ 8.86 (s, 1H), 8.75 (d, J=2.3 Hz, 1H), 8.69 (s, 1H), 8.02 (br s, 2H), 7.66-7.53 (m, 3H), 7.16 (br d, J=8.4 Hz, 1H), 4.37 (br d, J=13.3 Hz, 1H), 3.93-3.81 (m, 6H), 3.35-3.10 (m, 2H), 2.16 (dt, J=12.9.6.3 Hz, 2H), 1.86-1.74 (m, 2H), 1.69 (br d, J=13.7 Hz, 1H), 1.54 (br d, J=13.5 Hz, 1H); MS ESI m/z 433 (M+H); Anal. HPLC Retention time: 1.03 Method 2; ROCK2 IC$_{50}$=289 nM.

Example 72: Preparation of 2-[3-methoxy-4-(1H-pyrazol-4-yl)phenyl]-8-(6-methylpyridine-3-carbonyl)-2,8-diazaspiro[4.5]decan-1-one

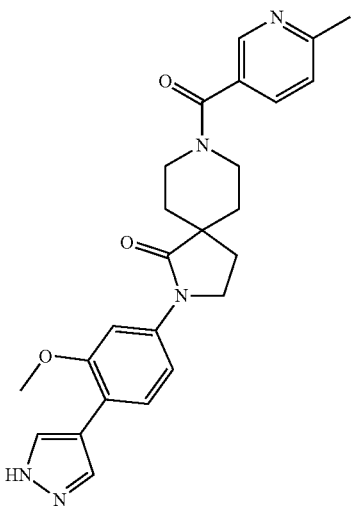

¹H NMR (500 MHz, DMSO-d₆) δ 8.47 (s, 1H), 8.01 (br s, 2H), 7.74 (dd, J=8.0, 1.9 Hz, 1H), 7.64-7.56 (m, 2H), 7.35 (d, J=8.0 Hz, 1H), 7.17-7.10 (m, 1H), 4.03 (dd, J=11.2, 4.2 Hz, 1H), 3.90-3.80 (m, 5H), 3.61 (br s, 1H), 3.37-3.22 (m, 2H), 2.14 (br d, J=6.2 Hz, 2H), 1.89 (s, 3H), 1.80-1.61 (m, 3H), 1.57-1.44 (m, 2H); MS ESI m/z 446 (M+H); Anal. HPLC Retention time: 1.12 (Method 2); ROCK2 IC$_{50}$=219 nM.

Example 73: Preparation of 2-[3-methoxy-4-(1H-pyrazol-4-yl)phenyl]-8-(pyridine-3-carbonyl)-2,8-diazaspiro[4.5]decan-1-one

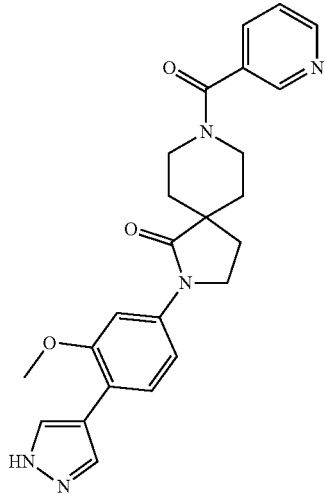 [SMILES: COc1cc(N2CCC3(CCN(C(=O)c4cccnc4)CC3)C2=O)ccc1-c1cn[nH]c1]

¹H NMR (500 MHz, DMSO-d₆) δ 8.69-8.64 (m, 1H), 8.62 (s, 1H), 8.02 (br s, 2H), 7.86 (br d, J=7.8 Hz, 1H), 7.65-7.57 (m, 2H), 7.50 (dd, J=7.6, 5.0 Hz, 1H), 7.15 (br d, J=8.4 Hz, 1H), 4.38-4.25 (m, 1H), 4.06-3.99 (m, 1H), 3.87 (s, 5H), 3.65-3.54 (m, 1H) 3.41 (br s, 1H), 2.15 (br d, J=6.0 Hz, 2H), 1.81-1.65 (m, 3H), 1.54 (br d, J=12.4 Hz, 1H); MS ESI m/z 432 (M+H); Anal. HPLC Retention time: 0.89 (Method 1); ROCK2 IC$_{50}$=414 nM.

Example 74: Preparation of 2-[3-methoxy-4-(1H-pyrazol-4-yl)phenyl]-8-(quinoline-3-carbonyl)-2,8-diazaspiro[4.5]decan-1-one

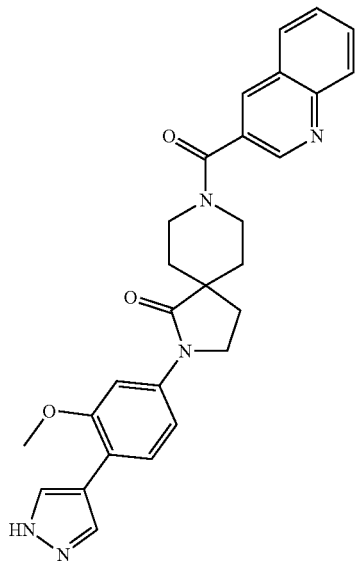 [SMILES: COc1cc(N2CCC3(CCN(C(=O)c4cnc5ccccc5c4)CC3)C2=O)ccc1-c1cn[nH]c1]

¹H NMR (500 MHz, DMSO-d₆) δ 8.92 (d, J=1.7 Hz, 1H), 8.50 (s, 1H), 8.09 (dd, J=11.8, 8.5 Hz, 2H), 8.02 (br s, 2H), 7.86 (t, J=7.3 Hz, 1H), 7.70 (t, J=7.4 Hz, 1H), 7.65-7.58 (m, 2H), 7.20-7.10 (m, 1H), 4.39 (br d, J=2.9 Hz, 1H), 3.92-3.82 (m, 5H), 3.71 (br d, J=9.3 Hz, 1H), 3.39-3.20 (m, 2H), 2.16 (br s, 2H), 1.82 (br s, 2H), 1.71 (br d, J=3.5 Hz, 1H), 1.61-1.51 (m, 1H)

MS ESI m/z 482.3 (M+H); Anal. HPLC Retention time: 1.16 (Method 1); ROCK2 IC$_{50}$=78 nM.

Example 75: Preparation of 8-(4-chloro-2-fluorobenzoyl)-2-[3-methoxy-4-(1H-pyrazol-4-yl)phenyl]-2,8-diazaspiro[4.5]decan-1-one

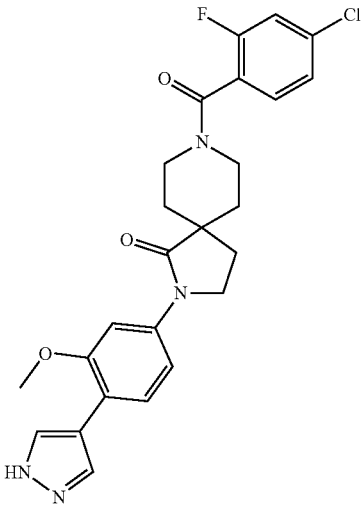 [SMILES: COc1cc(N2CCC3(CCN(C(=O)c4ccc(Cl)cc4F)CC3)C2=O)ccc1-c1cn[nH]c1]

¹H NMR (500 MHz, DMSO-d₆) δ 8.02 (br s, 2H), 7.65-7.56 (m, 3H), 7.47 (br s, 1H), 7.43-7.38 (m, 1H), 7.14 (br d, J=8.6 Hz, 1H), 4.35 (br d, J=13.5 Hz, 1H), 3.92-3.81 (m, 5H), 3.29-3.11 (m, 1H), 2.55 (s, 2H), 2.22-2.08 (m, 2H), 1.79-1.61 (m, 3H), 1.52 (br d, J=10.7 Hz, 1H); MS ESI m/z 483.18, 483.06 (M+H); ROCK2 IC$_{50}$=50 nM.

Example 76: Preparation of 8-(1-benzothiphene-2-carbonyl)-2-[3-methoxy-4-(1H-pyrazol-4-yl)phenyl]-2,8-diazaspiro[4.5]decan-1-one

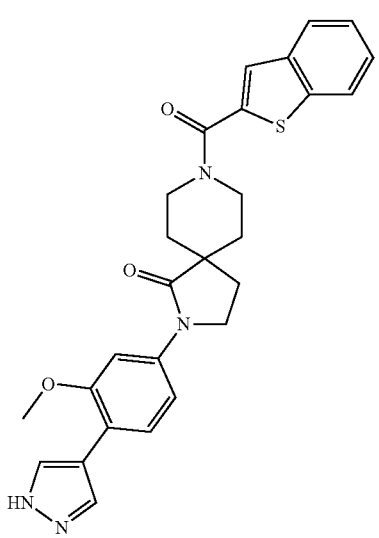 [SMILES: COc1cc(N2CCC3(CCN(C(=O)c4cc5ccccc5s4)CC3)C2=O)ccc1-c1cn[nH]c1]

¹H NMR (500 MHz, DMSO-d₆) δ 8.07-7.98 (m, 3H), 7.97-7.91 (m, 1H), 7.75 (s, 1H), 7.66-7.58 (m, 2H), 7.50-7.41 (m, 2H), 7.16 (dd, J=8.4, 1.8 Hz, 1H), 4.36-4.10 (m, 2H), 3.92-3.83 (m, 5H), 3.56-3.41 (m, 2H), 2.18 (br t, J=6.6 Hz, 2H), 1.85-1.75 (m, 2H), 1.66 (br d, J=13.4 Hz, 2H); MS ESI m/z 487.1 (M+H); Anal. HPLC Retention time: 1.68 (Method 2); ROCK2 IC₅₀=27 nM.

Example 77: Preparation of 2-[3-methoxy-4-(1H-pyrazol-4-yl)phenyl]-8-(1,2,3-thiadiazole-4-carbonyl)-2,8-diazaspiro[4.5]decan-1-one

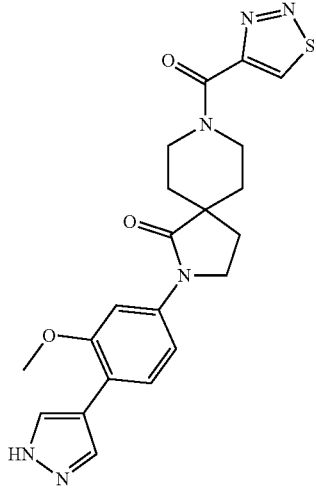 [SMILES: COc1cc(N2CCC3(CCN(C(=O)c4csnn4)CC3)C2=O)ccc1-c1cn[nH]c1]

¹H NMR (500 MHz, DMSO-d₆) δ 9.57 (s, 1H), 8.02 (br s, 2H), 7.67-7.53 (m, 2H), 7.16 (dd J=8.4, 1.6 Hz, 1H), 4.42 (br d, J=13.5 Hz, 1H), 3.93-3.84 (m, 5H), 3.42-3.21 (m, 2H), 3.17 (d, J=5.1 Hz, 1H), 2.22-2.10 (m, 2H), 1.85-1.75 (m, 2H), 1.71 (br d, J=13.0 Hz, 1H), 1.59 (br d, J=12.6 Hz, 1H); MS ESI m/z 439.2 (M+H); Anal. HPLC Retention time: 1.13 (Method 1); ROCK2 IC₅₀=453 nM.

Example 78: Preparation of 2-[3-methoxy-4-(1H-pyrazol-4-yl)phenyl]-8-[2-(pyridin-3-yl)-1,3-thiazole-4-carbonyl]-2,8-diazaspiro[4.5]decan-1-one

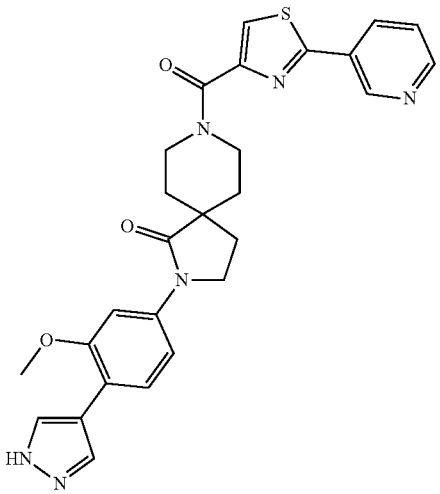

¹H NMR (500 MHz, DMSO-d₆) δ 9.17 (s, 1H), 8.70 (br d, J=3.9 Hz, 1H), 8.34 (br d, J=7.9 Hz, 1H), 8.26 (s, 1H), 8.02 (br s, 2H), 7.69-7.52 (m, 3H), 7.16 (br d, J=8.3 Hz, 1H), 4.39 (br d, J=10.4 Hz, 1H), 4.18 (br d, J=11.9 Hz, 1H), 3.95-3.81 (m, 5H), 3.74 (br d, J=4.1 Hz, 1H), 3.17 (br d, J=4.3 Hz, 1H), 2.19 (br d, J=6.1 Hz, 2H), 1.88-1.73 (m, 2H), 1.72-1.55 (m, 2H)
MS ESI m/z 515 (M+H); Anal. HPLC Retention time: 1.26 Method 2; ROCK2 IC₅₀=76 nM.

Example 79: Preparation of 2-[3-methoxy-4-(1H-pyrazol-4-yl)phenyl]-8-(5-methylpyrazine-2-carbonyl)-2,8-diazaspiro[4.5]decan-1-one

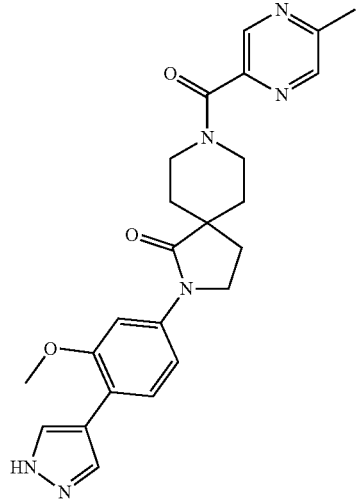

¹H NMR (500 MHz, DMSO-d₆) δ 8.72 (s, 1H), 8.57 (s, 1H), 8.02 (br s, 2H), 7.65-7.55 (m, 2H), 7.15 (dd, J=8.4, 1.6 Hz, 1H), 4.36 (br d, J=13.0 Hz, 1H), 3.96-3.80 (m, 5H), 3.74 (br d, J=13.3 Hz, 1H), 3.42 (br s, 1H), 3.21-3.12 (m, 1H), 2.51 (br s, 3H), 2.24-2.09 (m, 2H), 1.84-1.73 (m, 2H), 1.71-1.62 (m, 1H), 1.53 (br d, J=13.5 Hz, 1H); MS ESI m/z 447.1 (M+H); Anal. HPLC Retention time: 1.11 (Method 2); ROCK2 IC₅₀=110 nM.

Example 80: Preparation of 8-(2,6-dimethoxypyridine-3-carbonyl)-2-[3-methoxy-4-(1H-pyrazol-4-yl)phenyl]-2,8-diazaspiro[4.5]decan-1-one

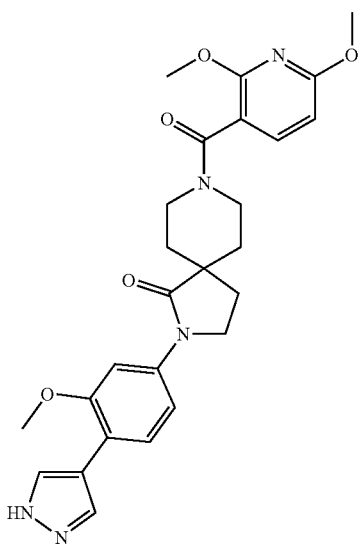

$^1$H NMR (500 MHz, DMSO-d$_6$) δ 8.02 (br s, 2H), 7.61 (br d, J=8.4 Hz, 3H), 7.14 (br d, J=8.3 Hz, 1H), 6.45 (d, J=8.0 Hz, 1H), 4.34 (br d, J=13.4 Hz, 1H), 4.10-3.99 (m, 1H), 3.94-3.82 (m, 1H), 3.17 (s, 1H), 3.12-3.03 (m, 1H), 2.14 (br d, J=5.5 Hz, 2H), 1.77-1.68 (m, 2H), 1.64-1.61 (m, 1H), 1.52-1.43 (m, 1H); MS ESI m/z 492.2 (M+H); Anal. HPLC Retention time: 1.44 (Method 1); ROCK2 IC$_{50}$=99 nM.

Example 81: Preparation of 2-[3-methoxy-4-(1H-pyrazol-4-yl)phenyl]-8-{5-oxo-2H,3H,5H-[1,3]thiazolo[3,2-a]pyrimidine-6-carbonyl}-2,8-diazaspiro[4.5]decan-1-one

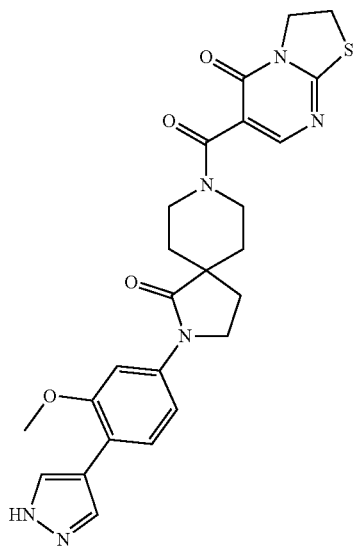 [SMILES: COc1cc(N2CCC3(CCN(C(=O)c4cnc5n(c4=O)CCS5)CC3)C2=O)ccc1-c1cn[nH]c1]

$^1$H NMR (500 MHz, DMSO-d$_6$) δ 8.02 (br s, 2H), 7.85 (s, 1H), 7.65-7.57 (m, 2H), 7.15 (br d, J=8.3 Hz, 1H), 4.40 (br t, J=7.9 Hz, 2H), 4.29 (br d, J=13.3 Hz, 1H), 4.03 (dd, J=11.1, 4.0 Hz, 1H), 3.90-3.81 (m, 5H), 3.61-3.52 (m, 1H), 3.06 (br t, J=11.0 Hz, 1H), 2.19-2.09 (m, 2H), 1.81-1.66 (m, 2H), 1.60 (br d, J=13.9 Hz, 1H), 1.65-1.57 (m, 1H), 1.54-1.49 (m, 1H), 1.51 (br d, J=13.0 Hz, 1H); MS ESI m/z 1013.2 (M+H); Anal. HPLC Retention time: 1.01 (Method 2); ROCK2 IC$_{50}$=57 nM.

Example 82: Preparation of 2-[3-methoxy-4-(1H-pyrazol-4-yl)phenyl]-8-(4-methylthiophene-2-carbonyl)-2,8-diazaspiro[4.5]decan-1-one

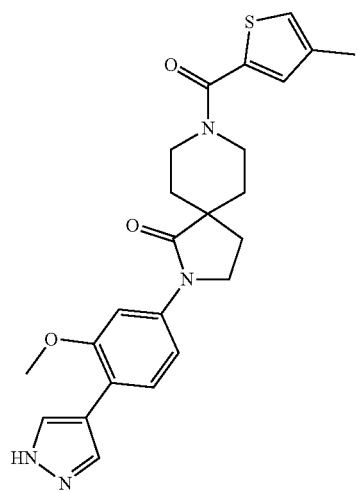

$^1$H NMR (500 MHz, DMSO-d$_6$) δ 8.02 (br s, 2H), 7.66-7.58 (m, 2H), 7.34 (s, 1H), 7.25 (s, 1H), 7.16 (dd, J=8.5, 1.6 Hz, 1H), 4.19 (br d, J=11.4 Hz, 2H), 3.94-3.84 (m, 5H), 3.62 (br d, J=5.1 Hz, 1H), 3.37 (br s, 1H), 2.24 (s, 3H), 2.16 (br t, J=6.8 Hz, 2H), 1.81-1.70 (m, 2H), 1.69-1.55 (m, 3H); MS ESI m/z 451.2 (M+H); Anal. HPLC Retention time: 1.47 (Method 1) ROCK2 IC$_{50}$=109 nM.

Example 83: Preparation of 8-(1,3-benzothiazole-6-carbonyl-2-[3-methoxy-4-(1H-pyrazol-4-yl)phenyl]-2,8-diazaspiro[4.5]decan-1-one

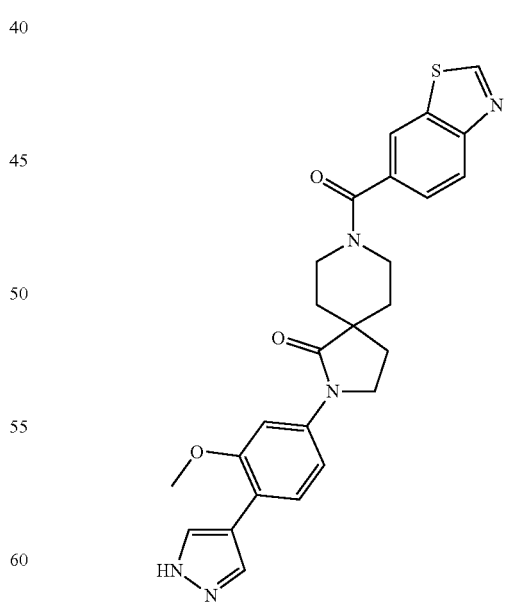

$^1$H NMR (500 MHz, DMSO-d$_6$) δ 9.47 (s, 1H), 8.28 (s, 1H), 8.15 (d, J=8.3 Hz, 1H), 8.02 (br s, 2H), 7.64-7.53 (m, 3H), 7.15 (br d, J=8.4 Hz, 1H), 4.44-4.32 (m, 1H), 3.86 (s, 5H), 3.52 (br s, 3H), 2.15 (br s, 2H), 1.72-1.62 (m, 1H), 1.57-1.44 (m, 1H), 1.25-1.05 (m, 2H); MS ESI m/z 488.1 (M+H); Anal. HPLC Retention time: 1.23 (Method 1); ROCK2 IC$_{50}$=26 nM.

Example 84: Preparation of 2-[3-methoxy-4-(1H-pyrazol-4-yl)phenyl]-8-(2-phenyl-1,3-thiazole-4-carbonyl)-2,8-diazaspiro[4.5]decan-1-one

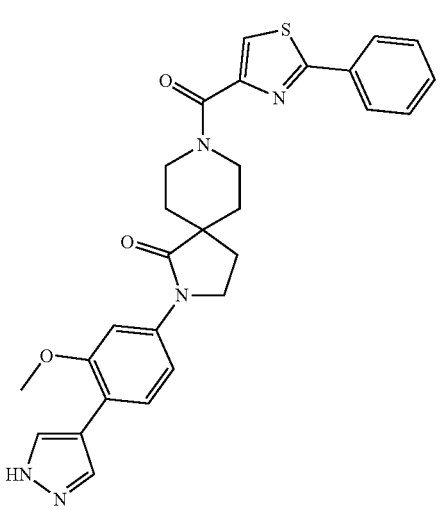 [SMILES: COc1cc(N2CCC3(CCN(C(=O)c4csc(-c5ccccc5)n4)CC3)C2=O)ccc1-c1cn[nH]c1]

$^1$H NMR (500 MHz, DMSO-d$_6$) δ 8.55-8.46 (m, 1H), 8.15 (s, 1H), 8.06 (br s, 11H), 8.00-7.93 (m, 2H), 7.65-7.58 (m, 2H), 7.53 (br d, J=5.4 Hz, 3H), 7.15 (br d, J=6.9 Hz, 1H), 4.38 (br d, J=9.8 Hz, 1H), 4.20 (br d, J=11.4 Hz, 1H), 3.86 (s, 5H), 3.61-3.48 (m, 1H), 3.46-3.34 (m, 1H), 2.18 (br d, J=4.0 Hz, 2H), 1.91-1.73 (m, 2H), 1.72-1.53 (m, 2H); MS ESI m/z 514.3 (M+H); Anal. HPLC Retention time: 1.65 (Method 1); ROCK2 IC$_{50}$=138 nM.

Example 85: Preparation of 2-[3-methoxy-4-(1H-pyrazol-4-yl)phenyl]-8-(5-phenylfuran-2-carbonyl)-2,8-diazaspiro[4.5]decan-1-one

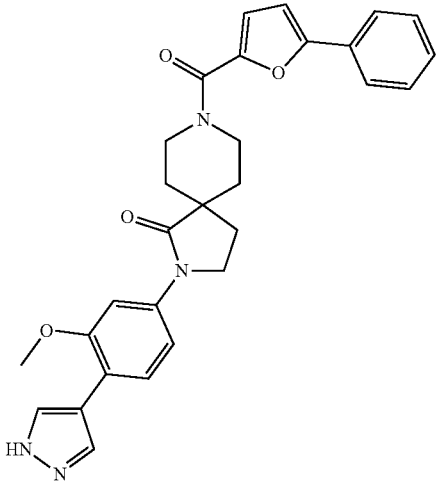 [SMILES: COc1cc(N2CCC3(CCN(C(=O)c4ccc(-c5ccccc5)o4)CC3)C2=O)ccc1-c1cn[nH]c1]

$^1$H NMR (500 MHz, DMSO-d$_6$) δ 8.09-7.95 (m, 2H), 7.78 (br d, J=7.7 Hz, 2H), 7.62 (br d, J=6.1 Hz, 2H), 7.48 (t, J=7.6 Hz, 2H), 7.38 (br d, J=7.3 Hz, 1H), 7.20-7.10 (m, 3H), 4.32 (br d, =13.4 Hz, 2H), 4.23-4.14 (m, 1H), 4.03 (dd, J=11.3, 4.0 Hz, 1H), 3.92-3.86 (m, 5H), 2.19 (br t, J=6.8 Hz, 2H), 1.91-1.77 (m, 2H), 1.68 (br d, J=12.8 Hz, 2H); MS ESI m/z 497.1 (M+H); Anal. HPLC Retention time: 1.69 (Method 1); ROCK2 IC$_{50}$=851 nM.

Example 86: Preparation of 2-[3-methoxy-4-(1H-pyrazol-4-yl)phenyl]-8-(1,3-thiazole-4-carbonyl)-2,8-diazaspiro[4.5]decan-1-one

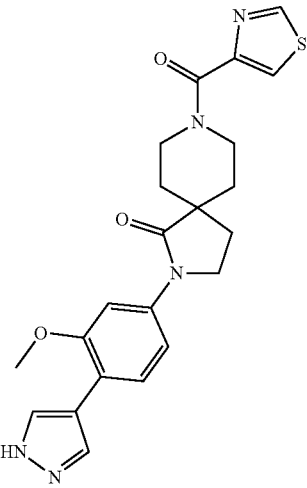 [SMILES: COc1cc(N2CCC3(CCN(C(=O)c4cscn4)CC3)C2=O)ccc1-c1cn[nH]c1]

$^1$H NMR (500 MHz, DMSO-d$_6$) δ 9.14 (s, 1H), 8.13 (d, J=1.4 Hz, 1H), 8.08-7.91 (m, 2H), 7.66-7.53 (m, 2H), 7.14 (br d, J=8.3 Hz, 1H), 4.35 (br d, J=11.6 Hz, 1H), 4.11-3.99 (m, 1H), 3.92-3.79 (m, 3H), 3.66 (br s, 2H), 3.33 (br s, 1H), 3.14-3.04 (m, 1H), 2.16 (br d, J=7.2 Hz, 2H), 1.75 (br t, J=10.9 Hz, 2H), 1.65 (br d, J=13.7 Hz, 1H), 1.55 (br d, J=11.8 Hz, 1H); MS ESI m/z 438 (M+H); Anal. HPLC Retention time: 1.09 (Method 2); ROCK2 IC$_{50}$=443 nM.

Example 87: Preparation of 2-[3-methoxy-4-(1H-pyrazol-4-yl)phenyl]-8-[6-(trifluoromethyl)pyridine-3-carbonyl]-2,8-diazaspiro[4.5]decan-1-one

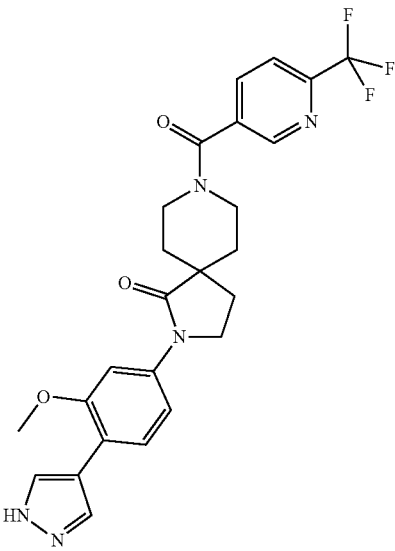 [SMILES: COc1cc(N2CCC3(CCN(C(=O)c4ccc(C(F)(F)F)nc4)CC3)C2=O)ccc1-c1cn[nH]c1]

$^1$H NMR (500 MHz, DMSO-d$_6$) δ 8.83 (s, 1H), 8.16 (br d, J=7.4 Hz, 1H), 8.01 (br d, J=8.0 Hz, 3H), 7.65-7.56 (m,

2H), 7.20-7.09 (m, 1H), 4.34 (br d, J=11.2 Hz, 1H), 4.03 (dd, J=11.1, 4.2 Hz, 1H), 3.94-3.79 (m, 5H), 3.37-3.17 (m, 2H), 2.14 (dt, J=13.1, 6.8 Hz, 2H), 1.86-1.65 (m, 3H), 1.54 (br d, J=13.3 Hz, 1H); MS ESI m/z 500.2 (M+H); Anal. HPLC Retention time: 1.42 (Method 1); ROCK2 IC$_{50}$=557 nM.

Example 88: Preparation of N-(4-{2-[3-methoxy-4-(1H-pyrazol-4-yl)phenyl]-1-oxo-2,8-diazaspiro[4.5]decane-8-carbonyl}phenyl)acetamide

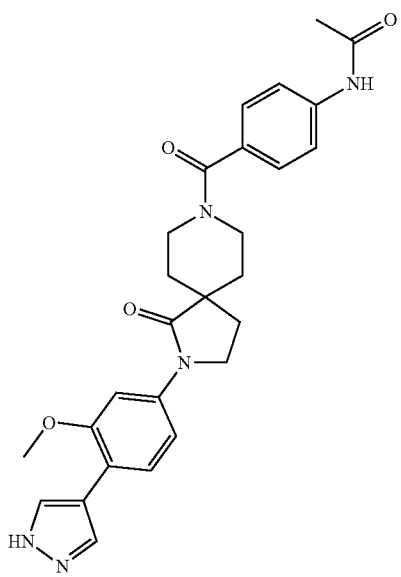

$^1$H NMR (500 MHz, DMSO-d$_6$) δ 10.16 (s, 1H), 8.02 (br s, 2H), 7.70-7.56 (m, 4H), 7.36 (d, J=8.4 Hz, 2H), 7.14 (br d, J=8.5 Hz, 1H), 4.37-4.22 (m, 2H), 3.86 (s, 5H), 3.50 (br s, 1H), 3.32-3.04 (m, 1H), 2.14 (br s, 2H), 2.06 (s, 3H), 1.78-1.65 (m, 2H), 1.65-1.47 (m, 2H); MS ESI m/z 488 (M+H); Anal. HPLC Retention time: 1.1 (Method 2); ROCK2 IC$_{50}$=73 nM.

Example 89: Preparation of 2-[3-methoxy-4-(1H-pyrazol-4-yl)phenyl]-8-(thiophene-2-carbonyl)-2,8-diazaspiro[4.5]decan-1-one

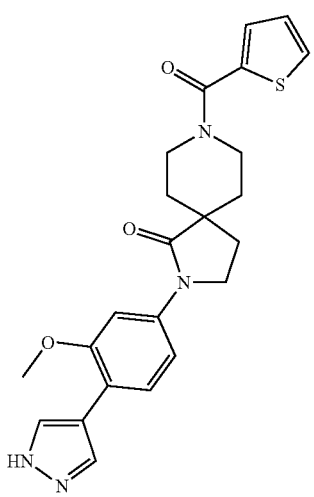 [SMILES: COc1cc(N2CCC3(CCN(C(=O)c4cccs4)CC3)C2=O)ccc1-c1cn[nH]c1]

$^1$H NMR (500 MHz, DMSO-d$_6$) δ 8.19-7.88 (m, 2H), 7.76 (d, J=5.0 Hz, 1H), 7.66-7.57 (m, 2H), 7.42 (d, J=3.4 Hz, 1H), 7.19-7.09 (m, 2H), 4.19 (br s, 2H), 3.91-3.83 (m, 5H), 3.52-3.37 (m, 2H), 2.16 (br t, J=6.8 Hz, 2H), 1.82-1.70 (m, 2H), 1.62 (br d, J=13.3 Hz, 2H); MS ESI m/z 437.2 (M+H); Anal. HPLC Retention time: 1.33 (Method 1); ROCK2 IC$_{50}$=117 nM.

Example 90: Preparation of 2-[3-methoxy-4-(1H-pyrazol-4-yl)phenyl]-8-(4-methoxyisoquinoline-1-carbonyl)-2,8-diazaspiro[4.5]decan-1-one

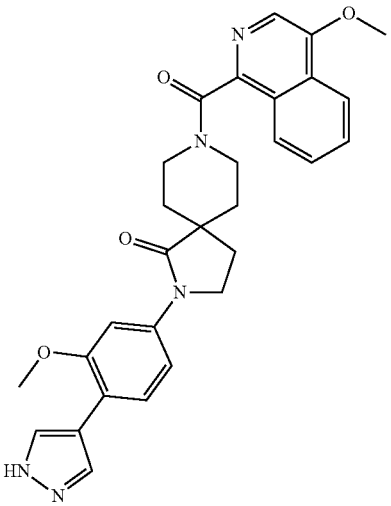

$^1$H NMR (500 MHz, DMSO-d$_6$) δ 8.27-8.16 (m, 2H), 8.01 (br s, 2H), 7.93 (br d, J=8.2 Hz, 1H), 7.84 (br d, J=7.9 Hz, 1H), 7.78 (br d, J=7.6 Hz, 1H), 7.60 (br d, J=5.2 Hz, 2H), 7.14 (br d, J=7.6 Hz, 1H), 4.52 (br d, J=13.1 Hz, 1H), 4.11 (s, 3H), 3.93-3.80 (m, 5H), 3.35-3.23 (m, 2H), 3.16 (br t, J=11.3 Hz, 1H), 2.26-2.17 (m, 1H), 2.16-2.05 (m, 1H), 1.94-1.81 (m, 1H), 1.74 (br d, J=13.1 Hz, 1H), 1.67 (br t, J=10.2 Hz, 1H), 1.43 (br d, J=13.1 Hz, 1H); MS ESI m/z 512 (M+H); Anal. HPLC Retention time: 1.48 (Method 1); ROCK2 IC$_{50}$=127 nM.

Example 91: Preparation of 2-[3-methoxy-4-(1H-pyrazol-4-yl)phenyl]-8-[(1R,2R)-2-phenylcyclopropanecarbonyl]-2,8-diazaspiro[4.5]decan-1-one

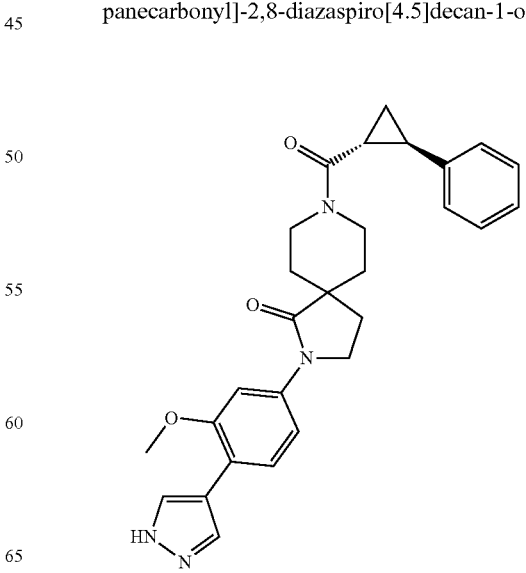

¹H NMR (500 MHz, DMSO-d₆) δ 8.02 (br s, 2H), 7.63-7.53 (m, 2H), 7.30-7.23 (m, 2H), 7.19 (br d, J=7.4 Hz, 3H), 7.13 (br t, J=7.1 Hz, 1H), 4.24 (br s, 1H), 4.13 (br t. J=14.2 Hz, 1H), 3.88-3.80 (m, 5H), 3.56-3.44 (m, 2H), 3.39-3.25 (m, 1H), 2.93 (br d, J=9.9 Hz, 1H), 2.30 (dt, J=19.3, 7.7 Hz, 2H), 2.13 (br s, 2H), 1.68-1.54 (m, 3H), 1.43 (br dd, J=9.0, 4.3 Hz, 1H); MS ESI m/z 471 (M+H); Anal. HPLC Retention time: 1.62 (Method 1); ROCK2 IC₅₀=436 nM.

Example 92: Preparation of 2-[3-methoxy-4-(1H-pyrazol-4-yl)phenyl]-8-[4-(propan-2-yl)benzoyl]-2,8-diazaspiro[4.5]decan-1-one

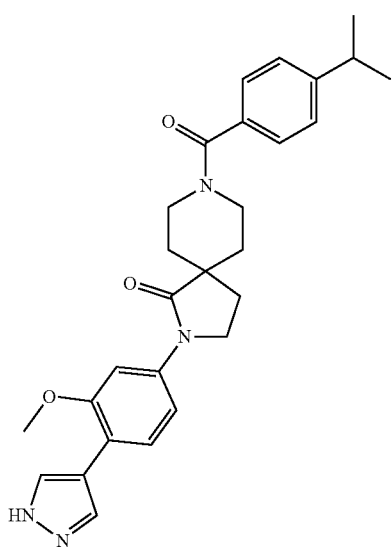

¹H NMR (500 MHz, DMSO-d₆) δ 8.02 (br s, 2H), 7.61 (dd, J=4.9, 3.3 Hz, 2H), 7.33 (s, 3H), 7.15 (dd, J=8.5.1.4 Hz, 1H), 4.37-4.29 (m, 1H), 4.21 (br d, J=11.8 Hz, 1H), 3.87 (s, 4H), 3.50-3.38 (m, 1H), 3.27-3.09 (m, 1H), 2.93 (quin, J=6.9 Hz, 1H). 2.15 (br d, J=6.3 Hz, 2H), 1.80-1.47 (m, 4H), 1.22 (d, J=7.0 Hz, 6H); MS ESI m/z 473.1 (M+H); Anal. HPLC Retention time: 1.76 Method 2; ROCK2 IC₅₀=12 nM.

Example 93: Preparation of 8-{6-bromopyrazolo[1,5-a]pyrimidine-2-carbonyl}-2-[3-methoxy-4-(1H-pyrazol-4-yl)phenyl]-2,8-diazaspiro[4.5]decan-1-one

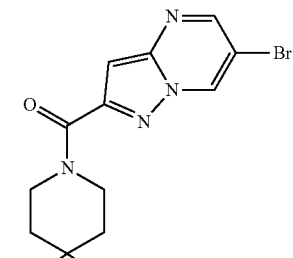

¹H NMR (500 MHz, DMSO-d₆) δ 9.62 (d, J=1.2 Hz, 1H), 8.70 (d, J=2.0 Hz, 1H), 8.19-7.88 (m, 2H), 7.70-7.53 (m, 2H), 7.15 (dd, J=8.4, 1.6 Hz, 1H), 7.02 (s, 1H), 4.39 (br d, J=13.0 Hz, 1H), 4.13 (br d, J=13.8 Hz, 1H), 3.94-3.77 (m, 5H), 3.42-3.31 (m, 1H), 3.22-3.16 (m, 1H), 2.21-2.10 (m, 2H), 1.82-1.72 (m, 2H), 1.71-1.64 (m, 1H), 1.56 (br d, J=13.0 Hz, 1H); MS ESI m/z 550.1 (M+H); Anal. HPLC Retention time: 1.35 (Method 1); ROCK2 IC₅₀=5 nM.

Example 94: Preparation of 2-[3-methoxy-4-(1H-pyrazol-4-yl)phenyl]-8-[4-(morpholin-4-yl)benzoyl]-2,8-diazaspiro[4.5]decan-1-one

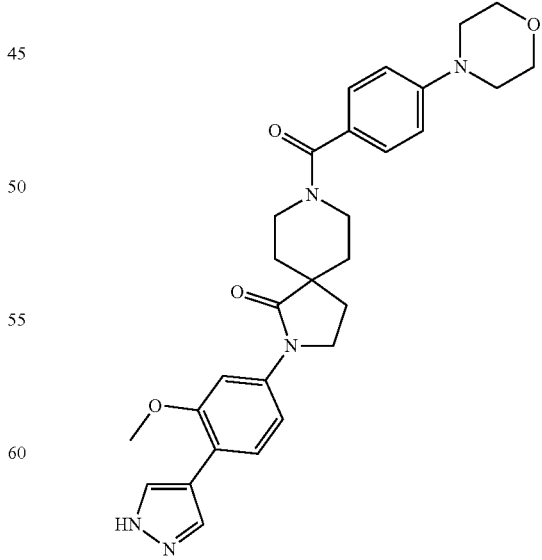

¹H NMR (500 MHz, DMSO-d₆) δ 8.02 (br s, 2H), 7.68-7.56 (m, 2H), 7.31 (br d, J=8.6 Hz, 2H), 7.20-7.10 (m,

1H), 6.98 (br d, J=8.7 Hz, 2H), 4.08-3.99 (m, 2H), 3.92-3.81 (m, 5H), 3.78-3.66 (m, 4H), 3.37 (br s, 2H), 3.22-3.11 (m, 4H), 2.14 (br t, J=6.6 Hz, 2H), 1.71 (br d, J=9.6 Hz, 2H), 1.59 (br s, 3H); MS ESI m/z 516 (M+H); Anal. HPLC Retention time: 1.33 (Method 2); ROCK2 IC$_{50}$=2 nM.

Example 95: Preparation of 8-[4-(1H-imidazol-1-yl)benzoyl]-2-[3-methoxy-4-(1H-pyrazol-4-yl)phenyl]-2,8-diazaspiro[4.5]decan-1-one

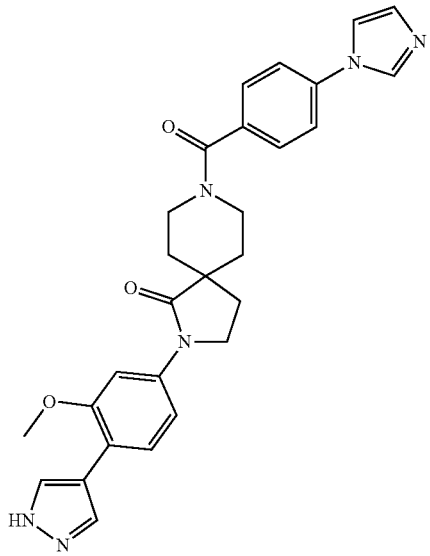 [SMILES: COc1cc(N2CCC3(CCN(C(=O)c4ccc(-n5ccnc5)cc4)CC3)C2=O)ccc1-c1cn[nH]c1]

$^1$H NMR (500 MHz, DMSO-d$_6$) δ 8.35 (s, 1H), 8.02 (br s, 2H), 7.83 (s, 1H), 7.76 (br d, J=8.3 Hz, 2H), 7.61 (br d, J=7.3 Hz, 2H), 7.57 (br d, J=8.4 Hz, 2H), 7.18-7.11 (m, 2H), 4.35 (br d, J=11.6 Hz, 2H), 3.87 (s, 5H), 3.72-3.60 (m, 2H), 2.16 (br s, 2H), 1.89-1.72 (m, 2H), 1.67 (br d, J=8.6 Hz, 1H), 1.55 (br d, J=6.0 Hz, 1H); MS ESI m/z 497 (M+H); Anal. HPLC Retention time: 1.16 (Method 2), ROCK2 IC$_{50}$=13 nM.

Example 96: Preparation of 4-{2-[3-methoxy-4-(1H-pyrazol-4-yl)phenyl]-1-oxo-2,8-diazaspiro[4.5]decane-8-carbonyl}pyridin-1-ium-1-olate

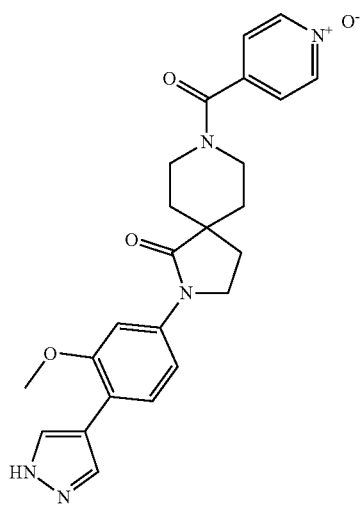

$^1$H NMR (500 MHz, DMSO-d$_6$) δ 8.27 (d, J=6.7 Hz, 2H), 8.02 (br s, 2H), 7.60 (d, J=8.4 Hz, 1H), 7.57 (d, J=1.4 Hz, 1H), 7.49 (d, J=6.7 Hz, 2H), 7.14 (dd, J=8.5, 1.6 Hz, 1H), 4.02 (dd, J=11.1, 4.0 Hz, 2H), 3.89-3.81 (m, 5H), 3.31 (dt, J=17.1, 6.3 Hz, 1H), 3.16 (br d, J=4.9 Hz, 1H), 2.13 (br d, J=4.6 Hz, 2H), 1.75 (br d, J=14.5 Hz, 2H), 1.69-1.59 (m, 1H), 1.59-1.44 (m, 1H); MS ESI m/z 448 (M+H); Anal. HPLC Retention time: 0.87 (Method 1); ROCK2 IC$_{50}$=1095 nM.

Example 97: Preparation of 2-[3-methoxy-4-(1H-pyrazol-4-yl)phenyl]-8-(1,2-oxazole-5-carbonyl)-2,8-diazaspiro[4.5]decan-1-one

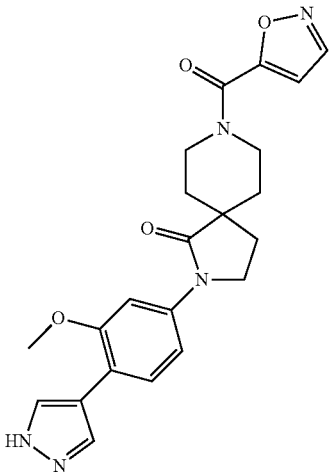 [SMILES: COc1cc(N2CCC3(CCN(C(=O)c4ccno4)CC3)C2=O)ccc1-c1cn[nH]c1]

$^1$H NMR (500 MHz, DMSO-d$_6$) δ 8.01 (br s, 2H), 7.60 (br d, J=8.4 Hz, 1H), 7.15 (br dd, J=16.7, 8.0 Hz, 2H), 6.86 (br d, J=8.5 Hz, 1H), 4.46 (br d, J=6.1 Hz, 1H), 4.35 (br d, J=3.2 Hz, 1H), 3.75 (br s, 5H), 3.43-3.27 (m, 2H), 2.15 (br d, J=5.8 Hz, 2H), 1.80-1.70 (m, 3H), 1.63 (br s, 1H); MS ESI m/z 422.2 (M+H); Anal. HPLC Retention time: 1.13 (Method 1); ROCK2 IC$_{50}$=427 nM.

Example 98: Preparation of 2-[3-methoxy-4-(1H-pyrazol-4-yl)phenyl]-8-[5-(trifluoromethyl)pyridine-2-carbonyl]-2,8-diazaspiro[4.5]decan-1-one

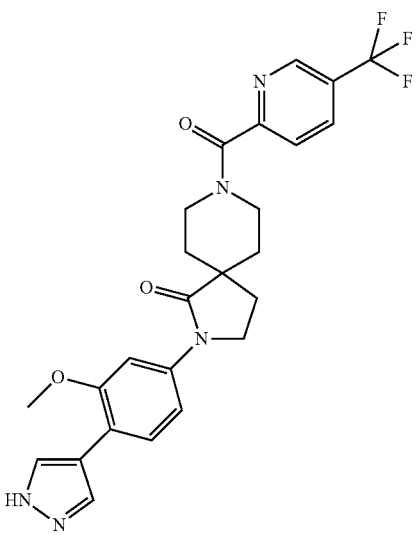 [SMILES: COc1cc(N2CCC3(CCN(C(=O)c4ccc(C(F)(F)F)cn4)CC3)C2=O)ccc1-c1cn[nH]c1]

¹H NMR (500 MHz, DMSO-d₆) δ 9.02 (s, 1H), 8.37 (br d, J=7.9 Hz, 1H), 8.02 (br s, 2H), 7.82 (d, J=8.2 Hz, 1H), 7.65-7.56 (m, 2H), 7.16 (br d, J=8.3 Hz, 1H), 4.37 (br d, J=13.1 Hz, 1H), 3.96-3.80 (m, 5H), 3.59 (br d, J=12.7 Hz, 1H), 3.27-3.16 (m, 2H), 2.25-2.09 (m, 2H), 1.87-1.74 (m, 2H), 1.68-1.65 (m, 1H), 1.52 (br d, J=13.8 Hz, 1H); MS ESI m/z 500.2 (M+H); Anal. HPLC Retention time: 1.43 (Method 1); ROCK2 IC₅₀=259 nM.

Example 99: Preparation of 2-[3-methoxy-4-(1H-pyrazol-4-yl)phenyl]-8-(2-methoxypyrimidine-5-carbonyl)-2,8-diazaspiro[4.5]decan-1-one

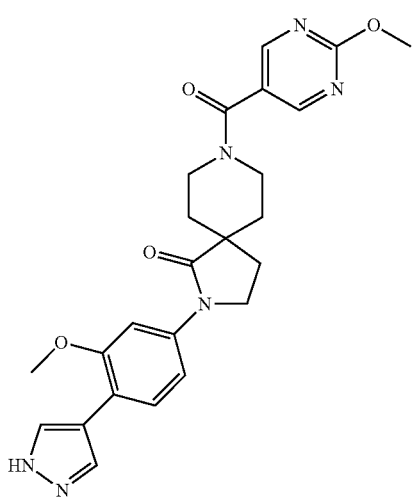 [SMILES: COc1ncc(C(=O)N2CCC3(CC2)CCN(c2ccc(-c4cn[nH]c4)c(OC)c2)C3=O)cn1]

¹H NMR (500 MHz, DMSO-d₆) δ 8.72 (s, 2H), 8.16-7.89 (m, 2H), 7.66-7.55 (m, 2H), 7.15 (dd, J=8.4, 1.6 Hz, 1H), 4.30 (br d, J=8.2 Hz, 1H), 3.97 (s, 3H), 3.87 (s, 5H), 3.73-3.62 (m, 1H), 3.49-3.32 (m, 1H), 3.17 (br d, J=5.2 Hz, 1H), 2.14 (br s, 2H), 1.77 (br s, 2H), 1.69-1.49 (m, 2H); MS ESI m/z 463.2 (M+H); Anal. HPLC Retention time: 1.1 (Method 2); ROCK2 IC₅₀=464 nM.

Example 100: Preparation of 8-(5-cyclopropyl-1,2-oxazole-3-carbonyl)-2-[3-methoxy-4-(1H-pyrazol-4-yl)phenyl]-2,8-diazaspiro[4.5]decan-1-one

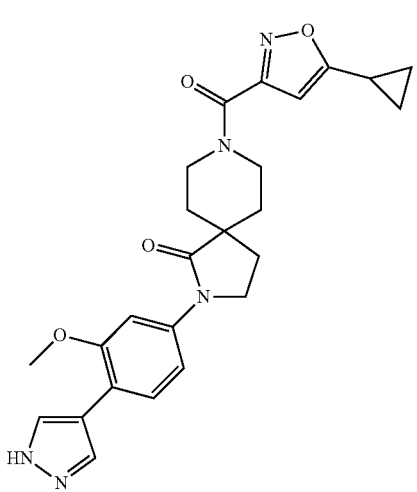 [SMILES: COc1cc(N2CCC3(CCN(C(=O)c4cc(C5CC5)on4)CC3)C2=O)ccc1-c1cn[nH]c1]

¹H NMR (500 MHz, DMSO-d₆) δ 8.02 (br s, 2H), 7.69-7.56 (m, 2H), 7.15 (br d, J=8.3 Hz, 1H), 6.44 (s, 1H), 4.31 (br d, J=13.1 Hz, 1H), 3.96-3.75 (m, 7H), 3.47-3.09 (m, 2H), 2.30-2.05 (m, 4H), 1.67-1.53 (m, 2H); MS ESI m/z 462.2 (M+H); Anal. HPLC Retention time: 1.42 (Method 1); ROCK2 IC₅₀=6 nM.

Example 101: Preparation of 2-[3-methoxy-4-(1H-pyrazol-4-yl)phenyl]-8-(5-methoxypyrazine-2-carbonyl)-2,8-diazaspiro[4.5]decan-1-one

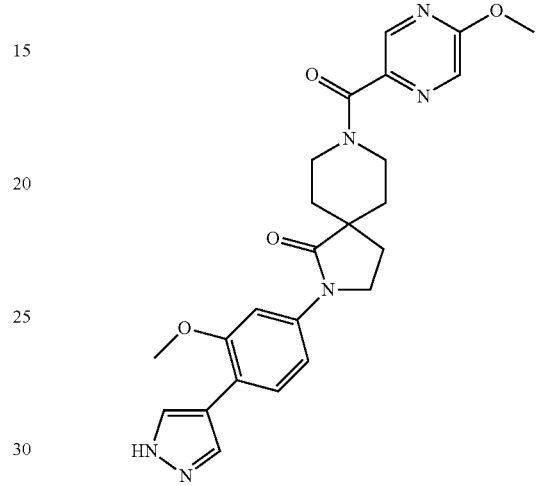

¹H NMR (500 MHz, DMSO-d₆) δ 8.47 (s, 1H), 8.31 (s, 1H), 8.02 (br s, 2H), 7.71-7.55 (m, 2H), 7.15 (dd, J=8.4, 1.6 Hz, 1H), 4.35 (br d, J=12.8 Hz, 1H), 3.96 (s, 3H), 3.86 (s, 6H), 3.44 (br s, 2H), 3.38-3.36 (m, 1H), 2.20-2.06 (m, 2H), 1.83-1.72 (m, 2H), 1.66 (br d, J=13.5 Hz, 1H), 1.53 (br d, J=12.5 Hz, 1H); MS ESI m/z 463 (M+H); Anal. HPLC Retention time: 1.22 (Method 1); ROCK2 IC₅₀=86 nM.

Example 102: Preparation of 8-(2,3-dihydro-1-benzofuran-2-carbonyl)-2-[3-methoxy-4-(1H-pyrazol-4-yl)phenyl]-2,8-diazaspiro[4.5]decan-1-one

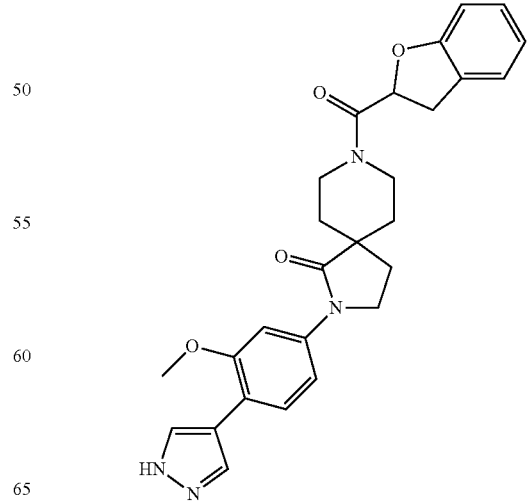

¹H NMR (500 MHz, DMSO-d₆) δ 8.02 (br s, 2H), 7.69-7.54 (m, 2H), 7.24 (br t, J=7.9 Hz, 1H), 7.16 (br d, J=8.2 Hz, 1H), 7.11 (s, 1H), 6.85 (s, 1H), 6.80 (s, 1H), 5.76-5.57 (m, 1H), 4.23 (br d, J=4.7 Hz, 1H), 4.01 (br d, J=13.4 Hz, 1H), 3.93-3.79 (m, 5H), 3.48-3.30 (m, 1H), 3.07-2.91 (m, 1H), 2.17 (br t, J=6.8 Hz, 2H), 1.83 (br s, 2H), 1.73-1.50 (m, 4H); MS ESI m/z 473.2 (M+H); Anal. HPLC Retention time: 1.48 (Method 2); ROCK2 IC$_{50}$=1966 nM.

Example 103: Preparation of 8-(4-fluoro-3-methyl-benzoyl)-2-[3-methoxy-4-(1H-pyrazol-4-yl)phenyl]-2,8-diazaspiro[4.5]decan-1-one

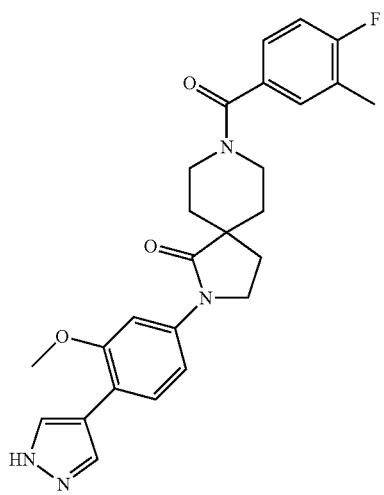 [SMILES: COc1cc(N2CCC3(CCN(C(=O)c4ccc(F)c(C)c4)CC3)C2=O)ccc1-c1cn[nH]c1]

¹H NMR (500 MHz, DMSO-d₆) δ 8.02 (br s, 2H), 7.66-7.55 (m, 2H), 7.36 (br d, J=6.7 Hz, 1H), 7.31-7.25 (m, 1H), 7.23-7.18 (m, 1H), 7.15 (dd, J=8.5, 1.5 Hz, 1H), 4.40-4.22 (m, 1H), 3.87 (s, 5H), 3.63-3.43 (m, 2H), 3.36-3.33 (m, 1H), 2.27 (s, 3H), 2.14 (br s, 2H), 1.73 (br s, 2H), 1.67-1.48 (m, 2H); MS ESI m/z 463 (M+H); Anal. HPLC Retention time: 1.51 (Method 1); ROCK2 IC$_{50}$=96 nM.

Example 104: Preparation of 2-[3-methoxy-4-(1H-pyrazol-4-yl)phenyl]-8-(5-methyl-1,2-oxazole-3-carbonyl)-2,8-diazaspiro[4.5]decan-1-one

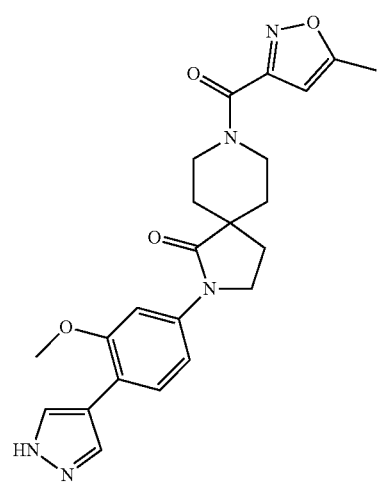 [SMILES: COc1cc(N2CCC3(CCN(C(=O)c4cc(C)on4)CC3)C2=O)ccc1-c1cn[nH]c1]

¹H NMR (500 MHz, DMSO-d₆) δ 8.02 (br s, 2H), 7.67-7.53 (m, 2H), 7.15 (dd, J=8.5, 1.6 Hz, 1H), 6.47 (s, 1H), 4.32 (br d, J=13.0 Hz, 1H), 3.96-3.78 (m, 6H), 3.35 (br t, J=11.3 Hz, 1H), 3.22-3.09 (m, 1H), 2.46 (s, 3H), 2.16 (q, J=6.6 Hz, 2H), 1.74-1.55 (m, 4H); MS ESI m/z 436 (M+H); Anal. HPLC Retention time: 1.23 (Method 1); ROCK2 IC$_{50}$=72 nM.

Example 105: Preparation of 2-[3-methoxy-4-(1H-pyrazol-4-yl)phenyl]-8-[4-(pyrimidin-2-yloxy)benzoyl]-2,8-diazaspiro[4.5]decan-1-one

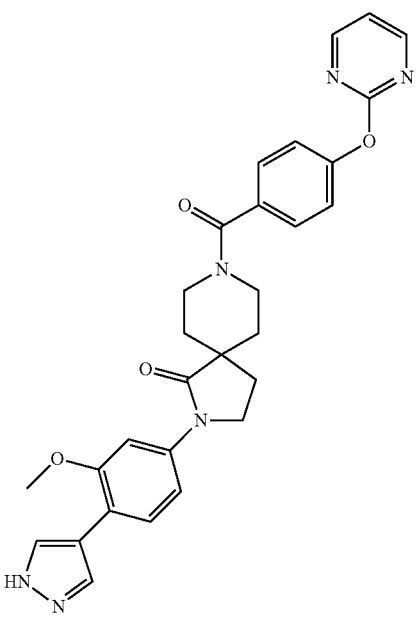 [SMILES: COc1cc(N2CCC3(CCN(C(=O)c4ccc(Oc5ncccn5)cc4)CC3)C2=O)ccc1-c1cn[nH]c1]

¹H NMR (500 MHz, DMSO-d₆) δ 8.67 (d, J=4.7 Hz, 2H), 8.02 (br s, 2H), 7.67-7.57 (m, 2H), 7.50 (br d, J=8.3 Hz, 2H), 7.35-7.23 (m, 4H), 7.16 (br d, J=7.6 Hz, 2H), 4.43-4.25 (m, 1H), 3.87 (s, 5H), 3.74-3.63 (m, 1H), 3.40 (br s, 1H), 3.17 (br s, 1H), 2.16 (br s, 2H), 1.76 (br s, 2H), 1.69-1.51 (m, 2H); MS ESI m/z 525.1 (M+H); Anal. HPLC Retention time: 1.22 (Method 1); ROCK2 IC$_{50}$=78 nM.

Example 106: Preparation of 2-[3-methoxy-4-(1H-pyrazol-4-yl)phenyl]-8-[4-(1H-1,2,4-triazol-1-yl)benzoyl]-2,8-diazaspiro[4.5]decan-1-one

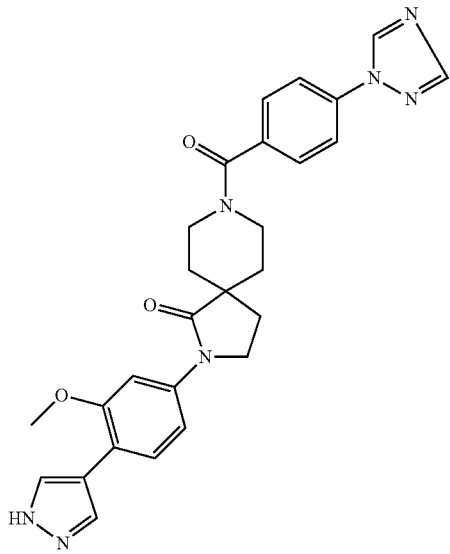 [SMILES: COc1cc(N2CCC3(CCN(C(=O)c4ccc(-n5cncn5)cc4)CC3)C2=O)ccc1-c1cn[nH]c1]

$^1$H NMR (500 MHz, DMSO-d$_6$) δ 9.35 (s, 1H), 8.27 (s, 1H), 7.95 (br d, J=8.5 Hz, 4H), 7.68-7.57 (m, 4H), 7.15 (br d, J=8.5 Hz, 1H), 4.34 (br d, J=6.4 Hz, 1H), 3.87 (s, 5H), 3.54-3.47 (m, 3H), 2.16 (br s, 2H), 1.84-1.50 (m, 4H); MS ESI m/z 498.2 (M+H); Anal. HPLC Retention time: 1.14 (Method 1); ROCK2 IC$_{50}$=25 nM.

Example 107: Preparation of 2-[3-methoxy-4-(1H-pyrazol-4-yl)phenyl]-8-[1-methyl-5-(trifluoromethyl)-1H-pyrazole-3-carbonyl]-2,8-diazaspiro[4.5]decan-1-one

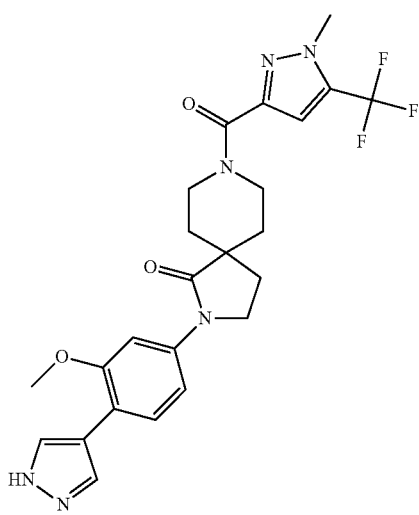 [SMILES: COc1cc(N2CCC3(CCN(C(=O)c4cc(C(F)(F)F)n(C)n4)CC3)C2=O)ccc1-c1cn[nH]c1]

$^1$H NMR (500 MHz, DMSO-d$_6$) δ 8.02 (br s, 2H), 7.61 (br d, J=5.8 Hz, 2H), 7.25-7.10 (m, 3H), 7.01 (s, 1H), 4.33 (br s, 2H), 4.02 (s, 3H), 3.87 (s, 5H), 3.44 (br d, J=11.0 Hz, 1H), 3.20-3.10 (m, 1H), 2.17 (br d, J=7.0 Hz, 2H), 1.81-1.70 (m, 2H), 1.68-1.56 (m, 2H); MS ESI m/z 503.2 (M+H); Anal. HPLC Retention time: 1.52 (Method 2); ROCK2 IC$_{50}$=67 nM.

Example 108: Preparation of 8-(5-ethylpyridine-2-carbonyl)-2-[3-methoxy-4-(1H-pyrazol-4-yl)phenyl]-2,8-diazaspiro[4.5]decan-1-one

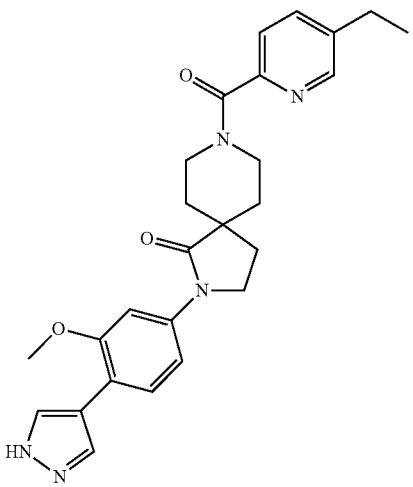 [SMILES: CCc1ccc(C(=O)N2CCC3(CC2)CCN(c2ccc(-c4cn[nH]c4)c(OC)c2)C3=O)nc1]

$^1$H NMR (500 MHz, DMSO-d$_6$) δ 8.46 (s, 1H), 8.02 (br s, 2H), 7.79 (br d, J=7.6 Hz, 1H), 7.66-7.57 (m, 2H), 7.51 (d, J=7.9 Hz, 1H), 7.15 (br d, J=8.5 Hz, 1H), 4.36 (br d, J=13.3 Hz, 1H), 3.91-3.80 (m, 5H), 3.74 (br d, J=13.2 Hz, 1H), 3.25 (br t, J=12.8 Hz, 1H), 3.18-3.08 (m, 1H), 2.68 (q, J=7.5 Hz, 2H), 2.23-2.06 (m, 2H), 1.81-1.71 (m, 2H), 1.66 (br d, J=13.8 Hz, 1H), 1.51 (br d, J=13.5 Hz, 1H), 1.22 (t, J=7.6 Hz, 3H); MS ESI m/z 460.2 (M+H); Anal. HPLC Retention time: 1.32 (Method 1); ROCK2 IC$_{50}$=12 nM.

Example 109: Preparation of 8-(3-chloro-1,2-oxazole-5-carbonyl)-2-[3-methoxy-4-(1H-pyrazol-4-yl)phenyl]-2,8-diazaspiro[4.5]decan-1-one

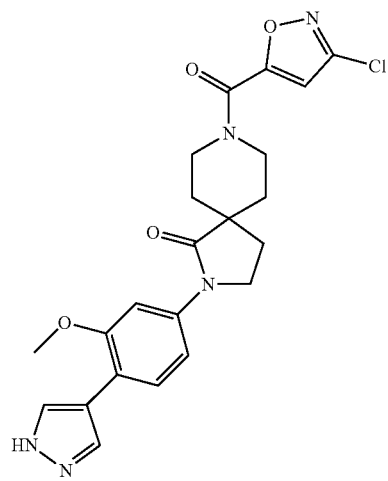 [SMILES: COc1cc(N2CCC3(CCN(C(=O)c4cc(Cl)no4)CC3)C2=O)ccc1-c1cn[nH]c1]

$^1$H NMR (500 MHz, DMSO-d$_6$) δ 8.02 (br s, 2H), 7.67-7.59 (m, 2H), 7.35 (s, 1H), 7.20-7.09 (m, 1H), 4.26 (br d, J=12.8 Hz, 1H), 3.87 (s, 6H), 2.25-2.10 (m, 2H), 1.86-1.74 (m, 2H), 1.63 (br d, J=13.5 Hz, 2H); MS ESI m/z 456.2 (M+H); Anal. HPLC Retention time: 1.4 (Method 2); ROCK2 IC$_{50}$=362 nM.

Example 110: Preparation of 2-[3-methoxy-4-(1H-pyrazol-4-yl)phenyl]-8-[3-(propan-2-yl)-1H-pyrazole-5-carbonyl]-2,8-diazaspiro[4.5]decan-1-one

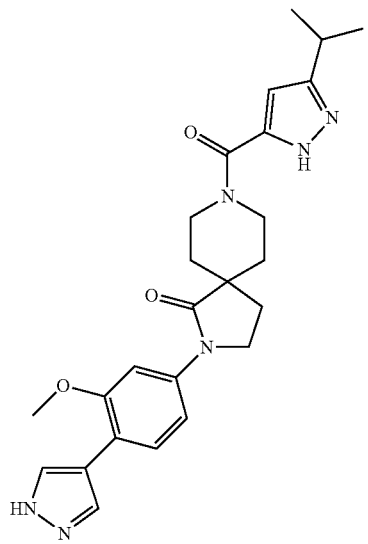 [SMILES: COc1cc(N2CCC3(CCN(C(=O)c4cc(C(C)C)n[nH]4)CC3)C2=O)ccc1-c1cn[nH]c1]

$^1$H NMR (500 MHz, DMSO-d$_6$) δ 8.26-7.88 (m, 2H), 7.69-7.53 (m, 2H), 7.25-7.02 (m, 1H), 6.32 (br s, 1H), 4.63 (br d, J=13.7 Hz, 1H), 4.36 (br d, J=12.2 Hz, 1H), 3.87 (s, 5H), 3.42 (br s, 1H), 3.11-3.02 (m, 1H), 3.04-2.91 (m, 2H), 2.16 (br d, J=5.3 Hz, 2H), 1.87-1.67 (m, 2H), 1.65-1.50 (m, 2H), 1.23 (br d, J=6.8 Hz, 6H); MS ESI m/z 463.3 (M+H); Anal. HPLC Retention time: 1.31 (Method 1); ROCK2 IC$_{50}$=34 nM.

Example 111: Preparation of 8-(3-cyclopropyl-1H-pyrazole-5-carbonyl)-2-[3-methoxy-4-(1H-pyrazol-4-yl)phenyl]-2,8-diazaspiro[4.5]decan-1-one

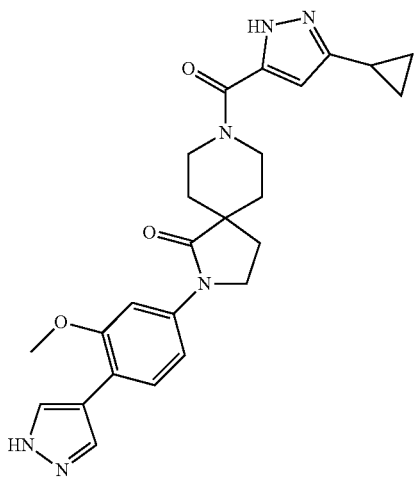 [SMILES: COc1cc(N2CCC3(CCN(C(=O)c4cc(C5CC5)n[nH]4)CC3)C2=O)ccc1-c1cn[nH]c1]

$^1$H NMR (500 MH, DMSO-d$_6$) δ 8.02 (br s, 2H), 7.67-7.56 (m, 2H), 7.15 (br d, J=8.4 Hz, 1H), 6.22 (br s, 1H), 4.58 (br d, J=3.3 Hz, 1H), 4.34 (br s, 1H), 3.87 (s, 5H), 3.17 (br d, J=4.4 Hz, 1H), 3.08-2.96 (m, 1H), 2.16 (br d, J=4.5 Hz, 2H), 1.91 (br s, 1H), 1.71 (br d, J=11.2 Hz, 2H), 1.60 (br d, J=19.9 Hz, 2H), 0.94 (br s, 2H), 0.71 (br d, J=3.0 Hz, 2H); MS ESI m/z 461.1 (M+H);

Anal. HPLC Retention time: 1.21 (Method 2); ROCK2 IC$_{50}$=17 nM.

Example 112: Preparation of 8-[4-(4-chlorophenoxy)benzoyl]-2-[3-methoxy-4-(1H-pyrazol-4-yl)phenyl]-2,8-diazaspiro[4.5]decan-1-one

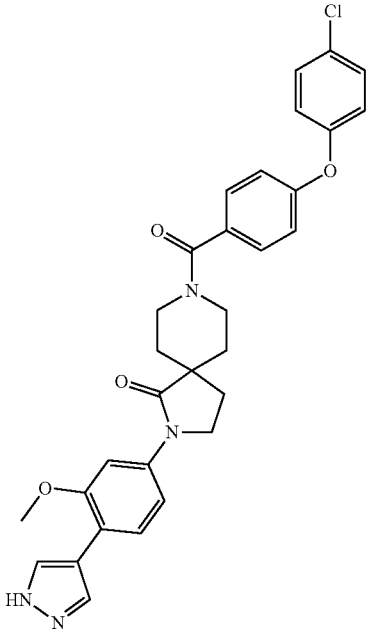 [SMILES: COc1cc(N2CCC3(CCN(C(=O)c4ccc(Oc5ccc(Cl)cc5)cc4)CC3)C2=O)ccc1-c1cn[nH]c1]

$^1$H NMR (500 MHz, DMSO-d$_6$) δ 8.01 (br s, 2H), 7.65-7.57 (m, 2H), 7.46 (br t, J=9.2 Hz, 5H), 7.12 (br d, J=8.9 Hz, 3H), 7.07 (br d, J=8.5 Hz, 2H), 4.40-4.20 (m, 1H), 3.86 (s, 6H), 3.34 (br s, 2H), 2.15 (br s, 2H), 1.74 (br s, 2H), 1.59 (br d, J=3.4 Hz, 2H); MS ESI m/z 557.2 (M+H); Anal. HPLC Retention time: 1.93 (Method 2); ROCK2 IC$_{50}$=39 nM.

Example 113: Preparation of 2-[3-methoxy-4-(1H-pyrazol-4-yl)phenyl]-8-[3-(4-methoxyphenyl)-1,2-oxazole-5-carbonyl]-2,8-diazaspiro[4.5]decan-1-one

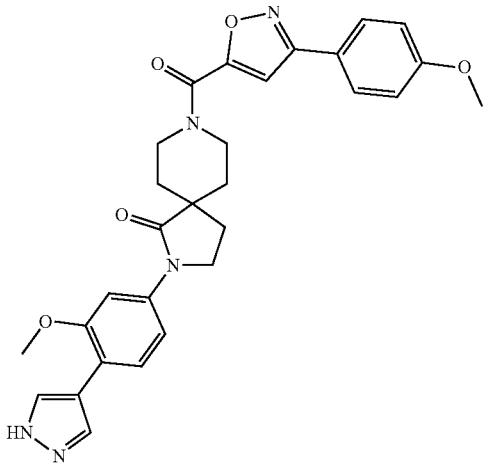

$^1$H NMR (500 MHz, DMSO-d$_6$) δ 8.09 (br s, 1H), 7.95 (br s, 1H), 7.88 (br d, J=8.5 Hz, 2H), 7.63-7.58 (m, 2H), 7.16 (s, 2H), 7.11 (br d, J=8.5 Hz, 2H), 4.36 (br d, J=12.8 Hz, 1H), 3.99 (br d, J=13.4 Hz, 1H), 3.87 (s, 5H), 3.84 (s, 3H), 3.50-3.40 (m, 2H), 2.22-2.14 (m, 2H), 1.78 (br d, J=12.5 Hz, 2H), 1.73-1.60 (m, 2H); MS ESI m/z 528.1 (M+H); Anal. HPLC Retention time: 1.68 (Method 2), ROCK2 IC$_{50}$=17 nM.

Example 114: Preparation of 2-[3-methoxy-4-(1H-pyrazol-4-yl)phenyl]-8-{4-oxo-4H,5H,6H,7H-pyrazolo[1,5-a]pyrazine-2-carbonyl}-2,8-diazaspiro[4.5]decan-1-one

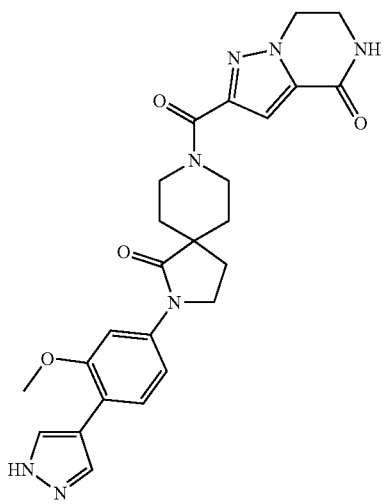 [SMILES: COc1cc(N2CCC3(CCN(C(=O)c4cc5n(n4)CCNC5=O)CC3)C2=O)ccc1-c1cn[nH]c1]

$^1$H NMR (500 MHz, DMSO-d$_6$) δ 8.33 (br s, 1H), 8.14-7.90 (m, 2H), 7.61 (dd, J=4.7, 3.2 Hz, 2H), 7.16 (dd, J=8.4, 1.7 Hz, 1H), 6.94 (s, 1H), 4.36 (br t, J=6.0 Hz, 4H), 3.87 (s, 5H), 3.65 (br s, 2H), 3.42 (br d, =10.7 Hz, 2H), 2.25-2.11 (m, 2H), 1.75 (br d, J=13.1 Hz, 2H), 1.68-1.53 (m, 2H); MS ESI m/z 489.9 (M+H); Anal. HPLC Retention time: 1.17 (Method 1); ROCK2 IC$_{50}$=6 nM.

Example 115: Preparation of 8-(5-chloropyrazine-2-carbonyl)-2-[3-methoxy-4-(1H-pyrazol-4-yl)phenyl]-2,8-diazaspiro[4.5]decan-1-one

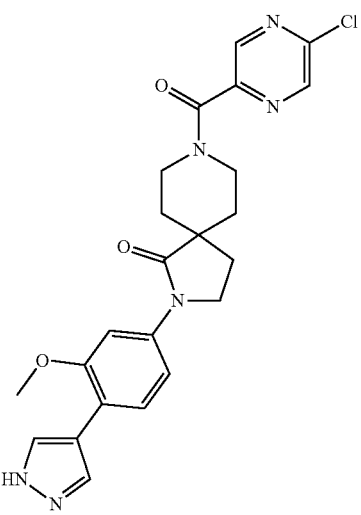 [SMILES: COc1cc(N2CCC3(CCN(C(=O)c4cnc(Cl)cn4)CC3)C2=O)ccc1-c1cn[nH]c1]

$^1$H NMR (500 MHz, DMSO-d$_6$) δ 8.84 (s, 1H), 8.74 (s, 1H), 8.02 (br s, 2H), 7.67-7.55 (m, 2H), 7.16 (br d, J=8.2 Hz, 1H), 4.35 (br d, J=13.5 Hz, 1H), 3.87 (s, 5H), 3.73 (br d, J=13.6 Hz, 1H), 3.34-3.12 (m, 2H), 2.26-2.09 (m, 2H), 1.84-1.74 (m, 2H), 1.68 (br d, J=13.7 Hz, 1H), 1.53 (br d, J=13.0 Hz, 1H); MS ESI m/z 467.2 (M+H); Anal. HPLC Retention time: 1.28 (Method 1); ROCK2 IC$_{50}$=200 nM.

Example 116: Preparation of 8-(5-bromopyrimidine-2-carbonyl)-2-[3-methoxy-4-(1H-pyrazol-4-yl)phenyl]-2,8-diazaspiro[4.5]decan-1-one

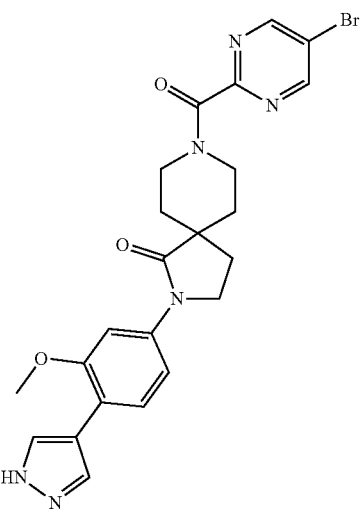 [SMILES: COc1cc(N2CCC3(CCN(C(=O)c4ncc(Br)cn4)CC3)C2=O)ccc1-c1cn[nH]c1]

$^1$H NMR (500 MHz, DMSO-d$_6$) δ 9.11 (s, 2H), 8.02 (br s, 2H), 7.67-7.54 (m, 2H), 7.15 (dd, J=8.4, 1.6 Hz, 1H), 4.33 (br d, J=12.9 Hz, 1H), 3.99-3.79 (m, 5H), 3.59-3.46 (m, 3H), 2.24-2.10 (m, 2H), 1.86-1.62 (m, 5H), 1.49 (br d, J=13.0 Hz, 1H); MS ESI m/z 511 (M+H); Anal. HPLC Retention time: 1.21 (Method 1); ROCK2 IC$_{50}$=88 nM.

Example 117: Preparation of 2-[3-methoxy-4-(1H-pyrazol-4-yl)phenyl]-8-[4-(2-oxo-1,2-dihydropyridin-1-yl)benzoyl]-2,8-diazaspiro[4.5]decan-1-one

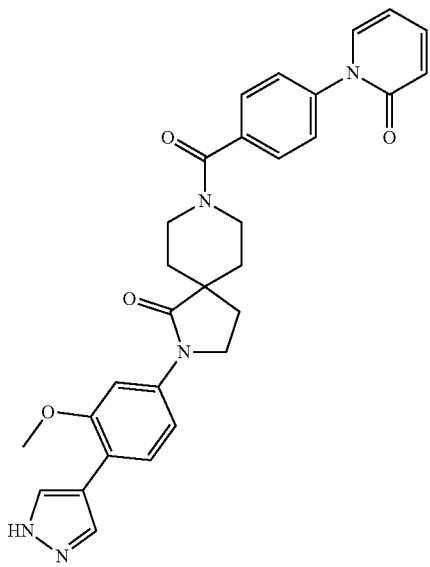 [SMILES: COc1cc(N2CCC3(CCN(C(=O)c4ccc(-n5ccccc5=O)cc4)CC3)C2=O)ccc1-c1cn[nH]c1]

$^1$H NMR (500 MHz, DMSO-d$_6$) δ 8.02 (br d, J=5.5 Hz, 2H), 7.75-7.67 (m, 1H), 7.62 (s, 2H), 7.53 (br d, =17.7 Hz, 5H), 7.16 (dd, J=8.5, 1.5 Hz, 1H), 6.51 (br d, J=9.5 Hz, 1H), 6.35 (br t, J=6.4 Hz, 1H), 4.35 (br d, =4.6 Hz, 1H), 3.87 (s, 5H), 3.65 (br s, 1H), 3.42 (br d, J=6.1 Hz, 2H), 2.16 (br s, 2H), 1.77 (br s, 2H), 1.67 (br s, 1H), 1.57 (br s, 1H); MS ESI m/z 524.3 (M+H); Anal. HPLC Retention time: 1.13 (Method 2), ROCK2 IC$_{50}$=7 nM.

Example 118: Preparation of 2-[3-methoxy-4-(1H-pyrazol-4-yl)phenyl]-8-[4-1H-1,2,3,4-tetrazol-1-yl)benzoyl]-2,8-diazaspiro[4.5]decan-1-one

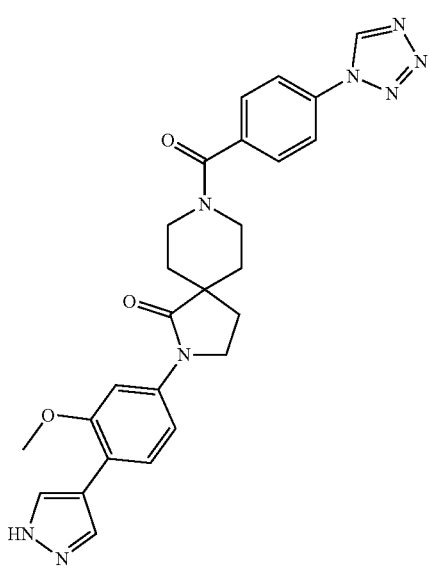 [SMILES: COc1cc(N2CCC3(CCN(C(=O)c4ccc(-n5cnnn5)cc4)CC3)C2=O)ccc1-c1cn[nH]c1]

$^1$H NMR (600 MHz, DMSO-d$_6$) δ 10.14 (s, 1H), 8.10 (br s, 1H), 8.01 (br d, J=8.1 Hz, 2H), 7.94 (br s, 1H), 7.70 (br d, J=8.3 Hz, 2H), 7.64-7.56 (m, 2H), 7.15 (br d, J=8.5 Hz, 1H), 4.66 (br d, J=5.0 Hz, 1H), 4.35 (br d, J=7.3 Hz, 1H), 3.94-3.86 (m, 5H), 3.70-3.57 (m, 1H), 3.32 (br dd, J=10.7, 5.7 Hz, 1H), 2.21-2.10 (m, 2H), 1.86-1.72 (m, 2H), 1.68 (br d, J=10.1 Hz, 1H), 1.58-1.47 (m, 1H); MS ESI m/z 499 (M+H); Anal. HPLC Retention time: 1.16 (Method 1); ROCK2 IC$_{50}$=57 nM.

Example 119: Preparation of 2-[3-methoxy-4-(1H-pyrazol-4-yl)phenyl]-8-(2-methyl-1,3-benzoxazole-5-carbonyl)-2,8-diazaspiro[4.5]decan-1-one

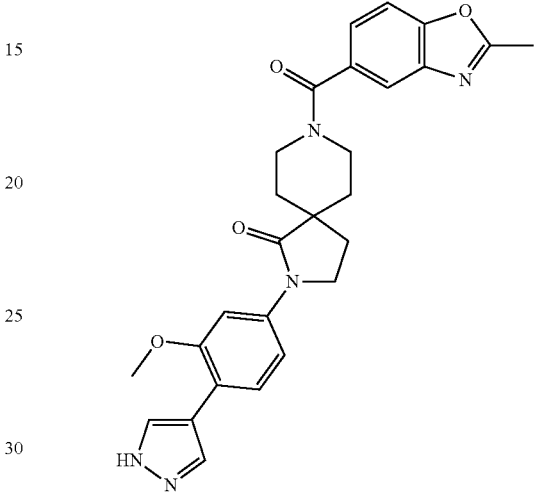

$^1$H NMR (500 MHz, DMSO-d$_6$) δ 8.02 (s, 2H), 7.73 (d, J=8.3 Hz, 1H), 7.68 (s, 1H), 7.63-7.57 (m, 2H), 7.39 (d, J=8.2 Hz, 1H), 7.14 (dd, J=8.5, 1.6 Hz, 1H), 4.03 (dd, J=11.1, 3.9 Hz, 1H), 3.93-3.81 (m, 5H), 3.62 (br s, 1H), 3.47 (br s, 1H), 3.33 (br s, 1H), 2.63 (s, 3H), 2.14 (br s, 2H), 1.81-1.61 (m, 3H), 1.51 (br d, J=5.6 Hz, 1H); MS ESI m/z 486.3 (M+H); Anal. HPLC Retention time: 1.27 (Method 2); ROCK2 IC$_{50}$=70 nM.

Example 120: Preparation of 2-[3-methoxy-4-(1H-pyrazol-4-yl)phenyl]-8-[4-(4-methylpiperazin-1-yl)benzoyl]-2,8-diazaspiro[4.5]decan-1-one

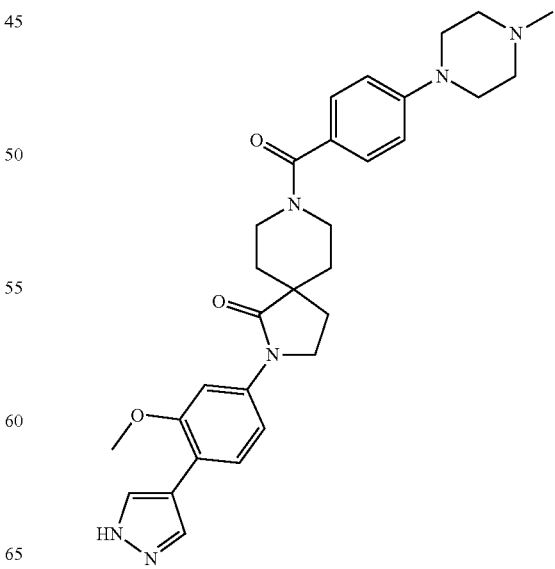

¹H NMR (500 MHz, DMSO-d₆) δ 8.18-7.91 (m, 2H), 7.61 (dd, J=5.0, 3.3 Hz, 2H), 7.29 (br d, J=8.6 Hz, 2H), 7.15 (dd, J=8.5, 1.6 Hz, 1H), 6.96 (br d, J=8.8 Hz, 2H), 4.03 (br dd, J=11.0, 4.0 Hz, 1H), 3.94-3.77 (m, 5H), 3.63 (br d, J=5.6 Hz, 1H), 3.40 (br s, 1H), 3.21 (br s, 2H), 3.17 (br d, J=4.4 Hz, 1H), 2.51 (br s, 8H), 2.46 (br d, J=4.4 Hz, 4H), 2.22 (s, 3H), 2.14 (br t, J=6.6 Hz, 2H), 1.77-1.66 (m, 2H), 1.57 (br d, J=10.7 Hz, 2H); MS ESI m/z 529.2 (M+H); Anal. HPLC Retention time: 0.98 (Method 2); ROCK2 IC$_{50}$=0.3 nM.

Example 121: Preparation of 2-[3-methoxy-4-(1H-pyrazol-4-yl)phenyl]-8-(2-methylpyrimidine-5-carbonyl)-2,8-diazaspiro[4.5]decan-1-one

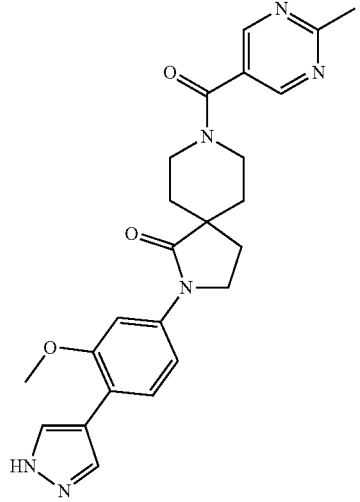

¹H NMR (500 MHz, DMSO-d₆) δ 8.78 (s, 2H), 8.02 (br s, 2H), 7.65-7.57 (m, 2H), 7.15 (br d, J=8.5 Hz, 1H), 4.32 (br d, J=11.0 Hz, 1H), 4.07-3.99 (m, 1H), 3.91-3.82 (m, 5H), 3.63 (br s, 1H), 3.39-3.27 (m, 1H), 2.67 (s, 3H), 2.14 (br d, J=6.6 Hz, 2H), 1.77 (br d, J=7.7 Hz, 2H), 1.67 (br d, J=10.9 Hz, 1H), 1.55 (br d, J=11.9 Hz, 1H); MS ESI m/z 447.2 (M+H); Anal. HPLC Retention time: 0.99 (Method 1); ROCK2 IC$_{50}$=585 nM.

Example 122: Preparation of 8-(2-chloro-4-methoxybenzoyl)-2-[3-methoxy-4-(1H-pyrazol-4-yl)phenyl]-2,8-diazaspiro[4.5]decan-1-one

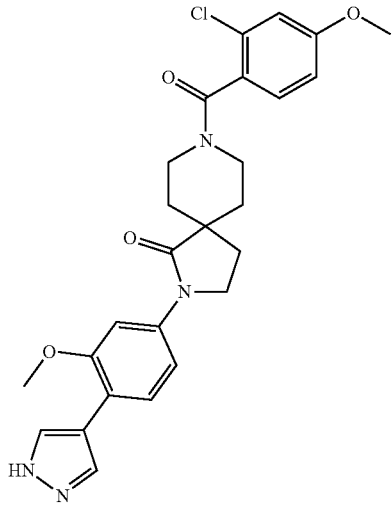

¹H NMR (500 MHz, DMSO-d₆) δ 8.16-7.88 (m, 2H), 7.67-7.58 (m, 2H), 7.36-7.24 (m, 1H), 7.12 (br d, J=9.3 Hz, 2H), 7.05-6.95 (m, 1H), 4.37 (br d, J=4.5 Hz, 1H) 4.03 (dd, J=11.1, 4.2 Hz, 1H), 3.86 (s, 4H), 3.81 (s, 3H), 3.17-3.07 (m, 2H), 2.12 (br dd. J=13.1, 6.9 Hz, 2H), 1.86-1.71 (m, 2H), 1.65 (br d, J=13.0 Hz, 1H), 1.49 (br d, J=13.4 Hz, 1H); MS ESI m/z 495 (M+H); Anal. HPLC Retention time: 1.47 (Method 1); ROCK2 IC$_{50}$=11 nM.

Example 123: Preparation of 8-(5-chloropyridine-2-carbonyl)-2-[3-methoxy-4-(1H-pyrazol-4-yl)phenyl]-2,8-diazaspiro[4.5]decan-1-one

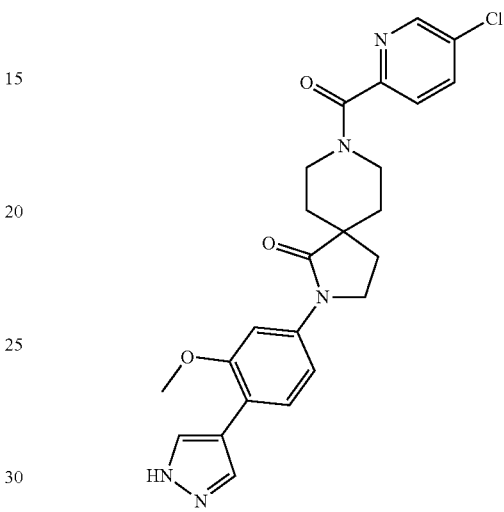

¹H NMR (500 MHz, DMSO-d₆) δ 8.67 (d, J=2.0 Hz, 1H), 8.08 (dd, J=8.4, 2.2 Hz, 1H), 8.02 (br s, 2H), 7.69-7.56 (m, 3H), 7.15 (dd, J=8.4, 1.4 Hz, 1H), 4.35 (br d, J=13.1 Hz, 1H), 3.94-3.80 (m, 5H), 3.67 (br d, J=13.3 Hz, 1H), 3.34-3.08 (m, 2H), 2.24-2.08 (m, 2H), 1.85-1.72 (m, 2H), 1.66 (br d, J=12.9 Hz, 1H), 1.52 (br d, J=13.0 Hz, 1H); MS ESI m/z 466 (M+H); Anal. HPLC Retention time: 1.33 Method 2; ROCK2 IC$_{50}$=65 nM.

Example 124: Preparation of 2-[3-methoxy-4-(1H-pyrazol-4-yl)phenyl]-8-[4-(1H-pyrazol-1-yl)benzoyl]-2,8-diazaspiro[4.5]decan-1-one

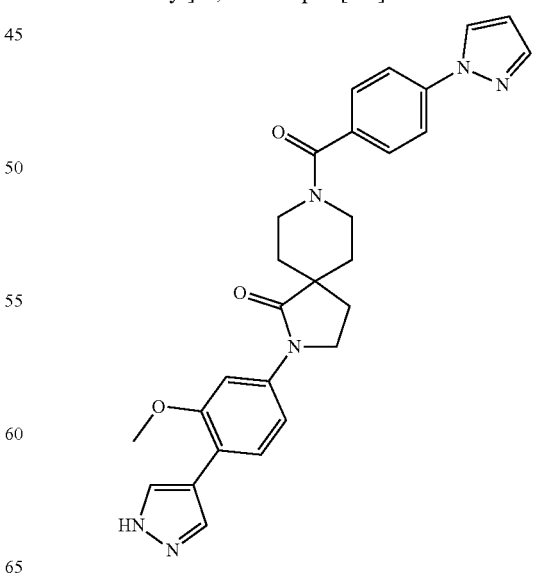

¹H NMR (500 MHz, DMSO-d₆) δ 8.58 (br s, 1H), 8.11 (br d, J=5.0 Hz, 1H), 8.01 (br d, J=9.0 Hz, 1H), 7.94 (br d, J=8.2

Hz, 2H), 7.79 (s, 1H), 7.62 (br s, 1H), 7.55 (br d, J=8.2 Hz, 1H), 7.16 (br d, J=8.4 Hz, 1H), 6.59 (br s, 1H), 4.57 (br d, J=8.6 Hz, 1H), 4.47-4.38 (m, 1H), 4.03 (br s, 1H), 3.87 (s, 3H), 3.73-3.59 (m, 1H), 3.39-3.31 (m, 2H), 2.15 (br s, 2H), 1.76 (br s, 2H), 1.66-1.45 (m, 2H); MS ESI m/z 496.9 (M+H); Anal. HPLC Retention time: 1.48 (Method 1); ROCK2 IC$_{50}$=62 nM.

Example 125: Preparation of 2-[3-methoxy-4-(1H-pyrazol-4-yl)phenyl]-8-[5-oxo-3-(pyridin-2-yl)-4,5-dihydro-1,2,4-triazine-6-carbonyl]-2,8-diazaspiro[4.5]decan-1-one

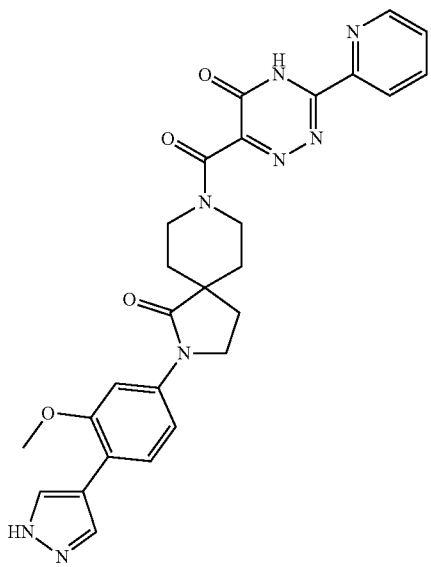 [SMILES: COc1cc(N2CCC3(CCN(C(=O)c4nnc(-c5ccccn5)[nH]c4=O)CC3)C2=O)ccc1-c1cn[nH]c1]

$^1$H NMR (500 MHz, DMSO-d$_6$) δ 8.82 (br d, J=4.3 Hz, 1H), 8.33 (br d, J=7.9 Hz, 1H), 8.12 (br t, J=7.8 Hz, 1H), 8.09-7.89 (m, 2H), 7.78-7.70 (m, 1H), 7.63-7.55 (m, 2H), 7.15 (br d, J=8.2 Hz, 1H), 4.31 (br d, J=13.4 Hz, 1H), 3.92-3.80 (m, 5H), 3.66 (br d, J=14.6 Hz, 1H), 3.35-3.22 (m, 1H), 3.13 (br s, 1H), 2.23-2.11 (m, 2H), 1.74 (br d, J=7.0 Hz, 2H), 1.66 (br d, J=11.9 Hz, 1H), 1.54 (br d, J=12.5 Hz, 1H); MS ESI m/z 527.1 (M+H); Anal. HPLC Retention time: 0.86 (Method 1); ROCK2 IC$_{50}$=26 nM.

Example 126: Preparation of 2-[3-methoxy-4-(1H-pyrazol-4-yl)phenyl]-8-[4-(2-oxo-1,3-diazinan-1-yl)benzoyl]-2,8-diazaspiro[4.5]decan-1-one

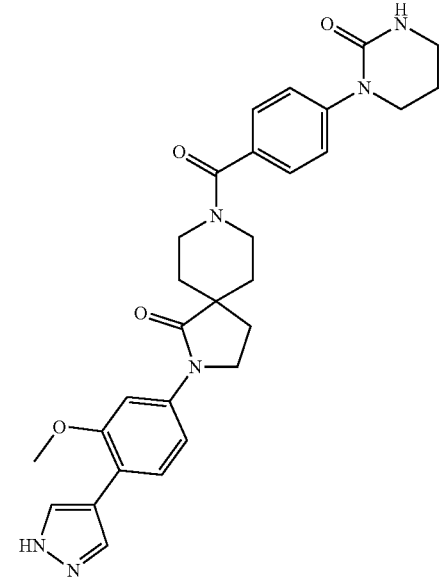 [SMILES: COc1cc(N2CCC3(CCN(C(=O)c4ccc(N5CCCNC5=O)cc4)CC3)C2=O)ccc1-c1cn[nH]c1]

$^1$H NMR (500 MHz, DMSO-d$_6$) δ 8.02 (br s, 2H), 7.68-7.55 (m, 2H), 7.42-7.28 (m, 5H), 7.24 (br d, J=8.2 Hz, 1H), 7.14 (br d, J=7.9 Hz, 1H), 6.66 (br s, 1H), 3.86 (s, 5H), 3.65 (br t, J=5.3 Hz, 1H), 3.55 (br s, 1H), 3.49 (br s, 2H), 3.23 (br s, 4H), 2.14 (br s, 2H), 1.94 (br d, J=5.3 Hz, 2H), 1.73 (br s, 2H), 1.65-1.48 (m, 2H), 1.12 (br s, 2H); MS ESI m/z 529 (M+H); Anal. HPLC Retention time: 1.22 (Method 1); ROCK2 IC$_{50}$=7.7 nM.

Example 127: Preparation of 8-[3-fluoro-4-(morpholin-4-yl)benzoyl]-2-[3-methoxy-4-(1H-pyrazol-4-yl)phenyl]-2,8-diazaspiro[4.5]decan-1-one

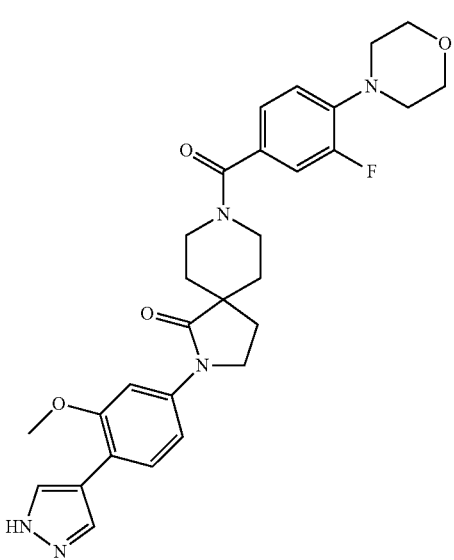 [SMILES: COc1cc(N2CCC3(CCN(C(=O)c4ccc(N5CCOCC5)c(F)c4)CC3)C2=O)ccc1-c1cn[nH]c1]

¹H NMR (500 MHz, DMSO-d₆) δ 8.14-7.85 (m, 2H), 7.60 (br d, J=6.7 Hz, 2H), 7.26-7.18 (m, 2H), 7.15 (br d, J=9.2 Hz, 1H), 7.08 (br t, J=8.5 Hz, 1H), 3.90 (s, 5H), 3.87 (s, 4H), 3.75 (br s, 4H), 3.18 (br s, 2H), 3.07 (br s, 4H), 2.14 (br s, 2H), 1.82-1.67 (m, 2H), 1.59 (br s, 2H); MS ESI m/z 534.3 (M+H); Anal. HPLC Retention time: 1.47 (Method 1); ROCK2 IC₅₀=11.2 nM.

Example 128: Preparation of 2-[3-methoxy-4-(1H-pyrazol-4-yl)phenyl]-8-[4-(2-oxopyrrolidin-1-yl)benzoyl]-2,8-diazaspiro[4.5]decan-1-one

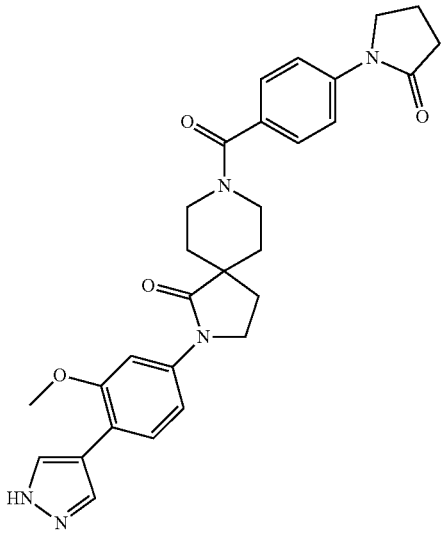 [SMILES: COc1cc(N2CCC3(CCN(C(=O)c4ccc(N5CCCC5=O)cc4)CC3)C2=O)ccc1-c1cn[nH]c1]

¹H NMR (500 MHz, DMSO-d₆) δ 8.17-7.87 (m, 2H), 7.75 (br d, J=8.4 Hz, 2H), 7.65-7.58 (m, 2H), 7.44 (br d, J=8.3 Hz, 2H), 7.15 (br d, J=8.7 Hz, 1H), 4.39-4.24 (m, 1H), 3.95-3.77 (m, 7H), 3.75-3.61 (m, 1H), 3.31 (br s, 1H), 3.18 (br dd, J=19.3, 4.2 Hz, 1H), 2.15 (br s, 2H), 2.08 (br t, J=7.4 Hz, 2H), 1.81-1.72 (m, 2H), 1.67-1.48 (m, 2H); MS ESI m/z 514.2 (M+H); Anal. HPLC Retention time: 1.27 (Method 1); ROCK2 IC₅₀=13 nM.

Example 129: Preparation of 2-[3-methoxy-4-(1H-pyrazol-4-yl)phenyl]-8-{7-oxo-4H,7H-[1,2,3,4]tetrazolo[1,5-a]pyrimidine-5-carbonyl}-2,8-diazaspiro[4.5]decan-1-one

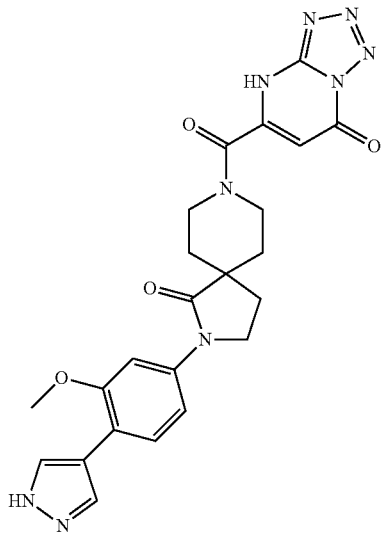 [SMILES: COc1cc(N2CCC3(CCN(C(=O)c4cc(=O)n5nnnc5[nH]4)CC3)C2=O)ccc1-c1cn[nH]c1]

¹H NMR (500 MHz, DMSO-d₆) δ 8.02 (br s, 2H), 7.60 (s, 2H), 7.22 (s, 1H), 7.14 (br s, 1H), 7.12 (s, 1H), 7.02 (s, 1H), 5.63 (s, 1H), 4.30 (br d, J=13.3 Hz, 1H), 3.93-3.78 (m, 4H), 3.66 (br d, J=12.3 Hz, 1H), 3.61 (br s, 1H), 3.37 (br d, J=5.6 Hz, 1H), 3.25-3.17 (m, 1H), 3.11 (br t, J=11.1 Hz, 1H), 2.21-2.08 (m, 2H), 1.82-1.68 (m, 2H), 1.64 (br d, J=13.3 Hz, 1H), 1.51 (br d, J=12.5 Hz, 1H); MS ESI m/z 490.18, 490.18 (M+H); Anal. HPLC Retention time; (Method 2); ROCK2 IC₅₀=292 nM.

Example 130: Preparation of 2-[3-methoxy-4-(1H-pyrazol-4-yl)phenyl]-8-[4-(piperazin-1-yl)benzoyl]-2,8-diazaspiro[4.5]decan-1-one

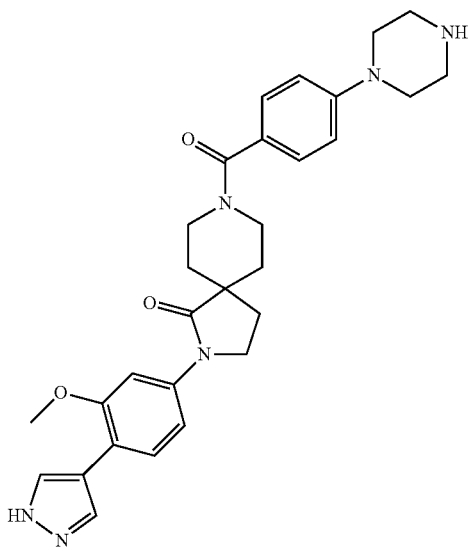 [SMILES: COc1cc(N2CCC3(CCN(C(=O)c4ccc(N5CCNCC5)cc4)CC3)C2=O)ccc1-c1cn[nH]c1]

¹H NMR (500 MHz, DMSO-d₆) δ 8.01 (br s, 2H), 7.67-7.56 (m, 2H), 7.34 (br d, J=8.5 Hz, 2H), 7.15 (br d, J=8.5 Hz, 1H), 7.03 (br d, J=8.5 Hz, 2H), 4.21-4.11 (m, 1H), 3.94-3.82 (m, 5H), 3.73-3.64 (m, 1H), 3.43 (br s, 2H), 3.29-3.12 (m, 8H), 2.14 (br t, J=6.4 Hz, 2H), 1.79-1.66 (m, 2H), 1.57 (br d, J=10.1 Hz, 2H); MS ESI m/z 515.2 (M+H); Anal. HPLC Retention time: 1.08 (Method 1); ROCK2 IC₅₀=0.4 nM.

Example 131: Preparation of 2-[3-methoxy-4-(1H-pyrazol-4-yl)phenyl]-8-{5-methyl-2-oxo-1H,2H-pyrazolo[1,5-a]pyrimidine-6-carbonyl}-2,8-diazaspiro[4.5]decan-1-one

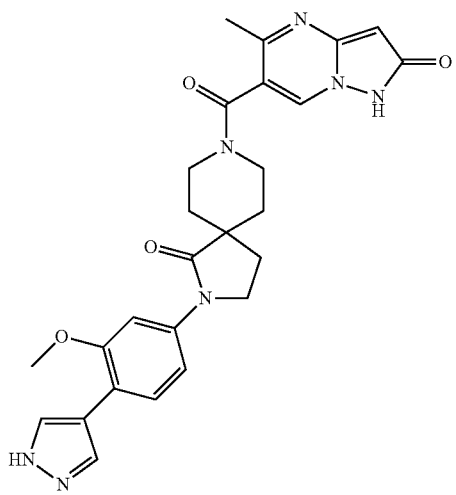 [SMILES: COc1cc(N2CCC3(CCN(C(=O)c4cn5[nH]c(=O)cc5nc4C)CC3)C2=O)ccc1-c1cn[nH]c1]

¹H NMR (500 MHz, DMSO-d₆) δ 8.25 (br s, 1H), 8.02 (br s, 2H), 7.70-7.55 (m, 2H), 7.14 (br d, J=8.5 Hz, 1H), 5.95 (s, 1H), 4.38 (br d, J=11.3 Hz, 1H), 3.87 (s, 5H), 3.62 (br s, 1H), 3.35-3.14 (m, 2H), 2.61 (br s, 3H), 2.15 (br d, J=5.8 Hz, 2H), 1.80 (br s, 1H), 1.70 (br s, 2H), 1.54 (br s, 1H); MS ESI m/z 502 (M+H); Anal. HPLC Retention time: 1.06 (Method 1); ROCK2 IC$_{50}$=2087 nM.

Example 132: Preparation of 2-[3-methoxy-4-(1H-pyrazol-4-yl)phenyl]-8-{7-methyl-4-oxo-3H,4H-pyrrolo[2,1-f][1,2,4]triazine-5-carbonyl}-2,8-diazaspiro[4.5]decan-1-one

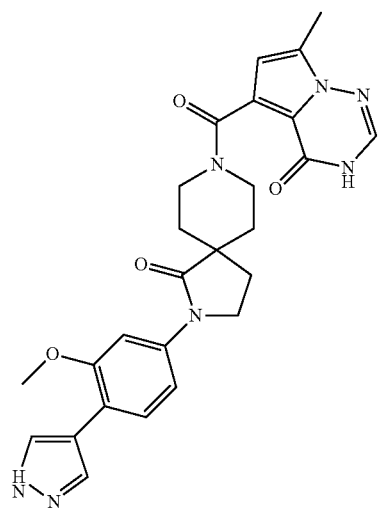 [SMILES: COc1cc(N2CCC3(CCN(C(=O)c4cc(C)n5nc[nH]c(=O)c45)CC3)C2=O)ccc1-c1cn[nH]c1]

¹H NMR (500 MHz, DMSO-d₆) δ 11.91-11.25 (m, 1H), 8.21-7.92 (m, 2H), 7.87 (br s, 1H), 7.67-7.55 (m, 2H), 7.14 (br d, J=8.2 Hz, 1H), 6.42 (s, 1H), 4.38 (br d, J=13.1 Hz, 1H), 3.89 (d, J=18.6 Hz, 6H), 3.61 (br d, J=14.0 Hz, 1H), 3.18-3.05 (m, 2H), 2.40 (s, 3H), 2.21-2.05 (m, 2H), 1.83-1.57 (m, 3H), 1.42 (br d, J=13.1 Hz, 1H); MS ESI m/z (M+H); Anal. HPLC Retention time: 1.25 (Method 1); ROCK2 IC$_{50}$=3 nM.

Example 133: Preparation of 2-[3-methoxy-4-(1H-pyrazol-4-yl)phenyl]-8-{5-methyl-4-oxo-3H,4H-pyrrolo[2,1-f][1,2,4]triazine-6-carbonyl}-2,8-diazaspiro[4.5]decan-1-one

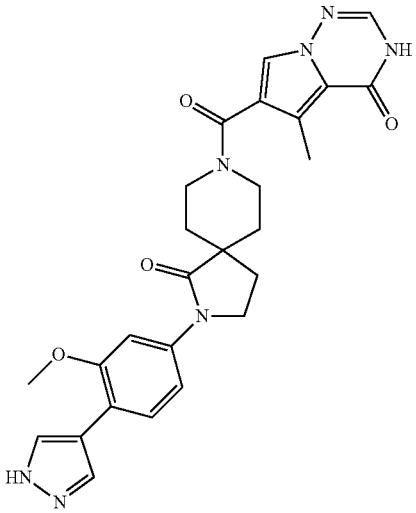 [SMILES: COc1cc(N2CCC3(CCN(C(=O)c4cn5nc[nH]c(=O)c5c4C)CC3)C2=O)ccc1-c1cn[nH]c1]

¹H NMR (500 MHz, DMSO-d₆) δ 8.01 (br s, 2H), 7.78 (s, 1H), 7.66 (s, 1H), 7.63-7.56 (m, 2H), 7.14 (br d, J=6.8 Hz, 1H), 3.86 (s, 5H), 3.63-3.42 (m, 4H), 2.40 (s, 3H), 2.14 (br s, 2H), 1.71 (br s, 2H), 1.58 (br s, 2H); MS ESI m/z 502.2 (M+H); Anal. HPLC Retention time: 1.18 (Method 1); ROCK2 IC$_{50}$=88 nM.

Example 134: Preparation of 2-[3-methoxy-4-(1H-pyrazol-4-yl)phenyl]-8-{4-[5-(propan-2-yl)-1,2,4-oxadiazol-3-yl]benzoyl}-2,8-diazaspiro[4.5]decan-1-one

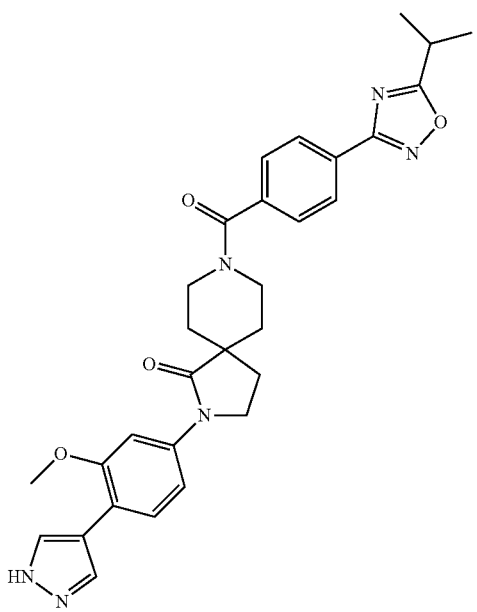 [SMILES: COc1cc(N2CCC3(CCN(C(=O)c4ccc(-c5noc(C(C)C)n5)cc4)CC3)C2=O)ccc1-c1cn[nH]c1]

¹H NMR (500 MHz, DMSO-d₆) δ 8.12 (s, 1H), 8.08 (br d, J=7.0 Hz, 2H), 8.03 (br s, 2H), 7.62-7.56 (m, 4H), 7.15 (br d, J=8.5 Hz, 1H), 4.41-4.30 (m, 1H), 3.94-3.78 (m, 5H), 3.51 (br s, 1H), 3.42-3.32 (m, 1H), 3.29 (br d, J=11.0 Hz, 1H), 3.18 (br s, 1H), 2.15 (br s, 2H), 1.84-1.65 (m, 3H), 1.53 (br d, J=7.6 Hz, 1H), 1.39 (br d, J=6.7 Hz, 6H); MS ESI m/z 541.1 (M+H); Anal. HPLC Retention time: 1.76 (Method 1); ROCK2 IC$_{50}$=75 nM.

Example 135: Preparation of 2-[3-methoxy-4-(1H-pyrazol-4-yl)phenyl]-8-[4-(pyrimidin-5-yl)benzoyl]-2,8-diazaspiro[4.5]decan-1-one

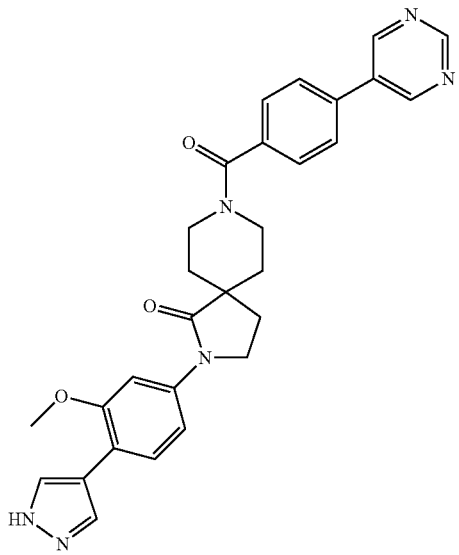 [SMILES: COc1cc(N2CCC3(CCN(C(=O)c4ccc(-c5cncnc5)cc4)CC3)C2=O)ccc1-c1cn[nH]c1]

¹H NMR (500 MHz, DMSO-d₆) δ 9.26-9.14 (m, 3H), 8.01 (br s, 2H), 7.91 (br d, J=8.0 Hz, 2H), 7.66-7.52 (m, 4H), 7.14 (br d, J=8.3 Hz, 1H), 4.43-4.27 (m, 1H), 3.86 (s, 4H), 3.58 (br s, 2H), 3.31 (br d, J=10.2 Hz, 1H), 3.17 (br d, J=5.0 Hz, 1H), 2.16 (br s, 2H), 1.88-1.61 (m, 3H), 1.53 (br d, J=10.1 Hz, 1H); MS ESI m/z 509 (M+H); Anal. HPLC Retention time: 1.29 (Method 1); ROCK2 IC$_{50}$=10 nM.

Example 136: Preparation of 8-[2-fluoro-4-(2-oxo-1,2-dihydropyrazin-1-yl)benzoyl]-2-[3-methoxy-4-(1H-pyrazol-4-yl)phenyl]-2,8-diazaspiro[4.5]decan-1-one

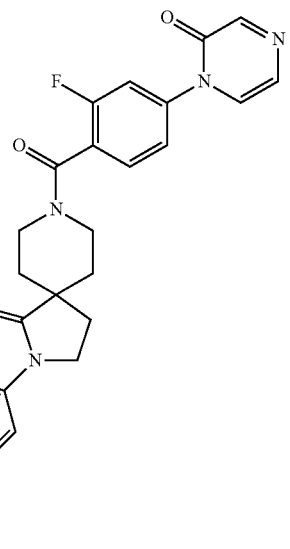

¹H NMR (500 MHz, DMSO-d₆) δ 8.19-7.87 (m, 2H), 7.70 (br d, J=6.1 Hz, 1H), 7.64-7.48 (m, 5H), 7.37 (br d, J=8.2 Hz, 1H), 7.15 (br d, J=7.9 Hz, 1H), 6.52 (br d, J=9.2 Hz, 1H), 6.59-6.48 (m, 1H), 6.37 (br t, J=6.4 Hz, 1H), 4.39 (br d, J=12.5 Hz, 1H), 3.87 (s, 5H), 3.74-3.65 (m, 1H), 3.30 (br d, J=9.2 Hz, 1H), 3.23-3.10 (m, 1H), 2.27-2.08 (m, 2H), 1.89-1.65 (m, 3H), 1.56 (br d, J=13.1 Hz, 1H); MS ESI m/z 543.2 (M+H); Anal. HPLC Retention time: 1.23 (Method 1); ROCK2 IC$_{50}$=4.2 nM.

Example 137: Preparation of 2-[3-methoxy-4-(1H-pyrazol-4-yl)phenyl]-8-[4-(2-oxo-1,3-oxazinan-3-yl)benzoyl]-2,8-diazaspiro[4.5]decan-1-one

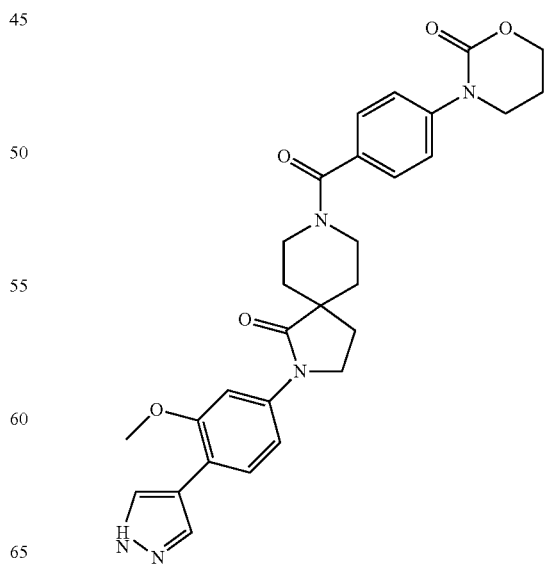

¹H NMR (500 MHz, DMSO-d₆) δ 8.01 (br s, 2H), 7.65-7.57 (m, 2H), 7.43 (br d, J=3.4 Hz, 4H), 7.14 (br d, J=8.5 Hz, 1H), 4.35 (br t, J=5.2 Hz, 2H), 3.86 (s, 5H), 3.70 (br t, J=6.0 Hz, 2H), 3.57-3.49 (m, 2H), 3.36-3.09 (m, 2H), 2.20-2.06 (m, 4H), 1.74 (br s, 2H), 1.67-1.50 (m, 2H); MS ESI m/z 530.4 (M+H); Anal. HPLC Retention time: 1.2 (Method 2); ROCK2 IC$_{50}$=7.1 nM.

Example 138: Preparation of 2-[3-methoxy-4-(1H-pyrazol-4-yl)phenyl]-8-[2-(trifluoromethyl)quinoxaline-6-carbonyl]-2,8-diazaspiro[4.5]decan-1-one

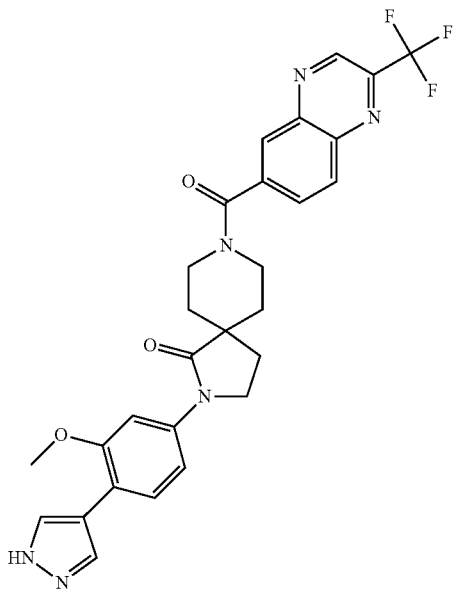 [SMILES: COc1cc(N2CCC3(CCN(C(=O)c4ccc5nc(C(F)(F)F)cnc5c4)CC3)C2=O)ccc1-c1cn[nH]c1]

MS ESI m/z 551.2 (M+H); Anal. HPLC Retention time: 1.58 Method 1; ROCK2 IC$_{50}$=63 nM.

Example 139: Preparation of 2-[3-methoxy-4-(1H-pyrazol-4-yl)phenyl]-8-[4-(2-oxoimidazolidin-1-yl)benzoyl]-2,8-diazaspiro[4.5]decan-1-one

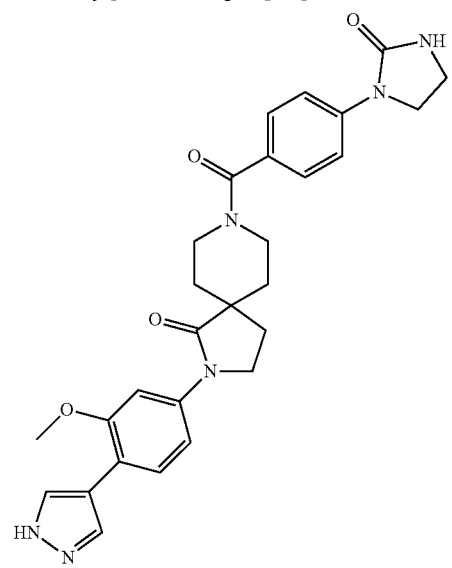

¹H NMR (500 MHz, DMSO-d₆) δ 8.02 (br s, 2H), 7.68-7.56 (m, 4H), 7.38 (br d, J=8.5 Hz, 2H), 7.14 (br d, J=8.2 Hz, 1H), 7.04 (s, 1H), 4.01 (br s, 1H), 3.92-3.81 (m, 7H), 3.76-3.68 (m, 1H), 3.47 (br s, 2H), 3.42 (br t, J=7.9 Hz, 1H), 3.17 (br d, J=4.6 Hz, 1H), 2.14 (br s, 2H), 1.73 (br s, 2H), 1.58 (br d, J=4.6 Hz, 2H); MS ESI m/z 515.3 (M+H); Anal. HPLC Retention time: 1.11 (Method 2); ROCK2 IC$_{50}$=3.7 nM.

Example 140: Preparation of 2-[3-methoxy-4-(1H-pyrazol-4-yl)phenyl]-8-[1-(pyrimidin-2-yl)piperidine-4-carbonyl]-2,8-diazaspiro[4.5]decan-1-one

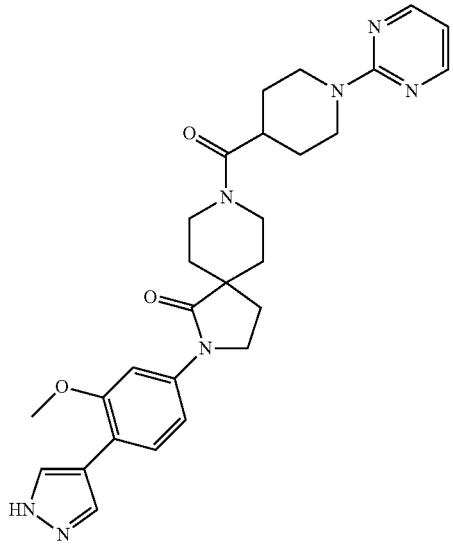 [SMILES: COc1cc(N2CCC3(CCN(C(=O)C4CCN(c5ncccn5)CC4)CC3)C2=O)ccc1-c1cn[nH]c1]

¹H NMR (500 MHz, DMSO-d₆) δ 8.34 (br d, J=4.5 Hz, 2H), 8.21-7.88 (m, 2H), 7.70-7.53 (m, 2H), 7.15 (br d, J=8.6 Hz, 1H), 6.59 (br t, J=4.5 Hz, 1H), 4.66 (br d, J=10.7 Hz, 2H), 4.25 (br d, J=12.5 Hz, 1H), 4.01 (br d, J=13.0 Hz, 1H), 3.87 (s, 5H), 3.28 (br t, J=11.4 Hz, 1H), 3.06-2.92 (m, 4H), 2.87 (br t, J=10.4 Hz, 1H), 2.14 (br t, J=6.5 Hz, 2H), 1.78-1.39 (m, 9H); MS ESI m/z 516.2 (M+H); Anal. HPLC Retention time: 1.41 (Method 1), ROCK2 IC$_{50}$=1240 nM.

Example 141: Preparation of 2-[3-methoxy-4-(1H-pyrazol-4-yl)phenyl]-8-[4-(2-oxo-1,3-oxazolidin-3-yl)benzoyl]-2,8-diazaspiro[4.5]decan-1-one

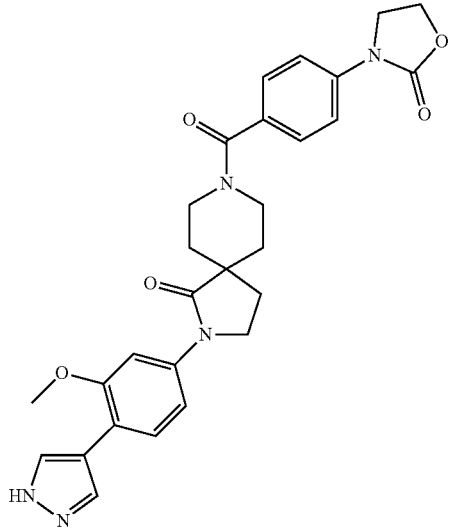 [SMILES: COc1cc(N2CCC3(CCN(C(=O)c4ccc(N5CCOC5=O)cc4)CC3)C2=O)ccc1-c1cn[nH]c1]

¹H NMR (500 MHz, DMSO-d₆) δ 8.01 (br s, 2H), 7.66-7.54 (m, 4H), 7.46 (br d, J=8.5 Hz, 2H), 7.14 (br d,

J=7.3 Hz, 1H), 4.46 (br t, J=7.9 Hz, 2H), 4.09 (br t, J=7.8 Hz, 2H), 3.86 (s, 5H), 3.56-3.45 (m, 2H), 3.32-3.17 (m, 2H), 2.14 (br s, 2H), 1.73 (br s, 2H), 1.65-1.49 (m, 2H); MS ESI m/z 515.9 (M+H); Anal. HPLC Retention time: 1.28 (Method 1); ROCK2 IC$_{50}$=3 nM.

Example 142: Preparation of 2-[3-methoxy-4-(1H-pyrazol-4-yl)phenyl]-8-[4-(2-oxopiperidin-1-yl)benzoyl]-2,8-diazaspiro[4.5]decan-1-one

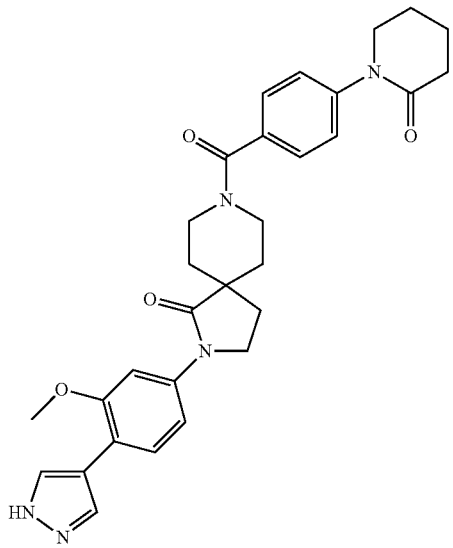 [SMILES: COc1cc(N2CCC3(CCN(C(=O)c4ccc(N5CCCCC5=O)cc4)CC3)C2=O)ccc1-c1cn[nH]c1]

$^1$H NMR (500 MHz, DMSO-d$_6$) δ 8.19-7.86 (m, 2H), 7.67-7.57 (m, 2H), 7.46-7.40 (m, 2H), 7.39-7.33 (m, 2H), 7.15 (br d, J=8.2 Hz, 1H), 4.42-4.25 (m, 1H), 3.87 (s, 5H), 3.63 (br t, J=5.5 Hz, 2H), 3.51-3.47 (m, 1H), 3.32-3.11 (m, 2H), 2.41 (br t, J=6.3 Hz, 2H), 2.15 (br s, 2H), 1.93-1.80 (m, 4H), 1.74 (br s, 2H), 1.68-1.50 (m, 2H); MS ESI m/z 528.2 (M+H); Anal. HPLC Retention time: 1.26 (Method 1); ROCK2 IC$_{50}$=8.8 nM.

Example 143: Preparation of 2-[3-methoxy-4-(1H-pyrazol-4-yl)phenyl]-8-[4-(2H-1,2,3,4-tetrazol-5-yl)benzoyl]-2,8-diazaspiro[4.5]decan-1-one

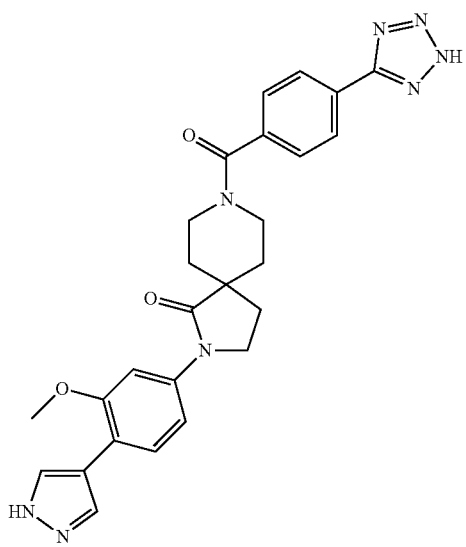 [SMILES: COc1cc(N2CCC3(CCN(C(=O)c4ccc(-c5nn[nH]n5)cc4)CC3)C2=O)ccc1-c1cn[nH]c1]

$^1$H NMR (500 MHz, DMSO-d$_6$) δ 8.07 (br d, J=7.9 Hz, 2H), 8.01 (br s, 2H), 7.64-7.56 (m, 2H), 7.48 (d, J=7.9 Hz, 2H), 7.18-7.09 (m, 1H), 4.41-4.27 (m, 1H), 3.87 (s, 5H), 3.75-3.61 (m, 1H), 3.33-3.10 (m, 2H), 2.15 (br s, 2H), 1.76 (br d, J=8.2 Hz, 2H), 1.68-1.50 (m, 2H); MS ESI m/z 499.3 (M+H); Anal. HPLC Retention time: 1.19 (Method 2); ROCK2 IC$_{50}$=1018 nM.

Example 144: Preparation of 2-[3-methoxy-4-(1H-pyrazol-4-yl)phenyl]-8-(1-oxo-2,3-dihydro-1H-isoindole-5-carbonyl)-2,8-diazaspiro[4.5]decan-1-one

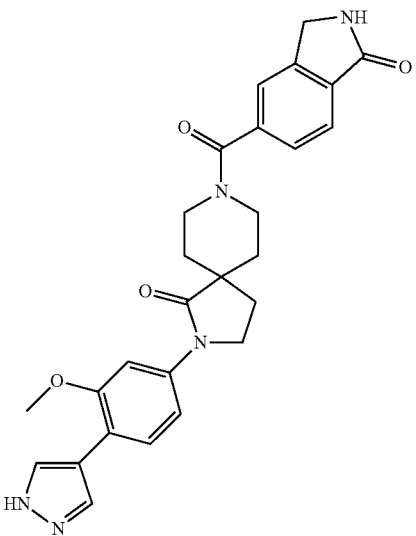 [SMILES: COc1cc(N2CCC3(CCN(C(=O)c4ccc5c(c4)CNC5=O)CC3)C2=O)ccc1-c1cn[nH]c1]

$^1$H NMR (500 MHz, DMSO-d$_6$) δ 8.67 (s, 1H), 8.02 (br s, 2H), 7.75 (d, J=7.6 Hz, 1H), 7.61 (br d, J=5.5 Hz, 3H), 7.49 (br d, J=7.6 Hz, 1H), 7.15 (br d, J=9.2 Hz, 1H), 4.43 (s, 2H), 4.38-4.27 (m, 1H), 3.90 (s, 5H), 3.65-3.52 (m, 1H), 3.40 (br s, 1H), 3.28-3.21 (m, 1H), 2.25-2.07 (m, 2H), 1.83-1.60 (m, 3H), 1.53 (br s, 1H); MS ESI m/z 486.02, 486.02 (M+H); ROCK2 IC$_{50}$=94 nM.

Example 145: Preparation of 2-[3-methoxy-4-(1H-pyrazol-4-yl)phenyl]-8-[6-(1H-1,2,4-triazol-1-yl)pyridine-3-carbonyl]-2,8-diazaspiro[4.5]decan-1-one

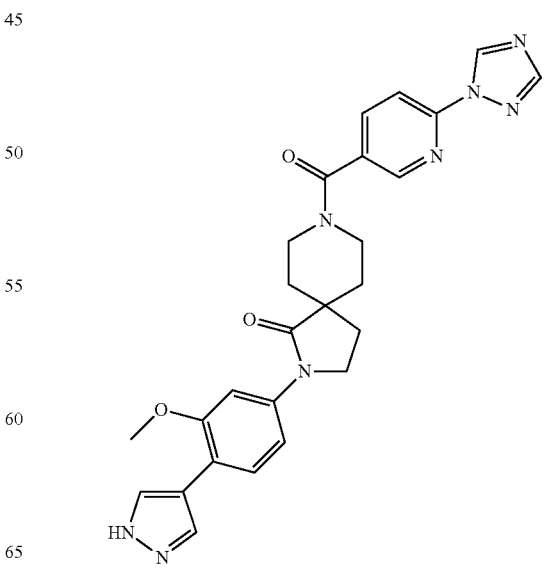

¹H NMR (500 MHz, DMSO-d₆) δ 9.42 (s, 1H), 8.61 (s, 1H), 8.34 (s, 1H), 8.14 (br d, J=8.5 Hz, 1H), 8.09-7.91 (m, 3H), 7.63-7.55 (m, 2H), 7.15 (br d, J=8.2 Hz, 1H), 4.34 (br d, J=8.5 Hz, 1H), 3.87 (s, 5H), 3.72-3.62 (m, 1H), 3.34 (br d, J=4.6 Hz, 1H), 3.23 (br d, J=12.2 Hz, 1H), 2.15 (br d, J=4.6 Hz, 2H), 1.79 (br s, 2H), 1.72-1.63 (m, 1H), 1.56 (br s, 1H); MS ESI m/z 499.1 (M+H); Anal. HPLC Retention time: 1.2 (Method 2); ROCK2 IC₅₀=54 nM.

Example 146: Preparation of 2-[3-methoxy-4-(1H-pyrazol-4-yl)phenyl]-8-[4-(2-oxo-1,2-dihydropyrazin-1-yl)benzoyl]-2,8-diazaspiro[4.5]decan-1-one

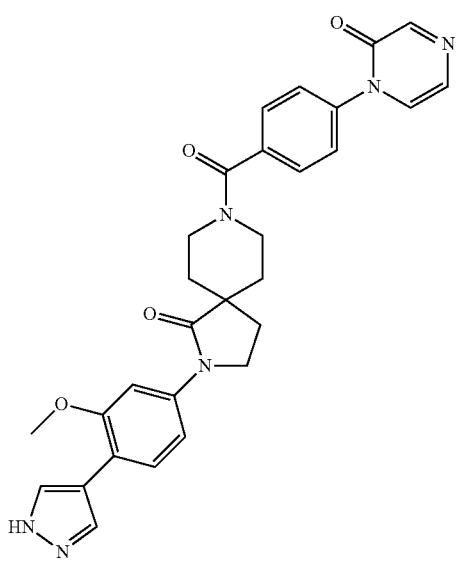 [SMILES: COc1cc(N2CCC3(CCN(C(=O)c4ccc(-n5ccncc5=O)cc4)CC3)C2=O)ccc1-c1cn[nH]c1]

¹H NMR (500 MHz, DMSO-d₆) δ 8.15 (s, 1H), 8.04 (br d, J=12.5 Hz, 2H), 7.71 (br d, J=4.3 Hz, 1H), 7.63-7.56 (m, 6H), 7.42 (br d, J=4.3 Hz, 1H), 7.16 (br d, J=8.2 Hz, 1H), 4.42-4.30 (m, 1H), 4.13 (br d, J=4.9 Hz, 1H), 3.87 (s, 5H), 3.39 (br d, J=4.0 Hz, 1H), 3.33-3.26 (m, 1H), 2.15 (br s, 2H), 1.77 (br s, 2H), 1.72-1.63 (m, 1H), 1.57 (br s, 1H); MS ESI m/z 525.3 (M+H):

Anal. HPLC Retention time: 1.16 (Method 2); ROCK2 IC₅₀=12 nM.

Example 147: Preparation of 1-(4-{2-[3-methoxy-4-(1H-pyrazol-4-yl)phenyl]-1-oxo-2,8-diazaspiro[4.5]decane-8-carbonyl}phenyl)imidazolidine-2,4-dione

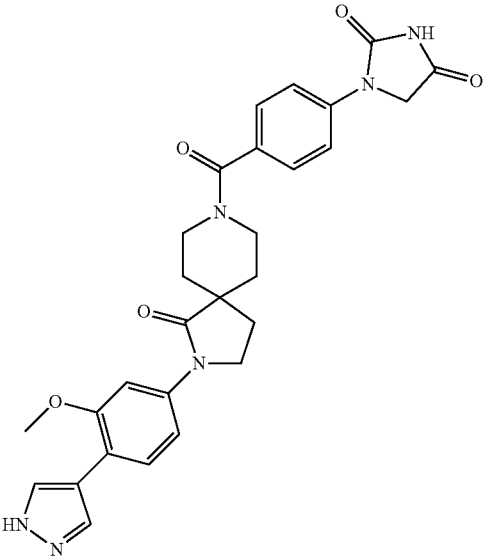 [SMILES: COc1cc(N2CCC3(CCN(C(=O)c4ccc(N5CC(=O)NC5=O)cc4)CC3)C2=O)ccc1-c1cn[nH]c1]

¹H NMR (500 MHz, DMSO-d₆) δ 8.18-7.90 (m, 2H), 7.68 (br d, J=8.5 Hz, 2H), 7.61 (br d, J=5.5 Hz, 2H), 7.44 (br d, J=8.5 Hz, 2H), 7.15 (br d, J=7.3 Hz, 1H), 4.48 (s, 2H), 4.37-4.19 (m, 1H), 3.87 (s, 5H), 3.74-3.60 (m, 1H), 3.44-3.34 (m, 1H), 3.29-3.21 (m, 1H), 2.15 (br s, 2H), 1.74 (br s, 2H), 1.57 (br d, J=8.2 Hz, 2H); MS ESI m/z 529.4 (M+H); Anal. HPLC Retention time: 1.18 (Method 1); ROCK2 IC₅₀=12 nM.

Example 148: Preparation of 4-{2-[3-methoxy-4-(H-pyrazol-4-yl)phenyl]-1-oxo-2,8-diazaspiro[4.5]decane-8-carbonyl}cyclohexane-1-carboxamide ¹H NMR (500 MHz, DMSO-d₆) δ 8.00 (br s, 2H), 7.59 (d, J=8.4 Hz, 1H), 7.55 (s, 1H), 7.34 (br s, 1H), 7.12 (br d, J=8.3

Hz, 1H), 6.69 (br s, 1H), 4.24 (br d, J=13.7 Hz, 1H), 3.91 (br d, J=12.4 Hz, 1H), 3.80 (br s, 6H), 3.29-3.15 (m, 1H), 2.81 (br t, J=10.3 Hz, 1H), 2.59 (br s, 1H), 2.11 (br t, J=6.6 Hz, 4H), 1.74 (br s, 2H), 1.67 (br s, 3H), 1.60-1.50 (m, 3H), 1.44-1.34 (m, 4H); MS ESI m/z 480.4 (M+H); Anal. HPLC Retention time: 0.94 (Method 2); ROCK2 IC$_{50}$=2165 nM.

Example 149: Preparation of 2-[3-methoxy-4-(1H-pyrazol-4-yl)phenyl]-8-(quinoline-8-carbonyl)-2,8-diazaspiro[4.5]decan-1-one

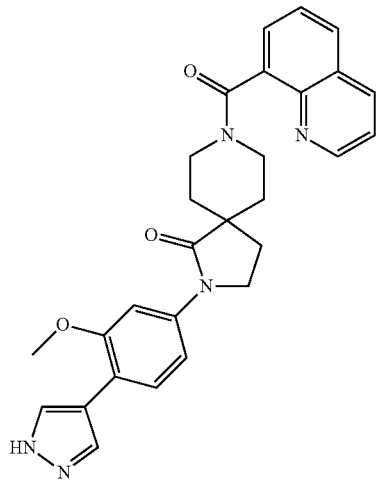 [SMILES: COc1cc(N2CCC3(CCN(C(=O)c4cccc5cccnc45)CC3)C2=O)ccc1-c1cn[nH]c1]

$^1$H NMR (500 MHz, DMSO-d$_6$) δ 8.96 (br dd, J=10.7, 3.1 Hz, 1H), 8.50-8.39 (m, 1H), 8.11-7.95 (m, 3H), 7.80-7.63 (m, 2H), 7.63-7.56 (m, 3H), 7.13 (br t, J=6.4 Hz, 1H), 4.63-4.39 (m, 1H), 3.94-3.71 (m, 5H), 3.33-2.97 (m, 3H), 2.19 (br dd, J=12.8, 5.2 Hz, 1H), 2.12-2.00 (m, 1H), 1.83-1.75 (m, 1H), 1.74-1.52 (m, 2H), 1.45-1.28 (m, 1H); MS ESI m/z 481.9 (M+H); Anal. HPLC Retention time: 1.42 (Method 1); ROCK2 IC$_{50}$=251 nM.

Example 150: Preparation of 2-[3-methoxy-4-(1H-pyrazol-4-yl)phenyl]-8-{4-methyl-1-oxo-1H,2H,3H,4H-pyrazino[1,2-a]indole-7-carbonyl}-2,8-diazaspiro[4.5]decan-1-one

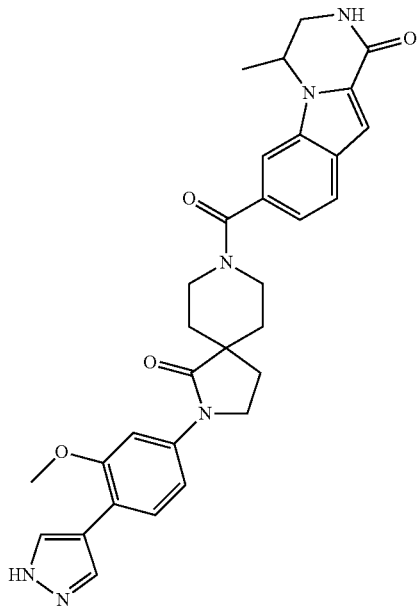 [SMILES: COc1cc(N2CCC3(CCN(C(=O)c4ccc5cc6n(c5c4)C(C)CNC6=O)CC3)C2=O)ccc1-c1cn[nH]c1]

$^1$H NMR (500 MHz, DMSO-d$_6$) δ 8.13 (br d, J=4.6 Hz, 1H), 8.01 (br s, 2H), 7.75 (d, J=8.2 Hz, 1H), 7.63 (s, 1H), 7.60 (br d, J=8.4 Hz, 1H), 7.56 (s, 1H), 7.17-7.06 (m, 3H), 4.98-4.86 (m, 1H), 3.85 (s, 2H), 3.74 (br s, 5H), 3.39 (br dd, J=12.5, 4.8 Hz, 1H), 3.32-3.22 (m, 1H), 3.15 (br dd, J=16.5, 4.2 Hz, 1H), 2.15 (br s, 2H), 1.84-1.60 (m, 3H), 1.50 (br d, J=9.3 Hz, 1H), 1.30 (br d, J=6.4 Hz, 3H); MS ESI m/z 553.3 (M+H); Anal. HPLC Retention time: 1.16 (Method 2); ROCK2 IC$_{50}$=144 nM.

Example 151: Preparation of 8-{1-[(4-fluoro-3-methoxyphenyl)methyl]piperidine-4-carbonyl}-2-[3-methoxy-4-(1H-pyrazol-4-yl)phenyl]-2,8-diazaspiro[4.5]decan-1-one

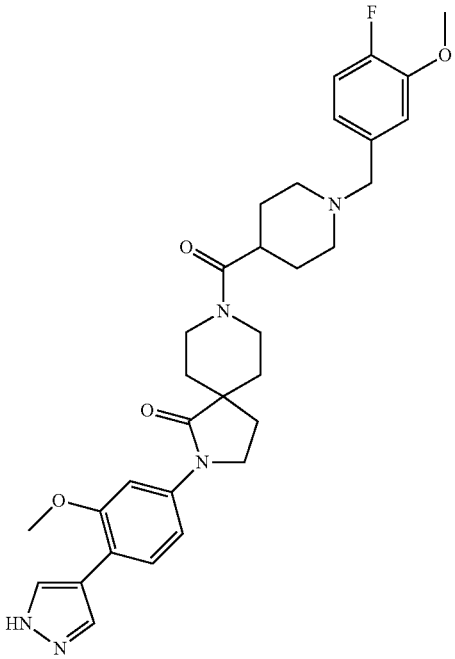 [SMILES: COc1cc(CN2CCC(C(=O)N3CCC4(CC3)CCN(c3ccc(-c5cn[nH]c5)c(OC)c3)C4=O)CC2)ccc1F]

$^1$H NMR (500 MHz, DMSO-d$_6$) δ 8.02 (br s, 2H), 7.65-7.56 (m, 2H), 7.17-7.10 (m, 2H), 7.07 (br d, J=8.6 Hz, 1H), 6.84 (br d, J=6.2 Hz, 1H), 4.25 (br d, J=13.2 Hz, 1H), 3.89 (br s, 1H), 3.88-3.83 (m, 5H), 3.82 (s, 3H), 3.22 (br t, J=12.3 Hz, 1H), 2.91-2.74 (m, 3H), 2.60 (br d, J=4.3 Hz, 1H), 2.12 (br t, J=6.7 Hz, 2H), 1.99 (br d, J=8.5 Hz, 2H), 1.85 (br s, 1H), 1.74-1.42 (m, 9H); MS ESI m/z 576.2 (M+H); Anal. HPLC Retention time: 1.46 (Method 1); ROCK2 IC$_{50}$=2472 nM.

Example 152: Preparation of 2-[3-methoxy-4-(1H-pyrazol-4-yl)phenyl]-8-(1-methyl-1H-indazole-5-carbonyl)-2,8-diazaspiro[4.5]decan-1-one

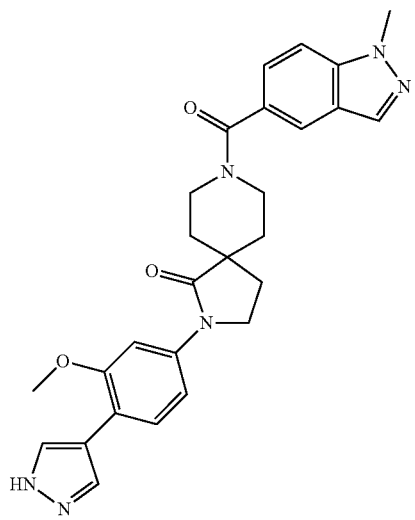 [SMILES: COc1cc(N2CCC3(CCN(C(=O)c4ccc5c(cnn5C)c4)CC3)C2=O)ccc1-c1cn[nH]c1]

¹H NMR (500 MHz, DMSO-d₆) δ 8.14 (s, 1H), 8.07-7.94 (m, 2H), 7.86 (s, 1H), 7.71 (d, J=8.6 Hz, 1H), 7.64-7.58 (m, 2H), 7.44 (d, J=8.7 Hz, 1H), 7.15 (br d, J=8.5 Hz, 1H), 4.35 (br d, J=8.7 Hz, 1H), 4.25-4.17 (m, 1H), 4.07 (s, 3H), 3.87 (s, 5H), 3.43 (br s, 1H), 3.31-3.12 (m, 1H), 2.15 (br s, 2H), 1.85-1.69 (m, 2H), 1.59 (br s, 2H); MS ESI m/z 485.2 (M+H); Anal. HPLC Retention time: 1.21 (Method 2); ROCK2 IC₅₀=6.2 nM.

Example 153: Preparation of 2-[3-methoxy-4-(1H-pyrazol-4-yl)phenyl]-8-(1-methyl-1H-indole-5-carbonyl)-2,8-diazaspiro[4.5]decan-1-one

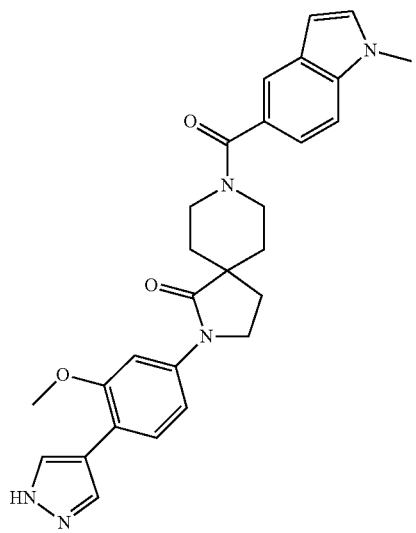 [SMILES: COc1cc(N2CCC3(CCN(C(=O)c4ccc5c(ccn5C)c4)CC3)C2=O)ccc1-c1cn[nH]c1]

¹H NMR (500 MHz, DMSO-d₆) δ 8.01 (br s, 2H), 7.66-7.54 (m, 3H), 7.49 (br d, J=8.4 Hz, 1H), 7.38 (br d, J=2.2 Hz, 1H), 7.20 (br d, J=8.3 Hz, 1H), 7.13 (br d, J=8.7 Hz, 1H), 6.51 (br d, J=2.1 Hz, 1H), 3.85 (s, 2H), 3.67 (br s, 9H), 3.19 (br d, J=18.9 Hz, 2H), 2.14 (br s, 2H), 1.72 (br s, 2H), 1.56 (br d, J=4.5 Hz, 2H); MS ESI m/z 484.3 (M+H); Anal. HPLC Retention time: 1.42 Method 2; ROCK2 IC₅₀=4.5 nM.

Example 154: Preparation of 8-(1-methanesulfonylpiperidine-4-carbonyl)-2-[3-methoxy-4-(1H-pyrazol-4-yl)phenyl]-2,8-diazaspiro[4.5]decan-1-one

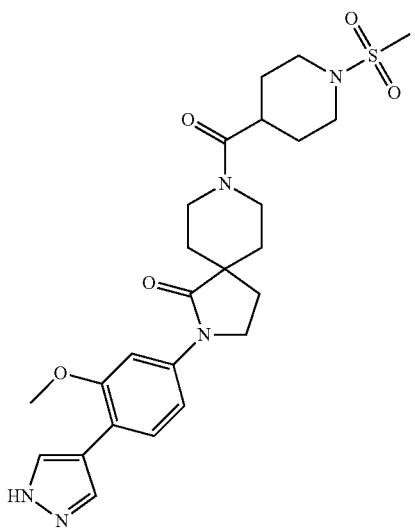 [SMILES: COc1cc(N2CCC3(CCN(C(=O)C4CCN(S(C)(=O)=O)CC4)CC3)C2=O)ccc1-c1cn[nH]c1]

¹H NMR (500 MHz, DMSO-d₆) δ 8.01 (br s, 2H), 7.65-7.55 (m, 0.2H), 7.14 (br d, J=8.5 Hz, 1H), 4.25 (br d, J=13.0 Hz, 1H), 3.93 (br d, J=13.8 Hz, 1H), 3.86 (s, 4H), 3.58 (br s, 5H), 3.25 (br t, J=11.6 Hz, 1H), 2.90-2.74 (m, 7H), 2.13 (br t, J=6.7 Hz, 2H), 1.73 (br s, 3H), 1.65-1.51 (m, 5H); MS ESI m/z 516.2 (M+H); Anal. HPLC Retention time: 1.07 (Method 2); ROCK2 IC₅₀=1995 nM.

Example 155: Preparation of 2-[3-methoxy-4-(1H-pyrazol-4-yl)phenyl]-8-(1-methyl-1H-indole-6-carbonyl)-2,8-diazaspiro[4.5]decan-1-one

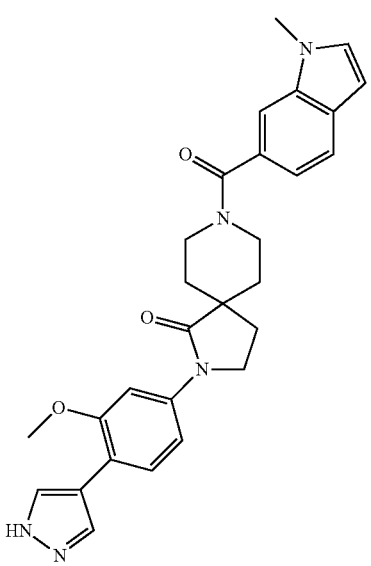 [SMILES: COc1cc(N2CCC3(CCN(C(=O)c4ccc5ccn(C)c5c4)CC3)C2=O)ccc1-c1cn[nH]c1]

¹H NMR (500 MHz, DMSO-d₆) δ 8.01 (br s, 2H), 7.63-7.54 (m, 3H), 7.50 (s, 1H), 7.41 (br d, J=2.6 Hz, 1H), 7.13 (br d, J=8.0 Hz, 1H), 7.06 (br d, J=8.2 Hz, 1H), 6.48 (br d, J=2.3 Hz, 1H), 3.85 (s, 2H), 3.69 (br s, 8H), 3.35-3.08 (m, 2H), 2.15 (br s, 2H), 1.73 (br d, J=2.0 Hz, 2H), 1.66-1.44 (m, 2H); MS ESI m/z 484.2 (M+H); Anal. HPLC Retention time: 1.47 (Method 2); ROCK2 IC₅₀=40 nM.

Example 156: Preparation of 8-(5-methoxy-1-methyl-1H-indole-2-carbonyl)-2-[3-methoxy-4-(1H-pyrazol-4-yl)phenyl]-2,8-diazaspiro[4.5]decan-1-one

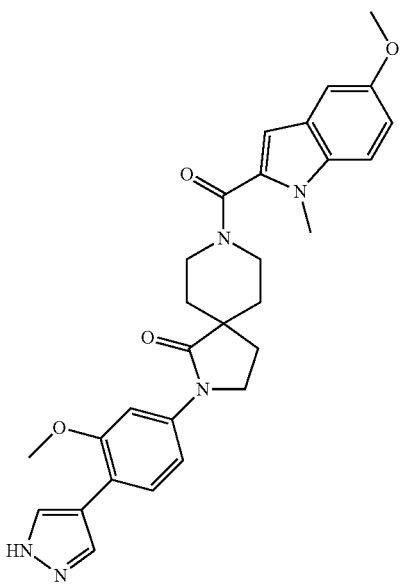 [SMILES: COc1ccc2c(c1)cc(C(=O)N1CCC3(CC1)CCN(c1ccc(-c4cn[nH]c4)c(OC)c1)C3=O)n2C]

¹H NMR (500 MHz, DMSO-d₆) δ 8.02 (br s, 2H), 7.67-7.57 (m, 2H), 7.42 (d, J=8.9 Hz, 1H), 7.15 (br d, J=8.5 Hz, 1H), 7.10 (d, J=1.7 Hz, 1H), 6.89 (dd, J=8.9, 2.0 Hz, 1H), 6.57 (s, 1H), 4.48-4.29 (m, 1H), 4.17-3.96 (m, 1H), 3.87 (s, 5H), 3.76 (s, 3H), 3.73 (s, 3H), 3.42 (br s, 1H), 3.17 (br s, 1H), 2.17 (br s, 2H), 1.83-1.71 (m, 2H), 1.63 (br s, 2H); MS ESI m/z 514.4 (M+H); Anal. HPLC Retention time: 1.61 (Method 1); ROCK2 IC₅₀=54 nM.

Example 157: Preparation of 7-{2-[3-methoxy-4-(1H-pyrazol-4-yl)phenyl]-1-oxo-2,8-diazaspiro[4.5]decane-8-carbonyl}-3,4-dihydro-2H-1,4-benzoxazin-3-one

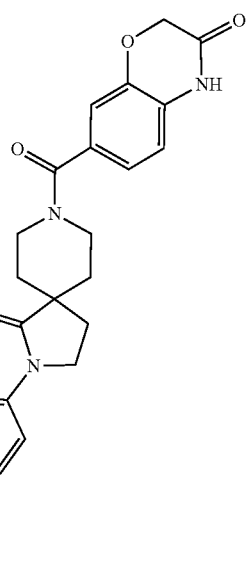

¹H NMR (500 MHz, DMSO-d₆) δ 8.02 (br s, 2H), 7.68-7.56 (m, 2H), 7.14 (br d, J=8.7 Hz, 1H), 7.05-6.91 (m, 3H), 4.62 (s, 2H), 4.34-4.19 (m, 1H), 4.01 (s, 1H), 3.86 (s, 5H), 3.42 (br s, 1H), 3.31-3.06 (m, 1H), 2.13 (br s, 2H), 1.71 (br s, 2H), 1.57 (br d, J=2.6 Hz, 2H); MS ESI m/z 502.1 (M+H); Anal. HPLC Retention time: 1.12 (Method 1); ROCK2 IC₅₀=22 nM.

Example 158: Preparation of 2-[3-methoxy-4-(1H-pyrazol-4-yl)phenyl]-8-[4-(pyridin-3-yl)benzoyl]-2,8-diazaspiro[4.5]decan-1-one

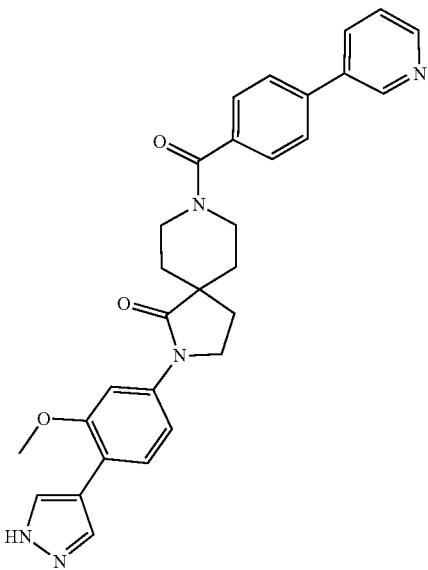 [SMILES: COc1cc(N2CCC3(CCN(C(=O)c4ccc(-c5cccnc5)cc4)CC3)C2=O)ccc1-c1cn[nH]c1]

¹H NMR (500 MHz, DMSO-d₆) δ 8.94 (br s, 1H), 8.60 (br d, J=3.8 Hz, 1H), 8.13 (br d, J=7.7 Hz, 1H), 8.11-7.91 (m, 2H), 7.83 (br d, J=7.8 Hz, 2H), 7.61 (br d, J=2.9 Hz, 2H), 7.55 (br d, J=8.2 Hz, 3H), 7.15 (br d, J=8.5 Hz, 1H), 4.35 (br d, J=7.0 Hz, 1H), 3.87 (s, 5H), 3.73-3.60 (m, 1H), 3.34-3.26 (m, 1H), 3.17 (br d, J=4.9 Hz, 1H), 2.16 (br s, 2H), 1.85-1.60 (m, 3H), 1.55 (br s, 1H); MS ESI m/z 508.2 (M+H); Anal. HPLC Retention time: 0.97 (Method 2); ROCK2 IC₅₀=4.1 nM.

Example 159: Preparation of 8-[2-methoxy-4-(1H-pyrazol-4-yl)benzoyl]-2-[3-methoxy-4-(1H-pyrazol-4-yl)phenyl]-2,8-diazaspiro[4.5]decan-1-one

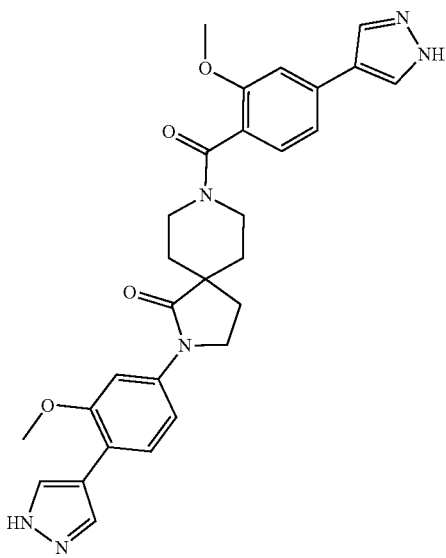 [SMILES: COc1cc(-c2cn[nH]c2)ccc1C(=O)N1CCC2(CC1)CCN(c1ccc(-c3cn[nH]c3)c(OC)c1)C2=O]

¹H NMR (500 MHz, DMSO-d₆) δ 8.41-8.19 (m, 1H), 8.16-7.98 (m, 2H), 7.61 (br d, J=7.3 Hz, 2H), 7.35 (br d, J=7.0 Hz, 1H), 7.29 (s, 1H), 7.25 (br s, 1H), 7.14 (br d, J=7.9 Hz, 2H), 4.92-4.80 (m, 1H), 4.48-4.31 (m, 1H), 3.96 (br d, J=6.4 Hz, 1H), 3.92-3.80 (m, 7H), 3.15-3.05 (m, 1H), 2.93 (br d, J=7.0 Hz, 1H), 2.21-2.09 (m, 2H), 1.84-1.69 (m, 2H), 1.63 (br d, J=12.5 Hz, 1H), 1.48 (br d, J=12.2 Hz, 1H); MS ESI m/z 527.1 (M+H); Anal. HPLC Retention time: 1.24 (Method 1); ROCK2 IC₅₀=29 nM.

Example 160: Preparation of 2-[3-methoxy-4-(1H-pyrazol-4-yl)phenyl]-8-[4-(1,3-oxazol-5-yl)benzoyl]-2,8-diazaspiro[4.5]decan-1-one

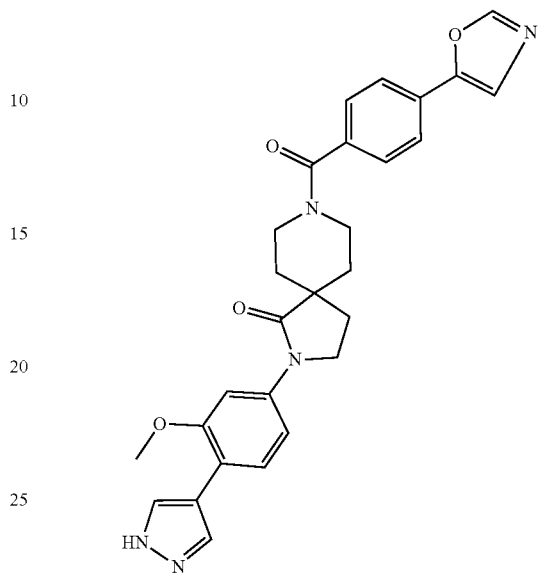

¹H NMR (500 MHz, DMSO-d₆) δ 8.50 (s, 1H), 8.21-7.90 (m, 2H), 7.86-7.74 (m, 3H), 7.67-7.57 (m, 2H), 7.52 (br d, J=7.8 Hz, 2H), 7.15 (br d, J=8.4 Hz, 1H), 4.33 (br d, J=6.6 Hz, 1H), 3.87 (s, 5H), 3.68-3.58 (m, 1H), 3.35-3.23 (m, 1H), 3.22-3.09 (m, 1H), 2.15 (br s, 2H), 1.75 (br d, J=4.1 Hz, 3H), 1.55 (br s, 1H); MS ESI m/z 497.9 (M+H); Anal. HPLC Retention time: 1.36 (Method 1), ROCK2 IC₅₀=23 nM.

Example 161: Preparation of 8-(2-bromo-4-methoxybenzoyl)-2-[3-methoxy-4-(1H-pyrazol-4-yl)phenyl]-2,8-diazaspiro[4.5]decan-1-one

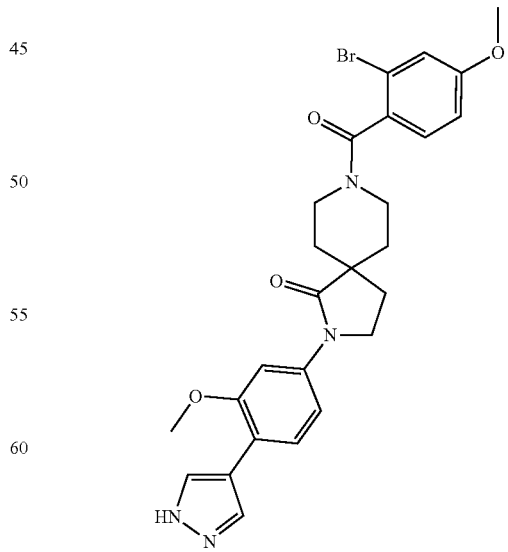

¹H NMR (500 MHz, DMSO-d₆) δ 8.01 (br s, 2H), 7.61-7.52 (m, 2H), 7.29-7.19 (m, 2H), 7.11 (br t, J=9.8 Hz,

1H), 7.03 (br t, J=9.0 Hz, 1H), 4.35 (br d, J=8.3 Hz, 1H), 3.90-3.63 (m, 8H), 3.31 (br d, J=9.4 Hz, 1H), 3.23-3.03 (m, 2H), 2.21-2.06 (m, 2H), 1.93-1.70 (m, 2H), 1.63 (br d, J=13.9 Hz, 1H), 1.48 (br d, J=9.6 Hz, 1H); MS ESI m/z 539.3 (M+H); Anal. HPLC Retention time: 1.47 (Method 2); ROCK2 IC$_{50}$=17 nM.

Example 162: Preparation of 2-[3-methoxy-4-(1H-pyrazol-4-yl)phenyl]-8-[4-(5-methyl-1,3,4-oxadiazol-2-yl)benzoyl]-2,8-diazaspiro[4.5]decan-1-one

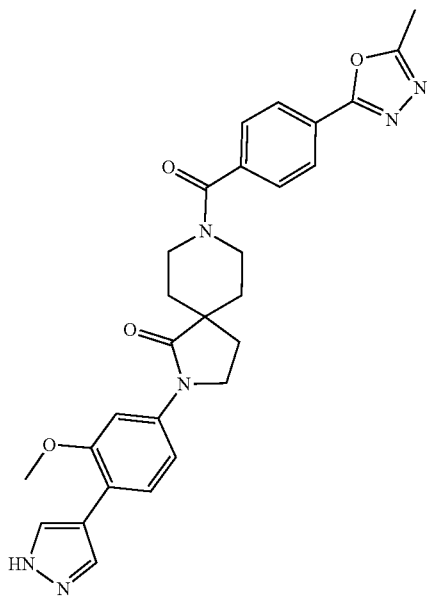 [SMILES: COc1cc(N2CCC3(CCN(C(=O)c4ccc(-c5nnc(C)o5)cc4)CC3)C2=O)ccc1-c1cn[nH]c1]

$^1$H NMR (500 MHz, DMSO-d$_6$) δ 8.05 (br d, J=8.1 Hz, 4H), 7.68-7.56 (m, 4H), 7.15 (br d, J=8.5 Hz, 1H), 4.41-4.26 (m, 1H), 3.87 (s, 5H), 3.63-3.54 (m, 1H), 3.27 (br d, J=11.0 Hz, 1H), 3.17 (br d, J=5.0 Hz, 1H), 2.60 (s, 3H), 2.16 (br d, J=5.2 Hz, 2H), 1.84-1.63 (m, 3H), 1.54 (br s, 1H); MS ESI m/z 513.3 (M+H); Anal. HPLC Retention time: 1.18 (Method 2); ROCK2 IC$_{50}$=27 nM.

Example 163: Preparation of 2-[3-methoxy-4-(1H-pyrazol-4-yl)phenyl]-8-[4-(1,3,4-oxadiazol-2-yl)benzoyl]-2,8-diazaspiro[4.5]decan-1-one

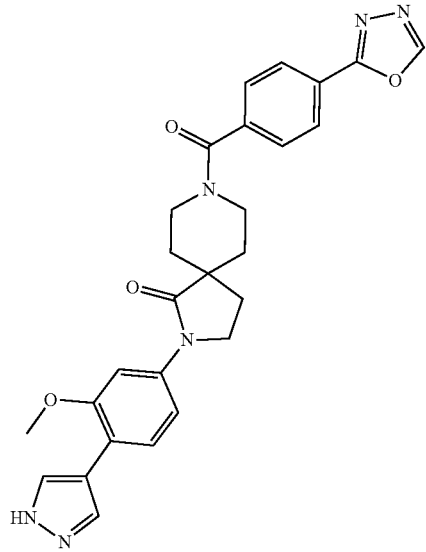 [SMILES: COc1cc(N2CCC3(CCN(C(=O)c4ccc(-c5nnco5)cc4)CC3)C2=O)ccc1-c1cn[nH]c1]

$^1$H NMR (500 MHz, DMSO-d$_6$) δ 9.26 (s, 1H), 8.11 (br d, J=8.1 Hz, 2H), 8.01 (br s, 2H), 7.62 (br d, J=8.1 Hz, 3H), 7.55 (s, 1H), 7.12 (br d, J=8.4 Hz, 1H), 4.35 (br d, J=11.2 Hz, 1H), 3.80 (br s, 5H), 3.57 (br d, J=13.1 Hz, 1H), 3.32-3.21 (m, 1H), 3.18-3.08 (m, 1H), 2.24-2.07 (m, 2H), 1.82-1.61 (m, 3H), 1.51 (br d, J=10.7 Hz, 1H), MS ESI m/z 499.1 (M+H); Anal. HPLC Retention time: 1.23 (Method 1); ROCK2 IC$_{50}$=16 nM.

Example 164: Preparation of 2-[3-methoxy-4-(1H-pyrazol-4-yl)phenyl]-8-(1-methyl-1H-1,3-benzodiazole-5-carbonyl)-2,8-diazaspiro[4.5]decan-1-one

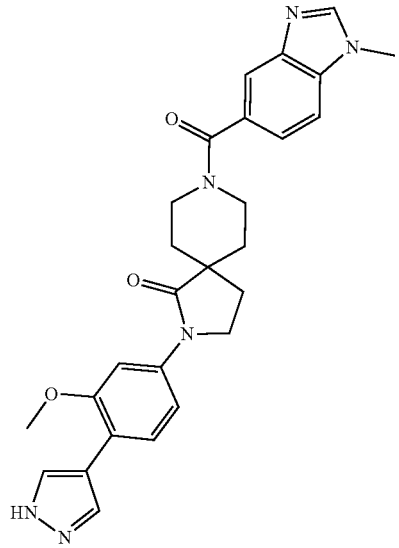

$^1$H NMR (500 MHz, DMSO-d$_6$) δ 8.29 (s, 1H), 8.02 (br d, J=1.8 Hz, 2H), 7.71-7.56 (m, 4H), 7.34 (br d, J=8.2 Hz, 1H), 7.15 (br d, J=8.2 Hz, 1H), 4.44-4.27 (m, 1H), 3.95-3.78 (m, 8H), 3.74-3.62 (m, 1H), 3.37 (br s, 1H), 3.17 (d, J=5.0 Hz, 1H), 2.15 (br s, 2H), 1.75 (br s, 2H), 1.59 (br d, J=9.9 Hz, 2H); MS ESI m/z 485 (M+H); Anal. HPLC Retention time: 1.17 (Method 1). ROCK2 IC$_{50}$=2.6 nM.

Example 165: Preparation of 2-[3-methoxy-4-(1H-pyrazol-4-yl)phenyl]-8-(2-methyl-1,6-naphthyridine-3-carbonyl)-2,8-diazaspiro[4.5]decan-1-one

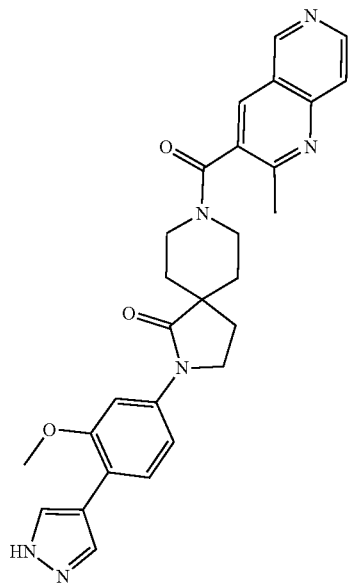 [SMILES: COc1cc(N2CCC3(CCN(C(=O)c4cc5cnccc5nc4C)CC3)C2=O)ccc1-c1cn[nH]c1]

$^1$H NMR (500 MHz, DMSO-d$_6$) δ 9.39 (br s, 1H), 8.74 (br d, J=5.8 Hz, 1H), 8.54-8.39 (m, 1H), 8.02 (br d, J=5.5 Hz, 2H), 7.87 (br d, J=5.8 Hz, 1H), 7.61 (br d, J=8.2 Hz, 2H), 7.15 (br s, 1H), 4.54-4.35 (m, 1H), 3.96-3.80 (m, 5H), 3.46 (s, 1H), 3.27 (br t, J=11.3 Hz, 2H), 2.66 (br s, 3H), 2.25-2.08 (m, 2H), 1.90-1.64 (m, 3H), 1.49 (br d, J=5.5 Hz, 1H); MS ESI m/z 496.9 (M+H); Anal. HPLC Retention time: 1.07 (Method 2); ROCK2 IC$_{50}$=896 nM.

Example 166: Preparation of 8-(isoquinoline-6-carbonyl)-2-[3-methoxy-4-(1H-pyrazol-4-yl)phenyl]-2,8-diazaspiro[4.5]decan-1-one

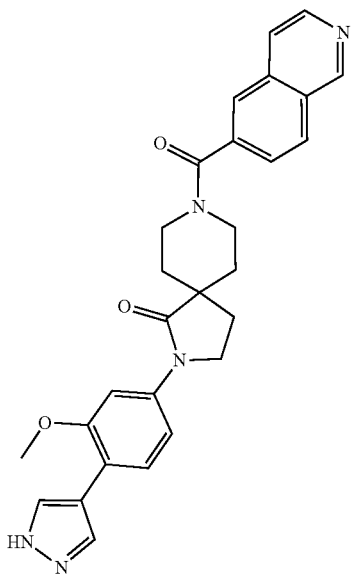 [SMILES: COc1cc(N2CCC3(CCN(C(=O)c4ccc5cnccc5c4)CC3)C2=O)ccc1-c1cn[nH]c1]

$^1$H NMR (500 MHz, DMSO-d$_6$) δ 9.38 (s, 1H), 8.57 (d, J=5.7 Hz, 1H), 8.22 (d, J=8.3 Hz, 1H), 8.03 (br d, J=12.2 Hz, 3H), 7.94 (br d, J=5.6 Hz, 1H), 7.69 (br d, J=8.2 Hz, 1H), 7.64-7.58 (m, 2H), 7.15 (br d, J=8.6 Hz, 1H), 4.39 (br s, 1H), 3.96-3.78 (m, 5H), 3.60 (br d, J=9.8 Hz, 1H), 3.26 (br dd, J=19.9, 12.8 Hz, 1H), 3.17 (s, 1H), 2.30-2.07 (m, 2H), 1.87-1.66 (m, 3H), 1.52 (br d, J=10.4 Hz, 1H); MS ESI m/z 482.2 (M+H); Anal. HPLC Retention time: 0.89 (Method 2); ROCK2 IC$_{50}$=33 nM.

Example 167: Preparation of 8-[4-(hydroxymethyl)benzoyl]-2-[3-methoxy-4-(1H-pyrazol-4-yl)phenyl]-2,8-diazaspiro[4.5]decan-1-one

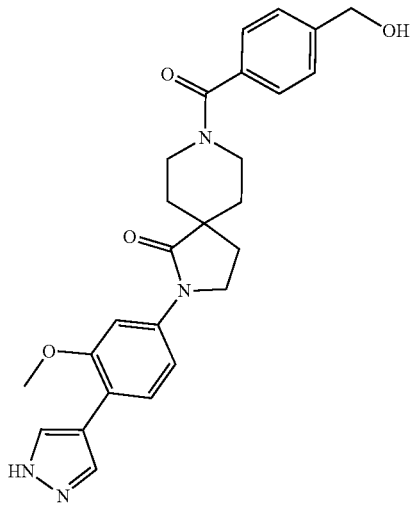 [SMILES: COc1cc(N2CCC3(CCN(C(=O)c4ccc(CO)cc4)CC3)C2=O)ccc1-c1cn[nH]c1]

$^1$H NMR (500 MHz, DMSO-d$_6$) δ 8.01 (br s, 2H), 7.59 (d, J=8.4 Hz, 1H), 7.56 (s, 1H), 7.43-7.29 (m, 4H), 7.12 (br d, J=8.3 Hz, 1H), 4.53 (br s, 2H), 4.38-4.28 (m, 1H), 3.84 (s, 2H), 3.75 (br s, 3H), 3.64-3.55 (m, 1H), 3.23 (br s, 1H), 3.09 (br d, J=2.6 Hz, 1H), 2.13 (br s, 2H), 1.80-1.58 (m, 3H), 1.50 (br d, J=7.5 Hz, 1H); MS ESI m/z 460.9 (M+H); Anal. HPLC Retention time: 1.2 (Method 1); ROCK2 IC$_{50}$=53 nM.

Example 168: Preparation of 2-[3-methoxy-4-(1H-pyrazol-4-yl)phenyl]-8-{4-[(pyrrolidin-1-yl)methyl]benzoyl}-2,8-diazaspiro[4.5]decan-1-one

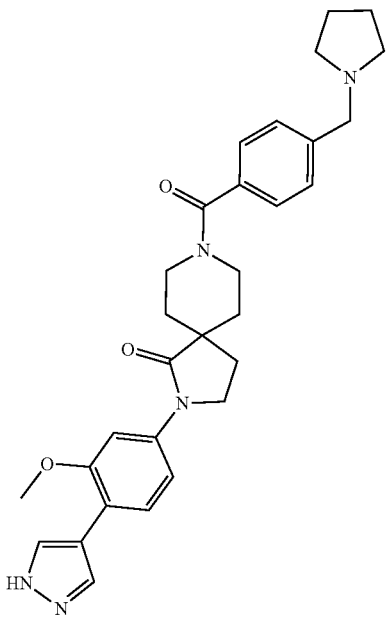 [SMILES: COc1cc(N2CCC3(CCN(C(=O)c4ccc(CN5CCCC5)cc4)CC3)C2=O)ccc1-c1cn[nH]c1]

¹H NMR (500 MHz, DMSO-d₆) δ 8.02 (s, 2H), 7.66-7.55 (m, 2H), 7.44-7.31 (m, 4H), 7.14 (br d, J=8.8 Hz, 1H), 4.38-4.26 (m, 1H), 3.93-3.78 (m, 5H), 3.60 (s, 1H), 3.44 (br d, J=11.8 Hz, 1H), 3.23 (br d, J=10.0 Hz, 1H), 3.17 (s, 1H), 3.15-3.06 (m, 1H), 2.43 (br s, 4H), 2.14 (br s, 2H), 1.89 (s, 4H), 1.69 (br s, 7H), 1.52 (br s, 1H); MS ESI m/z 514.2 (M+H); Anal. HPLC Retention time: 1.07 (Method 1); ROCK2 IC$_{50}$=17 nM.

Example 169: Preparation of 8-[4-(methanesulfonylmethyl)benzoyl]-2-[3-methoxy-4-(1H-pyrazol-4-yl)phenyl]-2,8-diazaspiro[4.5]decan-1-one

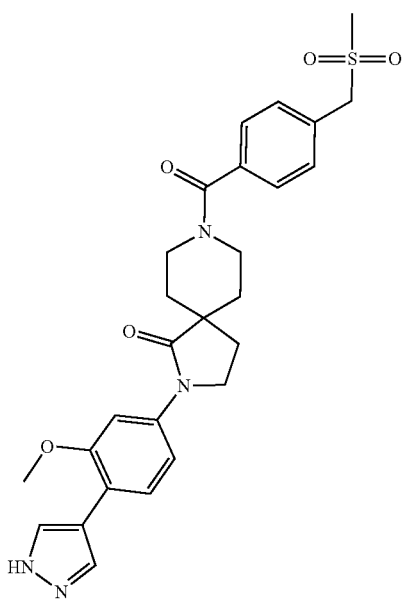 [SMILES: COc1cc(N2CCC3(CCN(C(=O)c4ccc(CS(C)(=O)=O)cc4)CC3)C2=O)ccc1-c1cn[nH]c1]

¹H NMR (500 MHz, DMSO-d₆) δ 8.02 (br s, 2H), 7.66-7.57 (m, 2H), 7.53-7.39 (m, 4H), 7.15 (br d, J=8.5 Hz, 1H), 4.55 (s, 2H), 4.34 (br s, 1H), 3.87 (s, 5H), 3.59 (br d, J=9.6 Hz, 1H), 3.25 (br d, J=10.9 Hz, 1H), 3.19-3.11 (m, 1H), 2.95 (s, 3H), 2.15 (br s, 2H), 1.83-1.61 (m, 3H), 1.53 (br s, 1H); MS ESI m/z 523.1 (M+H); Anal. HPLC Retention time: 1.19 (Method 1); ROCK2 IC$_{50}$=13 nM.

Example 170: Preparation of 8-(6-methoxy-1-methyl-1H-indole-2-carbonyl)-2-[3-methoxy-4-(1H-pyrazol-4-yl)phenyl]-2,8-diazaspiro[4.5]decan-1-one

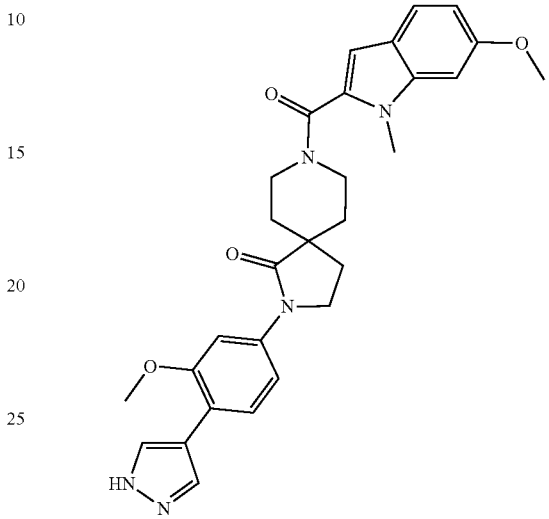

¹H NMR (500 MHz, DMSO-d₆) δ 8.18-7.91 (m, 2H), 7.61 (br d, J=6.1 Hz, 2H), 7.48 (d, J=8.7 Hz, 1H), 7.15 (br d, J=8.1 Hz, 1H), 7.02 (s, 1H), 6.75 (br d, J=8.8 Hz, 1H), 6.61 (s, 1H), 4.39-4.06 (m, 1H), 3.87 (s, 5H), 3.82 (s, 3H), 3.73 (s, 2H), 3.47 (br s, 5H), 2.25-2.13 (m, 2H), 1.83-1.70 (m, 2H), 1.63 (br d, J=10.2 Hz, 2H); MS ESI m/z 514.1 (M+H); Anal. HPLC Retention time: 1.62 (Method 1); ROCK2 IC$_{50}$=118 nM.

Example 171: Preparation of 2-[3-methoxy-4-(1H-pyrazol-4-yl)phenyl]-8-[4-(pyridin-4-yl)benzoyl]-2,8-diazaspiro[4.5]decan-1-one

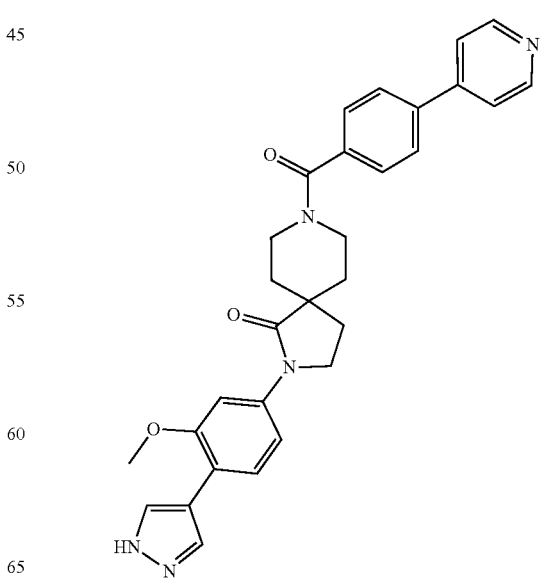

¹H NMR (500 MHz, DMSO-d₆) δ 8.66 (br d, J=5.3 Hz, 2H), 8.01 (br s, 2H), 7.89 (br d, J=8.0 Hz, 2H), 7.76 (br d, J=5.5 Hz, 2H), 7.65-7.52 (m, 4H), 7.14 (br d, J=8.6 Hz, 1H), 4.43-4.29 (m, 1H), 3.86 (s, 4H), 3.54 (br s, 2H), 3.29 (br s, 1H), 3.17 (br d, J=5.0 Hz, 1H), 2.15 (br s, 2H), 1.83-1.61 (m, 3H), 1.54 (br s, 1H); MS ESI m/z 508.1 (M+H); Anal. HPLC Retention time: 1.36 (Method 1); ROCK2 IC$_{50}$=5.5 nM.

Example 172: Preparation of 2-[3-methoxy-4-(1H-pyrazol-4-yl)phenyl]-8-(1-methylpiperidine-4-carbonyl)-2,8-diazaspiro[4.5]decan-1-one

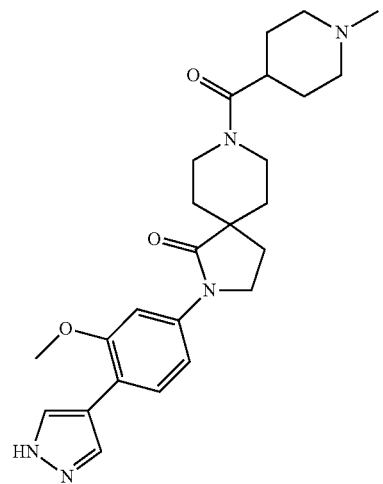 [SMILES: COc1cc(N2CCC3(CCN(C(=O)C4CCN(C)CC4)CC3)C2=O)ccc1-c1cn[nH]c1]

¹H NMR (500 MHz, DMSO-d₆) δ 8.01 (br s, 2H), 7.66-7.56 (m, 2H), 7.15 (br d, J=8.5 Hz, 1H), 4.25 (br d, J=12.2 Hz, 1H), 3.97-3.82 (m, 6H), 3.53-3.46 (m, 1H), 3.24 (br s, 1H), 2.86 (br s, 3H), 2.67-2.57 (m, 1H), 2.23 (s, 3H), 2.17-2.03 (m, 4H), 1.74-1.47 (m, 8H); MS ESI m/z 452.2 (M+H); Anal. HPLC Retention time: 1.01 (Method 2); ROCK2 IC$_{50}$=2068 nM.

Example 173: Preparation of 8-{4'-methanesulfonyl-[1,1'-biphenyl]-4-carbonyl}-2-[3-methoxy-4-(1H-pyrazol-4-yl)phenyl]-2,8-diazaspiro[4.5]decan-1-one

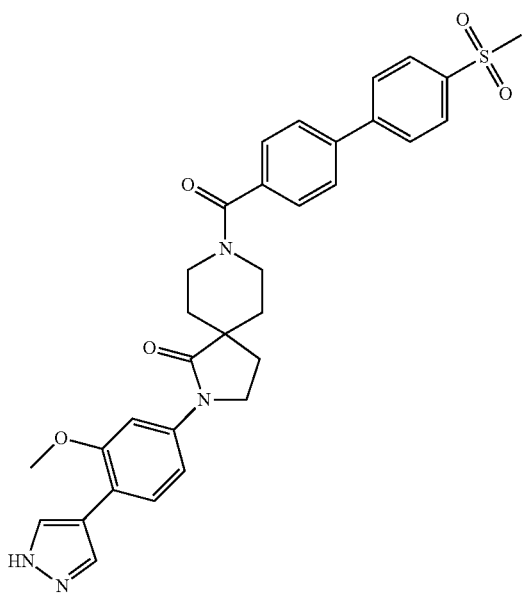 [SMILES: COc1cc(N2CCC3(CCN(C(=O)c4ccc(-c5ccc(S(C)(=O)=O)cc5)cc4)CC3)C2=O)ccc1-c1cn[nH]c1]

¹H NMR (500 MHz, DMSO-d₆) δ 8.20-7.90 (m, 6H), 7.85 (br d, J=8.0 Hz, 2H), 7.67-7.59 (m, 2H), 7.56 (br d, J=8.0 Hz, 2H), 7.15 (br d, J=8.4 Hz, 1H), 4.42-4.29 (m, 1H), 3.87 (s, 4H), 3.73-3.61 (m, 1H), 3.53-3.48 (m, 1H), 3.26 (s, 3H), 3.21-3.14 (m, 1H), 2.15 (br s, 2H), 1.87-1.63 (m, 3H), 1.55 (br s, 1H); MS ESI m/z 585.1 (M+H); Anal. HPLC Retention time: 1.46 (Method 2); ROCK2 IC$_{50}$=3.7 nM.

Example 174: Preparation of 8-(2,4-dimethoxybenzoyl)-2-[3-methoxy-4-(1H-pyrazol-4-yl)phenyl]-2,8-diazaspiro[4.5]decan-1-one

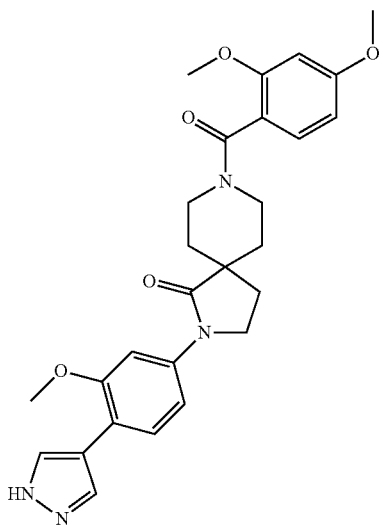 [SMILES: COc1ccc(C(=O)N2CCC3(CC2)CCN(c2ccc(-c4cn[nH]c4)c(OC)c2)C3=O)c(OC)c1]

¹H NMR (500 MHz, DMSO-d₆) δ 8.02 (s, 2H), 7.60 (br d, J=7.7 Hz, 2H), 7.27 (s, 1H), 7.17 (s, 1H), 7.13 (br d, J=8.0 Hz, 2H), 7.06 (s, 1H), 6.66-6.53 (m, 2H), 4.36 (br s, 1H), 3.95-3.74 (m, 9H), 3.59 (br s, 2H), 3.37 (br d, J=11.3 Hz, 1H), 3.12-2.89 (m, 2H), 2.11 (br d, J=17.0 Hz, 2H), 1.70 (br d, J=11.4 Hz, 2H), 1.60 (br d, J=13.0 Hz, 1H), 1.45 (br d, J=13.0 Hz, 1H); MS ESI m/z 490.9 (M+H); Anal. HPLC Retention time: 1.44 (Method 2); ROCK2 IC$_{50}$=29 nM.

Example 175: Preparation of 2-[3-methoxy-4-(1H-pyrazol-4-yl)phenyl]-8-[1-(pyridin-4-yl)piperidine-4-carbonyl]-2,8-diazaspiro[4.5]decan-1-one

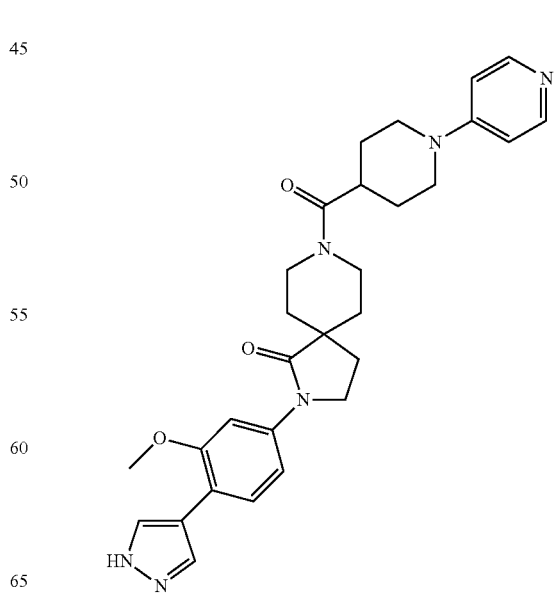

¹H NMR (500 MHz, DMSO-d₆) δ 8.11 (br d, J=4.2 Hz, 2H), 8.02 (br s, 2H), 7.66-7.55 (m, 2H), 7.14 (br d, J=8.4 Hz, 1H), 6.81 (br d, J=5.1 Hz, 2H), 4.25 (br d, J=13.4 Hz, 1H), 3.94 (br d, J=11.4 Hz, 3H), 3.86 (s, 4H), 3.26 (br t, J=11.5 Hz, 1H), 2.96 (br d, J=13.5 Hz, 4H), 2.14 (br t, J=6.6 Hz, 2H), 1.89 (s, 2H), 1.69 (br s, 3H), 1.57 (br d, J=14.6 Hz, 5H); MS ESI m/z 515.2 (M+H); Anal. HPLC Retention time: 1.02 (Method 1); ROCK2 IC$_{50}$=195 nM.

Example 176: Preparation of 2-[3-methoxy-4-(1H-pyrazol-4-yl)phenyl]-8-(6-methoxynaphthalene-2-carbonyl)-2,8-diazaspiro[4.5]decan-1-one

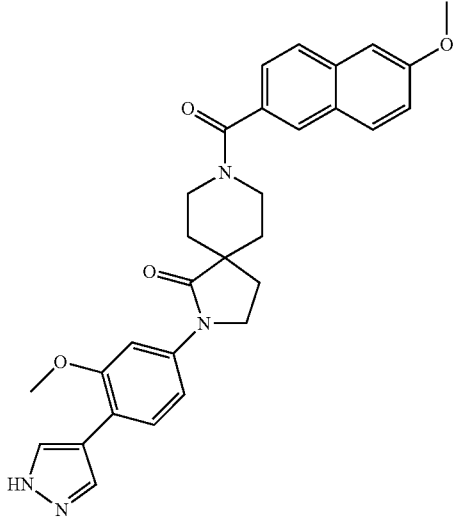 [SMILES: COc1ccc2cc(C(=O)N3CCC4(CC3)CCN(c3ccc(-c5cn[nH]c5)c(OC)c3)C4=O)ccc2c1]

¹H NMR (500 MHz, DMSO-d₆) δ 8.01 (br s, 2H), 7.95-7.86 (m, 3H), 7.66-7.56 (m, 2H), 7.47 (br d, J=8.5 Hz, 1H), 7.37 (s, 1H), 7.22 (dd, J=9.0, 2.0 Hz, 1H), 7.14 (br d, J=8.4 Hz, 1H), 3.87 (br d, J=12.4 Hz, 6H), 3.64-3.62 (m, 1H), 3.35-3.23 (m, 1H), 3.20-3.11 (m, 1H), 2.15 (br s, 2H), 1.84-1.49 (m, 4H); MS ESI m/z 511.2 (M+H); Anal. HPLC Retention time: 1.69 (Method 1); ROCK2 IC$_{50}$=20 nM.

Example 177: Preparation of 2-[3-methoxy-4-(1H-pyrazol-4-yl)phenyl]-8-(2-oxo-2,3-dihydro-1H-indole-5-carbonyl)-2,8-diazaspiro[4.5]decan-1-one

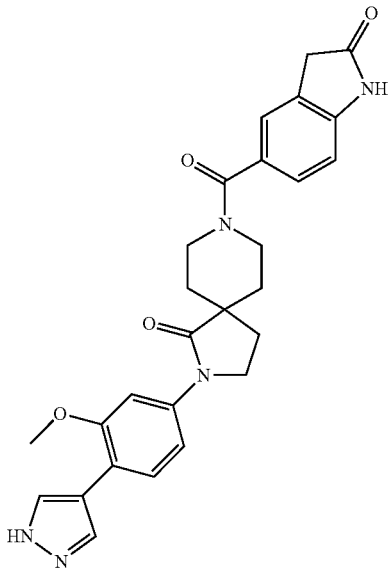 [SMILES: COc1cc(N2CCC3(CCN(C(=O)c4ccc5c(c4)CC(=O)N5)CC3)C2=O)ccc1-c1cn[nH]c1]

¹H NMR (500 MHz, DMSO-d₆) δ 8.01 (br s, 2H), 7.65-7.52 (m, 2H), 7.32-7.22 (m, 2H), 7.13 (br d, J=8.2 Hz, 1H), 6.89 (d, J=7.9 Hz, 1H), 3.85 (s, 3H), 3.71-3.51 (m, 8H), 2.14 (br s, 2H), 1.71 (br s, 2H), 1.57 (br s, 2H); MS ESI m/z 485.9 (M+H); Anal. HPLC Retention time: 1.13 (Method 2); ROCK2 IC$_{50}$=78 nM.

Example 178: Preparation of 8-(5,6-dimethoxy-1-methyl-1H-indole-2-carbonyl-2-[3-methoxy-4-(1H-pyrazol-4-yl)phenyl]-2,8-diazaspiro[4.5]decan-1-one

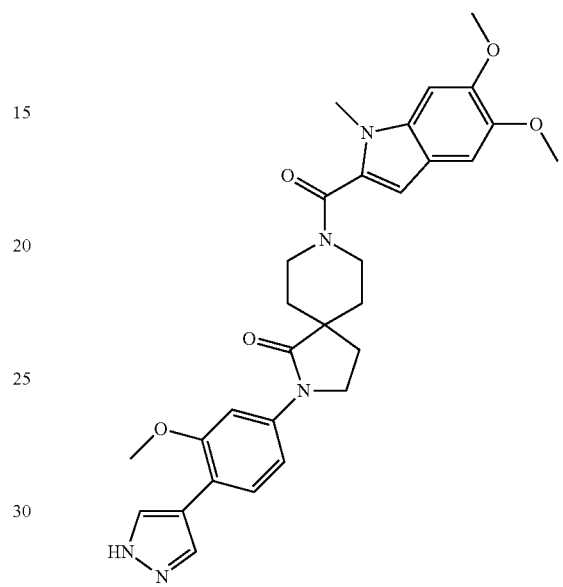

¹H NMR (500 MHz, DMSO-d₆) δ 8.02 (br s, 2H), 7.67-7.56 (m, 2H), 7.15 (br d, J=8.5 Hz, 1H), 7.08 (d, J=14.4 Hz, 2H), 6.55 (s, 1H), 4.35-4.11 (m, 1H), 3.87 (s, 5H), 3.84 (s, 3H), 3.75 (d, J=9.7 Hz, 6H), 2.17 (br t, J=6.4 Hz, 2H), 1.81-1.69 (m, 2H), 1.62 (br d, J=13.0 Hz, 2H); MS ESI m/z 544.1 (M+H); Anal. HPLC Retention time: 1.4 (Method 2); ROCK2 IC$_{50}$=14 nM.

Example 179: Preparation of 8-(1,2-dimethyl-1H-1,3-benzodiazole-5-carbonyl)-2-[3-methoxy-4-(1H-pyrazol-4-yl)phenyl]-2,8-diazaspiro[4.5]decan-1-one

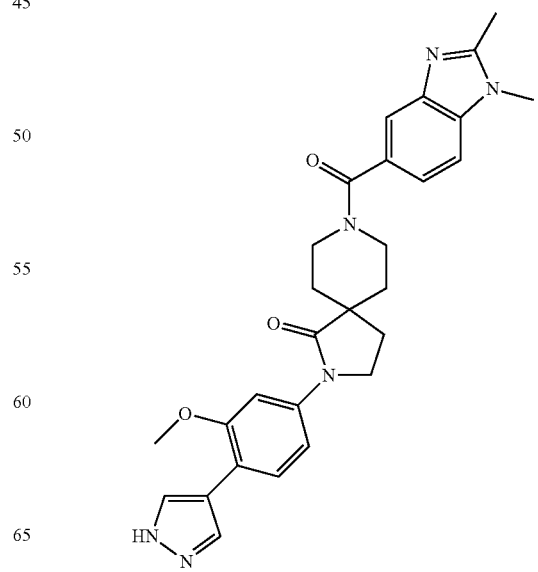

¹H NMR (500 MHz, DMSO-d₆) δ 8.19-7.87 (m, 2H), 7.66-7.58 (m, 2H), 7.56-7.50 (m, 2H), 7.25 (br d, J=8.5 Hz, 1H), 7.14 (br d, J=8.5 Hz, 1H), 3.86 (s, 7H), 3.75 (s, 4H), 3.42 (br s, 4H), 3.28-3.12 (m, 1H), 2.15 (br s, 2H), 1.83-1.43 (m, 4H); MS ESI m/z 499.1 (M+H); Anal. HPLC Retention time: 1.22 (Method 1); ROCK2 IC₅₀=2.3 nM.

Example 180: Preparation of 2-[3-methoxy-4-(1H-pyrazol-4-yl)phenyl]-8-{4-[(morpholin-4-yl)methyl]benzoyl}-2,8-diazaspiro[4.5]decan-1-one

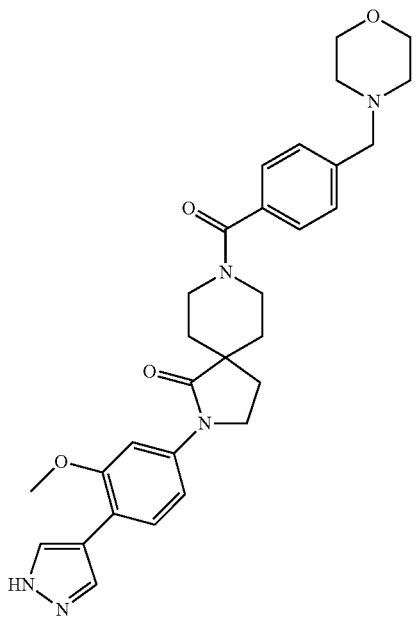 [SMILES: COc1cc(N2CCC3(CCN(C(=O)c4ccc(CN5CCOCC5)cc4)CC3)C2=O)ccc1-c1cn[nH]c1]

¹H NMR (500 MHz, DMSO-d₆) δ 8.02 (br s, 2H), 7.64-7.58 (m, 2H), 7.45-7.32 (m, 4H), 7.15 (br d, J=8.5 Hz, 1H), 4.34 (br d, J=10.1 Hz, 1H), 3.87 (s, 5H), 3.58 (br d, J=4.0 Hz, 4H), 3.50 (s, 2H), 3.40 (br s, 1H), 3.22 (br s, 1H), 3.15-3.09 (m, 1H), 2.37 (br s, 4H), 2.14 (br s, 2H), 1.80-1.47 (m, 4H); MS ESI m/z 530.2 (M+H); Anal. HPLC Retention time: 1.31 (Method 1); ROCK2 IC₅₀=27 nM.

Example 181: Preparation of 4-{2-[3-methoxy-4-(1H-pyrazol-4-yl)phenyl]-1-oxo-2,8-diazaspiro[4.5]decane-8-carbonyl}benzamide

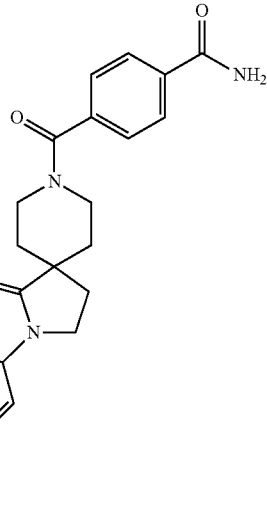

¹H NMR (500 MHz, DMSO-d₆) δ 8.13 (br s, 1H), 8.01 (br s, 2H), 7.91 (br d, J=8.0 Hz, 2H), 7.59 (d, J=8.4 Hz, 1H), 7.56 (s, 1H), 7.47 (br d, J=7.7 Hz, 3H), 7.12 (br d, J=8.1 Hz, 1H), 4.34 (br d, J=11.8 Hz, 1H), 3.74 (br s, 5H), 3.53 (br d, J=11.1 Hz, 1H), 3.23 (br d, J=10.0 Hz, 1H), 3.18-3.05 (m, 1H), 2.22-2.06 (m, 2H), 1.81-1.61 (m, 3H), 1.50 (br d, J=12.4 Hz, 1H); MS ESI m/z 474.1 (M+H); Anal. HPLC Retention time: 0.97 (Method 2); ROCK2 IC₅₀=35 nM.

Example 182: Preparation of 2-[3-methoxy-4-(1H-pyrazol-4-yl)phenyl]-8-[2-(pyridin-4-yl)-1H-1,3-benzodiazole-6-carbonyl]-2,8-diazaspiro[4.5]decan-1-one

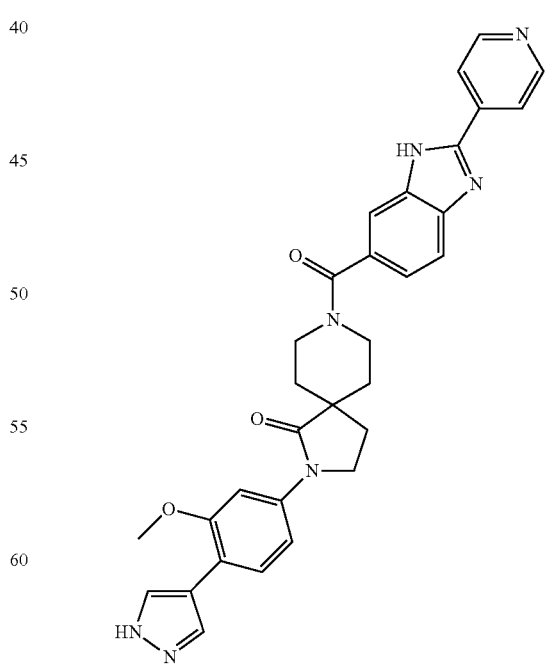

¹H NMR (500 MHz, DMSO-d₆) δ 8.79 (br d, J=5.1 Hz, 2H), 8.11 (br d, J=5.1 Hz, 2H), 8.02 (br s, 2H), 7.72 (br s,

2H), 7.65-7.57 (m, 2H), 7.34 (br d, J=7.9 Hz, 1H), 7.16 (br d, J=7.9 Hz, 1H), 4.44-4.24 (m, 1H), 3.96-3.79 (m, 5H), 3.31-3.22 (m, 1H), 3.17 (br s, 1H), 2.89 (s, 1H), 2.16 (br s, 2H), 1.76 (br s, 2H), 1.68-1.48 (m, 2H); MS ESI m/548.2 (M+H); Anal. HPLC Retention time: 1.21 (Method 1); ROCK2 IC$_{50}$=16 nM.

Example 183: Preparation of 8-{4-[(1H-imidazol-1-yl)methyl]benzoyl}-2-[3-methoxy-4-(1H-pyrazol-4-yl)phenyl]-2,8-diazaspiro[4.5]decan-1-one

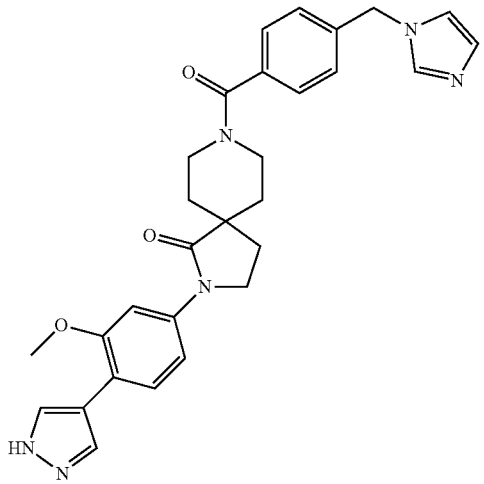 [SMILES: COc1cc(N2CCC3(CCN(C(=O)c4ccc(Cn5ccnc5)cc4)CC3)C2=O)ccc1-c1cn[nH]c1]

$^1$H NMR (500 MHz, DMSO-d$_6$) δ 8.01 (s, 2H), 7.80 (br s, 1H), 7.59 (d, J=8.4 Hz, 1H), 7.55 (s, 1H), 7.42-7.36 (m, 2H), 7.32 (br d, J=7.9 Hz, 2H), 7.22 (br s, 1H), 7.12 (br d, J=8.2 Hz, 1H), 6.93 (br s, 1H), 5.23 (s, 2H), 4.36-4.24 (m, 1H), 3.84 (s, 1H), 3.79-3.67 (m, 4H), 3.61-3.47 (m, 1H), 3.28-3.17 (m, 1H), 3.10 (br d, J=9.7 Hz, 1H), 2.12 (br d, J=6.3 Hz, 2H), 1.76-1.56 (m, 3H), 1.48 (br d, J=9.6 Hz, 1H); MS ESI m/z 511.2 (M+H); Anal. HPLC Retention time: 1.24 (Method 1), ROCK2 IC$_{50}$=23 nM.

Example 184: Preparation of 8-[2-(benzyloxy)-4-methoxybenzoyl]-2-[3-methoxy-4-(1H-pyrazol-4-yl)phenyl]-2,8-diazaspiro[4.5]decan-1-one

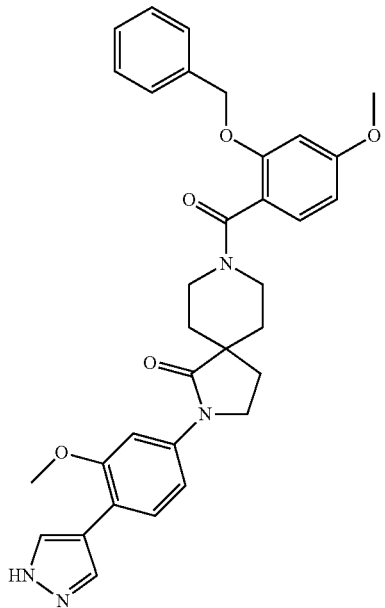 [SMILES: COc1ccc(C(=O)N2CCC3(CC2)CCN(c2ccc(-c4cn[nH]c4)c(OC)c2)C3=O)c(OCc2ccccc2)c1]

$^1$H NMR (500 MHz, DMSO-d$_6$) δ 8.02 (br s, 2H), 7.69-7.54 (m, 2H), 7.53-7.38 (m, 4H), 7.37-7.29 (m, 1H), 7.21-6.99 (m, 2H), 6.70 (br s, 1H), 6.64-6.53 (m, 1H), 5.16 (br s, 2H), 4.29 (br d, J=8.8 Hz, 1H), 3.92-3.72 (m, 8H), 3.46 (br s, 1H), 3.21-3.05 (m, 2H), 2.16-1.92 (m, 2H), 1.84-1.60 (m, 2H), 1.55 (br s, 1H), 1.50-1.37 (m, 1H); MS ESI m/z 567 (M+H); Anal. HPLC Retention time: 1.78 (Method 1); ROCK2 IC$_{50}$=12 nM.

Example 185: Preparation of 2-[3-methoxy-4-(1H-pyrazol-4-yl)phenyl]-8-[4-(3-methyl-1,2,4-oxadiazol-5-yl)benzoyl]-2,8-diazaspiro[4.5]decan-1-one

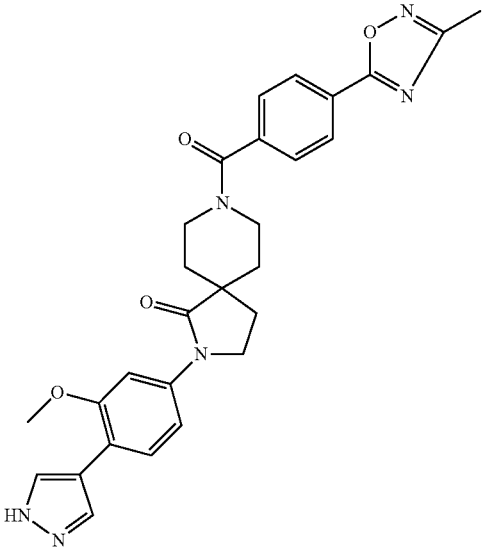 [SMILES: COc1cc(N2CCC3(CCN(C(=O)c4ccc(-c5nc(C)no5)cc4)CC3)C2=O)ccc1-c1cn[nH]c1]

$^1$H NMR (500 MHz, DMSO-d$_6$) δ 8.17 (br d, J=7.9 Hz, 2H), 8.12-7.85 (m, 2H), 7.72-7.54 (m, 4H), 7.15 (br d, J=8.4 Hz, 1H), 4.35 (br d, J=12.1 Hz, 1H), 3.86 (s, 5H), 3.63-3.52 (m, 1H), 3.28 (br s, 1H), 3.22-3.12 (m, 1H), 2.43 (s, 3H), 2.24-2.07 (m, 2H), 1.88-1.61 (m, 3H), 1.53 (br d, J=9.4 Hz, 1H); MS ESI m/z 513.3 (M+H); Anal. HPLC Retention time: 1.37 (Method 2); ROCK2 IC$_{50}$=37 nM.

Example 186: Preparation of 8-(4-{4-[(3-chlorophenyl)methyl]piperazin-1-yl}benzoyl)-2-[3-methoxy-4-(1H-pyrazol-4-yl)phenyl]-2,8-diazaspiro[4.5]decan-1-one

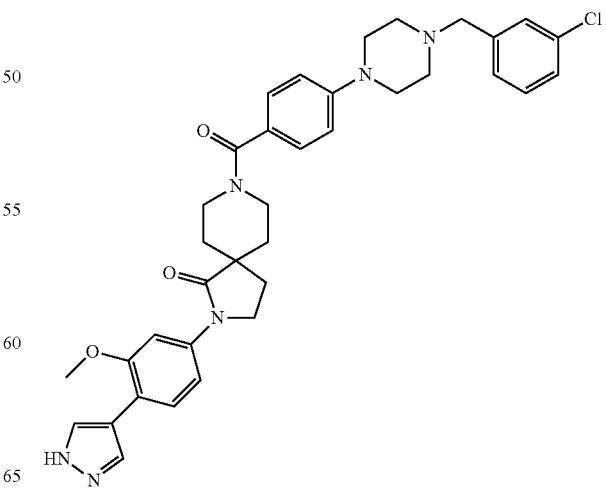

¹H NMR (500 MHz, DMSO-d₆) δ 8.02 (br d, J=2.3 Hz, 2H), 7.70-7.53 (m, 2H), 7.43-7.23 (m, 6H), 7.14 (br d, J=8.5 Hz, 1H), 6.95 (br d, J=8.5 Hz, 2H), 4.11-3.97 (m, 1H), 3.95-3.72 (m, 5H), 3.53 (s, 1H), 3.45 (br s, 2H), 3.30-3.07 (m, 4H), 2.51 (br s, 10H), 2.14 (br t, J=6.2 Hz, 2H), 1.79-1.65 (m, 2H), 1.56 (br d, J=10.2 Hz, 2H); MS ESI m/z 639.3 (M+H); Anal. HPLC Retention time: 1.28 (Method 2); ROCK2 IC$_{50}$=1.2 nM.

Example 187: Preparation of 2-[3-methoxy-4-(1H-pyrazol-4-yl)phenyl]-8-(5-methyl-1H-pyrazole-3-carbonyl)-2,8-diazaspiro[4.5]decan-1-one

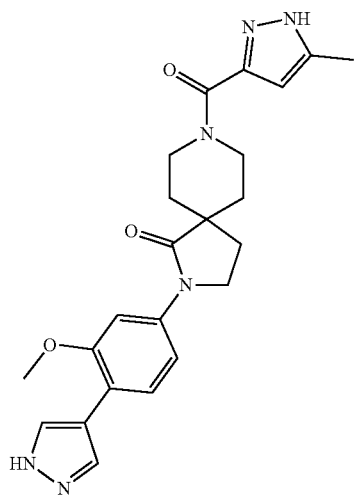

¹H NMR (500 MHz, DMSO-d₆) δ 8.02 (br s, 2H), 7.66-7.51 (m, 2H), 7.15 (br d, J=8.5 Hz, 1H), 6.30 (s, 1H), 4.57 (br s, 1H), 4.35 (br d, J=11.8 Hz, 1H), 3.86 (s, 5H), 3.41-3.29 (m, 1H), 3.04 (br d, J=10.6 Hz, 1H), 2.25 (s, 3H), 2.16 (br d, J=5.6 Hz, 2H), 1.71 (br d, J=10.4 Hz, 2H), 1.63-1.51 (m, 2H); MS ESI m/z 434.9 (M+H); Anal. HPLC Retention time: 1.18 (Method 1); ROCK2 IC$_{50}$=27 nM.

Example 188: Preparation of 8-(1,5-dimethyl-1H-pyrazole-3-carbonyl)-2-[3-methoxy-4-(1H-pyrazol-4-yl)phenyl]-2,8-diazaspiro[4.5]decan-1-one

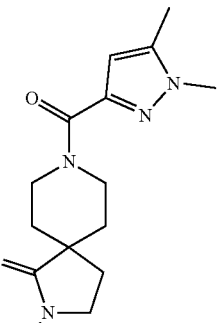
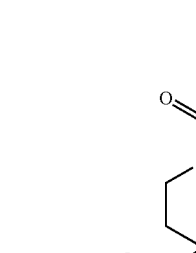
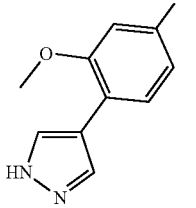

¹H NMR (500 MHz, DMSO-d₆) δ 8.02 (br s, 2H), 7.66-7.54 (m, 2H), 7.15 (br d, J=8.4 Hz, 1H), 6.33 (s, 1H), 4.55 (br d, J=12.7 Hz, 1H), 4.34 (br d, J=11.2 Hz, 1H), 3.86 (s, 5H), 3.75 (s, 3H), 3.40-3.32 (m, 1H), 3.09-2.98 (m, 1H), 2.26 (s, 3H), 2.16 (br d, J=5.6 Hz, 2H), 1.69 (br s, 2H), 1.63-1.48 (m, 2H); MS ESI m/z 449.1 (M+H); Anal. HPLC Retention time: 1.23 (Method 1); ROCK2 IC$_{50}$=31 nM.

Example 189: Preparation of 8-(4-amino-2-chlorobenzol)-2-[3-methoxy-4-(1H-pyrazol-4-yl)phenyl]-2,8-diazaspiro[4.5]decan-1-one

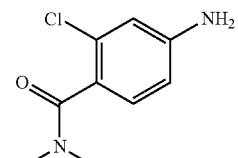
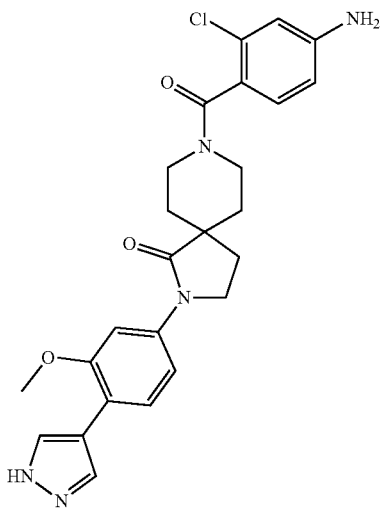 [SMILES: COc1cc(N2CCC3(CCN(C(=O)c4ccc(N)cc4Cl)CC3)C2=O)ccc1-c1cn[nH]c1]

¹H NMR (500 MHz, DMSO-d₆) δ 8.02 (br s, 2H), 7.70-7.52 (m, 2H), 7.12 (br s, 1H), 7.04-6.89 (m, 1H), 6.62 (br s, 1H), 6.54 (br s, 1H), 5.63 (br s, 2H), 4.40-4.26 (m, 1H), 3.86 (s, 5H), 3.52-3.45 (m, 1H), 3.29-3.01 (m, 2H), 2.13 (br s, 2H), 1.86-1.57 (m, 3H), 1.48 (br d, J=12.3 Hz, 1H); MS

ESI m/z 480.2 (M+H); Anal. HPLC Retention time: 1.12 (Method 2); ROCK2 IC$_{50}$=38 nM.

Example 190: Preparation of 8-[4-(dimethylamino)benzoyl]-2-[3-methoxy-4-(1H-pyrazol-4-yl)phenyl]-2,8-diazaspiro[4.5]decan-1-one

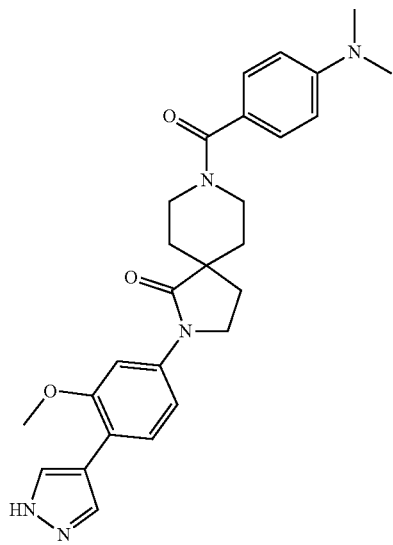

$^1$H NMR (500 MHz, DMSO-d$_6$) δ 8.19-7.85 (m, 2H), 7.65-7.54 (m, 2H), 7.29 (br d, J=8.4 Hz, 2H), 7.14 (br d, J=8.4 Hz, 1H), 6.72 (br d, J=8.4 Hz, 2H), 4.14-3.93 (m, 1H), 3.91-3.73 (m, 5H), 3.45 (br s, 2H), 3.17 (br d, J=4.3 Hz, 1H), 2.94 (s, 6H), 2.14 (br t, J=6.6 Hz, 2H), 1.70 (br d, J=9.2 Hz, 2H), 1.56 (br d, J=12.1 Hz, 2H); MS ESI m/z 474.4 (M+H); Anal. HPLC Retention time: 1.12 (Method 2); ROCK2 IC$_{50}$=16 nM.

Example 191: Preparation of 2-[3-methoxy-4-1H-pyrazol-4-yl)phenyl]-8-[4-(pyrrolidin-1-yl)benzoyl]-2,8-diazaspiro[4.5]decan-1-one

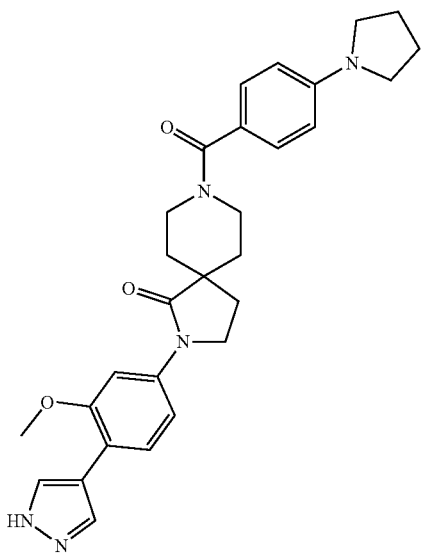 [SMILES: COc1cc(N2CCC3(CCN(C(=O)c4ccc(N5CCCC5)cc4)CC3)C2=O)ccc1-c1cn[nH]c1]

$^1$H NMR (500 MHz, DMSO-d$_6$) δ 8.02 (br s, 2H), 7.61 (br d, J=5.2 Hz, 2H), 7.28 (br d, J=7.9 Hz, 2H), 7.15 (br d, J=8.5 Hz, 1H), 6.55 (br d, J=8.2 Hz, 2H), 4.05 (br s, 1H), 3.90-3.79 (m, 5H), 3.41 (br s, 1H), 3.26 (br s, 4H), 3.18 (br d, J=4.0 Hz, 2H), 3.02 (br d, J=3.4 Hz, 1H), 2.15 (br t, J=6.6 Hz, 2H), 1.96 (br s, 4H), 1.78-1.67 (m, 3H), 1.56 (br d, J=12.5 Hz, 2H); MS ESI m/z 499.9 (M+H); Anal. HPLC Retention time: 1.62 (Method 2); ROCK2 IC$_{50}$=4 nM.

Example 192: Preparation of 8-(4-(1,1-dioxido-1,2-thiazinan-2-yl)benzoyl)-2-(3-methoxy-4-(1H-pyrazol-4-yl)phenyl)-2,8-diazaspiro[4.5]decan-1-one

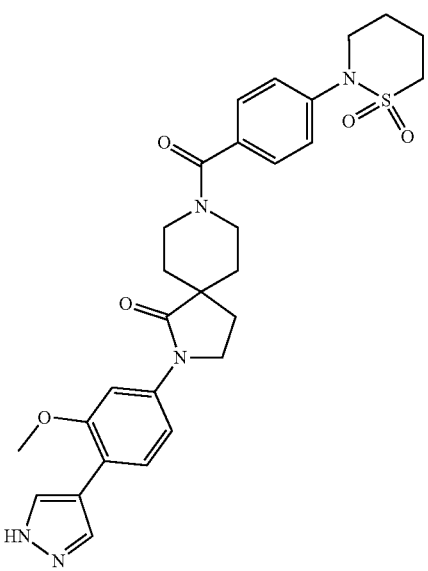 [SMILES: COc1cc(N2CCC3(CCN(C(=O)c4ccc(N5CCCCS5(=O)=O)cc4)CC3)C2=O)ccc1-c1cn[nH]c1]

$^1$H NMR (500 MHz, DMSO-d$_6$) δ 8.02 (br s, 2H), 7.65-7.56 (m, 2H), 7.48-7.35 (m, 4H), 7.15 (br d, J=8.1 Hz, 1H), 4.38-4.28 (m, 1H), 3.86 (s, 4H), 3.78-3.62 (m, 2H), 3.45 (br s, 1H), 3.36-3.24 (m, 1H), 3.21-3.17 (m, 1H), 3.14 (br s, 1H), 2.16 (br d, J=5.3 Hz, 4H), 1.89-1.46 (m, 6H); MS ESI m/z 564.1 (M+H); Anal. HPLC Retention time: 1.25 (Method 2); ROCK2 IC$_{50}$=3.3 nM.

Example 193: Preparation of 2-[3-methoxy-4-(1H-pyrazol-4-yl)phenyl]-8-[4-(1H-pyrrol-1-yl)benzoyl]-2,8-diazaspiro[4.5]decan-1-one

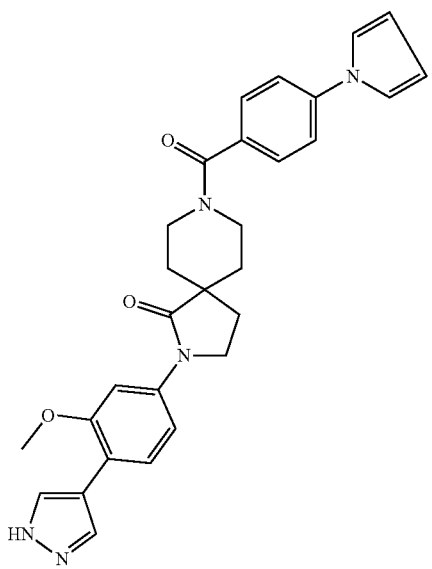 [SMILES: COc1cc(N2CCC3(CCN(C(=O)c4ccc(-n5cccc5)cc4)CC3)C2=O)ccc1-c1cn[nH]c1]

$^1$H NMR (500 MHz, DMSO-d$_6$) δ 8.01 (br s, 2H), 7.65 (br d, J=8.2 Hz, 2H), 7.59 (br d, J=5.4 Hz, 2H), 7.50 (br d, J=8.2 Hz, 2H), 7.42 (br s, 2H), 7.14 (br d, J=8.4 Hz, 1H), 6.30 (br s, 2H), 4.09-4.04 (m, 1H), 3.86 (s, 5H), 3.61 (br s, 1H), 3.37-3.23 (m, 1H), 3.16 (br s, 1H), 2.15 (br s, 2H), 1.73 (br d, J=6.3 Hz, 2H), 1.68-1.47 (m, 2H); MS ESI m/z 496.1 (M+H); Anal. HPLC Retention time: 1.61 (Method 2); ROCK2 IC$_{50}$=12 nM.

Example 194: Preparation of 8-[4-(diethylamino)benzoyl]-2-[3-methoxy-4-(1H-pyrazol-4-yl)phenyl]-2,8-diazaspiro[4.5]decan-1-one

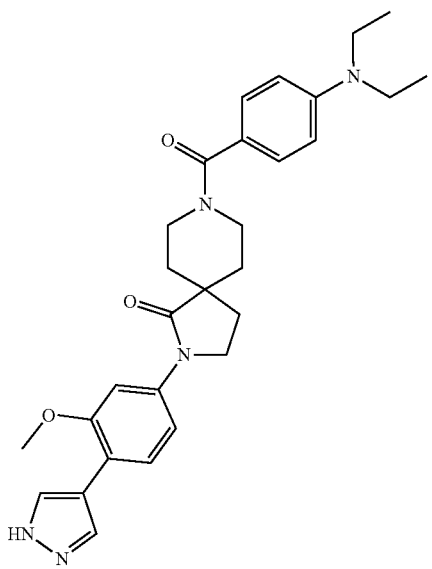 [SMILES: CCN(CC)c1ccc(C(=O)N2CCC3(CC2)CCN(c2ccc(-c4cn[nH]c4)c(OC)c2)C3=O)cc1]

$^1$H NMR (500 MHz, DMSO-d$_6$) δ 8.02 (br s, 2H), 7.66-7.52 (m, 2H), 7.27 (br d, J=8.5 Hz, 2H), 7.15 (br d, J=8.2 Hz, 1H), 6.66 (br d, J=8.5 Hz, 2H), 4.06 (br s, 2H), 3.91-3.79 (m, 5H), 3.47-3.29 (m, 3H), 3.18 (br d, J=4.3 Hz, 3H), 2.15 (br t, J=6.7 Hz, 2H), 1.71 (br d, J=9.2 Hz, 2H), 1.57 (br d, J=12.8 Hz, 2H), 1.11 (br t, J=7.0 Hz, 6H); MS ESI m/z 502.2 (M+H); Anal. HPLC Retention time: 1.76 (Method 1); ROCK2 IC$_{50}$=5.2 nM.

Example 195: Preparation of 8-(4-bromobenzoyl)-2-[3-methoxy-4-(1H-pyrazol-4-yl)phenyl]-2,8-diazaspiro[4.5]decan-1-one

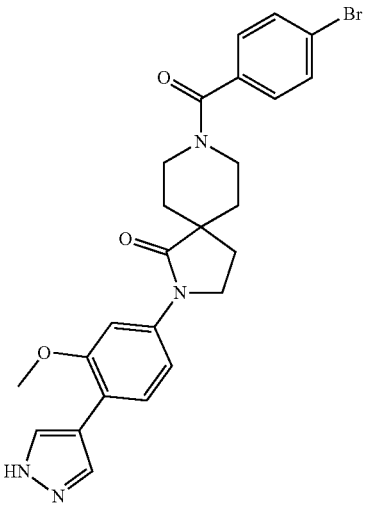

$^1$H NMR (500 MHz, DMSO-d$_6$) δ 8.02 (s, 2H), 7.67 (br d, J=8.2 Hz, 2H), 7.64-7.57 (m, 2H), 7.38 (br d, J=8.2 Hz, 2H), 7.15 (br d, J=8.2 Hz, 1H), 4.37-4.26 (m, 1H), 3.87 (s, 5H), 3.51 (br s, 1H), 3.30-3.21 (m, 1H), 3.18 (s, 1H), 2.14 (br s, 2H), 1.85-1.59 (m, 3H), 1.53 (br s, 1H); MS ESI m/z 509.1 (M+H); Anal. HPLC Retention time: 1.59 (Method 1); ROCK2 IC$_{50}$=33 nM.

Example 196: Preparation of 2-[3-methoxy-4-(1H-pyrazol-4-yl)phenyl]-8-(1-methyl-1H-1,2,3-benzotriazole-5-carbonyl)-2,8-diazaspiro[4.5]decan-1-one

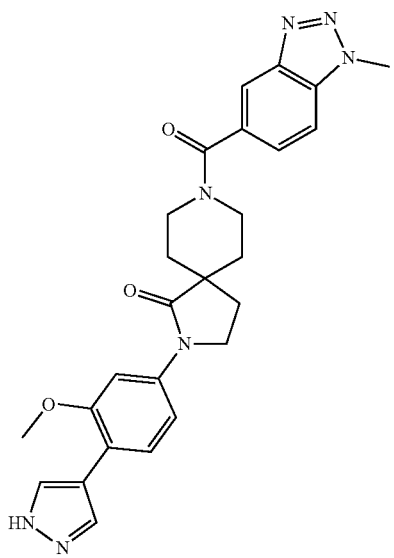

$^1$H NMR (500 MHz, DMSO-d$_6$) δ 8.08 (s, 1H), 8.01 (br s, 2H), 7.94 (d, J=8.9 Hz, 1H), 7.60 (br s, 3H), 7.15 (br d, J=8.5 Hz, 1H), 4.34 (s, 3H), 4.11-4.02 (m, 1H), 3.87 (s, 5H), 3.68-3.60 (m, 1H), 3.29 (br s, 1H), 3.24 (br s, 1H), 2.16 (br s, 2H), 1.84-1.50 (m, 4H); MS ESI m/z 486.2 (M+H); Anal. HPLC Retention time: 1.21 (Method 1); ROCK2 IC$_{50}$=9.1 nM.

Example 197: Preparation of 8-(1H-1,3-benzodiazole-4-carbonyl)-2-[3-methoxy-4-(1H-pyrazol-4-yl)phenyl]-2,8-diazaspiro[4.5]decan-1-one

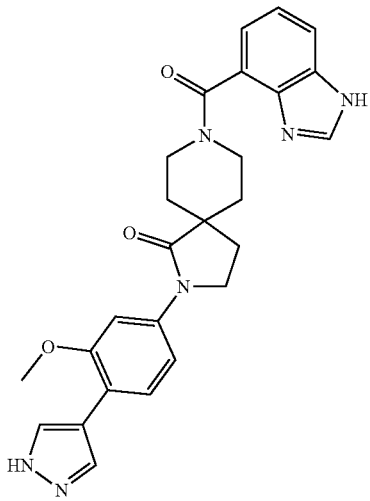 [SMILES: COc1cc(N2CCC3(CCN(C(=O)c4cccc5[nH]cnc45)CC3)C2=O)ccc1-c1cn[nH]c1]

$^1$H NMR (500 MHz, DMSO-d$_6$) δ 8.27 (s, 1H), 8.01 (s, 2H), 7.68-7.54 (m, 3H), 7.33-7.10 (m, 3H), 4.52-4.40 (m, 1H), 3.87 (s, 5H), 3.51 (br s, 1H), 3.31-3.10 (m, 2H), 2.16 (br s, 2H), 1.87-1.74 (m, 2H), 1.69 (br d, J=3.1 Hz, 1H), 1.43 (br s, 1H); MS ESI m/z 470.9 (M+H); Anal. HPLC Retention time: 1.27 (Method 1); ROCK2 IC$_{50}$=61 nM.

Example 198: Preparation of 2-[3-methoxy-4-(1H-pyrazol-4-yl)phenyl]-8-{pyrazolo[1,5-a]pyrimidine-3-carbonyl}-2,8-diazaspiro[4.5]decan-1-one

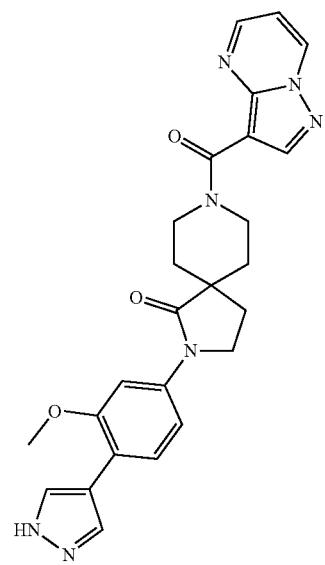 [SMILES: COc1cc(N2CCC3(CCN(C(=O)c4cnn5cccnc45)CC3)C2=O)ccc1-c1cn[nH]c1]

$^1$H NMR (500 MHz, DMSO-d$_6$) δ 9.18 (dd, J=7.0.1.5 Hz, 1H), 8.72 (br d, J=2.4 Hz, 1H), 8.44 (s, 1H), 8.15-7.87 (m, 2H), 7.61 (dd, J=4.7, 3.2 Hz, 2H), 7.25-7.09 (m, 2H), 4.46-4.29 (m, 1H), 3.87 (s, 5H), 3.38-3.25 (m, 1H), 3.21-3.09 (m, 1H), 2.17 (br s, 2H), 1.83 (br s, 2H), 1.72-1.48 (m, 2H); MS ESI m/z 472.2 (M+H); Anal. HPLC Retention time: 1.23 (Method 1); ROCK2 IC$_{50}$=1060 nM.

Example 199: Preparation of 8-(4,7-dimethoxynaphthalene-1-carbonyl)-2-[3-methoxy-4-(1H-pyrazol-4-yl)phenyl]-2,8-diazaspiro[4.5]decan-1-one

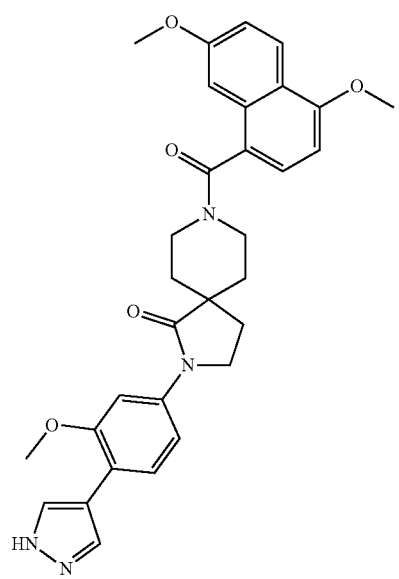

$^1$H NMR (500 MHz, DMSO-d$_6$) δ 8.13 (br d, J=9.3 Hz, 1H), 8.01 (br s, 2H), 7.60 (br d, J=8.2 Hz, 2H), 7.42-7.27 (m, 1H), 7.24-7.12 (m, 2H), 7.11-6.96 (m, 1H), 6.88 (br d, J=7.2 Hz, 1H), 4.60 (br d, J=10.2 Hz, 1H), 3.98 (s, 3H), 3.93 (br s, 3H), 3.86 (s, 5H), 3.56-3.49 (m, 1H), 3.31 (br d, J=10.8 Hz, 1H), 3.15-3.09 (m, 1H), 2.18 (br d, J=4.9 Hz, 1H), 2.11 (br s, 1H), 1.89-1.80 (m, 1H), 1.77-1.68 (m, 1H), 1.58 (br s, 1H), 1.38 (br d, J=10.6 Hz, 1H); MS ESI m/z 541 (M+H); Anal. HPLC Retention time: 1.74 (Method 2); ROCK2 IC$_{50}$=186 nM.

Example 200: Preparation of 8-[4-hydroxy-7-(propan-2-yl)pyrrolo[2,1-f][1,2,4]triazine-5-carbonyl]-2-[3-methoxy-4-(1H-pyrazol-4-yl)phenyl]-2,8-diazaspiro[4.5]decan-1-one

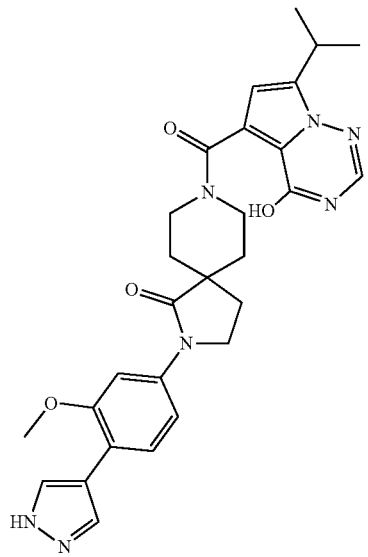 [SMILES: COc1cc(N2CCC3(CCN(C(=O)c4cc(C(C)C)n5ncnc(O)c45)CC3)C2=O)ccc1-c1cn[nH]c1]

$^{1}$H NMR (500 MHz, DMSO-d$_{6}$) δ 8.08 (br s, 1H), 7.94 (br s, 1H), 7.85 (s, 1H), 7.66-7.53 (m, 2H), 7.13 (br d, J=8.2 Hz, 1H), 6.41 (s, 1H), 4.39 (br d, J=12.8 Hz, 1H), 3.88-3.80 (m, 5H), 3.60 (br d, J=13.7 Hz, 1H), 3.37-3.26 (m, 1H), 3.20-3.02 (m, 2H), 2.20-2.00 (m, 2H), 1.81-1.66 (m, 2H), 1.62 (br d, J=6.7 Hz, 1H), 1.42 (br d, J=11.9 Hz, 1H), 1.28 (br d, J=6.7 Hz, 6H); MS ESI m/z 530 (M+H); Anal. HPLC Retention time: 1.51 (Method 1); ROCK2 IC$_{50}$=2.1 nM.

Example 201: Preparation of 3-{2-[3-methoxy-4-(1H-pyrazol-4-yl)phenyl]-1-oxo-2,8-diazaspiro[4.5]decane-8-carbonyl}-1H-indole-5-carbonitrile

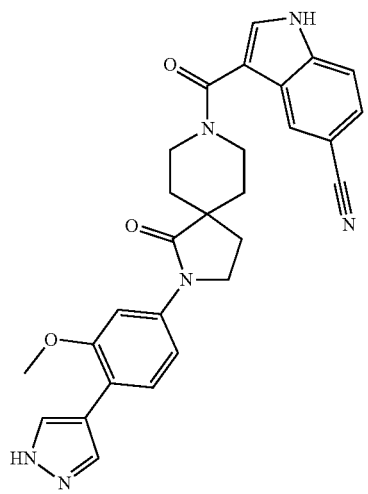 [SMILES: COc1cc(N2CCC3(CCN(C(=O)c4c[nH]c5ccc(C#N)cc45)CC3)C2=O)ccc1-c1cn[nH]c1]

$^{1}$H NMR (500 MHz, DMSO-d$_{6}$) δ 8.15 (s, 1H), 8.02 (br s, 2H), 7.95 (s, 1H), 7.68-7.58 (m, 3H), 7.54 (d, J=7.9 Hz, 1H), 7.16 (br d, J=8.2 Hz, 1H), 4.21 (br d, J=11.6 Hz, 2H), 3.94-3.82 (m, 5H), 3.44 (br s, 1H), 3.36-3.23 (m, 1H), 2.19 (br t, J=6.9 Hz, 2H), 1.83-1.72 (m, 2H), 1.61 (br d, J=12.5 Hz, 2H); MS ESI m/z 495.2 (M+H); Anal. HPLC Retention time: 1.42 (Method 1); ROCK2 IC$_{50}$=718 nM.

Example 202: Preparation of 2-[3-methoxy-4-(1H-pyrazol-4-yl)phenyl]-8-{4-oxo-3H,4H-pyrrolo[2,1-f][1,2,4]triazine-5-carbonyl}-2,8-diazaspiro[4.5]decan-1-one

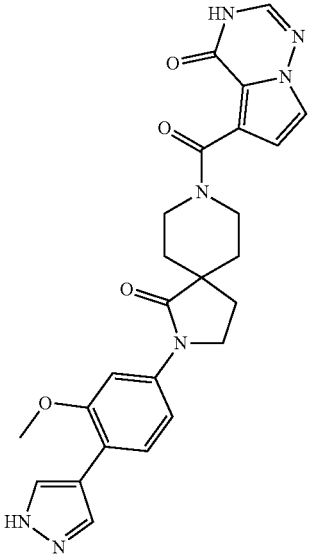 [SMILES: COc1cc(N2CCC3(CCN(C(=O)c4ccn5nc[nH]c(=O)c45)CC3)C2=O)ccc1-c1cn[nH]c1]

$^{1}$H NMR (500 MHz, DMSO-d$_{6}$) δ 8.02 (br s, 2H), 7.86 (br d, J=2.9 Hz, 1H), 7.69-7.57 (m, 3H), 7.13 (br d, J=8.1 Hz, 1H), 6.59 (br s, 1H), 4.39 (br d, J=12.8 Hz, 1H), 3.93-3.76 (m, 5H), 3.59 (br d, J=13.5 Hz, 1H), 3.22-3.04 (m, 2H), 2.22-2.01 (m, 2H), 1.82-1.66 (m, 2H), 1.62 (br d, J=13.4 Hz, 1H), 1.42 (br d, J=12.4 Hz, 1H); MS ESI m/z 487.9 (M+H); Anal. HPLC Retention time: 1.11 (Method 1); ROCK2 IC$_{50}$=5.4 nM.

Example 203: Preparation of 8-(isoquinoline-8-carbonyl)-2-[3-methoxy-4-(1H-pyrazol-4-yl)phenyl]-2,8-diazaspiro[4.5]decan-1-one

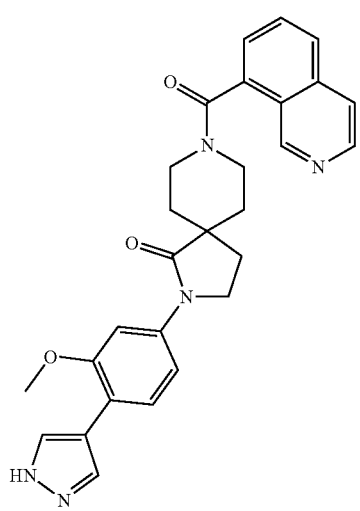 [SMILES: COc1cc(N2CCC3(CCN(C(=O)c4cccc5ccncc45)CC3)C2=O)ccc1-c1cn[nH]c1]

$^1$H NMR (500 MHz, DMSO-d$_6$) δ 9.26-9.08 (m, 1H), 8.57 (br d, J=5.2 Hz, 1H), 8.05 (br d, J=8.2 Hz, 1H), 8.00 (br s, 2H), 7.93 (d, J=5.8 Hz, 1H), 7.84 (br t, J=7.6 Hz, 1H), 7.68-7.55 (m, 3H), 7.12 (br s, 1H), 4.64-4.41 (m, 1H), 3.97-3.74 (m, 4H), 3.41-3.09 (m, 3H), 2.19 (br d, J=5.8 Hz, 1H), 2.15-2.05 (m, 1H), 1.86 (s, 2H), 1.80-1.71 (m, 1H), 1.42 (br d, J=12.5 Hz, 1H); MS ESI m/z 482.1 (M+H); Anal. HPLC Retention time: 1.26 (Method 1); ROCK2 IC$_{50}$=326 nM.

Example 204: Preparation of 2-[3-methoxy-4-(1H-pyrazol-4-yl)phenyl]-8-[2-(2-methoxyethyl)-3-oxo-2,3-dihydro-1H-isoindole-4-carbonyl]-2,8-diazaspiro[4.5]decan-1-one

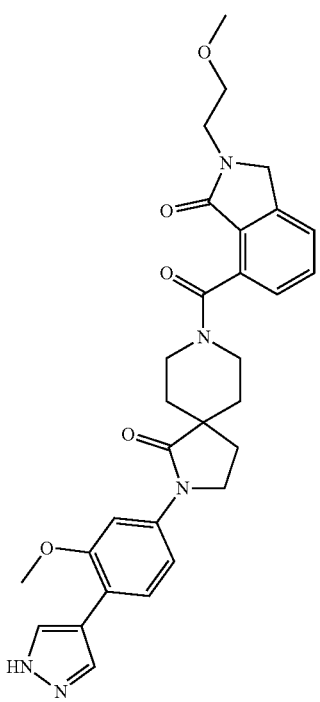 [SMILES: COCCN1Cc2cccc(C(=O)N3CCC4(CC3)CCN(c3ccc(-c5cn[nH]c5)c(OC)c3)C4=O)c2C1=O]

$^1$H NMR (500 MHz, DMSO-d$_6$) δ 8.13-7.88 (m, 2H), 7.66-7.54 (m, 4H), 7.38-7.25 (m, 1H), 7.17-7.06 (m, 1H), 4.55 (br s, 2H), 4.44-4.31 (m, 1H), 3.94-3.67 (m, 7H), 3.64-3.56 (m, 1H), 3.53-3.49 (m, 3H), 3.27 (br d, J=3.4 Hz, 4H), 3.16-3.00 (m, 2H), 2.14 (br dd, J=13.0, 6.9 Hz, 1H), 2.07 (br d, J=6.4 Hz, 1H), 1.78 (br d, J=11.6 Hz, 1H), 1.71 (br s, 1H), 1.64-1.54 (m, 1H), 1.50-1.30 (m, 1H); MS ESI m/z 544 (M+H); Anal. HPLC Retention time: 1.32 (Method 1); ROCK2 IC$_{50}$=50 nM.

Example 205: Preparation of tert-butyl 4-(4-{2-[3-methoxy-4-(1H-pyrazol-4-yl)phenyl]-1-oxo-2,8-diazaspiro[4.5]decane-8-carbonyl}phenyl)piperazine-1-carboxylate

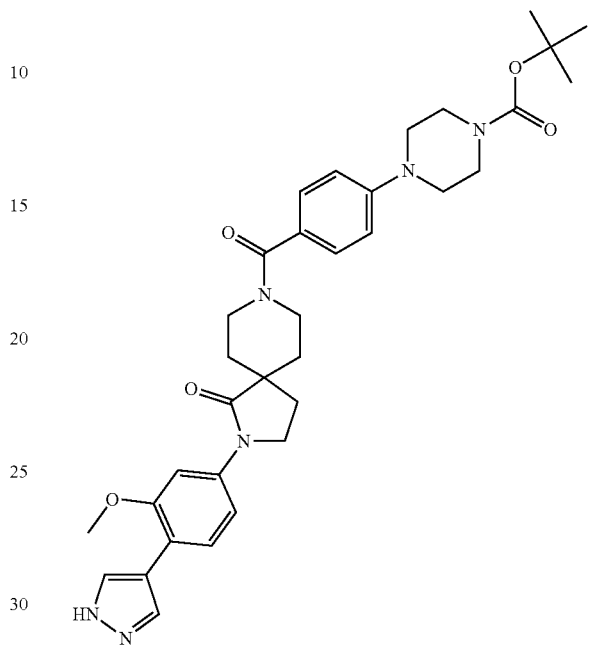

$^1$H NMR (500 MHz, DMSO-d$_6$) δ 8.02 (br d, J=2.4 Hz, 2H), 7.60 (br d, J=1.2 Hz, 2H), 7.31 (br d, J=8.5 Hz, 2H), 7.18-7.11 (m, 1H), 6.98 (br d, J=8.5 Hz, 2H), 4.01 (br d, J=3.1 Hz, 1H), 3.91-3.82 (m, 9H), 3.50-3.44 (m, 1H), 3.32-3.26 (m, 1H), 3.24-3.11 (m, 5H), 2.14 (br t, J=6.6 Hz, 2H), 1.79-1.68 (m, 2H), 1.57 (br d, J=11.9 Hz, 2H), 1.42 (s, 9H); MS ESI m/z 615.3 (M+H); Anal. HPLC Retention time: 1.76 (Method 1); ROCK2 IC$_{50}$=8.9 nM.

Preparation of Examples 206-208

The following compounds were made in a parallel manner using the following procedure: Reagents were weighed into stubby tubes. Stock solutions were made for reagent addition: Dissolved 63.0 mg 2-(3-methoxy-4-(1H-pyrazol-4-yl)phenyl)-2,8-diazaspiro[4.5]decan-1-one, 2 HCl in 2.5 ml of THF. To each vial containing sulfonyl chloride reagents was added 0.5 ml of the 2-(3-methoxy-4-(1H-pyrazol-4-yl)phenyl)-2,8-diazaspiro[4.5]decan-1-one, 2 HCl solution followed by DIEA (0.028 ml, 0.150 mmol). The reaction mixture vials were placed in a Bohdan Miniblock XT and were agitated overnight at 400 rpm.

Upon completion, reaction mixtures were purified via preparative LC/MS with the following conditions: Column: XBridge C18, 19×100 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 2-minute hold at 100% B; Flow: 20 mL/min. Fractions containing the desired product were combined and dried via centrifugal evaporation. **Gradient varied for each reaction depending on polarity of compound.

Compound purity was assigned based on the methods below.

Method 1: Column: Waters Acquity UPLC BEH C18.2.1× 50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method 2: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min: Detection: UV at 220 nm.

Example 206: Preparation of 2-[3-methoxy-4-(1H-pyrazol-4-yl)phenyl]-8-(4-methoxybenzenesulfonyl)-2,8-diazaspiro[4.5]decan-1-one

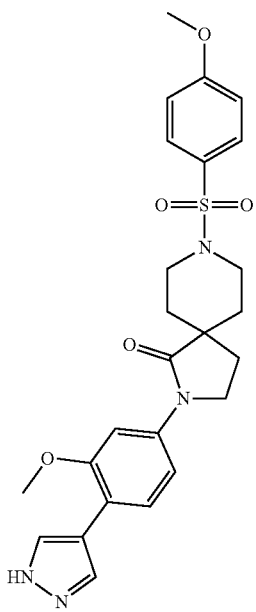 [SMILES: COc1ccc(S(=O)(=O)N2CCC3(CCN(c4ccc(-c5cn[nH]c5)c(OC)c4)C3=O)CC2)cc1]

$^1$H NMR (500 MHz, DMSO-d$_6$) δ 8.09 (br s, 1H), 7.93 (br s, 1H), 7.71 (d, J=8.8 Hz, 2H), 7.58 (d, J=8.5 Hz, 1H), 7.53 (s, 1H), 7.18 (d, J=8.8 Hz, 2H), 7.12-7.06 (m, 1H), 4.22-4.14 (m, 1H), 3.86 (d, J=11.8 Hz, 6H), 3.76 (br t, J=6.9 Hz, 2H), 3.51 (br s, 1H), 3.43 (br s, 1H), 3.17 (d, J=5.2 Hz, 1H), 1.88 (br t, J=6.8 Hz, 2H), 1.83-1.75 (m, 2H), 1.62 (br d, J=13.4 Hz, 2H); MS ESI m/z 497.2 (M+H); Anal. HPLC Retention time: 1.55 (Method 1); ROCK2 IC$_{50}$=497 nM.

Example 207: Preparation of 2-[3-methoxy-4-(1H-pyrazol-4-yl)phenyl]-8-(3-methoxybenzenesulfonyl)-2,8-diazaspiro[4.5]decan-1-one

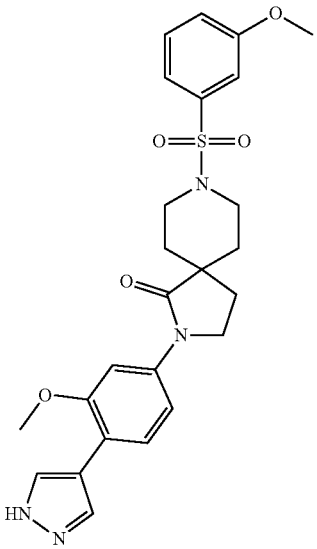

$^1$H NMR (500 MHz, DMSO-d$_6$) δ 8.08 (br s, 1H), 7.93 (br s, 1H), 7.63-7.56 (m, 2H), 7.54 (s, 1H), 7.38-7.28 (m, 2H), 7.22 (s, 1H), 7.10 (br d, J=8.5 Hz, 1H), 4.68 (t, J=5.8 Hz, 1H), 4.17 (q, J=5.0 Hz, 1H), 3.85 (d, J=5.5 Hz, 6H), 3.76 (br t, J=6.8 Hz, 2H), 3.54 (br d, J=12.3 Hz, 1H), 3.17 (d, J=5.3 Hz, 1H), 1.89 (br t, J=6.8 Hz, 2H), 1.84-1.73 (m, 2H), 1.63 (br d, J=13.5 Hz, 2H); MS ESI m/z 497.3 (M+H); Anal. HPLC Retention time: 1.64 (Method 1); ROCK2 IC$_{50}$=266 nM.

Example 208: Preparation of methyl 5-({2-[3-methoxy-4-(1H-pyrazol-4-yl)phenyl]-1-oxo-2,8-diazaspiro[4.5]decan-8-yl}sulfonyl)furan-2-carboxylate

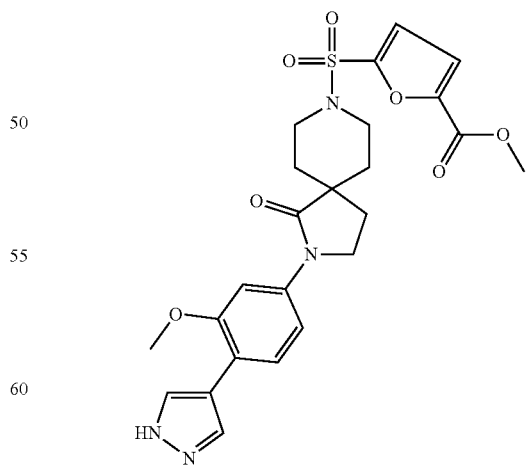

$^1$H NMR (500 MHz, DMSO-d$_6$) δ 8.01 (br s, 2H), 7.60 (d, J=8.5 Hz, 1H), 7.55 (d, J=1.4 Hz, 1H), 7.51 (d, J=3.7 Hz, 1H), 7.37 (d, J=3.6 Hz, 1H), 7.11 (dd, J=8.5, 1.7 Hz, 1H), 3.86 (d, J=11.5 Hz, 6H), 3.80 (br t, J=6.8 Hz, 2H), 3.65 (br d, J=12.7 Hz, 2H), 2.97 (br t, J=10.6 Hz, 2H), 2.00 (br t, J=6.8 Hz, 2H), 1.81-1.70 (m, 2H), 1.63 (br d, J=13.7 Hz, 2H); MS ESI m/z 515.2 (M+H); Anal. HPLC Retention time: 1.5 (Method 1); ROCK2 $IC_{50}$=2072 nM.

Preparation of Examples 209-218

The following compounds were made in a parallel manner using the following procedure: Reagents were weighed into stubby tubes. Stock solutions were made for reagent addition: Dissolved 360 mg 2-(3-methoxy-4-(1H-pyrazol-4-yl) phenyl)-2,8-diazaspiro[4.5]decan-1-one, 2 HCl in 12 ml of DCM. To each vial containing sulfonyl chloride reagents or isocyanide reagents was added 0.5 ml of the 2-(3-methoxy-4-(1H-pyrazol-4-yl)phenyl)-2,8-diazaspiro[4.5]decan-1-one, 2 HCl solution followed by DIEA (0.033 ml, 0.188 mmol). The reaction mixture vials were placed in a Bohdan Miniblock XT and were agitated overnight at 400 rpm.

Upon completion, reaction mixtures were purified via preparative LC/MS with the following conditions: Column: XBridge C18, 19×100 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 2-minute hold at 100% B: Flow: 20 mL/min. Fractions containing the desired product were combined and dried via centrifugal evaporation. **Gradient varied for each reaction depending on polarity of compound.

Compound purity was assigned based on the methods below.

Method 1: Column: Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate: Temperature: 50° C.; Gradient: 0-100% B over 3 minutes, then a 0.75-minute hold at 100% B: Flow: 1.0 mL/min; Detection: UV at 220 nm.

Method 2: Column: Waters Acquit) UPLC BEH C18, 2.1×50 mm, 1.7-µm particles; Mobile Phase A: 5:95 acetonitrile:water with 0.1% trifluoroacetic acid:Mobile Phase B: 95:5 acetonitrile:water with 0.1% trifluoroacetic acid; Temperature: 50° C.; Gradient: 0-100% B over 3 minutes, then a 0.75-minute hold at 100% B: Flow: 1.0 mL/min; Detection: UV at 220 nm.

Example 209: Preparation of 6-({2-[3-methoxy-4-(1H-pyrazol-4-yl)phenyl]-1-oxo-2,8-diazaspiro[4.5]decan-8-yl}sulfonyl)-1,2,3,4-tetrahydroquinazoline-2,4-dione

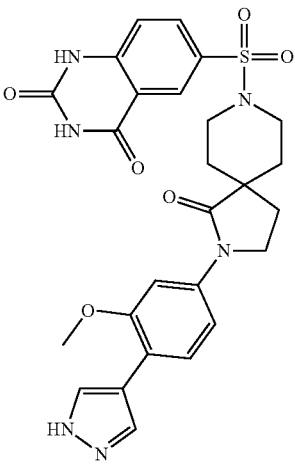 [SMILES: COc1cc(N2CCC3(CCN(S(=O)(=O)c4ccc5[nH]c(=O)[nH]c(=O)c5c4)CC3)C2=O)ccc1-c1cn[nH]c1]

$^1$H NMR (500 MHz, DMSO-$d_6$) δ 8.14 (d, J=1.5 Hz, 1H), 8.05-7.92 (m, 3H), 7.57 (d, J=8.2 Hz, 1H), 7.51 (s, 1H), 7.35 (d, J=8.5 Hz, 1H), 7.09 (br d, J=8.2 Hz, 1H), 3.83 (s, 3H), 3.75 (br t, J=6.7 Hz, 2H), 3.50 (br d, J=15.3 Hz, 2H), 2.60 (br t, J=11.0 Hz, 2H), 1.89 (br t, J=6.6 Hz, 2H), 1.83-1.72 (m, 2H), 1.63 (br d, J=13.1 Hz, 2H); MS ESI m/z 551.2 (M+H); Anal. HPLC Retention time: 1.15 (Method 1); ROCK2 $IC_{50}$=410 nM.

Example 210: Preparation of 5-({2-[3-methoxy-4-(1H-pyrazol-4-yl)phenyl]-1-oxo-2,8-diazaspiro[4.5]decan-8-yl}sulfonyl)-2,3-dihydro-1H-isoindole-1,3-dione

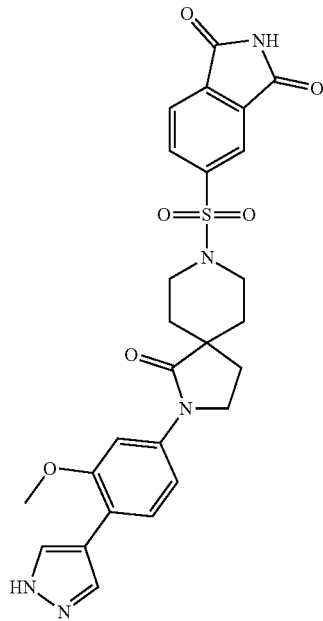 [SMILES: COc1cc(N2CCC3(CCN(S(=O)(=O)c4ccc5c(c4)C(=O)NC5=O)CC3)C2=O)ccc1-c1cn[nH]c1]

$^1$H NMR (500 MHz, DMSO-$d_6$) δ 8.00 (br d, J=4.6 Hz, 3H), 7.78 (br d, J=11.0 Hz, 2H), 7.61-7.50 (m, 2H), 7.10 (br d, J=7.6 Hz, 1H), 3.88-3.79 (m, 3H), 3.76 (br t, J=6.1 Hz, 2H), 3.64-3.52 (m, 2H), 2.66-2.59 (m, 2H), 1.94-1.86 (m, 2H), 1.84-1.78 (m, 2H), 1.64 (br d, J=13.7 Hz, 2H); MS ESI n/z 536.1 (M+H); Anal. HPLC Retention time: 1.37 (Method 1); ROCK2 $IC_{50}$=2305 nM.

Example 211: Preparation of 8-(1,3-benzothiazole-6-sulfonyl)-2-[3-methoxy-4-(1H-pyrazol-4-yl)phenyl]-2,8-diazaspiro[4.5]decan-1-one

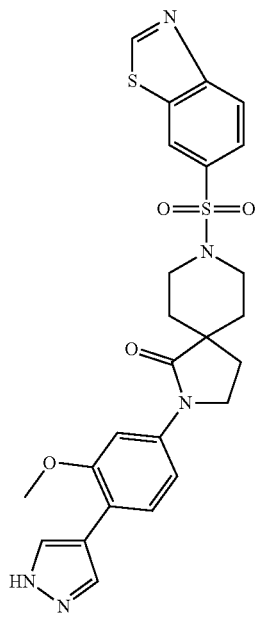 [SMILES: COc1cc(N2CCC3(CCN(S(=O)(=O)c4ccc5ncsc5c4)CC3)C2=O)ccc1-c1cn[nH]c1]

$^1$H NMR (500 MHz, DMSO-d$_6$) δ 9.65 (s, 1H), 8.74 (s, 1H), 8.33 (d, J=8.5 Hz, 1H), 7.99 (br s, 2H), 7.90 (br d, J=8.5 Hz, 1H), 7.57 (d, J=8.5 Hz, 1H), 7.50 (s, 1H), 7.14-7.01 (m, 1H), 3.83 (s, 3H), 3.74 (br t, J=6.7 Hz, 2H), 3.64-3.53 (m, 2H), 2.66 (br t, J=10.4 Hz, 2H), 1.87 (br t, J=6.9 Hz, 2H), 1.83-1.76 (m, 2H), 1.63 (br d, J=13.4 Hz, 2H); MS ESI m/z 524 (M+H); Anal. HPLC Retention time: 1.42 (Method 1); ROCK2 IC$_{50}$=46 nM.

Example 212: Preparation of 8-(3-fluoro-4-methoxybenzenesulfonyl)-2-[3-methoxy-4-(1H-pyrazol-4-yl)phenyl]-2,8-diazaspiro[4.5]decan-1-one

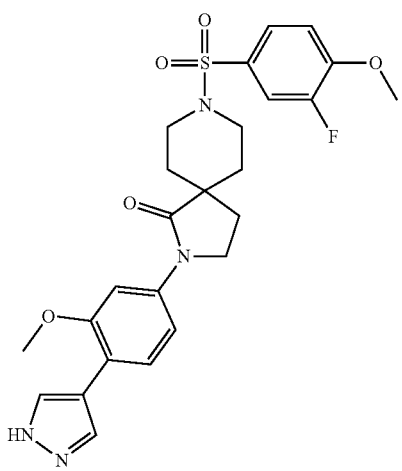

$^1$H NMR (500 MHz, DMSO-d$_6$) δ 7.99 (br s, 2H), 7.65-7.53 (m, 3H), 7.50 (s, 1H), 7.41 (br t, J=8.7 Hz, 1H), 7.09 (br d, J=8.2 Hz, 1H), 3.94 (s, 3H), 3.83 (s, 3H), 3.75 (br t, J=6.7 Hz, 2H), 3.51 (br d, J=11.9 Hz, 2H), 2.65-2.56 (m, 2H), 1.89 (br t, J=6.9 Hz, 2H), 1.78 (br t, J=10.4 Hz, 2H), 1.62 (br d, J=13.4 Hz, 2H); MS ESI m/z 515 (M+H); Anal. HPLC Retention time: 1.58 (Method 1); ROCK2 IC$_{50}$=285 nM.

Example 213: Preparation of 4-({2-[3-methoxy-4-(1H-pyrazol-4-yl)phenyl]-1-oxo-2,8-diazaspiro[4.5]decan-8-yl}sulfonyl)benzene-1-sulfonamide

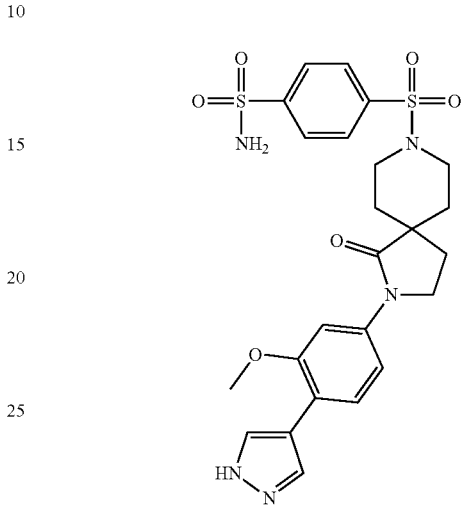

$^1$H NMR (500 MHz, DMSO-d$_6$) δ 8.07 (br d, J=8.2 Hz, 3H), 7.98 (br d, J=8.5 Hz, 2H), 7.66 (br s, 1H), 7.57 (d, J=8.5 Hz, 1H), 7.50 (s, 1H), 7.09 (br d, J=8.5 Hz, 1H), 3.83 (s, 3H), 3.76 (br t, J=6.6 Hz, 2H), 3.52-3.50 (m, 2H), 2.69 (br t, J=10.4 Hz, 2H), 1.90 (br t, J=6.7 Hz, 2H), 1.79 (br d, J=10.1 Hz, 2H), 1.64 (br d, J=13.4 Hz, 2H); MS ESI m/z 546.2 (M+H); Anal. HPLC Retention time: 1.34 (Method 2), ROCK2 IC$_{50}$=456 nM.

Example 214: Preparation of 2-[3-methoxy-4-(1H-pyrazol-4-yl)phenyl]-1-oxo-N-(pyridin-3-yl)-2,8-diazaspiro[4.5]decane-8-carboxamide

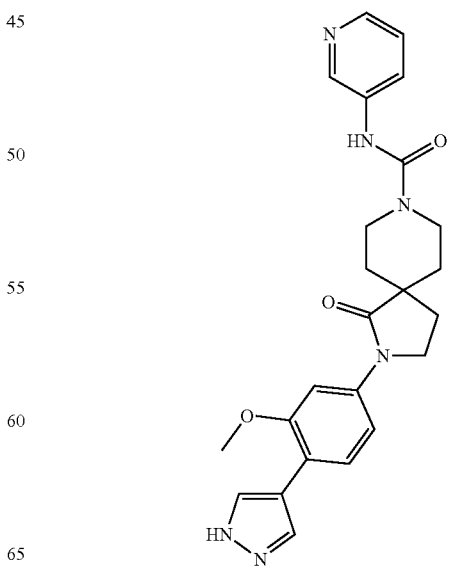

¹H NMR (500 MHz, DMSO-d₆) δ 8.76 (s, 1H), 8.62 (br s, 1H), 8.14 (br d, J=4.0 Hz, 1H), 8.09-7.90 (m, 2H), 7.87 (br d, J=8.2 Hz, 1H), 7.64-7.54 (m, 2H), 7.28 (br dd, J=8.2, 4.6 Hz, 1H), 7.15 (br d, J=8.2 Hz, 1H), 4.05 (br d, J=13.7 Hz, 2H), 3.86 (s, 5H), 3.08 (br t, J=12.2 Hz, 2H), 2.14 (br t, J=6.7 Hz, 2H), 1.81-1.65 (m, 2H), 1.57 (br d, J=12.8 Hz, 2H); MS ESI m/z 447 (M+H); Anal. HPLC Retention time: 0.86 (Method 1); ROCK2 IC₅₀=1483 nM.

Example 215: Preparation of N-[4-(dimethylamino)phenyl]-2-[3-methoxy-4-(1H-pyrazol-4-yl)phenyl]-1-oxo-2,8-diazaspiro[4.5]decane-8-carboxamide

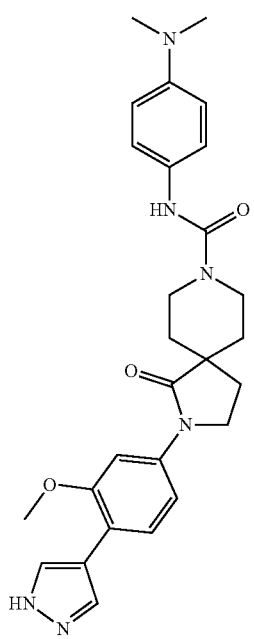 [SMILES: COc1cc(N2CCC3(CCN(C(=O)Nc4ccc(N(C)C)cc4)CC3)C2=O)ccc1-c1cn[nH]c1]

¹H NMR (500 MHz, DMSO-d₆) δ 8.23 (s, 1H), 8.01 (br s, 2H), 7.66-7.53 (m, 2H), 7.23 (br d, J=8.9 Hz, 2H), 7.15 (br d, J=8.2 Hz, 1H), 6.66 (br d, J=8.5 Hz, 2H), 4.02 (br d, J=13.7 Hz, 2H), 3.91-3.81 (m, 5H), 3.00 (br d, J=9.8 Hz, 2H), 2.82 (s, 6H), 2.13 (br t, J=6.6 Hz, 2H), 1.74-1.66 (m, 2H), 1.53 (br d, J=12.8 Hz, 2H); MS ESI m/z 489.2 (M+H); Anal. HPLC Retention time: 1.29 (Method 1); ROCK2 IC₅₀=791 nM.

Example 216: Preparation of 2-[3-methoxy-4-(1H-pyrazol-4-yl)phenyl]-N-(3-methoxyphenyl)-1-oxo-2,8-diazaspiro[4.5]decane-8-carboxamide

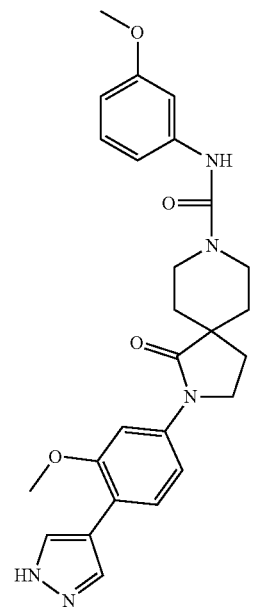 [SMILES: COc1cccc(NC(=O)N2CCC3(CC2)CCN(c2ccc(-c4cn[nH]c4)c(OC)c2)C3=O)c1]

¹H NMR (500 MHz, DMSO-d₆) δ 8.52 (s, 1H), 8.02 (br s, 2H), 7.70-7.55 (m, 2H), 7.21-7.03 (m, 4H), 6.51 (br d, J=7.0 Hz, 1H), 4.05 (br d, J=13.4 Hz, 3H), 3.88-3.83 (m, 5H), 3.71 (s, 3H), 3.09-3.03 (m, 2H), 2.14 (br t, J=6.9 Hz, 2H), 1.72 (br d, J=11.3 Hz, 2H), 1.56 (br d, J=12.5 Hz, 2H); MS ESI m/z 476.1 (M+H); Anal. HPLC Retention time: 1.33 (Method 1); ROCK2 IC₅₀=2252 nM.

Example 217: Preparation of 2-[3-methoxy-4-(1H-pyrazol-4-yl)phenyl]-N-(4-methoxyphenyl)-1-oxo-2,8-diazaspiro[4.5]decane-8-carboxamide

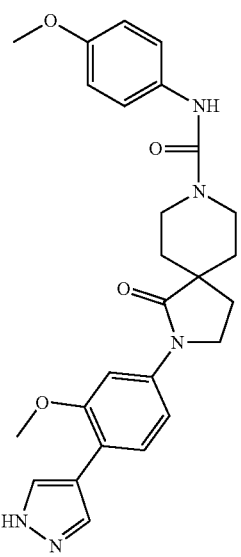 [SMILES: COc1ccc(NC(=O)N2CCC3(CC2)CCN(c2ccc(-c4cn[nH]c4)c(OC)c2)C3=O)cc1]

¹H NMR (500 MHz, DMSO-d₆) δ 8.37 (s, 1H), 7.68-7.56 (m, 2H), 7.35 (br d, J=8.5 Hz, 2H), 7.15 (br d, J=7.6 Hz, 1H), 6.82 (br d, J=8.9 Hz, 2H), 4.04 (br d, J=13.4 Hz, 2H), 3.94-3.81 (m, 5H), 3.74-3.68 (m, 3H), 3.03 (br t, J=11.9 Hz, 2H), 2.13 (br t, J=6.7 Hz, 2H), 1.72 (br t, J=10.7 Hz, 2H), 1.54 (br d, J=13.1 Hz, 2H); MS ESI m/z 476.11, 476.11 (M+H); ROCK2 $IC_{50}$=2460 nM.

Example 218: Preparation of 8-(4-methanesulfonyl-benzenesulfonyl)-2-[3-methoxy-4-(1H-pyrazol-4-yl)phenyl]-2,8-diazaspiro[4.5]decan-1-one

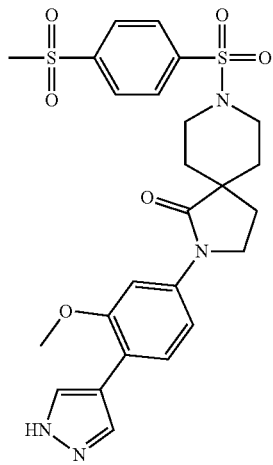 [SMILES: COc1cc(N2CCC3(CCN(S(=O)(=O)c4ccc(S(C)(=O)=O)cc4)CC3)C2=O)ccc1-c1cn[nH]c1]

$^1$H NMR (500 MHz, DMSO-$d_6$) δ 8.20 (br d, J=8.2 Hz, 2H), 8.05 (br d, J=8.2 Hz, 4H), 7.58 (br d, J=8.5 Hz, 1H), 7.51 (s, 1H), 7.09 (br d, J=8.2 Hz, 1H), 3.83 (s, 3H), 3.76 (br t, J=6.6 Hz, 2H), 3.31 (s, 3H), 3.17 (d, J=4.9 Hz, 2H), 2.71 (br t, J=10.8 Hz, 2H), 1.92 (br t, J=6.7 Hz, 2H), 1.79 (br t, J=10.2 Hz, 2H), 1.63 (br d, J=13.1 Hz, 2H); MS ESI m/z 545 (M+H); Anal. HPLC Retention time: 1.42 (Method 1); ROCK2 $IC_{50}$=843 nM.

Preparation of Examples 219-246

The following compounds were made in a parallel manner using the following procedure: Reagents were weighed into stubby tubes. Stock solutions were made for reagent addition: Dissolved 510 mg 2-(3-methoxy-4-(H-pyrazol-4-yl)phenyl)-8-(4-(piperazin-1-yl)benzoyl)-2,8-diazaspiro[4.5]decan-1-one, HCl in 14.50 ml of DCE. To each stubby tube containing aldehyde/ketone reagent (0.072 mmol) was added 0.25 ml of the 2-(3-methoxy-4-(H-pyrazol-4-yl)phenyl)-8-(4-(piperazin-1-yl)benzoyl)-2,8-diazaspiro[4.5]decan-1-one, HCl solution and trimethyl orthoformate (0.020 ml, 0.180 mmol) followed by acetic acid (1.039 ul, 0.018 mmol). The reaction mixture vials were placed in a Bohdan Miniblock XT and were agitated at 400 rpm on an Innova platform shaker at rt for 1 hr. To each vial was then added MP-cyanoborohydride (30.1 mg, 0.072 mmol) and continued agitation overnight.

Upon completion, reaction mixtures were purified via preparative LC/MS with the following conditions: Column: XBridge C18, 19×100 mm, 5-μm particles; Mobile Phase A: 5:95 acetonitrile:water with 10 mM ammonium acetate; Mobile Phase B: 95:5 acetonitrile:water with 10 mM ammonium acetate; Gradient: 10-50% B over 20 minutes, then a 2-minute hold at 100% B; Flow: 20 mL/min. Fractions containing the desired product were combined and dried via centrifugal evaporation. **Gradient varied for each reaction depending on polarity of compound.

Compound purity was assigned based on the methods below.

Method 1: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Method 2: Column: Waters Acquity UPLC BEH C18, 2.1×50 mm, 1.7-μm particles; Mobile Phase A: 5:95 acetonitrile:water with 0.1% trifluoroacetic acid: Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Example 219: Preparation of 2-[3-methoxy-4-(1H-pyrazol-4-yl)phenyl]-8-(4-{4-[(quinoxalin-2-yl)methyl]piperazin-1-yl}benzoyl)-2,8-diazaspiro[4.5]decan-1-one

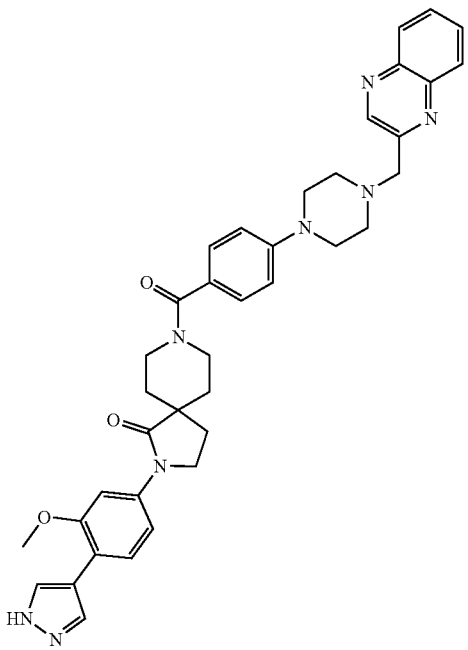 [SMILES: COc1cc(N2CCC3(CCN(C(=O)c4ccc(N5CCN(Cc6cnc7ccccc7n6)CC5)cc4)CC3)C2=O)ccc1-c1cn[nH]c1]

$^1$H NMR (500 MHz, DMSO-$d_6$) δ 9.05 (s, 1H), 8.41-8.26 (m, 1H), 8.23-8.11 (m, 2H), 7.97-7.89 (m, 2H), 7.65-7.54 (m, 2H), 7.36-7.26 (m, 3H), 7.13 (br d, J=8.7 Hz, 1H), 7.03 (br d, J=8.2 Hz, 2H), 4.63 (br s, 2H), 3.85 (s, 5H), 3.74 (br s, 6H), 3.33 (br d, J=6.6 Hz, 2H), 3.25-3.20 (m, 1H), 2.97-2.86 (m, 3H), 2.14 (br s, 2H), 1.70 (br s, 2H), 1.61-1.47 (m, 2H); MS ESI m/z 657.3 (M+H); Anal. HPLC Retention time: 1.62 (Method 2); ROCK2 $IC_{50}$=1.9 nM.

Example 220: Preparation of 8-[4-(4-{[4-(1H-imidazol-1-yl)phenyl]methyl}piperazin-1-yl)benzoyl]-2-[3-methoxy-4-(1H-pyrazol-4-yl)phenyl]-2,8-diazaspiro[4.5]decan-1-one

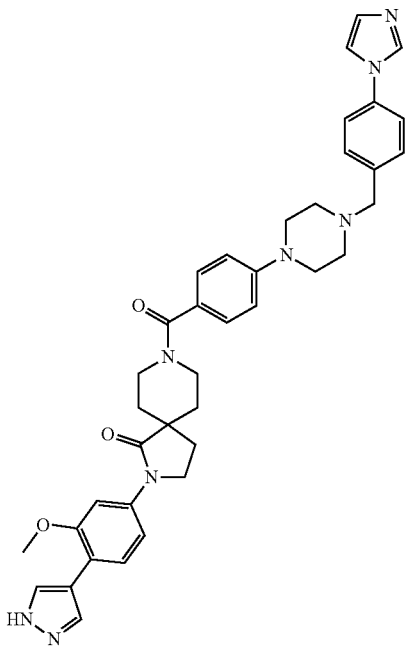 [SMILES: COc1cc(N2CCC3(CCN(C(=O)c4ccc(N5CCN(Cc6ccc(-n7ccnc7)cc6)CC5)cc4)CC3)C2=O)ccc1-c1cn[nH]c1]

$^1$H NMR (500 MHz, DMSO-d$_6$) δ 8.17 (br s, 2H), 8.02 (s, 2H), 7.91 (br d, J=8.1 Hz, 2H), 7.76 (br d, J=8.2 Hz, 2H), 7.63-7.58 (m, 2H), 7.35 (br d, J=8.4 Hz, 2H), 7.19-7.12 (m, 2H), 7.08-7.01 (m, 2H), 4.47 (br s, 2H), 3.86 (s, 6H), 3.59-3.47 (m, 1H), 3.36-3.25 (m, 1H), 3.21-3.12 (m, 1H), 2.51 (br s, 6H), 2.15 (br s, 2H), 1.71 (br d, J=9.5 Hz, 2H), 1.58 (br s, 2H); MS ESI m/z 671.5 (M+H); Anal. HPLC Retention time: 0.93 (Method 1); ROCK2 IC$_{50}$=0.3 nM.

Example 221: Preparation of 8-(4-{4-[2-(benzyloxy)ethyl]piperazin-1-yl}benzoyl)-2-[3-methoxy-4-(1H-pyrazol-4-yl)phenyl]-2,8-diazaspiro[4.5]decan-1-one

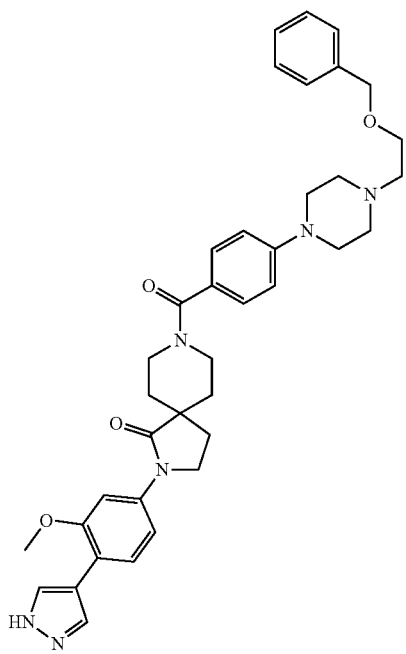 [SMILES: COc1cc(N2CCC3(CCN(C(=O)c4ccc(N5CCN(CCOCc6ccccc6)CC5)cc4)CC3)C2=O)ccc1-c1cn[nH]c1]

$^1$H NMR (500 MHz, DMSO-d$_6$) δ 8.02 (br s, 2H), 7.64-7.58 (m, 2H), 7.39-7.31 (m, 8H), 7.15 (br d, J=8.4 Hz, 1H), 7.05 (br d, J=8.4 Hz, 1H), 4.72 (br d, J=4.5 Hz, 1H), 4.57 (br d, J=5.6 Hz, 3H), 3.86 (s, 4H), 3.78 (br s, 2H), 3.60 (br d, J=5.6 Hz, 2H), 3.57-3.46 (m, 8H), 3.39 (br s, 1H), 3.33 (br d, J=7.0 Hz, 1H), 2.15 (br s, 2H), 1.70 (br d, J=9.2 Hz, 2H), 1.58 (br s, 2H); MS ESI m/z 649.2 (M+H); Anal. HPLC Retention time: 1.68 (Method 2); ROCK2 IC$_{50}$=0.4 nM.

Example 222: Preparation of 8-{4-[4-(2,2-diphenylethyl)piperazin-1-yl]benzoyl}-2-[3-methoxy-4-(1H-pyrazol-4-yl)phenyl]-2,8-diazaspiro[4.5]decan-1-one

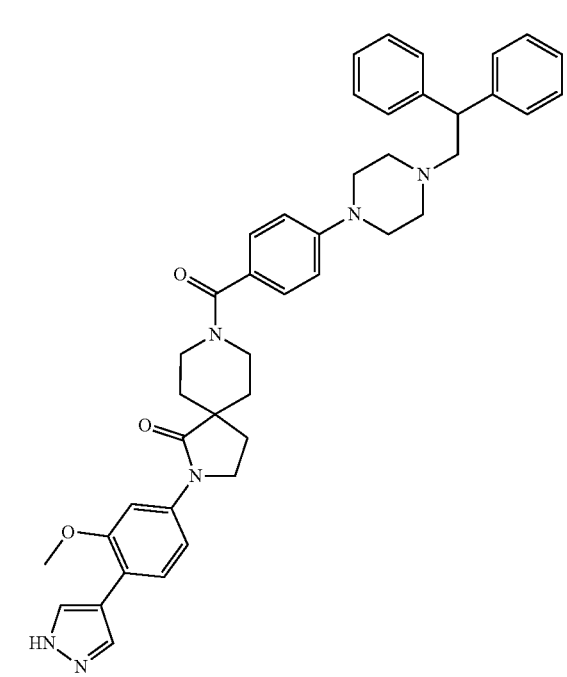 [SMILES: COc1cc(N2CCC3(CCN(C(=O)c4ccc(N5CCN(CC(c6ccccc6)c6ccccc6)CC5)cc4)CC3)C2=O)ccc1-c1cn[nH]c1]

$^1$H NMR (500 MHz, DMSO-d$_6$) δ 8.01 (br s, 2H), 7.66-7.56 (m, 2H), 7.39-7.24 (m, 15H), 7.21-7.09 (m, 4H), 6.92 (br d, J=8.5 Hz, 2H), 4.30 (br s, 2H), 3.86 (s, 6H), 3.48 (br s, 10H), 3.25 (s, 1H), 3.20-3.16 (m, 1H), 3.11 (br d, J=4.6 Hz, 4H), 3.00 (br d, J=7.6 Hz, 2H), 2.58 (br s, 4H), 2.14 (br s, 2H), 1.73-1.65 (m, 2H), 1.56 (br d, J=12.5 Hz, 2H); MS ESI m/z 695.3 (M+H); Anal. HPLC Retention time: 1.51 (Method 1); ROCK2 IC$_{50}$=9.3 nM.

Example 223: Preparation of 8-(4-{4-[(2-chlorophenyl)methyl]piperazin-1-yl}benzoyl)-2-[3-methoxy-4-(1H-pyrazol-4-yl)phenyl]-2,8-diazaspiro[4.5]decan-1-one

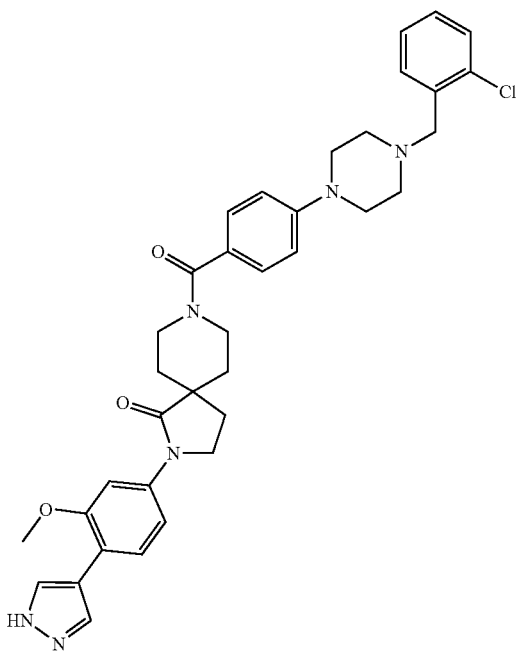 [SMILES: COc1cc(N2CCC3(CCN(C(=O)c4ccc(N5CCN(Cc6ccccc6Cl)CC5)cc4)CC3)C2=O)ccc1-c1cn[nH]c1]

¹H NMR (500 MHz, DMSO-d₆) δ 8.08-7.88 (m, 2H), 7.65-7.56 (m, 2H), 7.53 (br d, J=7.4 Hz, 1H), 7.44 (br d, J=7.7 Hz, 1H), 7.38-7.26 (m, 4H), 7.14 (br d, J=8.5 Hz, 1H), 6.96 (br d, J=8.6 Hz, 2H), 3.92-3.80 (m, 5H), 3.69-3.63 (m, 4H), 3.23 (br s, 4H), 2.57 (br s, 4H), 2.14 (br t, J=6.3 Hz, 2H), 1.81-1.66 (m, 4H), 1.58 (br s, 2H); MS ESI m/z 639.1 (M+H); Anal. HPLC Retention time: 1.28 (Method 1); ROCK2 IC₅₀=1.1 nM.

Example 224: Preparation of 2-[3-methoxy-4-(1H-pyrazol-4-yl)phenyl]-8-(4-{4-[(1,2,3-thiadiazol-4-yl)methyl]piperazin-1-yl}benzoyl)-2,8-diazaspiro[4.5]decan-1-one

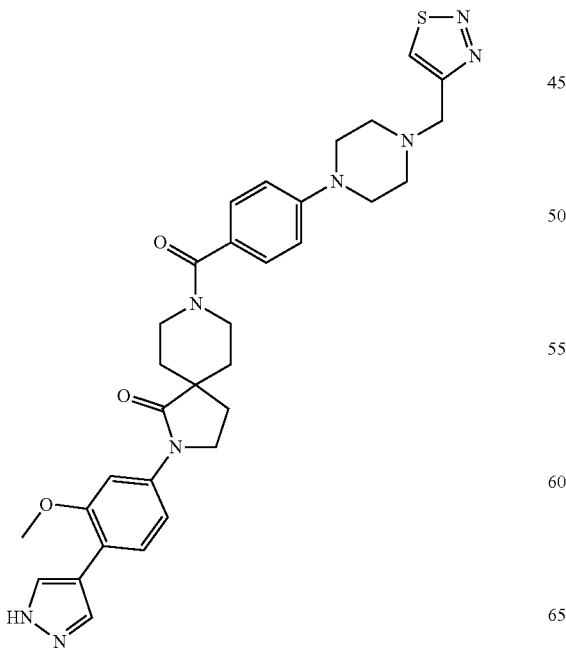

¹H NMR (500 MHz, DMSO-d₆) δ 9.10 (s, 1H), 8.02 (br d, J=3.4 Hz, 2H), 7.64-7.54 (m, 2H), 7.30 (br d, J=8.5 Hz, 2H), 7.16 (br d, J=7.3 Hz, 1H), 6.96 (br d, J=8.5 Hz, 2H), 4.11 (s, 3H), 3.93-3.81 (m, 5H), 3.57 (br d, J=6.7 Hz, 1H), 3.38 (s, 1H), 3.24 (br s, 5H), 2.61 (br s, 4H), 2.15 (br t, J=6.6 Hz, 2H), 1.72 (br d, J=9.5 Hz, 2H), 1.57 (br d, J=11.3 Hz, 2H); MS ESI m/z 612.9 (M+H):
Anal. HPLC Retention time: 1.37 (Method 2); ROCK2 IC₅₀=1.5 nM.

Example 225: Preparation of 8-{4-[4-({[1,1'-biphenyl]-4-yl}methyl)piperazin-1-yl]benzoyl}-2-[3-methoxy-4-(1H-pyrazol-4-yl)phenyl]-2,8-diazaspiro[4.5]decan-1-one

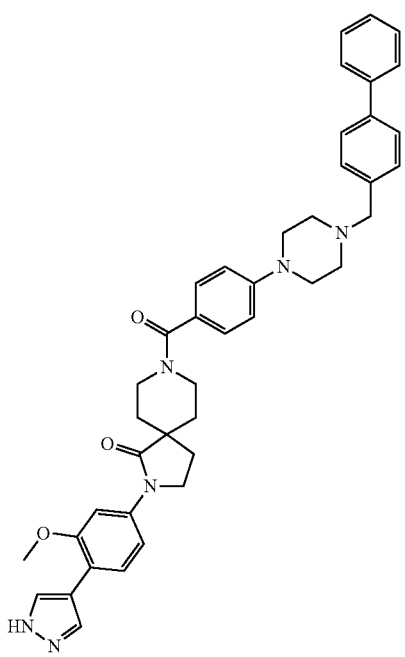 [SMILES: COc1cc(N2CCC3(CCN(C(=O)c4ccc(N5CCN(Cc6ccc(-c7ccccc7)cc6)CC5)cc4)CC3)C2=O)ccc1-c1cn[nH]c1]

¹H NMR (500 MHz, DMSO-d₆) δ 8.02 (br s, 2H), 7.80 (br d, J=7.8 Hz, 2H), 7.72 (br d, J=7.6 Hz, 2H), 7.67-7.57 (m, 4H), 7.50 (t, J=7.6 Hz, 2H), 7.45-7.38 (m, 1H), 7.34 (br d, J=8.3 Hz, 2H), 7.18-7.12 (m, 1H), 7.10-6.99 (m, 2H), 4.43 (br s, 2H), 3.86 (s, 5H), 3.63-3.42 (m, 6H), 3.38-3.29 (m, 1H), 3.26 (br s, 1H), 2.59-2.55 (m, 4H), 2.14 (br s, 2H), 1.70 (br d, J=10.5 Hz, 2H), 1.58 (br s, 2H); MS ESI m/z 681.3 (M+H); Anal. HPLC Retention time: 1.52 (Method 1); ROCK2 IC₅₀=4.5 nM.

Example 226: Preparation of 8-[4-(4-cyclohexylpiperazin-1-yl)benzoyl]-2-[3-methoxy-4-(1H-pyrazol-4-yl)phenyl]-2,8-diazaspiro[4.5]decan-1-one

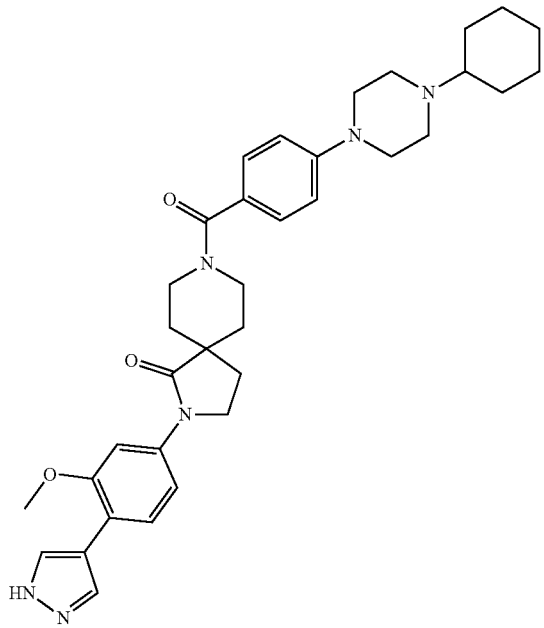 [SMILES: COc1cc(N2CCC3(CCN(C(=O)c4ccc(N5CCN(C6CCCCC6)CC5)cc4)CC3)C2=O)ccc1-c1cn[nH]c1]

$^1$H NMR (500 MHz, DMSO-d$_6$) δ 8.01 (br s, 2H), 7.65-7.54 (m, 2H), 7.34 (br d, J=8.5 Hz, 2H), 7.14 (br d, J=8.5 Hz, 1H), 7.04 (br d, J=8.5 Hz, 2H), 3.86 (s, 5H), 3.69-3.60 (m, 13H), 2.14 (br s, 2H), 2.09-2.03 (m, 2H), 1.83 (br d, J=12.5 Hz, 2H), 1.70 (br d, J=11.0 Hz, 2H), 1.60 (br s, 3H), 1.46-1.33 (m, 2H), 1.27 (br d, J=12.8 Hz, 2H), 1.18-1.08 (m, 1H); MS ESI m/z 597.2 (M+H); Anal. HPLC Retention time: 1.17 (Method 1); ROCK2 IC$_{50}$=0.7 nM.

Example 227: Preparation of 8-(4-{4-[(4-chlorophenyl)methyl]piperazin-1-yl}benzoyl)-2-[3-methoxy-4-(1H-pyrazol-4-yl)phenyl]-2,8-diazaspiro[4.5]decan-1-one

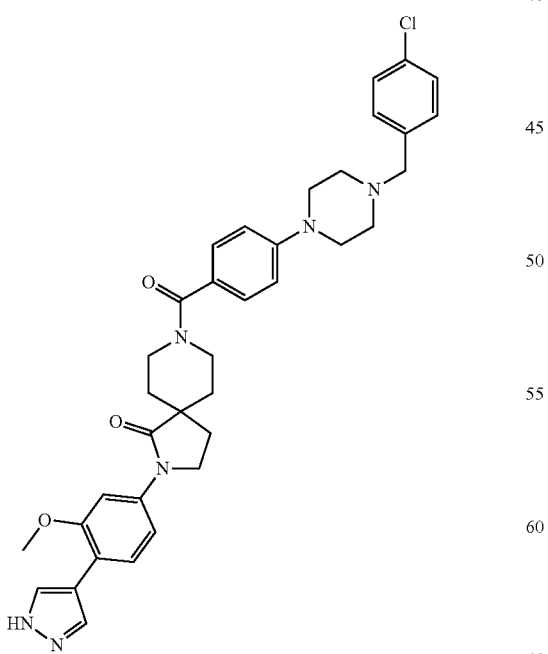

$^1$H NMR (500 MHz, DMSO-d$_6$) δ 8.01 (br s, 2H), 7.65-7.55 (m, 2H), 7.42-7.34 (m, 4H), 7.28 (br d, J=8.2 Hz, 2H), 7.14 (br d, J=7.6 Hz, 1H), 6.95 (br d, J=8.5 Hz, 2H), 3.85 (s, 5H), 3.67-3.63 (m, 8H), 3.55-3.50 (m, 1H), 3.29-3.11 (m, 7H), 2.14 (br t, J=6.3 Hz, 2H), 1.70 (br s, 2H), 1.56 (br d, J=12.8 Hz, 2H); MS ESI m/z 639.1 (M+H); Anal. HPLC Retention time: 1.96 (Method 2); ROCK2 IC$_{50}$=2.2 nM.

Example 228: Preparation of 2-[3-methoxy-4-(1H-pyrazol-4-yl)phenyl]-8-(4-{4-[(1-methyl-1H-pyrrol-2-yl)methyl]piperazin-1-yl}benzoyl)-2,8-diazaspiro[4.5]decan-1-one

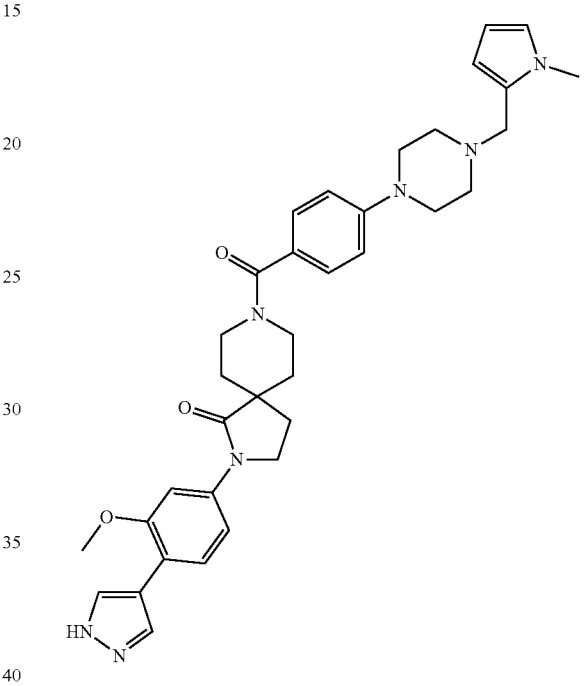

$^1$H NMR (500 MHz, DMSO-d$_6$) δ 8.02 (s, 2H), 7.66-7.57 (m, 2H), 7.29 (br d, J=8.5 Hz, 2H), 7.16 (br d, J=8.2 Hz, 1H), 6.96 (br d, J=8.5 Hz, 2H), 6.68 (br s, 1H), 5.90 (br d, J=9.5 Hz, 2H), 3.91 (s, 2H), 3.87 (s, 5H), 3.61 (s, 3H), 3.45 (br s, 6H), 3.24-3.18 (m, 6H), 2.15 (br s, 2H), 1.72 (br d, J=9.8 Hz, 2H), 1.57 (br d, J=11.9 Hz, 2H); MS ESI m/z 608.2 (M+H); Anal. HPLC Retention time: 1.66 (Method 2); ROCK2 IC$_{50}$=0.9 nM.

Example 229: Preparation of 8-(4-{4-[(1,3-benzo-thiazol-2-yl)methyl]piperazin-1-yl}benzoyl)-2-[3-methoxy-4-(1H-pyrazol-4-yl)phenyl]-2,8-diazaspiro[4.5]decan-1-one

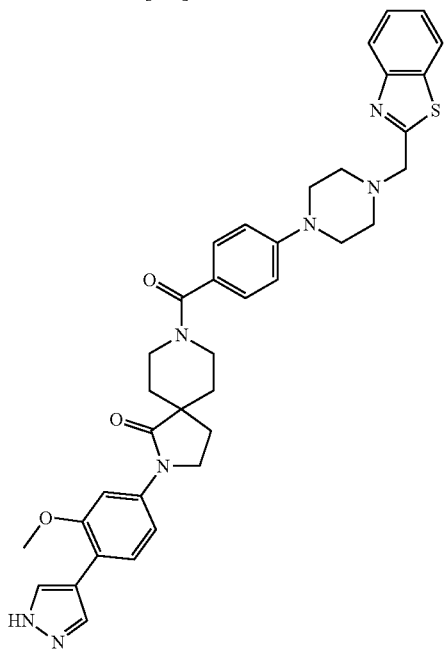

$^1$H NMR (500 MHz, DMSO-d$_6$) δ 8.06 (br d, J=7.6 Hz, 1H), 8.01 (br s, 2H), 7.94 (br d, J=8.2 Hz, 1H), 7.65-7.57 (m, 2H), 7.49 (br d, J=7.6 Hz, 1H), 7.45-7.39 (m, 1H), 7.30 (br d, J=8.5 Hz, 2H), 7.14 (br d, J=7.9 Hz, 1H), 6.98 (br d, J=8.5 Hz, 2H), 4.02 (s, 2H), 3.86 (s, 5H), 3.49-3.44 (m, 2H), 3.28 (br s, 4H), 3.17 (br s, 2H), 2.72 (br s, 4H), 2.14 (br t, J=6.3 Hz, 2H), 1.76-1.69 (m, 2H), 1.57 (br d, J=12.8 Hz, 2H); MS ESI m/z 662.1 (M+H); Anal. HPLC Retention time: 1.36 (Method 1); ROCK2 IC$_{50}$=1.9 nM.

Example 230: Preparation of 8-{4-[4-(cyclopentyl-methyl)piperazin-1-yl]benzoyl}-2-[3-methoxy-4-(1H-pyrazol-4-yl)phenyl]-2,8-diazaspiro[4.5]decan-1-one

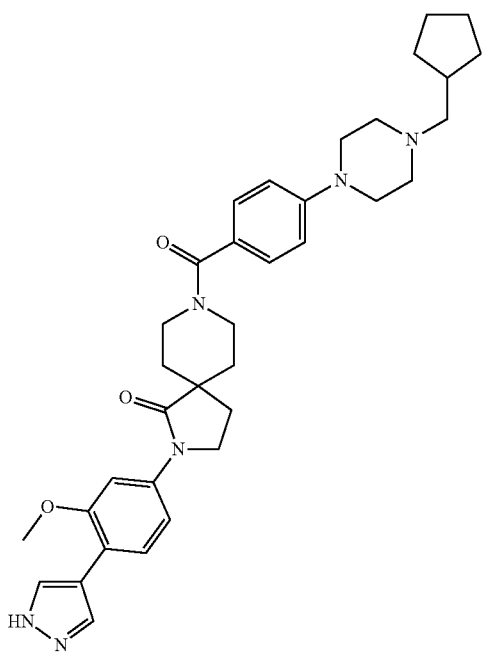 [SMILES: COc1cc(N2CCC3(CCN(C(=O)c4ccc(N5CCN(CC6CCCC6)CC5)cc4)CC3)C2=O)ccc1-c1cn[nH]c1]

$^1$H NMR (500 MHz, DMSO-d$_6$) δ 8.24 (s, 1H), 7.98 (s, 1H), 7.68-7.59 (m, 2H), 7.34 (br d, J=8.4 Hz, 2H), 7.16 (br d, J=8.8 Hz, 1H), 7.04 (br d, J=8.3 Hz, 2H), 3.89-3.84 (m, 5H), 3.21-3.09 (m, 6H), 2.31-2.20 (m, 2H), 2.15 (br s, 2H), 1.83 (br d, J=6.1 Hz, 3H), 1.70 (br d, J=9.5 Hz, 2H), 1.65-1.44 (m, 12H), 1.19-1.13 (m, 1H), 1.09-0.98 (m, 1H); MS ESI m/z 597.1 (M+H); Anal. HPLC Retention time: 2.56 (Method 2); ROCK2 IC$_{50}$=2.2 nM.

Example 231: Preparation of 8-{4-[4-(3,3-dimethyl-butyl)piperazin-1-yl]benzoyl}-2-[3-methoxy-4-(1H-pyrazol-4-yl)phenyl]-2,8-diazaspiro[4.5]decan-1-one

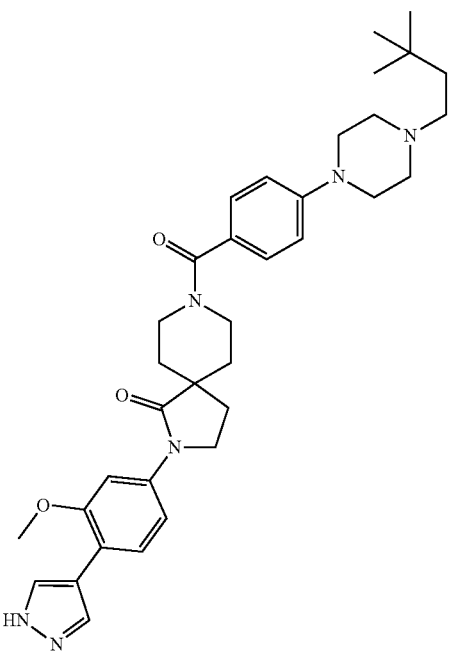 [SMILES: COc1cc(N2CCC3(CCN(C(=O)c4ccc(N5CCN(CCC(C)(C)C)CC5)cc4)CC3)C2=O)ccc1-c1cn[nH]c1]

$^1$H NMR (500 MHz, DMSO-d$_6$) δ 8.02 (br s, 2H), 7.65-7.58 (m, 2H), 7.30 (br d, J=8.2 Hz, 2H), 7.16 (br d, J=10.4 Hz, 1H), 6.96 (br d, J=8.5 Hz, 2H), 3.87 (s, 5H), 3.35 (br s, 1H), 3.19 (br d, J=15.3 Hz, 5H), 2.35-2.26 (m, 2H), 2.15 (br s, 2H), 1.70 (br s, 4H), 1.58 (br d, J=9.8 Hz, 2H), 1.44-1.35 (m, 2H), 0.94-0.85 (m, 9H); MS ESI m/z 599.2 (M+H); Anal. HPLC Retention time: 1.27 (Method 1); ROCK2 IC$_{50}$=2.2 nM.

Example 232: Preparation of 8-(4-{4-[1-(dimethyl-amino)propan-2-yl]piperazin-1-yl}benzoyl)-2-[3-methoxy-4-(1H-pyrazol-4-yl)phenyl]-2,8-diazaspiro[4.5]decan-1-one

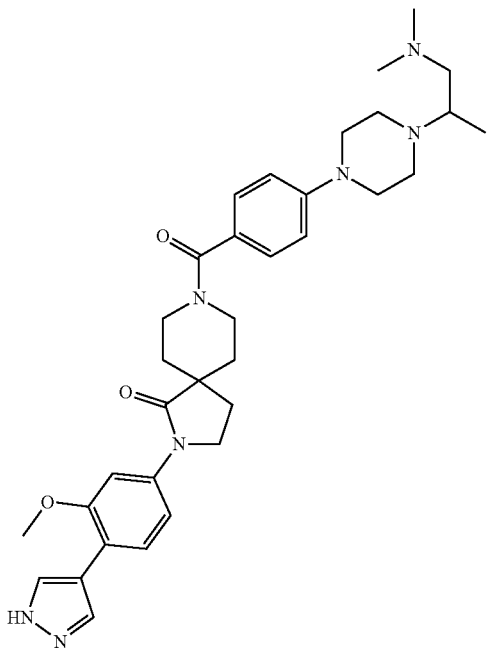 [SMILES: COc1cc(N2CCC3(CCN(C(=O)c4ccc(N5CCN(C(C)CN(C)C)CC5)cc4)CC3)C2=O)ccc1-c1cn[nH]c1]

¹H NMR (500 MHz, DMSO-d₆) δ 8.02 (br s, 2H), 7.66-7.58 (m, 2H), 7.34-7.27 (m, 3H), 7.19 (s, 1H), 6.98 (br d, J=8.5 Hz, 1H), 3.87 (s, 5H), 3.33-3.11 (m, 4H), 2.93 (br s, 2H), 2.81 (s, 6H), 2.15 (br t, J=6.4 Hz, 2H), 1.71 (br d, J=11.8 Hz, 2H), 1.57 (br d, J=10.4 Hz, 2H), 1.24 (s, 1H), 1.17 (br d, J=6.6 Hz, 1H), 0.93 (br d, J=5.5 Hz, 3H); Anal. HPLC Retention time: 1.18 (Method 2); MS ESI m/z 600.4 (M+H); ROCK2 IC₅₀=3.1 nM.

Example 233: Preparation of 2-[3-methoxy-4-(1H-pyrazol-4-yl)phenyl]-8-{4-[4-(propan-2-yl)piper-azin-1-yl]benzoyl}-2,8-diazaspiro[4.5]decan-1-one

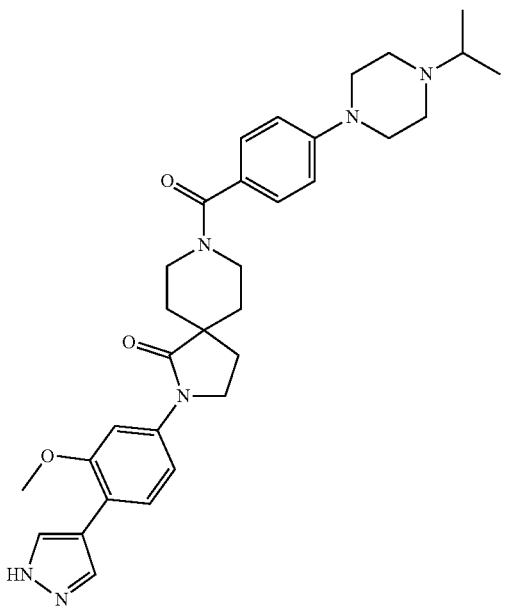 [SMILES: COc1cc(N2CCC3(CCN(C(=O)c4ccc(N5CCN(C(C)C)CC5)cc4)CC3)C2=O)ccc1-c1cn[nH]c1]

¹H NMR (500 MHz, DMSO-d₆) δ 8.01 (br s, 2H), 7.66-7.53 (m, 2H), 7.29 (br d, J=8.4 Hz, 2H), 7.14 (br d, J=8.3 Hz, 1H), 6.95 (br d, J=8.5 Hz, 2H), 3.93-3.79 (m, 5H), 3.26-3.12 (m, 5H), 2.65 (br d, J=5.9 Hz, 1H), 2.55 (s, 5H), 2.19-2.10 (m, 2H), 1.81-1.65 (m, 4H), 1.56 (br d, J=11.4 Hz, 2H), 1.00 (d, J=6.4 Hz 6H); MS ESI m/z 557.4 (M+H); Anal. HPLC Retention time: 1.05 (Method 1); ROCK2 IC₅₀=0.2 nM.

Example 234: Preparation of 2-[3-methoxy-4-(1H-pyrazol-4-yl)phenyl]-8-[4-(4-{[4-(trifluoromethyl)phenyl]methyl}piperazin-1-yl)benzoyl]-2,8-diaz-aspiro[4.5]decan-1-one

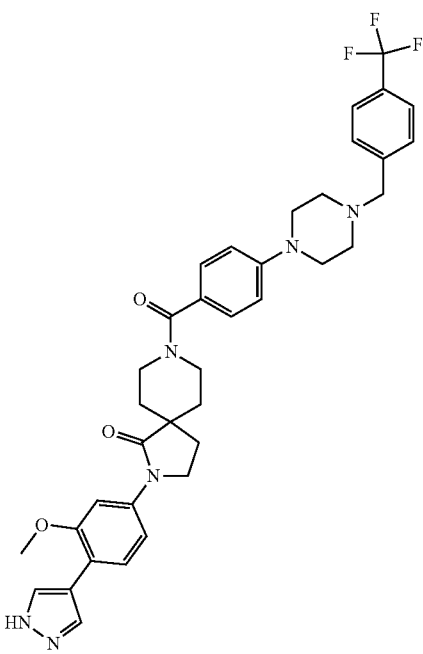 [SMILES: COc1cc(N2CCC3(CCN(C(=O)c4ccc(N5CCN(Cc6ccc(C(F)(F)F)cc6)CC5)cc4)CC3)C2=O)ccc1-c1cn[nH]c1]

¹H NMR (500 MHz, DMSO-d₆) δ 8.03 (br s, 2H), 7.88 (br d, J=7.9 Hz, 2H), 7.77 (br d, J=7.6 Hz, 2H), 7.64-7.55 (m, 2H), 7.34 (br d, J=8.2 Hz, 2H), 7.19-7.13 (m, 2H), 7.03 (br d, J=8.5 Hz, 1H), 4.49-3.24 (m, 19H), 2.15 (br s, 2H), 1.72 (br s, 2H), 1.63-1.49 (m, 2H); MS ESI m/z 673.2 (M+H); Anal. HPLC Retention time: 1.39 (Method 1); ROCK2 IC₅₀=4.1 nM.

Example 235: Preparation of N-(3-{[4-(4-{2-[3-methoxy-4-(1H-pyrazol-4-yl)phenyl]-1-oxo-2,8-diazaspiro[4.5]decane-8-carbonyl}phenyl)piperazin-1-yl]methyl}phenyl)methanesulfonamide

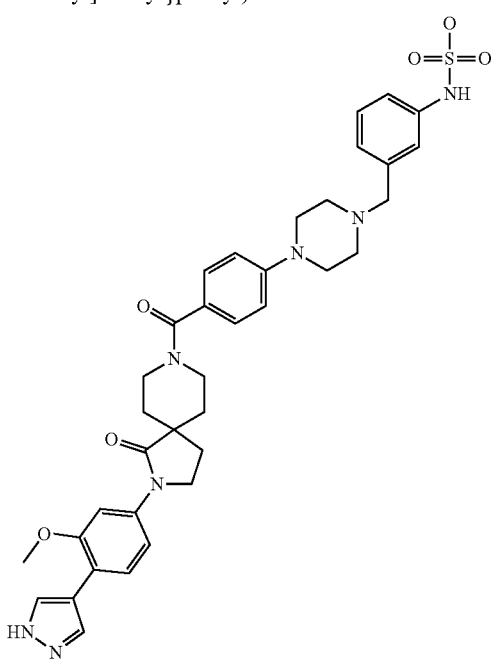

$^1$H NMR (500 MHz, DMSO-d$_6$) δ 9.98 (br s, 1H), 8.09-7.88 (m, 2H), 7.65-7.55 (m, 2H), 7.49-7.42 (m, 1H), 7.38 (br s, 1H), 7.34 (br d, J=8.2 Hz, 1H), 7.29-7.24 (m, 2H), 7.20-7.11 (m, 2H), 7.09-7.00 (m, 2H), 4.36 (br s, 2H), 3.86 (s, 5H), 3.60 (br s, 12H), 3.04 (s, 3H), 2.14 (br s, 2H), 1.71 (br s, 2H), 1.57 (br d, J=6.9 Hz, 2H); MS ESI m/z 698.2 (M+H); Anal. HPLC Retention time: 1.13 (Method 1); ROCK2 IC$_{50}$=0.2 nM.

Example 236: Preparation of 2-[3-methoxy-4-(1H-pyrazol-4-yl)phenyl]-8-(4-{4-[(1,3-thiazol-2-yl)methyl]piperazin-1-yl}benzoyl)-2,8-diazaspiro[4.5]decan-1-one

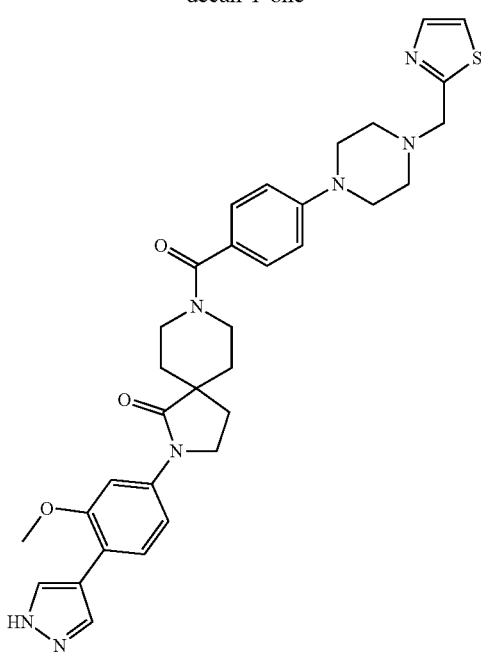

$^1$H NMR (500 MHz, DMSO-d$_6$) δ 8.02 (br s, 2H), 7.74 (br d, J=3.0 Hz, 1H), 7.68 (br s, 1H), 7.63-7.57 (m, 2H), 7.29 (br d, J=8.3 Hz, 2H), 7.14 (br d, J=8.2 Hz, 1H), 6.97 (br d, J=8.4 Hz, 2H), 3.95-3.79 (m, 7H), 3.52 (br s, 2H), 3.36-3.11 (m, 6H), 2.64 (br s, 4H), 2.14 (br s, 2H), 1.70 (br d, J=10.3 Hz, 2H), 1.57 (br d, J=8.5 Hz, 2H); MS ESI m/z 612.2 (M+H); Anal. HPLC Retention time: 1.16 (Method 1); ROCK2 IC$_{50}$=2.7 nM.

Example 237: Preparation of 8-{4-[4-({4-[3-(dimethylamino)propoxy]phenyl}methyl)piperazin-1-yl]benzoyl}-2-[3-methoxy-4-(1H-pyrazol-4-yl)phenyl]-2,8-diazaspiro[4.5]decan-1-one

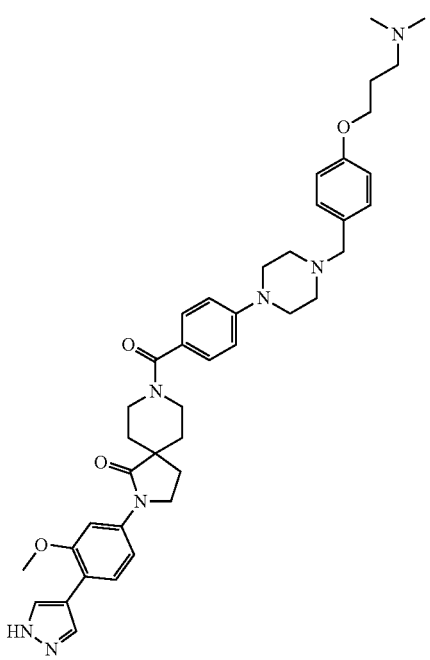

$^1$H NMR (500 MHz, DMSO-d$_6$) δ 8.01 (br s, 2H), 7.62-7.55 (m, 2H), 7.28 (br d, J=8.2 Hz, 2H), 7.22 (br d, J=8.2 Hz, 2H), 7.14 (br d, J=7.6 Hz, 1H), 6.94 (br d, J=8.5 Hz, 2H), 6.87 (br d, J=8.2 Hz, 2H), 4.00-3.91 (m, 2H), 3.89-3.79 (m, 5H), 3.58-3.33 (m, 6H), 3.25-3.16 (m, 4H), 2.49-2.42 (m, 6H), 2.21 (s, 6H), 2.13 (br t, J=6.4 Hz, 2H), 1.88-1.80 (m, 2H), 1.70 (br d, J=10.7 Hz, 2H), 1.56 (br d, J=11.3 Hz, 2H); MS ESI m/z 706.3 (M+H); Anal. HPLC Retention time: 0.92 (Method 1); ROCK2 IC$_{50}$=0.1 nM.

Example 238: Preparation of 2-[3-methoxy-4-(1H-pyrazol-4-yl)phenyl]-8-{4-[4-(3-methylbutyl)piperazin-1-yl]benzoyl}-2,8-diazaspiro[4.5]decan-1-one

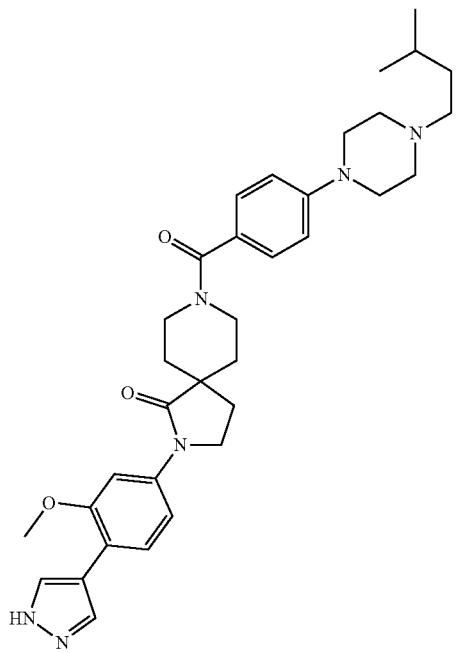 [SMILES: COc1cc(N2CCC3(CCN(C(=O)c4ccc(N5CCN(CCC(C)C)CC5)cc4)CC3)C2=O)ccc1-c1cn[nH]c1]

$^1$H NMR (500 MHz, DMSO-d$_6$) δ 8.01 (br s, 2H), 7.65-7.56 (m, 2H), 7.29 (br d, J=8.5 Hz, 2H), 7.15 (br d, J=8.5 Hz, 1H), 6.95 (br d, J=8.5 Hz, 2H), 3.93-3.80 (m, 5H), 3.60 (br s, 1H), 3.57-3.52 (m, 1H), 3.35 (br s, 1H), 3.29-3.09 (m, 5H), 2.32 (br t, J=7.5 Hz, 2H), 2.14 (br s, 2H), 2.05 (br d, J=4.3 Hz, 1H), 1.70 (br s, 1H), 1.63-1.52 (m, 3H), 1.35 (br d, J=7.6 Hz, 2H), 1.00 (d, J=6.1 Hz, 2H), 0.89 (br d, J=6.7 Hz, 8H); MS ESI m/z 585.2 (M+H); Anal. HPLC Retention time: 1.53 (Method 2); ROCK2 IC$_{50}$=1.6 nM.

Example 239: Preparation of 2-[3-methoxy-4-(1H-pyrazol-4-yl)phenyl]-8-{4-[4-(2-phenylethyl)piperazin-1-yl]benzoyl}-2,8-diazaspiro[4.5]decan-1-one

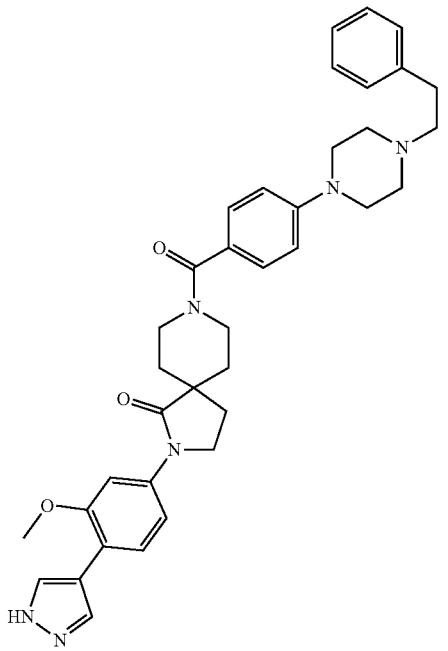 [SMILES: COc1cc(N2CCC3(CCN(C(=O)c4ccc(N5CCN(CCc6ccccc6)CC5)cc4)CC3)C2=O)ccc1-c1cn[nH]c1]

$^1$H NMR (500 MHz, DMSO-d$_6$) δ 8.01 (br s, 2H), 7.65-7.55 (m, 2H), 7.35 (br d, J=7.9 Hz, 4H), 7.29 (br d, J=7.9 Hz, 3H), 7.14 (br d, J=8.9 Hz, 1H), 7.06 (br d, J=8.5 Hz, 2H), 3.86 (s, 6H), 3.46 (br s, 5H), 3.40-3.31 (m, 1H), 3.23 (br d, J=13.4 Hz, 1H), 3.06-2.98 (m, 2H), 2.50 (br s, 6H), 2.14 (br s, 2H), 1.71 (br d, J=9.8 Hz, 2H), 1.57 (br d, J=10.1 Hz, 2H); MS ESI m/z 619.2 (M+H); Anal. HPLC Retention time: 1.79 (Method 2); ROCK2 IC$_{50}$=0.6 nM.

Example 240: Preparation of 2-[3-methoxy-4-(1H-pyrazol-4-yl)phenyl]-8-{4-[4-(3,3,3-trifluoropropyl)piperazin-1-yl]benzoyl}-2,8-diazaspiro[4.5]decan-1-one

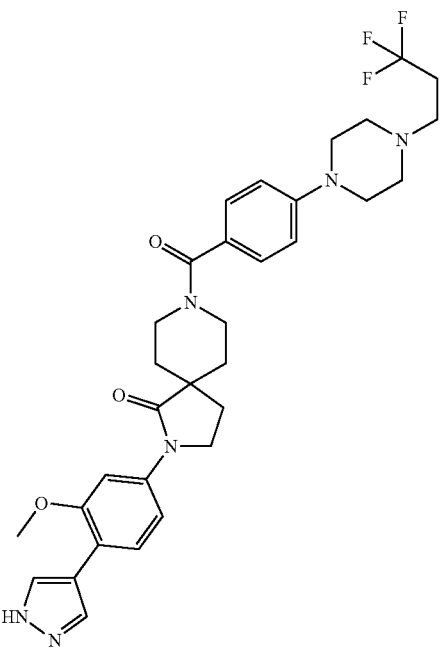 [SMILES: COc1cc(N2CCC3(CCN(C(=O)c4ccc(N5CCN(CCC(F)(F)F)CC5)cc4)CC3)C2=O)ccc1-c1cn[nH]c1]

$^1$H NMR (500 MHz, DMSO-d$_6$) δ 8.01 (br s, 2H), 7.64-7.57 (m, 2H), 7.30 (br d, J=8.2 Hz, 2H), 7.15 (br d, J=8.5 Hz, 1H), 6.97 (br d, J=8.5 Hz, 2H), 3.92-3.80 (m, 5H), 3.55-3.47 (m, 4H), 3.27-3.13 (m, 6H), 2.51-2.44 (m, 4H), 2.14 (br t, J=6.4 Hz, 2H), 1.80-1.64 (m, 4H), 1.57 (br d, J=11.6 Hz, 2H); MS ESI m/z 611.1 (M+H); Anal. HPLC Retention time: 1.12 (Method 1); ROCK2 IC$_{50}$=1.0 nM.

Example 241: Preparation of 8-{4-[4-(2,2-dimethyl-propyl)piperazin-1-yl]benzoyl}-2-[3-methoxy-4-(1H-pyrazol-4-yl)phenyl]-2,8-diazaspiro[4.5]decan-1-one

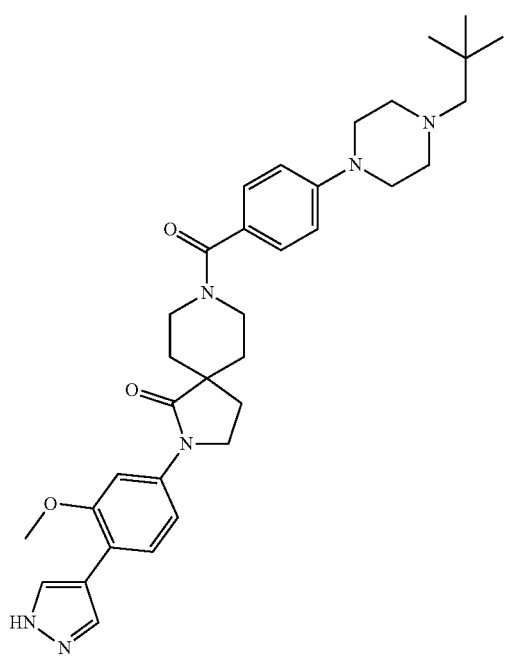 [SMILES: COc1cc(N2CCC3(CCN(C(=O)c4ccc(N5CCN(CC(C)(C)C)CC5)cc4)CC3)C2=O)ccc1-c1cn[nH]c1]

$^1$H NMR (500 MHz, DMSO-d$_6$) δ 8.01 (br s, 2H), 7.64-7.55 (m, 2H), 7.28 (br d, J=8.4 Hz, 2H), 7.14 (br d, J=8.2 Hz, 1H), 6.94 (br d, J=8.5 Hz, 2H), 3.86 (s, 5H), 3.55 (br s, 2H), 3.24-3.13 (m, 4H), 2.63-2.53 (m, 6H), 2.19-2.11 (m, 2H), 2.09 (s, 2H), 1.73-1.66 (m, 2H), 1.57 (br s, 2H), 0.87 (s, 9H); MS ESI m/z 293.2 (M+H); Anal. HPLC Retention time: 2.18 (Method 2); ROCK2 IC$_{50}$=0.4 nM.

Example 242: Preparation of 8-{4-[4-(1-hydroxy-propan-2-yl)piperazin-1-yl]benzoyl}-2-[3-methoxy-4-(1H-pyrazol-4-yl)phenyl]-2,8-diazaspiro[4.5]decan-1-one

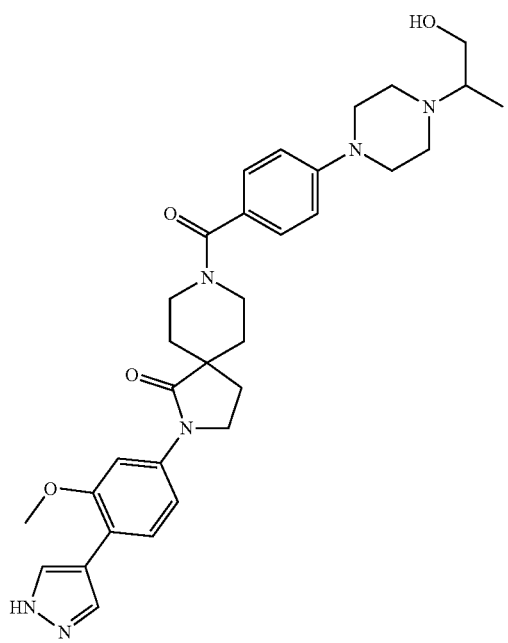 [SMILES: COc1cc(N2CCC3(CCN(C(=O)c4ccc(N5CCN(C(C)CO)CC5)cc4)CC3)C2=O)ccc1-c1cn[nH]c1]

$^1$H NMR (500 MHz, DMSO-d$_6$) δ 8.01 (br s, 2H), 7.65-7.57 (m, 2H), 7.29 (br d, J=8.2 Hz, 2H), 7.15 (br d, J=7.6 Hz, 1H), 6.95 (br d, J=8.2 Hz, 2H), 3.87 (s, 5H), 3.49 (br s, 1H), 3.43 (br d, J=8.9 Hz, 1H), 3.32 (br d, J=4.0 Hz, 1H), 3.20 (br s, 5H), 3.00 (s, 1H), 2.72-2.58 (m, 4H), 2.45 (br s, 1H), 2.22 (s, 1H), 2.15 (br, J=6.4 Hz, 2H), 1.78-1.67 (m, 2H), 1.57 (br d, J=11.3 Hz, 2H), 0.96 (br d, J=6.7 Hz, 3H); MS ESI m/z 573.3 (M+H); Anal. HPLC Retention time: 1.09 (Method 2); ROCK2 IC$_{50}$=0.7 nM.

Example 243: Preparation of 2-[3-methoxy-4-(1H-pyrazol-4-yl)phenyl]-8-(4-{4-[(pyridin-3-yl)methyl]piperazin-1-yl}benzoyl)-2,8-diazaspiro[4.5]decan-1-one

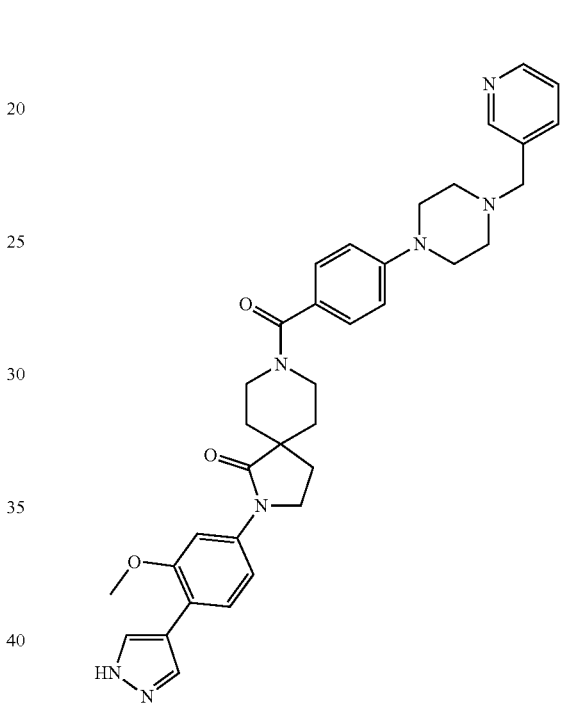

$^1$H NMR (500 MHz, DMSO-d$_6$) δ 8.51 (s, 1H), 8.47 (br d, J=4.3 Hz, 1H), 8.00 (s, 2H), 7.75 (br d, J=7.6 Hz, 1H), 7.62-7.55 (m, 2H), 7.38 (dd, J=7.3, 4.9 Hz, 1H), 7.28 (br d, J=8.5 Hz, 2H), 7.13 (br d, J=9.5 Hz, 1H), 6.95 (br d, J=8.9 Hz, 2H), 4.02 (br dd, J=11.0, 4.0 Hz, 1H), 3.91-3.78 (m, 5H), 3.57 (br d, J=10.4 Hz, 4H), 3.34 (br s, 1H), 3.29-3.11 (m, 6H), 2.27 (br t, J=7.5 Hz, 1H), 2.13 (br t, =6.4 Hz, 2H), 1.69 (br d, J=9.5 Hz, 2H), 1.56 (br d, J=10.4 Hz, 2H); MS ESI m/z 606 (M+H); Anal. HPLC Retention time: 1.44 (Method 2); ROCK2 IC$_{50}$=1.0 nM.

Example 244: Preparation of 2-[3-methoxy-4-(1H-pyrazol-4-yl)phenyl]-8-{4-[4-(1-methylpiperidin-4-yl)piperazin-1-yl]benzoyl}-2,8-diazaspiro[4.5]decan-1-one

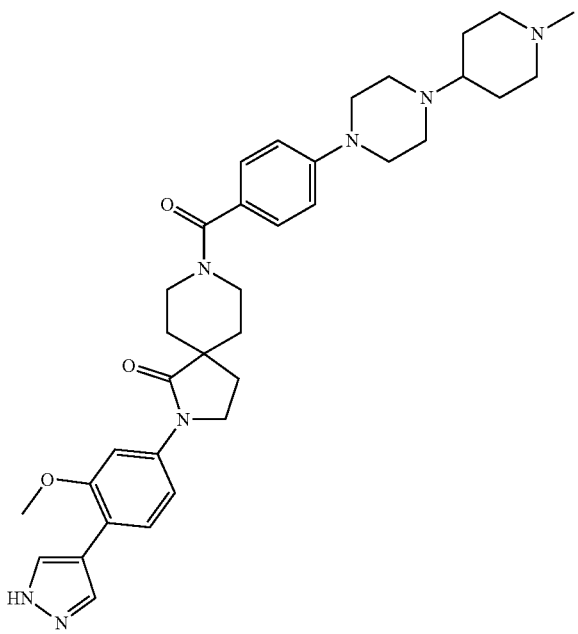

$^1$H NMR (500 MHz, DMSO-$d_6$) δ 8.02 (s, 2H), 7.64-7.55 (m, 2H), 7.35 (br d, J=8.4 Hz, 2H), 7.14 (br d, J=8.5 Hz, 1H), 7.06 (br d, J=8.4 Hz, 2H), 3.86 (s, 5H), 3.62 (br s, 6H), 3.46-3.40 (m, 1H), 3.34 (br d, J=6.3 Hz, 1H), 3.25-3.09 (m, 2H), 3.06-2.93 (m, 2H), 2.78 (br s, 3H), 2.51-2.47 (m, 5H), 2.35 (br d, J=12.2 Hz, 2H), 2.14 (br s, 2H), 1.96-1.82 (m, 2H), 1.71 (br t, J=9.5 Hz, 2H), 1.58 (br s, 2H); MS ESI m/z 612.1 (M+H); Anal. HPLC Retention time: 1.06 Method 1; ROCK2 IC$_{50}$=0.9 nM.

Example 245: Preparation of 8-[4-(4-{[4-(dimethylamino)phenyl]methyl}piperazin-1-yl)benzoyl]-2-[3-methoxy-4-(1H-pyrazol-4-yl)phenyl]-2,8-diazaspiro[4.5]decan-1-one

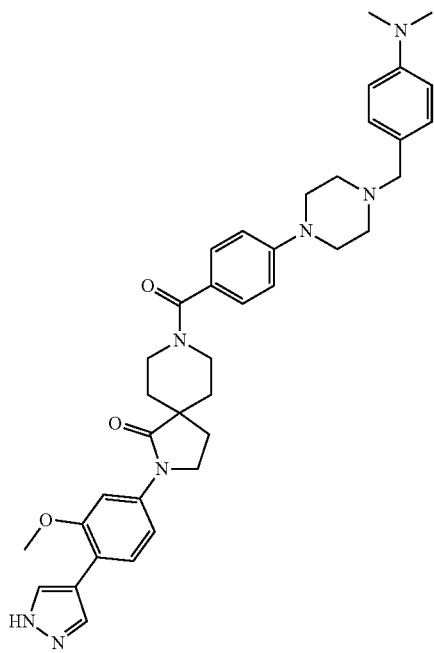

$^1$H NMR (500 MHz, DMSO-$d_6$) δ 8.02 (br s, 2H), 7.60 (s, 2H), 7.28 (br d, J=8.3 Hz, 2H), 7.12 (br d, J=8.5 Hz, 3H), 6.94 (br d, J=8.4 Hz, 2H), 6.69 (br d, J=8.2 Hz, 2H), 3.86 (s, 5H), 3.59-3.54 (m, 5H), 3.25-3.11 (m, 5H), 2.87 (s, 6H), 2.46 (br s, 4H), 2.14 (br s, 2H), 1.70 (br d, J=9.3 Hz, 2H), 1.56 (br d, J=10.9 Hz, 2H); MS ESI m/z 648.2 (M+H); Anal. HPLC Retention time: 1.75 (Method 2); ROCK2 IC$_{50}$=0.1 nM.

Example 246: Preparation of 2-[3-methoxy-4-(1H-pyrazol-4-yl)phenyl]-8-(4-{4-[(oxolan-3-yl)methyl]piperazin-1-yl}benzoyl)-2,8-diazaspiro[4.5]decan-1-one

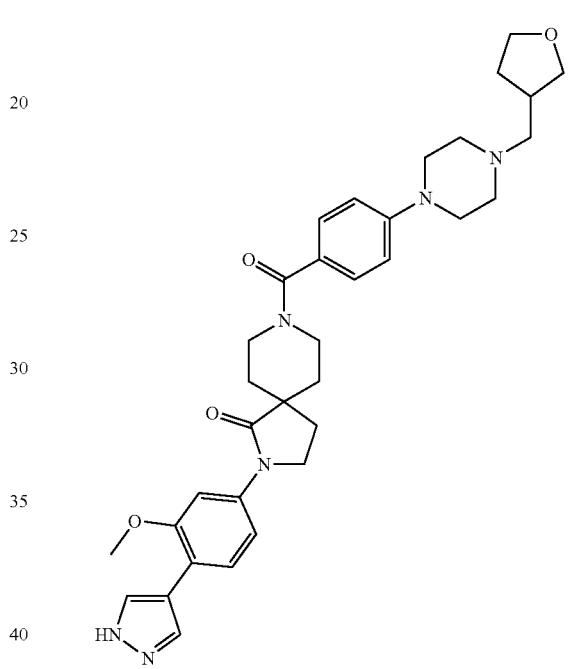

$^1$H NMR (500 MHz, DMSO-$d_6$) δ 8.02 (br s, 2H), 7.66-7.55 (m, 2H), 7.29 (br d, J=8.5 Hz, 2H), 7.14 (br d, J=8.4 Hz, 1H), 6.95 (br d, J=8.6 Hz, 2H), 4.03 (br dd, J=11.3, 4.0 Hz, 1H), 3.91-3.79 (m, 5H), 3.77-3.66 (m, 3H), 3.64-3.58 (m, 5H), 3.42-3.33 (m, 1H), 3.25-3.16 (m, 4H), 2.49-2.43 (m, 3H), 2.30 (br d, J=7.3 Hz, 2H), 2.14 (br t, J=6.3 Hz, 2H), 1.95 (br dd, J=12.3, 5.0 Hz, 1H), 1.78-1.65 (m, 3H), 1.62-1.47 (m, 3H); MS ESI m/z 599.2 (M+H); Anal. HPLC Retention time: 1.38 (Method 2); ROCK2 IC$_{50}$=0.7 nM.

What is claimed is:

1. A compound according to Formula (I):

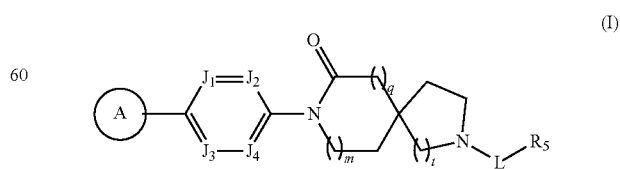

or a stereoisomer, a tautomer, or a pharmaceutically acceptable salt thereof, wherein Ring A is selected from

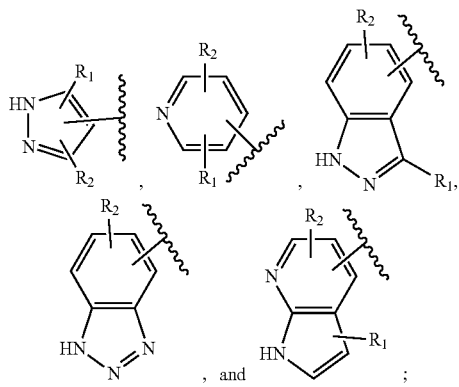

, and ;

$J_1$, $J_2$, $J_3$, and $J_4$ are independently selected from N, $CR_3$, and $CR_4$; provided no more than two of $J_1$, $J_2$, $J_3$, and $J_4$ are N;

L is selected from —C(O)—, —C(O)NH—, and —S(O)$_p$—;

$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$C(=O)NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 $R_e$, and —(CH$_2$)$_r$-heterocyclyl substituted with 0-3 $R_e$;

$R_3$, at each occurrence, is independently selected from H, F, Cl, Br, CN, $C_{1-4}$ alkyl substituted with 0-3 $R_e$, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$C(=O)(CH$_2$)$_r$NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 $R_e$, and —(CH$_2$)$_r$-heterocyclyl substituted with 0-3 $R_e$;

$R_4$, at each occurrence, is independently selected from H, F, Cl, Br, OH, CN, $OC_{1-4}$ alkyl substituted with 0-3 $R_e$, $NR_aR_a$, and $C_{1-4}$ alkyl substituted with 0-3 $R_e$;

$R_5$ is selected from $C_{3-10}$ carbocyclyl substituted with 0-5 $R_6$ and heterocyclyl comprising carbon atoms and 1-6 heteroatoms selected from N, $NR_{6a}$, S, and O, and substituted with 0-6 $R_6$;

$R_6$, at each occurrence, is independently selected from F, Cl, Br, =O, $C_{1-4}$alkyl, $C_{2-4}$alkenyl, $C_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_7$R$_7$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$C(=O)R$_b$, —(CHR$_d$)$_r$C(=O)NR$_a$R$_a$, —(CHR$_d$)$_r$OC(=O)R$_b$, —(CHR$_d$)$_r$—C$_{3-6}$cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 $R_e$;

$R_{6a}$ is selected from H, $C_{1-4}$alkyl, $C_{2-4}$alkenyl, $C_{2-4}$alkynyl, —S(O)$_p$R$_c$, —S(O)$_p$NR$_a$R$_a$, —C(=O)OR$_b$, —C(=O)R$_b$, —C(=O)NR$_a$R$_a$, —(CHR$_d$)$_r$—C$_{3-6}$cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 $R_e$;

$R_7$, at each occurrence, is independently selected from H, $C_{1-6}$ alkyl substituted with 1-5 $R_a$, $C_{2-6}$ alkenyl substituted with 1-5 $R_a$, $C_{2-6}$ alkynyl substituted with 1-5 $R_a$, —(CH$_2$)$_r$—C$_{3-10}$carbocyclyl substituted with 1-5 $R_a$, and —(CH$_2$)$_r$-heterocyclyl substituted with 1-5 $R_a$; or $R_7$ and $R_7$ together with the nitrogen atom to which they are both attached form a heterocyclic ring substituted with 1-5 $R_a$;

$R_a$, at each occurrence, is independently selected from H, C(=O)OR$_b$, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from F, Cl, Br, CN, NO$_2$, =O, $C_{1-6}$ alkyl substituted with 1-5 $R_f$, $C_{2-6}$ alkenyl, $C_{2-6}$ alkynyl, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$, —(CH$_2$)$_r$NR$_f$R$_f$, —(CH$_2$)$_r$—C$_{3-6}$cycloalkyl substituted with 1-5 $R_f$, —O(CH$_2$)$_r$—C$_{3-6}$ cycloalkyl substituted with 1-5 $R_f$, —(CH$_2$)$_r$-heterocyclyl substituted with 1-5 $R_f$, —O(CH$_2$)$_r$-heterocyclyl substituted with 1-5 $R_f$, —(CH$_2$)$_r$-aryl substituted with 1-5 $R_f$, —O(CH$_2$)$_r$-aryl substituted with 1-5 $R_f$, —(CH$_2$)$_r$-heteroaryl substituted with 1-5 $R_f$, and —O(CH$_2$)$_r$-heteroaryl substituted with 1-5 $R_f$;

$R_f$ at each occurrence, is independently selected from H, F, Cl, Br, CN, NO$_2$, =O, $C_{1-5}$alkyl (optionally substituted with F, Cl, Br, OH, $OC_{1-4}$ alkyl, $NR_gR_g$), —(CH$_2$)$_r$—C$_{3-10}$carbocyclyl and —(CH$_2$)$_r$-heterocyclyl, or $R_f$ and $R_f$ together with the nitrogen atom to which they are both attached form a heterocyclic ring optionally substituted with $C_{1-4}$alkyl;

$R_g$, at each occurrence, is independently selected from H and $C_{1-5}$alkyl;

m is an integer of zero, 1 or 2;
p is an integer of zero, 1 or 2;
q is an integer of zero or 1;
r is an integer of zero, 1, 2, 3 or 4; and
t is an integer of zero, 1 or 2.

2. The compound of claim 1 or a stereoisomer, a tautomer, or a pharmaceutically acceptable salt thereof, wherein
$R_1$, at each occurrence, is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

R$_2$, at each occurrence, is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$CN, —(CH$_2$)$_r$NR$_a$C(=O)OR$_b$, —(CH$_2$)$_r$OC(=O)NR$_a$R$_a$, —(CH$_2$)$_r$C(=O)OR$_b$, —(CH$_2$)$_r$NR$_a$S(O)$_p$NR$_a$R$_a$, and —(CH$_2$)$_r$NR$_a$S(O)$_p$R$_c$;

R$_3$, at each occurrence, is independently selected from H, F, Cl, Br, CN, C$_{1-4}$ alkyl substituted with 0-3 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$NR$_a$C(=O)R$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

R$_4$, at each occurrence, is independently selected from H, F, Cl, Br, OH, CN, and C$_{1-4}$ alkyl substituted with 0-3 R$_e$;

R$_5$ is selected from

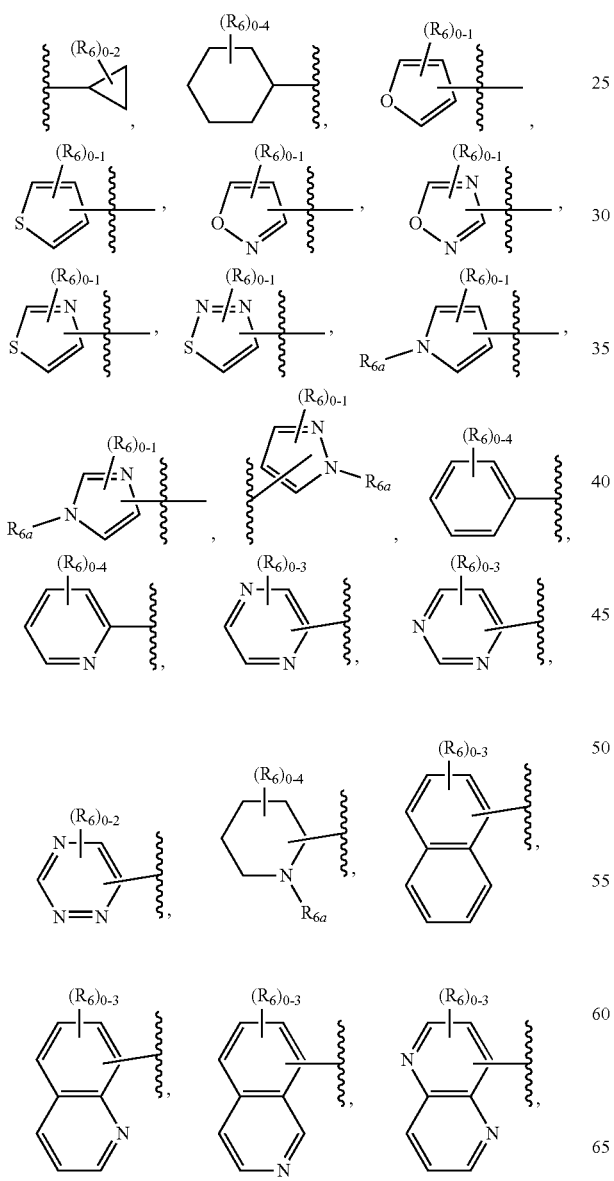

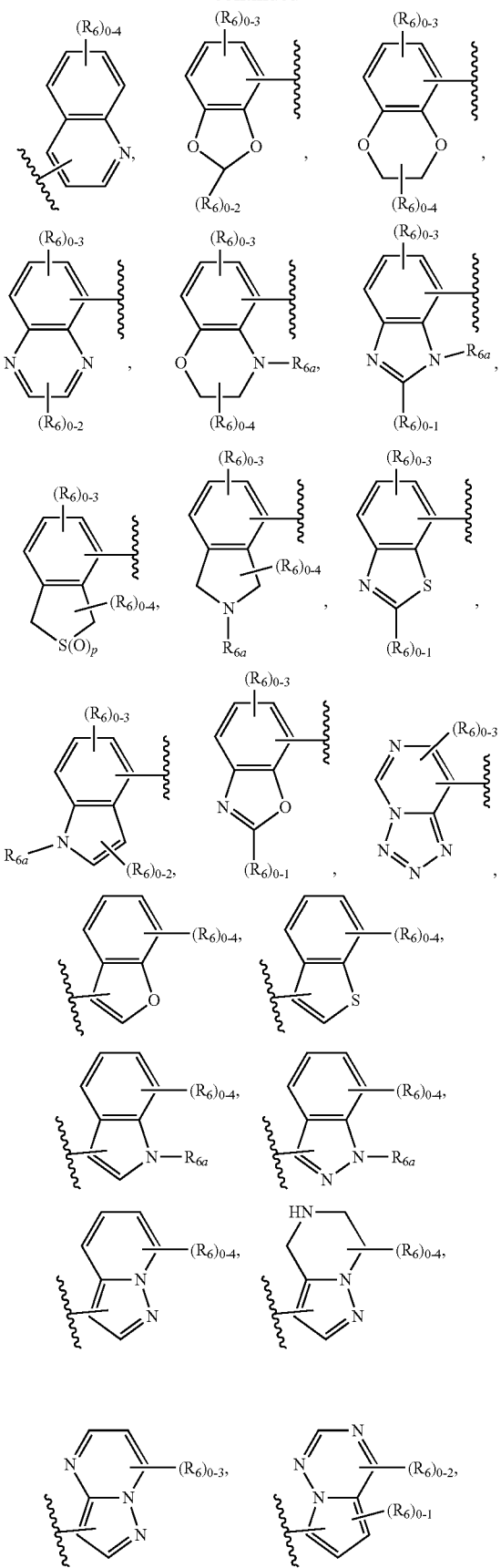

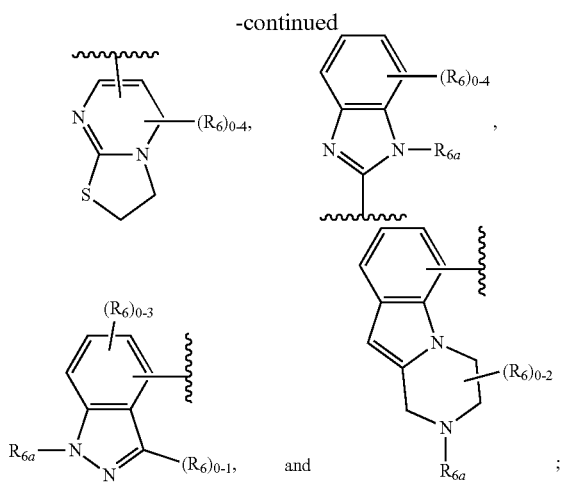

R$_6$, at each occurrence, is independently selected from F, Cl, Br, =O, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O)NR$_a$R$_a$, —(CHR$_d$)$_r$C(=O)OR$_b$, —(CHR$_d$)$_r$(=O)R$_b$, —C(=O)NR$_a$R$_a$—(CHR$_d$)$_r$OC(=O)R$_b$, —(CHR$_d$)$_r$—C$_{3-6}$ cycloalkyl, —(CHR$_d$)$_r$-heterocyclyl, —(CHR$_d$)$_r$-aryl, and —(CHR$_d$)$_r$-heteroaryl, wherein said alkyl, alkenyl, alkynyl, cycloalkyl, heterocyclyl, aryl, or heteroaryl is substituted with 0-4 R$_e$;

R$_{6a}$, at each occurrence, is independently selected from H, C$_{1-4}$alkyl, —S(O)$_p$R$_c$, —S(O)$_p$NR$_a$R$_a$, —C(=O)OR$_b$, —C(=O)R$_b$, —C(=O)NR$_a$R$_a$, —(CHR$_d$)$_r$—C$_{3-6}$ cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_7$, at each occurrence, is independently selected from H, C$_{1-6}$ alkyl substituted with 1-5 R$_a$, C$_{2-6}$ alkenyl substituted with 1-5 R$_a$, C$_{2-6}$ alkynyl substituted with 1-5 R$_a$, —(CH$_2$)$_r$—C$_{3-10}$carbocyclyl substituted with 1-5 R$_a$, and —(CH$_2$)$_r$-heterocyclyl substituted with 1-5 R$_a$; or R$_7$ and R$_7$ together with the nitrogen atom to which they are both attached form a heterocyclic ring substituted with 1-5 R$_a$;

R$_a$, at each occurrence, is independently selected from H, $_r$C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, —(CH$_2$)$_r$OR$_f$, S(O)$_p$R$_f$, C(=O)NR$_f$R$_f$, NR$_f$C(=O)R$_d$, S(O)$_p$NR$_f$R$_f$, NR$_f$S(O)$_p$R$_d$, NR$_f$C(=O)OR$_d$, OC(=O)NR$_f$R$_f$, —(CH$_2$)$_r$NR$_f$R$_f$, —(CH$_2$)$_r$—C$_{3-6}$cycloalkyl substituted with 1-5 R$_f$, —O(CH$_2$)$_r$—C$_{3-6}$cycloalkyl substituted with 1-5 R$_f$, —(CH$_2$)$_r$-heterocyclyl substituted with 1-5 R$_f$, —O(CH$_2$)$_r$-heterocyclyl substituted with 1-5 R$_f$, —(CH$_2$)$_r$-aryl substituted with 1-5 R$_f$, —O(CH$_2$)$_r$-aryl substituted with 1-5 R$_f$, —(CH$_2$)$_r$-heteroaryl substituted with 1-5 R$_f$, and —O(CH$_2$)$_r$-heteroaryl substituted with 1-5 R$_f$;

R$_f$, at each occurrence, is independently selected from H, F, Cl, Br, CN, OH, C$_{1-5}$alkyl (optionally substituted with F, Cl, Br, OH, and OC$_{1-4}$ alkyl, —NR$_g$R$_g$), —(CH$_2$)$_r$—C$_{3-10}$carbocyclyl, and —(CH$_2$)$_r$-heterocyclyl, or R$_f$ and R$_f$ together with the nitrogen atom to which they are both attached form a heterocyclic ring optionally substituted with C$_{1-4}$alkyl; and R$_g$, at each occurrence, is independently selected from H and C$_{1-5}$alkyl.

3. The compound of claim 2, having Formula (II):

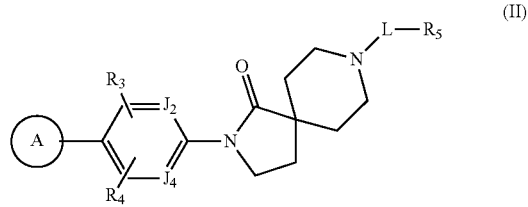

or a stereoisomer, a tautomer, or a pharmaceutically acceptable salt thereof, wherein
Ring A is selected from

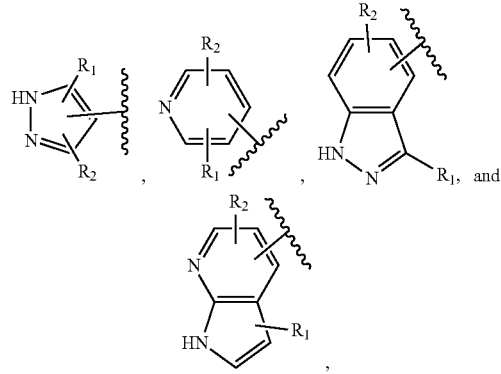

J$_2$ and J$_4$ are independently selected from N, CR$_3$, and CR$_4$;

L is selected from —C(O)— and —S(O)$_p$—;

R$_1$ at each occurrence, is independently selected from H, F, Cl, Br, CN, NR$_a$R$_a$, and C$_{1-4}$alkyl substituted with 0-4 R$_e$;

R$_2$, at each occurrence, is independently selected from H, F, Cl, Br, OH, CN, NR$_a$R$_a$, and C$_{1-4}$alkyl substituted with 0-4 R$_e$;

R$_3$, at each occurrence, is independently selected from H, F, Cl, Br, CN, C$_{1-4}$ alkyl substituted with 0-3 R$_e$, —(CH$_2$)$_r$OR$_b$, and —C$_{3-6}$cycloalkyl;

R₄, at each occurrence, is independently selected from H, F, Cl, Br, OH, CN, OC₁₋₄ alkyl substituted with 0-3 R_e, and C₁₋₄ alkyl substituted with 0-3 R_e;

R₅ is selected from

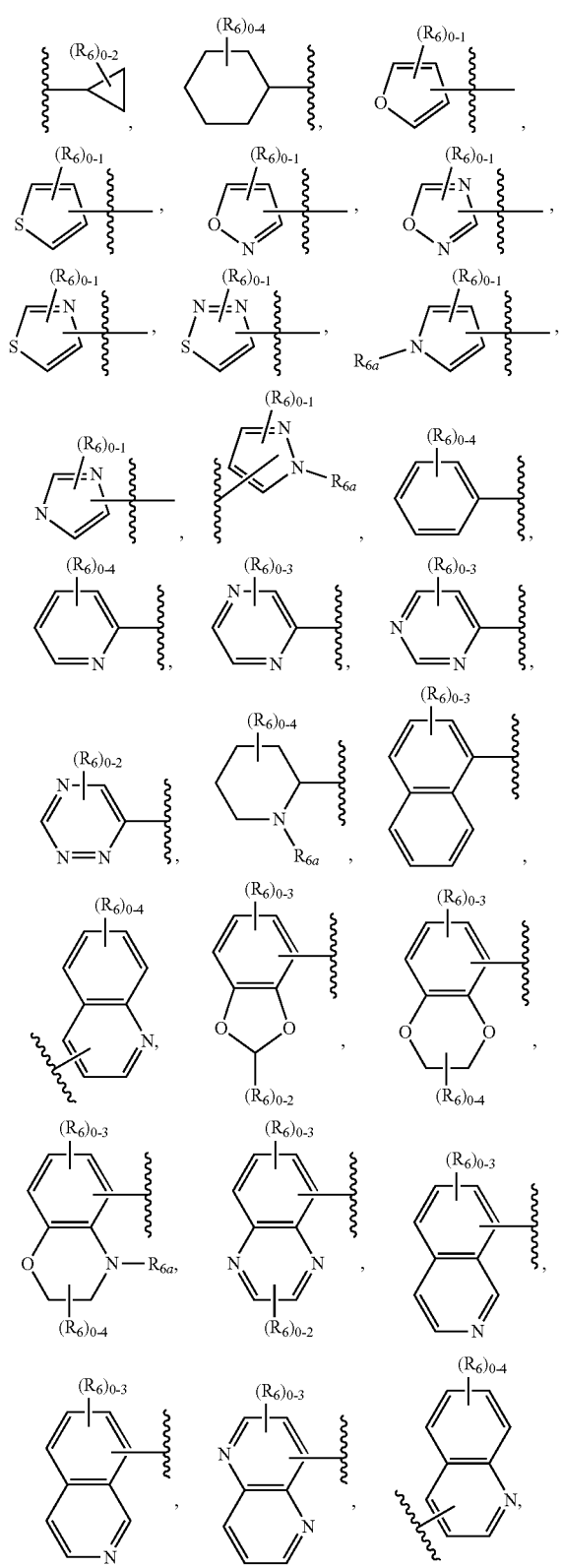

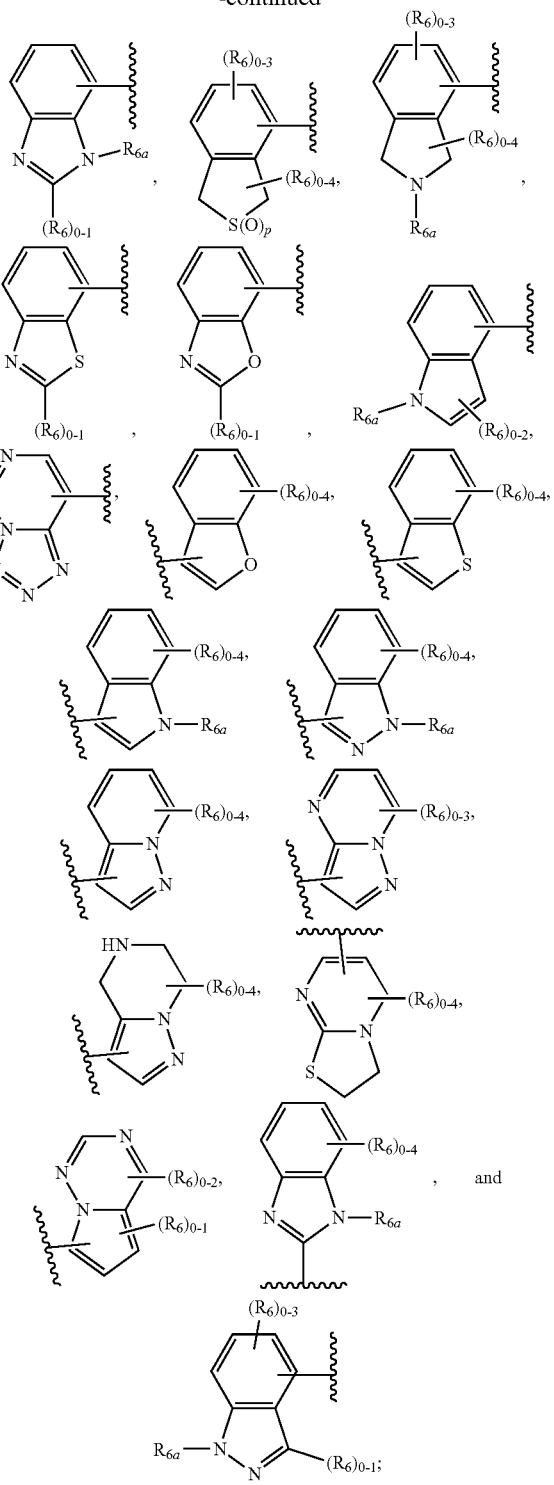

R₆, at each occurrence, is independently selected from F, Cl, Br, C₁₋₄alkyl, C₂₋₄ alkenyl, C₂₋₄ alkynyl, nitro, —(CHR_d)_rS(O)_pR_c, —(CHR_d)_rS(O)_pNR_aR_a, —(CHR_d)_rNR_aS(O)_pR_c, —(CHR_d)_rOR_b, —(CHR_d)_rCN, —(CHR_d)_rNR_aR_a, —(CHR_d)_rNR_aC(=O)R_b, —(CHR_d)_rNR_aC(=O)NR_aR_a, —(CHR_d)_rC(=O)OR_b, —(CHR_d)_rC(=O)R_b, —C(=O)NR_aR_a— (CHR_d)_r OC(=O)R_b, —(CHR_d)_r—C₃₋₆cycloalkyl, —(CHR_d)_r-heterocyclyl, —(CHR_d)_r-aryl, and —(CHR$_d$)$_r$-heteroaryl, wherein said alkyl, alkenyl, alkynyl, cycloalkyl, heterocyclyl, aryl, or heteroaryl is substituted with 0-4 R$_e$;

R$_{6a}$, at each occurrence, is independently selected from H, C$_{1-4}$alkyl, —S(O)$_p$R$_c$, —S(O)$_p$NR$_a$R$_a$, —C(=O)OR$_b$, —C(=O)R$_b$, —C(=O)NR$_a$R$_a$, —(CHR$_d$)$_r$—C$_{3-6}$cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

R$_7$, at each occurrence, is independently selected from H, C$_{1-6}$ alkyl substituted with 0-5 R$_a$, C$_{2-6}$ alkenyl substituted with 1-5 R$_a$, C$_{2-6}$ alkynyl substituted with 1-5 R$_a$, —(CH$_2$)$_r$—C$_{3-10}$carbocyclyl substituted with 1-5 R$_a$, and —(CH$_2$)$_r$-heterocyclyl substituted with 1-5 R$_a$; or R$_7$ and R$_7$ together with the nitrogen atom to which they are both attached form a heterocyclic ring substituted with 1-5 R$_a$;

R$_a$, at each occurrence, is independently selected from H, C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, CO$_2$H, —(CH$_2$)$_r$OR$_f$, S(O)$_p$R$_f$, S(O)$_p$NR$_f$R$_f$, NR$_f$S(O)$_p$R$_f$, —(CH$_2$)$_r$NR$_f$R$_f$, —(CH$_2$)$_r$—C$_{3-6}$cycloalkyl, —O(CH$_2$)$_r$—C$_{3-6}$cycloalkyl, —(CH$_2$)$_r$-heterocyclyl, —O(CH$_2$)$_r$-heterocyclyl, —(CH$_2$)$_r$-aryl, and —O(CH$_2$)$_r$-aryl;

R$_f$, at each occurrence, is independently selected from H, F, Cl, Br, CN, OH, C$_{1-5}$ alkyl (optionally substituted with F, Cl, Br, OH, and OC$_{1-4}$ alkyl, —NR$_g$R$_g$), —(CH$_2$)$_r$—C$_{3-6}$cycloalkyl, and —(CH$_2$)$_r$-phenyl; and R$_g$, at each occurrence, is independently selected from H and C$_{1-5}$ alkyl.

4. The compound of claim 3, having Formula (III):

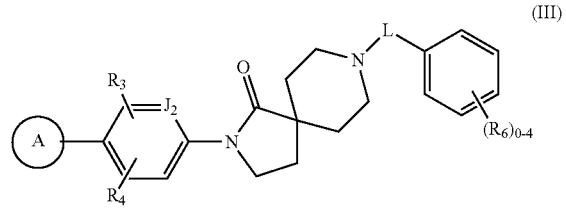

(III)

or a stereoisomer, a tautomer, or a pharmaceutically acceptable salt thereof, wherein Ring A is selected from

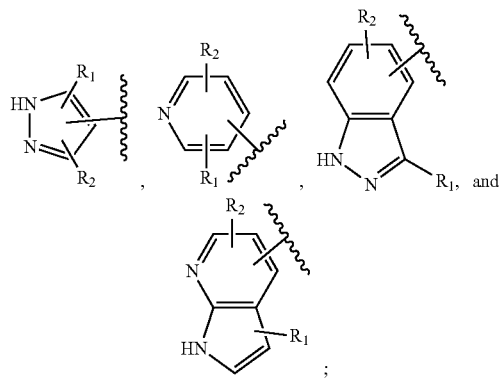

J$_2$ is selected from N, CR$_3$, and CR$_4$;
L is selected from —C(O)— and —S(O)$_p$—;
R$_1$, at each occurrence, is independently selected from H, F, Cl, Br, CN, NR$_a$R$_a$, and C$_{1-4}$alkyl substituted with 0-4 R$_e$;
R$_2$, at each occurrence, is independently selected from H and C$_{1-4}$alkyl substituted with 0-4 R$_e$;
R$_3$, at each occurrence, is independently selected from H, F, Cl, Br, CN, C$_{1-4}$ alkyl substituted with 0-3 R$_e$, —(CH$_2$)$_r$OR$_b$, and —C$_{3-6}$cycloalkyl;
R$_4$, at each occurrence, is independently selected from H, F, Cl, Br, OH, CN, OC$_{1-4}$ alkyl substituted with 0-3 R$_e$, and C$_{1-4}$ alkyl substituted with 0-3 R$_e$;
R$_6$, at each occurrence, is independently selected from F, Cl, Br, C$_{1-4}$ alkyl, —(CH$_2$)$_r$OR$_b$, —(CH$_2$)$_r$CN, —(CH$_2$)$_r$NR$_7$R$_7$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$, —(CH$_2$)$_r$OC(=O)R$_b$, —(CH$_2$)$_r$C(=O)NR$_a$R$_a$, —(CH$_2$)$_r$—C$_{3-6}$cycloalkyl, —(CH$_2$)$_r$-heterocyclyl, —(CH$_2$)$_r$-aryl, and —(CH$_2$)$_r$-heteroaryl, wherein said alkyl, cycloalkyl, aryl, or heteroaryl is substituted with 0-4 R$_e$;
R$_7$, at each occurrence, is independently selected from H, C$_{1-6}$ alkyl substituted with 1-5 R$_a$, C$_{2-6}$ alkenyl substituted with 1-5 R$_a$, C$_{2-6}$ alkynyl substituted with 1-5 R$_a$, —(CH$_2$)$_r$—C$_{3-10}$carbocyclyl substituted with 1-5 R$_a$, and —(CH$_2$)$_r$-heterocyclyl substituted with 1-5 R$_a$; or R$_7$ and R$_7$ together with the nitrogen atom to which they are both attached form a heterocyclic ring substituted with 1-5 R$_a$;
R$_a$, at each occurrence, is independently selected from H, C(=O)OR$_b$, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;
R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;
R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;
R$_e$, at each occurrence, is independently selected from F, Cl, Br, CN, NO$_2$, =O, C$_{1-6}$ alkyl substituted with 1-5

$R_f$, $C_{2-6}$ alkenyl, $C_{2-6}$ alkynyl, $CO_2H$, —$(CH_2)_rOR_f$, $S(O)_pR_f$, $S(O)_pNR_fR_f$, $NR_fS(O)_pR_a$, —$(CH_2)_rNR_fR_f$, —$(CH_2)_r$—$C_{3-6}$cycloalkyl, —$O(CH_2)_r$—$C_{3-6}$cycloalkyl, —$(CH_2)_r$-heterocyclyl, —$O(CH_2)_r$-heterocyclyl, —$(CH_2)_r$-aryl, and —$O(CH_2)_r$-aryl;

$R_f$, at each occurrence, is independently selected from H, F, Cl, Br, CN, OH, $C_{1-5}$ alkyl (optionally substituted with F, Cl, Br, OH, $OC_{1-4}$ alkyl, $NR_gR_g$), —$(CH_2)_r$—$C_{3-6}$cycloalkyl, and —$(CH_2)_r$-phenyl; and $R_g$, at each occurrence, is independently selected from H and $C_{1-5}$alkyl.

5. The compound of claim 4, having Formula (IV):

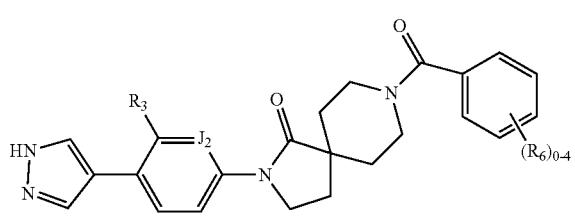

(IV)

or a stereoisomer, a tautomer, or a pharmaceutically acceptable salt thereof, wherein $J_2$ is selected from N and CH;

$R_3$ is selected from H, CN, $C_{1-4}$ alkyl, —$OC_{1-3}$ alkyl, and —$C_{3-6}$cycloalkyl;

$R_6$, at each occurrence, is independently selected from F, Cl, Br, $C_{1-4}$ alkyl, —$(CH_2)_rOR_b$, —$(CH_2)_rNR_7R_7$, —$(CH_2)_rNR_aC(=O)R_b$, —$(CH_2)_rNR_aC(=O)NR_aR_a$, —$(CH_2)_rC(=O)OR_b$, —$(CH_2)_rC(=O)R_b$, —$C(=O)NR_aR_a$, —$(CH_2)_rOC(=O)R_b$, —$(CH_2)_rC(=O)NR_aR_a$, —$(CH_2)_r$—$C_{3-6}$cycloalkyl, —$(CH_2)_r$-heterocyclyl, —$(CH_2)_r$-aryl, and —$(CH_2)_r$-heteroaryl, wherein said alkyl, cycloalkyl, heterocyclyl, aryl, or heteroaryl is substituted with 0-4 $R_e$;

$R_7$, at each occurrence, is independently selected from H, $C_{1-6}$ alkyl substituted with 1-5 $R_a$, $C_{2-6}$ alkenyl substituted with 1-5 $R_a$, $C_{2-6}$ alkynyl substituted with 1-5 $R_a$, —$(CH_2)_r$—$C_{3-10}$carbocyclyl substituted with 1-5 $R_a$, and —$(CH_2)_r$-heterocyclyl substituted with 1-5 $R_a$; or $R_7$ and $R_7$ together with the nitrogen atom to which they are both attached form a heterocyclic ring substituted with 1-5 $R_a$;

$R_a$, at each occurrence, is independently selected from H, $C(=O)OR_b$, $C_{1-6}$ alkyl substituted with 0-5 $R_e$, —$(CH_2)_r$—$C_{3-6}$cycloalkyl substituted with 0-5 $R_e$, —$(CH_2)_r$-aryl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_e$, at each occurrence, is independently selected from F, Cl, Br, CN, $NO_2$, =O, $C_{1-6}$ alkyl substituted with 1-5 $R_f$, $CO_2H$, $OR_f$, $NHS(O)_pC_{1-4}$alkyl, $NR_fR_f$ —$(CH_2)_r$—$C_{3-6}$cycloalkyl, —$O(CH_2)_r$—$C_{3-6}$cycloalkyl, —$(CH_2)_r$-heterocyclyl, —$O(CH_2)_r$-heterocyclyl, —$(CH_2)_r$-aryl, and —$O(CH_2)_r$-aryl;

$R_f$, at each occurrence, is independently selected from H, F, Cl, Br, CN, =O, $C_{1-5}$ alkyl (optionally substituted with F, Cl, Br, OH, $OC_{1-4}$ alkyl, $NR_gR_g$), —$(CH_2)_r$—$C_{3-6}$cycloalkyl, and —$(CH_2)_r$-phenyl;

$R_g$, at each occurrence, is independently selected from H and $C_{1-5}$alkyl; and r is an integer of zero, 1, 2 or 3.

6. The compound of claim 4, having Formula (V):

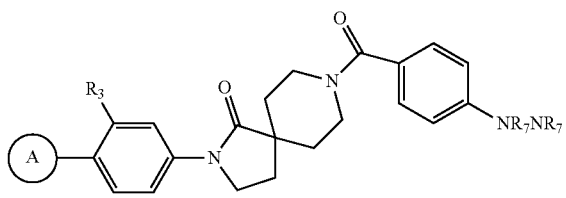

(V)

or a stereoisomer, a tautomer, or a pharmaceutically acceptable salt thereof, wherein Ring A is selected from

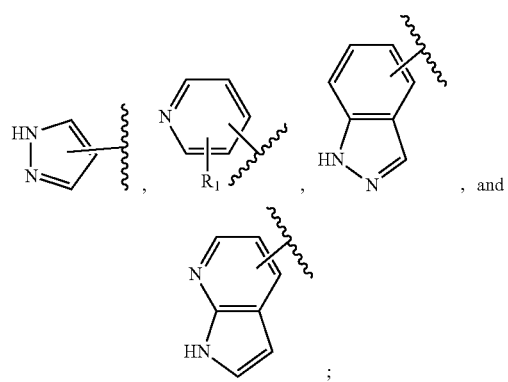

;

$R_1$ selected from H, F, Cl, Br, $NR_aR_a$, and $C_{1-4}$alkyl;

$R_3$ is —$OC_{1-3}$ alkyl;

$R_7$, at each occurrence, is independently selected from H, $C_{1-6}$ alkyl substituted with 1-5 $R_a$; or $R_7$ and $R_7$ together with the nitrogen atom to which they are both attached form a heterocyclic ring selected from

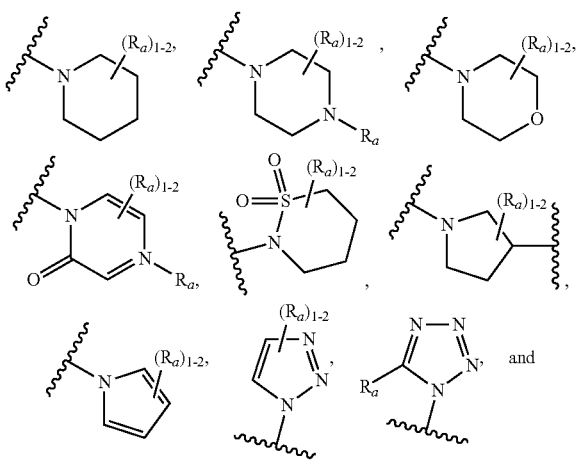

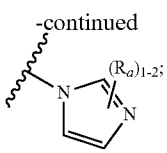

$R_a$, at each occurrence, is independently selected from H, C(=O)OR$_b$, C$_{1-6}$ alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;

$R_b$, at each occurrence, is independently selected from H, C$_{1-6}$ alkyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

$R_e$, at each occurrence, is independently selected from F, Cl, Br, CN, NO$_2$, =O, C$_{1-6}$ alkyl substituted with 1-4 R$_f$, CO$_2$H, OR$_f$, NHS(O)$_p$C$_{1-4}$alkyl, NR$_f$R$_f$, —(CH$_2$)$_r$—C$_{3-6}$cycloalkyl, —(CH$_2$)$_r$-heterocyclyl, —(CH$_2$)$_r$-aryl, —O(CH$_2$)$_r$—C$_{3-6}$cycloalkyl, —O(CH$_2$)$_r$-heterocyclyl, and —O(CH$_2$)$_r$-aryl;

$R_f$, at each occurrence, is independently selected from H, H, F, Cl, Br, CN, OH, C$_{1-5}$ alkyl (optionally substituted with F, Cl, Br, OH, OC$_{1-4}$ alkyl, NR$_g$R$_g$), —(CH$_2$)$_r$—C$_{3-6}$cycloalkyl, and —(CH$_2$)$_r$-phenyl;

$R_g$, at each occurrence, is independently selected from H and C$_{1-5}$alkyl; and r is an integer of zero, 1, 2 or 3.

7. The compound of claim 6, having Formula (VI):

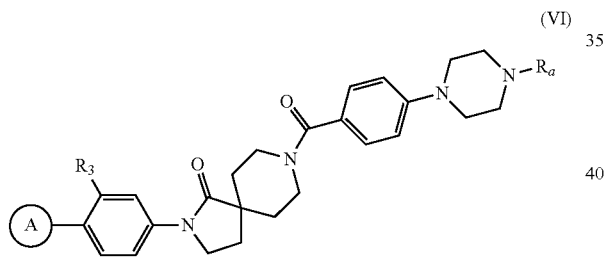

(VI)

or a stereoisomer, a tautomer, or a pharmaceutically acceptable salt thereof, wherein Ring A is selected from

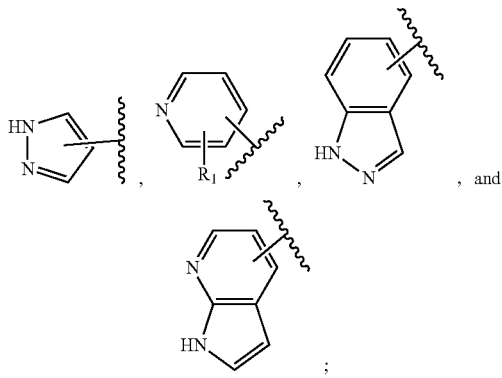

$R_1$ is selected from H, F, Cl, Br, NR$_a$R$_a$, and C$_{1-4}$alkyl;
$R_3$ is OC$_{1-4}$ alkyl;

$R_a$ is selected from H, C(=O)OC$_{1-4}$alkyl, C$_{1-6}$alkyl substituted with 0-5 R$_e$, —(CH$_2$)$_r$—C$_{3-6}$cycloalkyl substituted with 0-5 R$_e$, —(CH$_2$)$_r$-aryl substituted with 0-5 R$_e$, and —(CH$_2$)$_r$-heterocyclyl substituted with 0-5 R$_e$;

$R_e$, at each occurrence, is independently selected from F, Cl, Br, CN, NO$_2$, =O, C$_{1-4}$ alkyl CO$_2$H, OR$_f$, NHS(O)$_p$C$_{1-4}$alkyl, NR$_f$R$_f$, —(CH$_2$)$_r$—C$_{3-6}$cycloalkyl, —(CH$_2$)$_r$-heterocyclyl, —(CH$_2$)$_r$-aryl, —O(CH$_2$)$_r$—C$_{3-6}$cycloalkyl, —O(CH$_2$)$_r$-heterocyclyl, and —O(CH$_2$)$_r$-aryl;

$R_f$, at each occurrence, is independently selected from H, F, Cl, Br, CN, OH, C$_{1-5}$ alkyl (optionally substituted with F, Cl, Br, OH, OC$_{1-4}$ alkyl, NR$_g$R$_g$), and —(CH$_2$)$_r$-phenyl; and $R_g$, at each occurrence, is independently selected from H and C$_{1-5}$alkyl.

8. The compound of claim 7 or a stereoisomer, a tautomer, or a pharmaceutically acceptable salt thereof, wherein $R_a$ is selected from H, C(=O)OC$_{1-4}$alkyl, C$_{1-6}$ alkyl substituted with 0-5 R$_e$, —(CH$_2$)$_r$—C$_{3-6}$cycloalkyl substituted with 0-5 R$_e$, —(CH$_2$)$_r$-phenyl substituted with 0-5 R$_e$, and —(CH$_2$)$_r$-heterocyclyl wherein the heterocyclyl is selected from

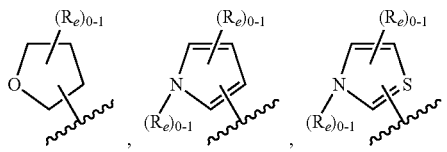

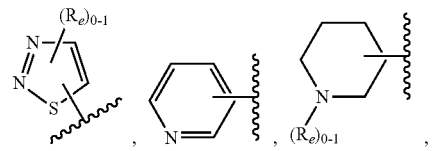

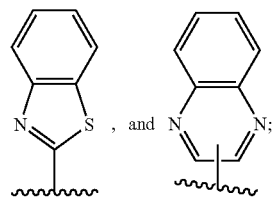

$R_e$, at each occurrence, is independently selected from F, Cl, Br, CN, NO$_2$, =O, C$_{1-6}$ alkyl substituted with 1-4 R$_f$, OR$_f$NHS(O)$_p$C$_{1-4}$alkyl, NR$_f$R$_f$, —(CH$_2$)$_r$—C$_{3-6}$cycloalkyl, —(CH$_2$)$_r$-heterocyclyl, —(CH$_2$)$_r$-aryl, —O(CH$_2$)$_r$—C$_{3-6}$cycloalkyl, —O(CH$_2$)$_r$-heterocyclyl, and —O(CH$_2$)$_r$-aryl;

$R_f$, at each occurrence, is independently selected from H, F, Cl, Br, CN, OH, and C$_{1-5}$ alkyl (optionally substituted with F, Cl, Br, OH, OC$_{1-4}$ alkyl, and NR$_g$R$_g$), and —(CH$_2$)$_r$-phenyl;

$R_g$, at each occurrence, is independently selected from H and C$_{1-4}$alkyl.

9. The compound of claim 3, having Formula (VII):
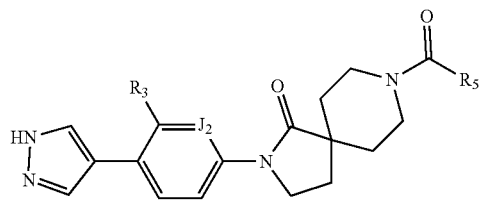
(VII)
or an enantiomer, a diastereomer, a stereoisomer, a tautomer, or a pharmaceutically acceptable salt thereof, wherein
$R_5$ is selected from
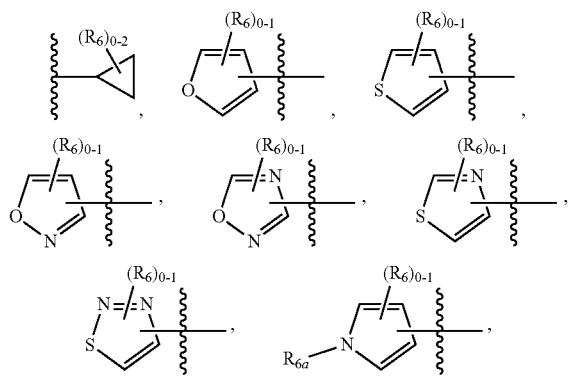
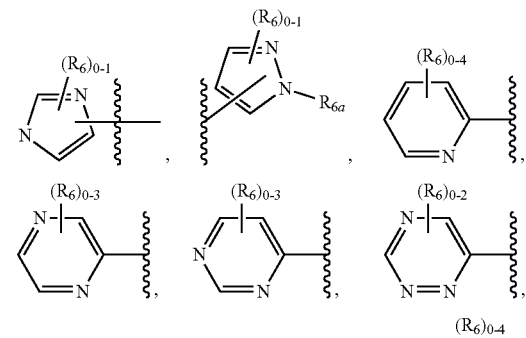
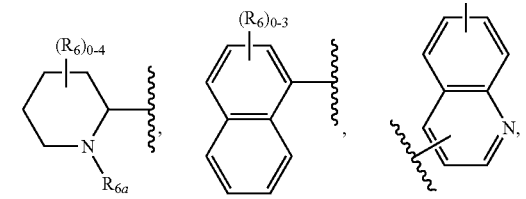
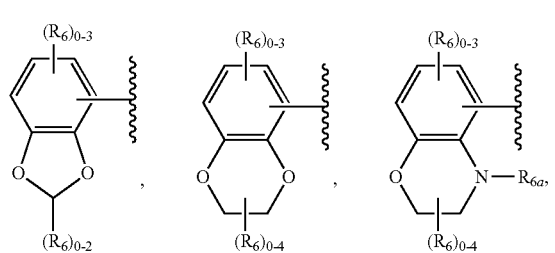
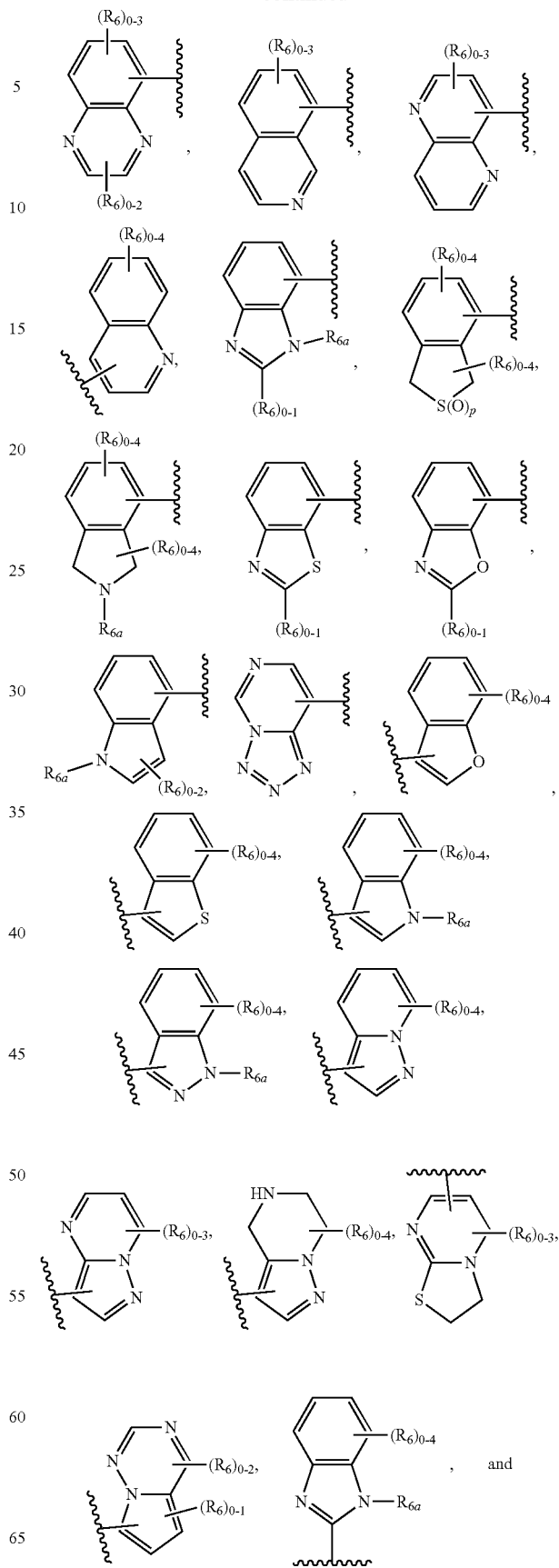
, and -continued

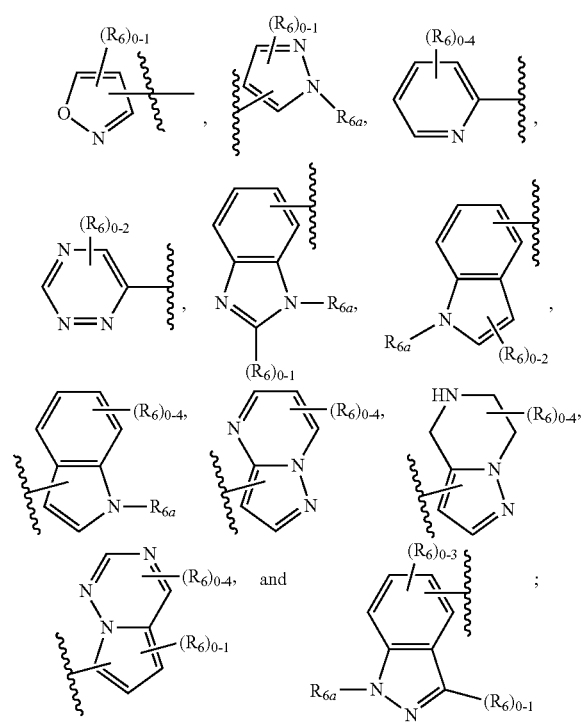

R$_6$, at each occurrence, is independently selected from F, Cl, Br, C$_{1-4}$alkyl, C$_{2-4}$alkenyl, C$_{2-4}$alkynyl, nitro, —(CH$_2$)$_r$S(O)$_p$R$_c$, —(CH$_2$)$_r$S(O)$_p$NR$_a$R$_a$, —(CH$_2$)$_r$NR$_a$S(O)$_p$R$_c$, —(CH$_2$)$_r$OR$_b$, —(CH$_2$)$_r$CN, —(CH$_2$)$_r$NR$_a$R$_a$, —(CH$_2$)$_r$NR$_a$C(=O)R$_b$, —(CH$_2$)$_r$NR$_a$C(=O)NR$_a$R$_a$, —(CH$_2$)$_r$C(=O)OR$_b$, —(CH$_2$)$_r$C(=O)R$_b$, —C(=O)NR$_a$R$_a$—(CH$_2$)$_r$OC(=O)R$_b$, —(CH$_2$)$_r$—C$_{3-6}$cycloalkyl, —(CH$_2$)$_r$-heterocyclyl, —(CH$_2$)$_r$-aryl, and —(CH$_2$)$_r$-heteroaryl, wherein said alkyl, alkenyl, alkynyl, cycloalkyl, heterocyclyl, aryl, or heteroaryl is substituted with 0-4 R$_e$; and R$_{6a}$, at each occurrence, is independently selected from H, C$_{1-4}$alkyl, —S(O)$_p$R$_c$, —S(O)$_p$NR$_a$R$_a$, —C(=O)OR$_b$, —C(=O)R$_b$, —C(=O)NR$_a$R$_a$, —(CH$_2$)$_r$—C$_{3-6}$cycloalkyl, —(CH$_2$)$_r$-heterocyclyl, —(CH$_2$)$_r$-aryl, and —(CH$_2$)$_r$-heteroaryl, wherein said alkyl, cycloalkyl, heterocyclyl, aryl, or heteroaryl is substituted with 0-4 R$_e$.

10. The compound of claim 9, or a stereoisomer, a tautomer, or a pharmaceutically acceptable salt thereof, wherein R$_5$ is selected from

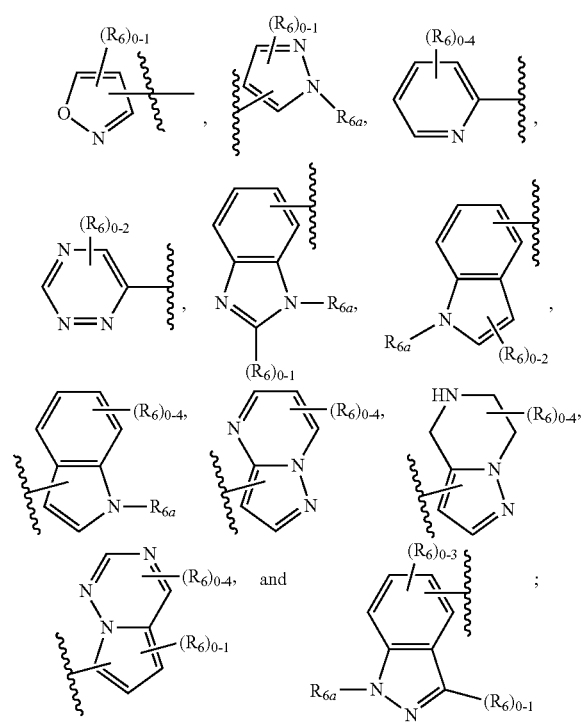

R$_6$, at each occurrence, is independently selected from F, Cl, Br, =O, C$_{1-4}$alkyl, OR$_b$, C$_{3-6}$cycloalkyl, heterocyclyl, aryl and heteroaryl wherein said alkyl, cycloalkyl, heterocyclyl, aryl, or heteroaryl is substituted with 0-4 R$_e$; and R$_{6a}$, at each occurrence, is independently selected from H and C$_{1-4}$ alkyl.

11. The compound of claim 2, having Formula (VIII):

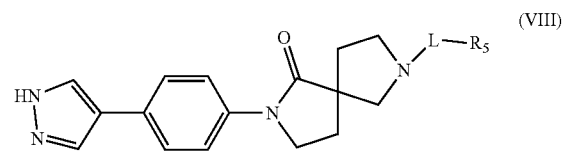

or a stereoisomer, a tautomer, or a pharmaceutically acceptable salt thereof, wherein L is selected from —C(O)— and —S(O)$_p$—;

R$_5$ is selected from

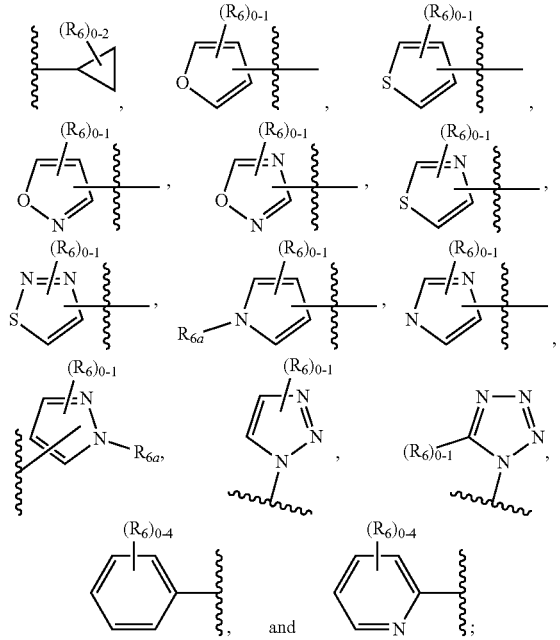

R$_6$, at each occurrence, is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, and —(CHR$_d$)$_r$NR$_a$R$_a$;

R$_{6a}$, at each occurrence, is independently selected from H and C$_{1-4}$alkyl;

R$_a$, at each occurrence, is independently selected from H and C$_{1-6}$ alkyl substituted with 0-5 R$_e$;

R$_b$, at each occurrence, is independently selected from H and C$_{1-6}$ alkyl substituted with 0-5 R$_e$;

R$_c$, at each occurrence, is independently selected from C$_{1-6}$ alkyl substituted with 0-5 R$_e$, C$_{2-6}$alkenyl substituted with 0-5 R$_e$, C$_{2-6}$alkynyl substituted with 0-5 R$_e$, C$_{3-6}$carbocyclyl, and heterocyclyl;

R$_e$, at each occurrence, is independently selected from F, Cl, Br, CN, NO$_2$, =O, C$_{1-6}$ alkyl substituted with 1-5 R$_f$, C$_{2-6}$ alkenyl, C$_{2-6}$ alkynyl, CO$_2$H, —(CH$_2$)$_r$OR$_f$, S(O)$_p$R$_f$, S(O)$_p$NR$_f$R$_f$, NR$_f$S(O)$_p$C$_{1-4}$alkyl, —(CH$_2$)$_r$NR$_f$R$_f$, —(CH$_2$)$_r$—C$_{3-6}$cycloalkyl, —(CH$_2$)$_r$-heterocyclyl, and —(CH$_2$)$_r$-aryl;

R$_f$, at each occurrence, is independently selected from H, F, Cl, Br, CN, OH, C$_{1-5}$ alkyl (optionally substituted with F, Cl, Br, OH, and OC$_{1-4}$ alkyl, NR$_g$R$_g$), C$_{3-6}$cycloalkyl, and phenyl;

$R_g$, at each occurrence, is independently selected from H and $C_{1-5}$alkyl; and r is an integer of zero, 1, 2 or 3.

12. A pharmaceutical composition comprising one or more compounds according to claim 1 and a pharmaceutically acceptable carrier or diluent.

* * * * *